United States Patent
Ding et al.

(10) Patent No.: US 8,134,001 B2
(45) Date of Patent: Mar. 13, 2012

(54) SPIROINDOLINONE DERIVATIVES

(75) Inventors: Qingjie Ding, Bridgewater, NJ (US); Nan Jiang, Fairfield, NJ (US); Song Yang, Shanghai (CN); Jing Zhang, Parsippany, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 606 days.

(21) Appl. No.: 12/272,870

(22) Filed: Nov. 18, 2008

(65) Prior Publication Data

US 2009/0156610 A1    Jun. 18, 2009

Related U.S. Application Data

(60) Provisional application No. 61/107,431, filed on Oct. 22, 2008, provisional application No. 61/013,691, filed on Dec. 14, 2007.

(51) Int. Cl.
*C07D 471/10* (2006.01)
*A61K 31/44* (2006.01)
(52) U.S. Cl. .................................. 546/17; 514/278
(58) Field of Classification Search ............ 546/17; 514/278
See application file for complete search history.

(56) References Cited

U.S. PATENT DOCUMENTS

| | | | |
|---|---|---|---|
| 7,495,007 B2 * | 2/2009 | Chen et al. | 514/278 |
| 2007/0213341 A1* | 9/2007 | Chen et al. | 514/253.03 |
| 2008/0009486 A1 | 1/2008 | Chen et al. | |
| 2008/0114013 A1 | 5/2008 | Liu et al. | |

FOREIGN PATENT DOCUMENTS

| WO | WO 2007/104664 | 9/2007 |
| WO | WO 2007104714 | 9/2007 |

OTHER PUBLICATIONS

J. Am Chem. Soc., 2005, 127, 10130.

* cited by examiner

*Primary Examiner* — Robert Havlin
(74) *Attorney, Agent, or Firm* — George W. Johnston; Patricia S. Rocha-Tramaloni

(57) ABSTRACT

There are provided compounds of the formula

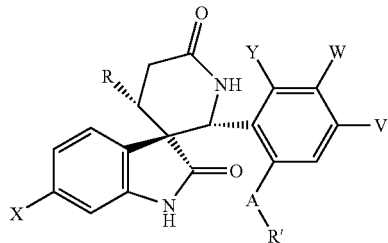

and pharmaceutically acceptable salts and esters thereof wherein W, V, X, Y, A, R and R' are as described herein. The compounds are useful as anticancer agents.

22 Claims, No Drawings

SPIROINDOLINONE DERIVATIVES

PRIORITY TO RELATED APPLICATION(S)

This application claims the benefit of U.S. Provisional Application No. 61/107,431, filed Oct. 22, 2008, and U.S. Provisional Application No. 61/013,691, filed Dec. 14, 2007. The entire contents of the above-identified applications are hereby incorporated by reference.

SUMMARY OF THE INVENTION

The present invention relates to spiroindolinone derivatives of the formula

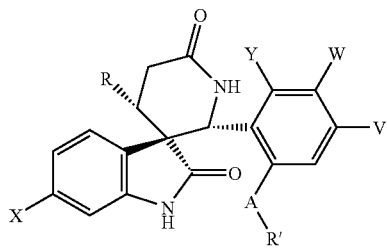

I and pharmaceutically acceptable salts and esters thereof wherein W, V, X, Y, A, R and R' are as described herein.

The compounds have utility as antiproliferative agents, especially, as anticancer agents.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am Chem. Soc., 2005, 127, 10130.

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

DETAILED DESCRIPTION OF THE INVENTION

The present invention relates to spiroindolinones of the formula

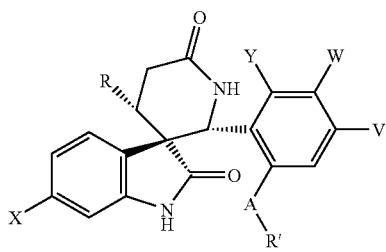

I wherein
X is Cl, F or Br
R is a substituted phenyl or substituted heteroaryl with the substituted phenyl or substituted heteroaryl selected from group consisting of:

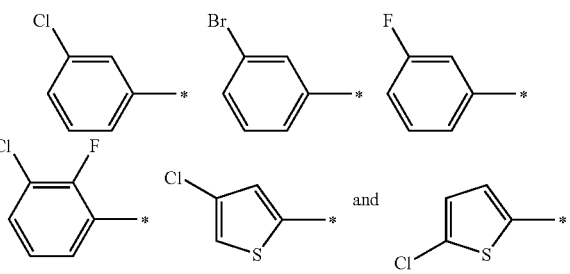

W is selected from the group consisting of F, Cl, Br, I, methyl, ethyl, cyclopropyl, cyano, methoxy, hydroxymethyl, COOMe, ethynyl, $CF_3$, vinyl, isopropenyl, 1-propynyl, 3-methyl-1-butynyl, 3,3-dimethyl-1-butynyl, 3-trifluoroethynyl, phenyl, 2-furany, 2-thiophenyl and 4-thiazolyl,
Y is hydrogen, F, Cl or Me,
V is hydrogen, F, Cl or methyl,
A is selected from the group consisting of a bond, O, NH, $CH_2$, C(=O), C(=O)NH, NHC(=O), NHC(=O)NH, S, $S(=O)_2$, and $O(CH_2)_n$
n=1, 2 or 3

R' is selected from the group consisting of heterocycle, substituted heterocyle, heteroaryl, substitluted heteroaryl, aryl, substituted aryl, substituted cycloalkyl and $CR_1R_2C(=O)NR_3R_4$ wherein $R_1$, $R_2$ are hydrogen or lower alkyl, or $R_1$ and $R_2$ may independently link to form a cyclic structure selected from a substituted or unsubstituted cycloalkyl and $R_3$, $R_4$ is independently selected from the group consisting of hydrogen, lower alkyl, aryl, lower alkenyl, substituted aryl, heteroaryl, substituted heteroaryl, heterocycle, substituted heterocycle, cycloalkyl and substituted cycloalkyl with the proviso that $R_3$, $R_4$ are not both hydrogen, or $R_3$ and $R_4$ may independently link to form a cyclic structure selected from substituted or unsubstituted heteroaryl, substituted or unsubstituted cycloalkyl, substituted or unsubstituted cycloalkenyl or substituted or unsubstituted heterocycle and the pharmaceutically acceptable salts and esters thereof.

Preferred are compounds of formula I wherein W, X, Y, A, R and R' are as described above and V is hydrogen or F.

Further preferred are compounds of formula I wherein W, X, A, R and R' are as described above, V is hydrogen or F and Y is hydrogen or F.

Yet further preferred are compounds of formula I wherein X, A, R and R' are as described above, W is F, Cl, Br, I or ethynyl, Y is hydrogen or F and V is hydrogen or F.

Still further preferred are compounds of formula I wherein X, R and R' are as described above, W is F, Cl, Br, I or ethynyl, Y is hydrogen or F, V is hydrogen or F and A is O or NH with the proviso that V and Y are not both F.

Most preferred compounds are those of the formula: racemic(2'R,3R,4'S)-2'-[2-(1-(tert-butoxycarbonyl)-4-piperidinylmethoxy)-5-iodo-phenyl]-6-chloro-4'-(3-chlorophenyl)spiro[3H-indole-3,3'-piperidine]-2,6'(1H)-dione, racemic (2'R,3R,4'S)-2'-[2-(1-(tert-butoxycarbonyl)-4-piperidinylmethoxy)-5-ethynyl -phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinylmethoxy)-5-ethynyl-phenyl]-6chloro-4'-(3-chlorophenyl)spiro[3H-indole-3,3'-piperidine]-2,6'(1H)-dione, racemic(2'R,3R,4'S)-2'-[2-(1-(tert-butoxycarbonyl)-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione, chiral(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione, chiral(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-iodo-2-(1-methyl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione, racemic(2'R,3R,4'S)-2'-[2-(1-acetyl-4-piperidinylamino)-5-iodo-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinylamino)-5-ethynyl-phenyl]-6-chloro-4'-(3-chlorophenyl)spiro[3H-indole-3,3'-piperidine]-2,6'(1H)-dione, racemic(2'R,3R,4'S)-6-chloro -4'-(3-chlorophenyl)-2'-[5-ethynyl-2-(1-propionyl-4-piperidinyloxy)-phenyl]spiro[3H-indole-3,3'-piperidine]-2, 6'(1H)-dione, racemic(2'R,3R,4'S)-6-chloro-4'-(3-chlorophenyl)-2'-{5-ethynyl-2-[1-(3-methanesulfonyl-propyl)-4-piperidinyloxy]-phenyl}spiro[3H-indole-3,3'-piperidine]-2,6'(1H)-dione, racemic(2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H) -dione, chiral(2'R,3R,4'S)-6-chloro-4'-(3-chlorophenyl)-2'-[5-ethynyl-2-(1-methanesulfonyl -4-piperidinyloxy)phenyl]spiro[3H-indole-3,3'-piperidine]-2,6'(1H)-dione, racemic(2'R,3R,4'S)-6-chloro-4'-(3-chlorophenyl)-2'-[2-(1-dimethylcarbamoyl-4-piperidinyloxy)-5-ethynyl-phenyl]spiro[3H-indole-3,3'-piperidine]-2,6'(1H)-dione, racemic(2'R,3R,4'S)-2'-[5-bromo-2-(1-(tert-butoxycarbonyl)-4-piperidinyloxy) -phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione, chiral(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione, racemic(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione, chiral(2'R,3R,4'S)-2'-[3-bromo-6-(1-(tert-butoxycarbonyl)-4-piperidinyloxy)-2-fluoro -phenyl]-6-chloro-4'-(3-chlorophenyl)spiro[3H-indole-3,3'-piperidine]-2,6'(1H)-dione, racemic(2'R,3R,4'S)-2'-[6-(1-acetyl-4-piperidinyloxy)-3-bromo-2-fluoro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-ethyl-4-piperidinyloxy) -5-ethynyl-phenyl]spiro[3H-indole-3,3'-piperidine]-2,6' (1H)-dione, racemic(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione, chiral(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione, racemic(2'R,3R,4'S)-2'-[3-bromo-6-(1-dimethylcarbamoyl-4-piperidinyloxy) -2-fluoro-phenyl]-6-chloro-4'-(3-chlorophenyl)spiro[3H-indole-3,3'-piperidine]-2,6'(1H)-dione, chiral(2'R,3R,4'S)-2'-[3-bromo-6-(1-dimethylcarbamoyl-4-piperidinyloxy) -2-fluoro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-diethylcarbamoyl -4-piperidinyloxy)-5-ethynyl-phenyl]spiro[3H-indole-3,3'-piperidine]-2,6'(1H)-dione, racemic(2'R,3R,4'S)-6-chloro-4'-(3-chlorophenyl)-2'-{5-iodo-2-[1-(pyrrolidine-1-carbonyl)-4-piperidinyloxy]-phenyl}spiro[3H-indole-3,3'-piperidine]-2,6'(1H)-dione, racemic(2'R,3R,4'S)-6-chloro-4'-(3-chlorophenyl)-2'-{5-ethynyl-2-[1-(pyrrolidine-1-carbonyl)-4-piperidinyloxy]-phenyl}spiro[3H-indole-3,3'-piperidine]-2,6'(1H)-dione, racemic(2'R,3R,4'S)-6-chloro-4'-(3-chlorophenyl)-2'-[5-ethynyl-2-(1-isopropyl-4-piperidinyloxy)-phenyl]spiro[3H-indole-3,3'-piperidine]-2, 6'(1H)-dione, racemic(2'R,3R,4'S)-6-chloro-4'-(3-chlorophenyl)-2'-{5-ethynyl-2-[1-(2-oxo-imidazolidine-1-carbonyl)-4-piperidinyloxy]-phenyl}spiro[3H-indole-3,3'-piperidine]-2,6'(1H)-dione, racemic(2'R,3R,4'S)-2'-[6-(1-(tert-butoxycarbonyl)-4-piperidinyloxy)-3-chloro-2-fluoro-phenyl]-6-chloro-4'-(3-chlorophenyl)spiro[3H-indole-3,3'-piperidine]-2,6'(1H)-dione, racemic(2'R,3R,4'S)-2'-[6-(1-acetyl-4-piperidinyloxy)-3-chloro-2-fluoro-phenyl]-6- chloro-4'-(3-chlorophenyl)spiro[3H-indole-3,3'-piperidine]-2,6'(1H)-dione, racemic(2'R,3R,4'S)-6-chloro-2'-[3-chloro-6-(1-dimethylcarbamoyl-4-piperidinyloxy)-2-fluoro-phenyl]-4'-(3-chlorophenyl)spiro[3H-indole-3,3'-piperidine]-2,6'(1H)-dione, racemic(2'R,3R,4'S)-6-chloro-2'-[3-chloro-6-(1-methylcarbamoyl-4-piperidinyloxy)-2-fluoro-phenyl]-4'-(3-chlorophenyl)spiro[3H-indole-3,3'-piperidine]-2,6'(1H)-dione, racemic(2'R,3R,4'S)-2'-[3-bromo-6-(1-methylcarbamoyl-4-piperidinyloxy)-2-fluoro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H) dione, racemic(2'R,3R,4'S)-6-chloro-4'-(3-chlorophenyl)-2'-{5-ethynyl-2-[1-(4-methylpiperazine-1-carbonyl)-4-piperidinyloxy]-phenyl}spiro[3H-indole-3,3'-piperidine]-2,6'(1H)-dione, racemic(2'R,3R,4'S)-6-chloro-4'-(3-chlorophenyl)-2'-[5-Iodo-2-(tetrahydro-pyran-4-yloxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-tetrahydro-pyran-4-yloxy)-phenyl]spiro[3H-indole-3,3'-piperidine]-2,6'(1H)-dione, racemic(2'R,3R,4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione, chiral(2'R,3R,4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione, racemic(2'R,3R,4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione, chiral(2'R,3R,4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione, racemic(2'R,3R,4'S)-2'-[5-bromo-2-(1-dimethylcarbamoyl-4-piperidinyloxy)-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-ethoxycarbonyl-4-piperidinyloxy)-5-iodo-phenyl]spiro[3H-indole-3,3'-piperidine]-2,6'(1H)-dione, racemic(2'R,3R,4'S)-2'-[5-bromo-2-(1-ethoxycarbonyl-4-piperidinyloxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-isobutyryl-4-piperidinyloxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-isopropoxycarbonyl-4-piperidinyloxy)-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-iodo-2-(1-isobutyryl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-[5-iodo-2-(1-isopropoxycarbonyl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-{2-[1-(2-hydroxy-ethyl)-4-piperidinyloxy]-5-iodo-phenyl}spiro[3H-indole-3,3'-piperidine]-2,6'(1H)-dione, racemic(2'R,3R,4'S)-6-chloro-4'-(3-chlorophenyl)-2'-[5-iodo-2-(1-methoxycarbonylmethyl-4-piperidinyloxy)-phenyl]spiro[3H-indole-3,3'-piperidine]-2,6'(1H)-dione, racemic(2'R,3R,4'S)-2'-[2-(1-tert-butoxycarbonylmethyl-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-hydroxycarbonylmethyl-4-piperidinyloxy)-5-iodo-phenyl]spiro[3H-indole-3,3'-piperidine]-2,6'(1H)-dione, racemic(2'R,3R,4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione, chiral(2'R,3R,4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-tert-butoxycarbonyl-3-pyrrolidinyloxy)-phenyl]-6-chloro-4'-(3-chlorophenyl)spiro[3H-indole-3,3'-piperidine]-2,6'(1H)-dione, racemic(2'R,3R,4'S)-2'-[2-(1-tert-butoxycarbonyl-3-pyrrolidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione, chiral(2'R,3R,4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-methoxy-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2,5dimethyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2-methoxy-4-methoxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-hydroxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-2'-{5-Bromo-2-[4-(2-hydroxy-1,1-dimethyl-ethylcarbamoyl)-phenoxy]-phenyl}-6-chloro-4'-(3-chlorophenyl)spiro[3H-indole-3,3'-piperidine]-2,6'(1H)-dione, racemic(2'R,3R,4'S)-2'-{5-bromo-2-[4-(2-pyrrolidin-1-yl-ethylcarbamoyl)-phenoxy]-phenyl}-6-chloro-4'-(3-chlorophenyl)spiro[3H-indole-3,3'-piperidine]-2,6'(1H)-dione, racemic(2'R,3R,4'S)-2'-[5-bromo-2-(4-carbamoyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2-chloro-4-methoxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-6-chloro-2'-[5-chloro-2-(4-methoxycarbonyl-phenoxy)-phenyl]-4'-(3-chlorophenyl)spiro[3H-indole-3,3'-piperidine]-2,6'(1H)-dione, racemic(2'R,3R,4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione, chiral(2'R,3R,4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione, racemic(2'R,3R,4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione, chiral(2'R,3R,4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione, racemic(2'R,3R,4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione, chiral(2'R,3R,4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione, racemic(2'R,3R,4'S)-2'-[5-bromo-2-(2,6-dimethyl-4-pyridinyloxy)-phenyl]-6-chloro-4'-(3-chlorophenyl)spiro[3H-indole-3,3'-piperidine]-2,6'(1H)-dione, racemic(2'R,3R,4'S)-6-chloro-2'-(5-chloro-2-imidazol-1-yl-phenyl)-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(4-cyano-phenoxy)-5-iodo-phenyl]spiro[3H-indole-3,3'-piperidine]-2,6'(1H)-dione, chiral(2'R,3R,4'S)-6-chloro-4'-(3- chlorophenyl)-2'-[2-(4-cyano-phenoxy)-5-iodo-phenyl]spiro[3H-indole-3,3'-piperidine]-2,6'(1H)-dione, racemic(2'R,3R,4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione, chiral(2'R,3R,4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione, racemic(2'R,3R,4'S)-6-chloro-4'-(3-chlorophenyl)-2'-[5-iodo-2-(4-methoxy-phenoxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione, racemic(2'R,3R,4'S)-6-chloro-4'-(3-chlorophenyl)-2'-[5-iodo-2-(4-methoxycarbonyl-phenoxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(4-methoxycarbonyl-phenoxy)-phenyl]spiro[3H-indole-3,3'-piperidine]-2,6'(1H)-dione, racemic(2'R,3R,4'S)-6-chloro-4'-(3-chlorophenyl)-2'-[2-(4-hydroxycarbonyl-phenoxy) -5-iodo-phenyl]spiro[3H-indole-3,3'-piperidine]-2,6'(1H)-dione, racemic(2'R,3R,4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione, chiral(2'R,3R,4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(2,6-dimethyl-4-pyridinyloxy)-5-iodo-phenyl]spiro[3H-indole-3,3'-piperidine]-2,6'(1H)-dione, racemic(2'R,3R,4'S)-6-chloro-4'-(3-chlorophenyl)-2'-[2-(2,6-dimethyl-4-pyridinyloxy)-5-ethynyl-phenyl]spiro[3H-indole-3,3'-piperidine]-2,6'(1H)-dione, racemic(2'R,3R,4'S)-2'-[5-bromo-2-(4-fluoro-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-trifluoromethyl-phenoxy)-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-chloro-2-(4-trifluoromethyl-phenoxy)-phenyl]spiro[3H-indole-3,3'-piperidine]-2,6'(1H)-dione, racemic(2'R,3R,4'S)-2'-[5-bromo-2-(3-cyano-phenoxy)-phenyl]-6-chloro-4'-(3-chlorophenyl)spiro[3H-indole-3,3'-piperidine]-2,6'(1H)-dione, racemic(2'R,3R,4'S)-2'-{5-bromo-2-[4-(3-hydroxy-propyl)-phenoxy]-phenyl}-6-chloro-4'-(3-chlorophenyl)spiro[3H-indole-3,3'-piperidine]-2,6'(1H)-dione, racemic(2'R,3R,4'S)-6-chloro-2'-[5-chloro-2-(4-cyano-phenoxy)-phenyl]-4'-(3-chlorophenyl)spiro[3H-indole-3,3'-piperidine]-2,6'(1H)-dione, chiral(2'R,3R,4'S)-6-chloro-2'-[5-chloro-2-(4-cyano-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-methylsulfanyl-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-methylsulfonyl-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-methylsulfinyl-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-nitro-phenoxy)-phenyl]-4'-(3-chlorophenyl)spiro[3H-indole-3,3'-piperidine]-2,6'(1H)-dione, racemic(2'R,3R,4'S)-2'-[2-(4-amino-phenoxy)-5-chloro-phenyl]-6-chloro-4'-(3-chlorophenyl)spiro[3H-indole-3,3'-piperidine]-2,6'(1H)-dione, chiral(2'R,3R,4'S)-2'-[2-(4-amino-phenoxy)-5-chloro-phenyl]-6-chloro-4'-(3-chlorophenyl)spiro[3H-indole-3,3'-piperidine]-2,6'(1H)-dione, racemic(2'R,3R,4'S)-2'-[2-(4-acetylamino-phenoxy)-5-chloro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-iodo-2-(1,3,5-trimethyl-1H-pyrazol-4-yloxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(1,3,5-trimethyl -1H-pyrazol-4-yloxy)-phenyl]spiro[3H-indole-3,3'-piperidine]-2,6'(1H) dione, racemic(2'R,3R,4'S)-2'-[5-bromo-2-(1,3,5-trimethyl-1H-pyrazol-4-yloxy)-phenyl]-6-chloro-4'-(3-chlorophenyl)spiro[3H-indole-3,3'-piperidine]-2,6'(1H)-dione, racemic(2'R,3R,4'S)-6-chloro-2'-[5-chloro-2-(1,4-dioxa-spiro[4.5]dec-8-yloxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-oxo-cyclohexyloxy)-phenyl]-4'-(3-chlorophenyl)spiro[3H-indole-3,3'-piperidine]-2,6'(1H)-dione, racemic(2'S,3R,4'S)-6-chloro-2'-[2-chloro-6-(4-methoxy-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione, chiral(2'R,3R,4S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione, chiral(2'R,3R,4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione, racemic(2'R,3R,4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'S)-6-chloro-2'-[5-chloro-4-methyl-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-chloro-2-(2,2,6,6-tetramethyl -tetrahydro-pyran-4-yloxy)-phenyl]spiro[3H-indole-3,3'-piperidine]-2,6'(1H)-dione, chiral(2'R,3R,4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione, racemic(2'R,3R,4'S)-6-chloro-2'-[5-chloro-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'R)-6-chloro-4'-(3-chloro-2-fluoro-phenyl)-2'-[5-chloro-2-(tetrahydro-pyran-4-yloxy)-phenyl]]spiro[3H-indole-3,3'-piperidine]-2,6'(1H)-dion, racemic(2'R,3R,4'R)-6-chloro-4'-(3-chloro-4-fluoro-phenyl)-2'-[5-chloro-2-(tetrahydro-pyran-4-yloxy)-phenyl]]spiro[3H-indole-3,3'-piperidine]-2,6'(1H)-dione, racemic(2'R,3R,4'S)-2'-{5-bromo-2-[2-(4-acetyl-piperazin-1-yl)-1,1-dimethyl-2-oxo-ethoxy]-phenyl}-6-chloro-4'-(3-chlorophenyl)spiro[3H-indole-3,3'-piperidine]-2,6'(1H)-dione, racemic(2'R,3R,4'S)-2'-{5-bromo-2-[2-(4,4-difluoro-piperidin-1-yl)-1,1-dimethyl-2-oxo-ethoxy]-phenyl}-6-chloro-4'-(3-chlorophenyl)spiro[3H-indole-3,3'-piperidine]-2,6'(1H)-dione, racemic(2'R,3R,4'S)-2'-{5-bromo-2-[1-methyl-1-(2,2,2-trifluoro-ethylcarbamoyl) -ethoxy]-phenyl}-6-chloro-4'-(3-chlorophenyl)spiro[3H-indole-3,3'-piperidine]-2,6'(1H)-dione, racemic(2'R,3R,4'S)-2'-[5-bromo-2-(1-dimethylcarbamoyl-1-methyl-ethoxy)-phenyl]-6-chloro-4'-

(3-chlorophenyl)spiro[3H-indole-3,3'-piperidine]-2,6'(1H)-dione, racemic(2'R,3R,4'S)-2'-[5-bromo-2-(2-dimethylcarbamoyl-2-methyl-propoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2,2-dimethyl-3-oxo-3-pyrrolidin-1-yl-propoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(3-methyl-oxetan-3-ylmethoxy)-phenyl]-6-chloro-4'-(3-chlorophenyl)spiro[3H-indole-3,3'-piperidine]-2,6'(1H)-dione, chiral(2'R,3R,4'S)-6-chloro-4'-(3-chlorophenyl)-2'-[5-bromo-2-(3-methyl-oxetan-3-ylmethoxy)phenyl]spiro[3H-indole-3,3'-piperidine]-2,6'(1H)-dione, racemic(2'R,3R,4'S)-2'-[5-bromo-2-(4-fluoro-benzyloxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(3-ethyl-oxetan-3-ylmethoxy)-phenyl]-6-chloro-4'-(3-chlorophenyl)spiro[3H-indole-3,3'-piperidine]-2,6'(1H)-dione, racemic(2'R,3R,4'S)-2'-[2-(1-tert-butoxycarbonyl-piperidin-4-yloxy)]-5-trifluoromethyl-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-methyl-piperidin-4-ylamino)-phenyl]-6-chloro -4'-(5-chloro-2-methyl-phenyl)spiro[3H-indole-3,3'-piperidine]-2,6'(1H)-dione, racemic(2'R,3'R,4'S)-6-chloro-4'-(3-chlorophenyl)-2'-[2-(2-hydroxy-ethoxy)-5-(2-thiophenyl)-phenyl]-spiro[3H-indole-3,3'-piperidine]-2,6'-dione, chiral(2'R,3'R,4'S)-6-chloro-4'-(3-chlorophenyl)-2'-[2-(2-hydroxy-ethoxy) -5-(2-furanyl)-phenyl]-spiro[3H-indole-3,3'-piperidine]-2,6'-dione, racemic(2'R,3'R,4'S)-6-chloro-4'-(3-chlorophenyl)-2'-[2-(2-hydroxy-ethoxy) -5-phenyl-phenyl]-spiro[3H-indole-3,3'-piperidine]-2,6'-dione, racemic(2'R,3R,4'S)-6-chloro-4'-(3-chlorophenyl)-2'-[5-chloro-2-(2-pyrazinyloxy)-phenyl]-spiro-[3H-indole-3,3'-piperidine]-2,6'-dione, racemic(2'R,3R,4'S)-6-chloro-4'-(3-chlorophenyl)-2'-[2-hydroxy-5-iodo-phenyl]spiro[3H-indole-3,3'-piperidine]-2,6'-dione, racemic(2'R,3'R,4'S)-6-chloro-4'-(3-chlorophenyl)-2'-[5-(2-furanyl)2-hydroxy-phenyl]-spiro[3H-indole-3,3'-piperidine]-2,6'-dione, racemic(2'R,3'R,4'S)-6-chloro-4'-(3-chlorophenyl)-2'-[2-hydroxy-5-(2-thiofuranyl)-phenyl]-spiro[3H-indole-3,3'-piperidine]-2,6'-dione, racemic(2'R,3'R,4'S)-6-chloro-4'-(3-chlorophenyl)-2'-[2-hydroxy-5-phenyl]-phenyl-spiro[3H-indole-3,3'-piperidine]-2,6'-dione, racemic(2'R,3'R,4'S)-6-chloro-4'-(3-chlorophenyl)-2'-[2-hydroxy-5-(2-thiazolylyl)-phenyl]-spiro[3H-indole-3,3'-piperidine]-2,6'-dione, racemic(2'R,3'R,4'S)-6-chloro-4'-(3-chlorophenyl)-2'-[2-hydroxy-5-(2-thiazolyl)-phenyl]-spiro[3H-indole-3,3'-piperidine]-2,6'-dione, chiral(2'R,3R,4'S)-2'-{2-[3-(tert-butoxycarbonyl)-pyrolidinyloxy]-5-chloro-phenyl}-6-chloro-4'-(3-chlorophenyl)spiro[3H-indole-3,3'-piperidine]-2,6'-dione, chiral(2'R,3R,4'S)-6-chloro-4'-(3-chlorophenyl)-2'-[5-chloro-(3-pyrolidinyloxy)-phenyl}spiro[3H-indole-3,3'-piperidine]-2,6'-dione, chiral(2'R,3R,4'S)-6-chloro-2'-[5-chloro-2-(3-methanesulfonyl-pyrolidinyloxy)-phenyl]-4'-(3-chlorophenyl)spiro[3H-indole-3,3'-piperidine]-2,6'-dione, chiral(2'R,3R,4'S)-6-chloro-2'-[5-chloro-2-(3-ethylcarbamoyl-pyrolidinyloxy)-phenyl}-4'-(3-chlorophenyl)spiro[3H-indole-3,3'-piperidine]-2,6'-dione, chiral(2'R,3R,4'S)-2'-[2-(1-acetyl-3-pyrolidinyloxy)-5-chloro-phenyl]-6-chloro-4'-(3-chlorophenyl)spiro[3H-indole-3,3'-piperidine]-2,6'-dione, racemic(2'R,3R,4'S)-6-chloro-4'-(3-chlorophenyl)-2'-[trans-4-(3-hydroxy-1-methanesulfonyl-piperidinyloxy)-5-iodo-phenyl]spiro[3H-indole-3,3'-piperidine]-2,6'-dione, racemic(2'R,3'R,4'S)-6-chloro-4'-(3-chloro-phenyl)-2'-[5-fluoro-2-(tetrahydro-pyran-4-yloxy)-phenyl]spiro[3H-indole-3,3'-piperidine]-2,6'-dione, chiral(2'R,3'R,4'S)-6-chloro-4'-(3-fluoro-phenyl)-2'-[5-fluoro-2-(tetrahydro-pyran-4-yloxy)-phenyl]spiro[3H-indole-3,3'-piperidine]-2,6'-dione, racemic(2'R,3'R,4'S)-6-chloro-4'-(3-chlorophenyl)-2'-[5-fluoro-2-(tetrahydro-thiopyran-4-yloxy)-phenyl]spiro[3H-indole-3,3'-piperidine]-2,6'-dione, chiral(2'R,3'R,4'S)-6-chloro-4'-(3-chlorophenyl)-2'-[5-fluoro-2-(1,1-dioxo-tetrahydro-thiopyran-4-yloxy)-phenyl]spiro[3H-indole-3,3'-piperidine]-2,6'-dione, chiral(2'R,3'R,4'S)-6-chloro-4'-(3-chlorophenyl)-2'-[5-fluoro-2-(cyclohexyloxy)-phenyl]spiro[3H-indole-3,3'-piperidine]-2,6'-dione, chiral(2'R,3'R,4'S)-6-chloro-4'-(3-chlorophenyl)-2'-[5-fluoro-2-(cyclopentyloxy)-phenyl]spiro[3H-indole-3,3'-piperidine]-2,6'-dione, racemic(2'R,3'R,4'S)-6-chloro-2'-[5-chloro-2-(cyclohexyloxy-phenyl)]-4'-(3-chloro-phenyl)spiro[3H-indole-3,3'-piperidine]-2,6'-dione, racemic(2'R,3'R,4'S)-6-chloro2'-[5-chlororo-2-(tetrahydro-thiopyran-4-yloxy)-phenyl]-4'-(3-fluoro-phenyl)-spiro[3H-indole-3,3'-piperidine]-2,6'-dione, racemic(2'R,3'R,4'S)-6-chloro-2'-[5-chloro-2-(1,1-dioxo-tetrahydro-thiopyran -4-yloxy)-phenyl]-4'-(3-fluoro-phenyl)spiro[3H-indole-3,3'-piperidine]-2,6'-dione, racemic(2'R,3'R,4'S)-6-chloro-4'-(3-fluoro-phenyl)-2'-[5-fluoro-2-(4-fuloro-phenoxy-phenyl)]spiro[3H-indole-3,3'-piperidine]-2,6'-dione, racemic(2'R,3'R,4'S)-4'-(3-chloro-phenyl)-6-fluoro-2'-[2-(2,4-difluoro-phenyloxy)-5-fluoro-phenyl]spiro[3H-indole-3,3'-piperidine]-2,6'-dione, racemic(2'R,3'R,4'R)-6-chloro-2'-[5-chloro-2-(2-chloro-6-fluoro-benzyloxy)-phenyl]-4'-(2,5-difluoro-phenyl)spiro[3H-indole-3,3'-piperidine]-2,6'-dione, racemic(2'R,3'R,4'R)-6-chloro-2'-[2-(4-cyano-phenyloxy)-5-fluoro-phenyl]-4'-(2,5-difluoro-phenyl)spiro[3H-indole-3,3'-piperidine]-2,6'-dione, racemic(2'R,3'R,4'S)-6-chloro-2'-[2-(4-cyano-phenyloxy)-5-fluoro-phenyl]-4'-(3-fluoro-phenyl)spiro[3H-indole-3,3'-piperidine]-2,6'-dione, racemic(2'R,3'R,4'S)-4'-(3-chloro-phenyl)-2'-[2-(4-cyano-phenyloxy)-5-fluoro-phenyl]-6-fluoro spiro[3H-indole-3,3'-piperidine]-2,6'-dione, racemic(2'R,3'R,4'S)-6-chloro-2'-[5-fluoro-2-(4-methoxy-phenyloxy)-phenyl]-4'-(3-fluoro-phenyl)spiro[3H-indole-3,3'-piperidine]-2,6'-dione, racemic(2'R,3'R,4'S)-4'-(3-chloro-phenyl)-6-fluoro-2'-[5-fluoro-2-(4-methoxy-phenyloxy)-phenyl]spiro[3H-indole-3,3'-piperidine]-2,6'-dione, racemic(2'R,3'R,4'R)-6-chloro-2'-[5-fluoro-2-(4-methoxy-phenyloxy)-phenyl]-4'-(2,5-difluoro-phenyl)spiro[3H-indole-3,3'-piperidine]-2,6'-dione, chiral(2'R,3'R,4'S)-6-chloro-4'-(3-chloro-phenyl)-2'-[5-fluoro-2-(4-methoxy-phenyloxy)-phenyl]spiro[3H-indole-3,3'-piperidine]-2,6'-dione, chiral(2'R,3'R,4'R)-6-chloro-4'-(5-chloro-2-fluoro-phenyl)-2'-[5-fluoro-2-(4-methoxy-phenyloxy)-phenyl]spiro[3H-indole-3,3'-piperidine]-2,6'-dione, racemic(2'R,3'R,4'R)-6-chloro-2'-{5-fluoro-2-[4-(2-hydroxy-ethoxy)-phenoxy]phenyl}-4'-(2,5-difluoro-phenyl)spiro[3H-indole-3,3'-piperidine]-2,6'-dione, racemic(2'R,3'R,4'R)-6-chloro-4'-(5-chloro-2-fluoro-phenyl)-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-6-chloro-4'-(3-fluoro-phenyl)-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-4'-(3-chloro-phenyl)-6-fluoro-2'-{5-fluoro-2-[4-(2-hydroxy-ethoxy)-phenoxy] phenyl}spiro[3H-indole-3,3'-piperidine]-2,6'-dione, racemic (2'R,3'R,4'S)-6-chloro-4'-(3-chloro-phenyl)-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-6-chloro-2'-[5-chloro-2-(tetrahydro-pyran-4-yloxy)-phenyl]-4'-(5-chloro-2-trifluoromethyl-phenyl)spiro[3H-indole-3,3'-piperidine]-2,6'-dione, racemic(2'R,3'R,4'S)-6-chloro-4'-(5-chloro-2-trifluoromethyl-phenyl)-2'-[5-iodo-2-(tetrahydro-pyran-4-yloxy)-phenyl]spiro[3H-indole-3,3'-piperidine]-2, 6'-dione, (2'R,3'R,4'S)-6-chloro-4'-(5-chloro-2-trifluoromethyl-phenyl)-2'-[2-(cyclohexyloxy)-5-fluoro-phenyl]spiro[3H-indole-3,3'-piperidine]-2,6'-dione, chiral (2'R,3'R,4'S)-6-chloro-2'-[5-chloro-2-(tetrahydro-pyran-4-yloxy)-phenyl]-4'-(3-fluoro-phenyl)spiro[3H-indole-3,3'-piperidine]-2,6'-dione, chiral(2'R,3'R,4'S)-6-chloro-2'-[5-fluoro-2-(cyclopentyloxy)-phenyl]-4'-(3-fluoro-phenyl)spiro[3H-indole-3,3'-piperidine]-2,6'-dione, racemic(2'R,3'R,4'S)-6-chloro-2'-[2-(cyclohexyloxy-5-iodo)-phenyl]-4'-(3-fluoro-phenyl)spiro[3H-indole-3,3'-piperidine]-2,6'-dione, racemic(2'R,3'R,4'S)-6-chloro-2'-[2-(cyclohexyloxy-5-fluoro)-phenyl]-4'-(3-fluoro-phenyl)spiro[3H-indole-3,3'-piperidine]-2,6'-dione, racemic(2'R,3'R,4'S)-6-chloro-2'-[2-(cyclohexyloxy-5-ethynyl)-phenyl]-4'-(3-fluoro-phenyl)spiro[3H-indole-3,3'-piperidine]-2,6'-dione, racemic(2'R,3'R,4'S)-6-chloro-4'-(3-chloro-phenyl)-2'-[2-(cyclohexyloxy) -5-iodo-phenyl]spiro[3H-indole-3,3'-piperidine]-2,6'-dione, racemic(2'R,3'R,4'S)-6-chloro-4'-(3-chloro-phenyl)-2'-[2-(cyclohexyloxy) -5-ethynyl-phenyl]spiro[3H-indole-3,3'-piperidine]-2,6'-dione, racemic(2'R,3'R,4'R)-6-chloro-2'-[5-chloro-2-(tetrahydro-thiopyran-4-yloxy)-phenyl]-4'-(2,5-difluoro-phenyl)spiro[3H-indole-3,3'-piperidine]-2,6'-dione, chiral(2'R,3'R,4'R)-6-chloro-2'-[2-cyclohexyloxy-5-fluoro-phenyl]-4'-(2,5-difluoro-phenyl) spiro[3H-indole-3,3'-piperidine]-2,6'-dione, racemic(2'R, 3'R,4'S)-2'-[5-chloro-2-(cyclohexyloxy)-phenyl]-4'-(3-chloro-phenyl)-6-fluoro spiro[3H-indole-3,3'-piperidine]-2,6'-dione, racemic(2'R,3'R,4'S)-4'-(3-chloro-phenyl)-2'-[5-chloro-2-(tetrahedro-thiopyran-4-yloxy-phenyl)]-6-fluoro spiro[3H-indole-3,3'-piperidine]-2,6'-dione, racemic(2'R, 3'R,4'S)-6-chloro-2'-[5-chloro-2-(cyclohexyloxy-phenyl)]-4'-(3-fluoro-phenyl)spiro[3H-indole-3,3'-piperidine]-2,6'-dione, chiral(2'R,3'R,4'R)-6-chloro-2'-[5-chloro-2-(tetrahydro-pyran-4-yloxy)-phenyl]-4'-(2,5-difluoro-phenyl)spiro[3H-indole-3,3'-piperidine]-2,6'-dione and chiral(2'R,3'R,4'R)-6-chloro-4'-(2,5-difluoro-phenyl)-2'-[5-fluoro-2-(tetrahydro-pyran-4-yloxy)-phenyl]spiro[3H-indole-3,3'-piperidine]-2,6'-dione.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkyl-sufonyl, aminosulfonyl, lower-alkylcarbonyl, lower-alkyl-carbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-(alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl -1-butenyl, 3-methyl-2-butenyl, 1-pentenyl, 2-pentenyl, 3-pentenyl, 4-pentenyl, 4-methyl -3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains,e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts have at least one asymmetric carbon atom and therefore may be present as racemic mixtures or different stereoisomers. The various isomers can be isolated by known separation methods, e.g., chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC$_{50}$" refers to the concentration of a particular compound required to inhibit 50% of a specific measured activity. IC$_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compounds of formulas I and are cleaved in vivo (in the organism) to the corresponding active carboxylic acid or alcohol respectively.

Synthesis

Compounds of this invention in formula I can be synthesized according to the following general schemes. It will be readily apparent to those of ordinary skill in the art that compounds in formula I can be prepared by substitution of the reagents or agents in the general synthesis routes. Using purification by chiral chromatography, compounds in formula I can be obtained as an optically pure or enriched enantiomers.

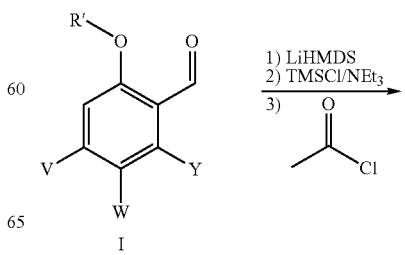

Scheme 1

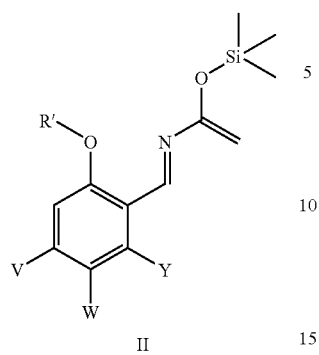

II

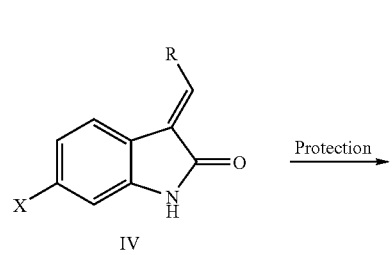

IV

In general an appropriately selected aldehyde I can be reacted with lithium hexamethyldisilamide, chlorotrialkylsilane and acteyl chloride in a one-pot, multi-steps manner to generate 2-aza-1,3-butadiene II (Scheme I) and can be used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited therein). The appropriately selected aldehyde I are either commercially available or can be synthesized by well-established multiple literature methods.

Scheme 2

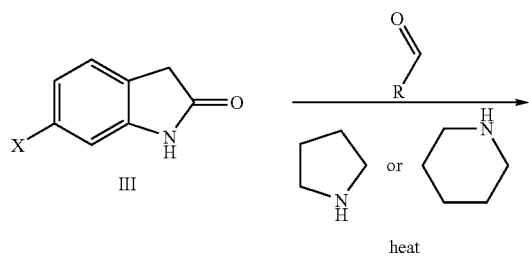

V

Oxindole III can be reacted with an appropriately substituted aldehyde or ketone in the presence of base under heated condition in either a protic like methanol, ethanol or an aprotic solvent like toluene, o-xylene to give intermediate IV. The commonly used base is either pyrrolidine or piperidine. Intermediate IV can be protected to give intermediate V. The protective group can be attached by using ethyl chloroformate, di-tert-butyl dicarbonate, SEM-Cl, benzyl bromide, and a base like 4-(dimethylamine)pyridine (DMAP), triethylamine, NaH, or LiH according to well established literature procedures. Examples of protective group formation and their deprotection have been described and reviewed comprehensively by Greene, T. W. et al in "Protective Groups in Organic Synthesis, $2^{nd}$ Edition. John Wiley & Sons Inc.

Scheme 3

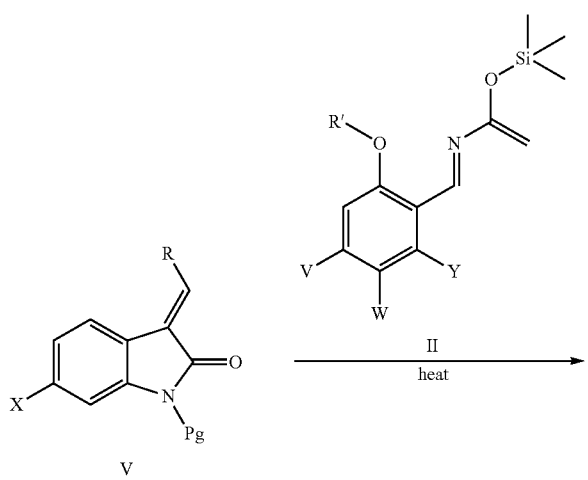

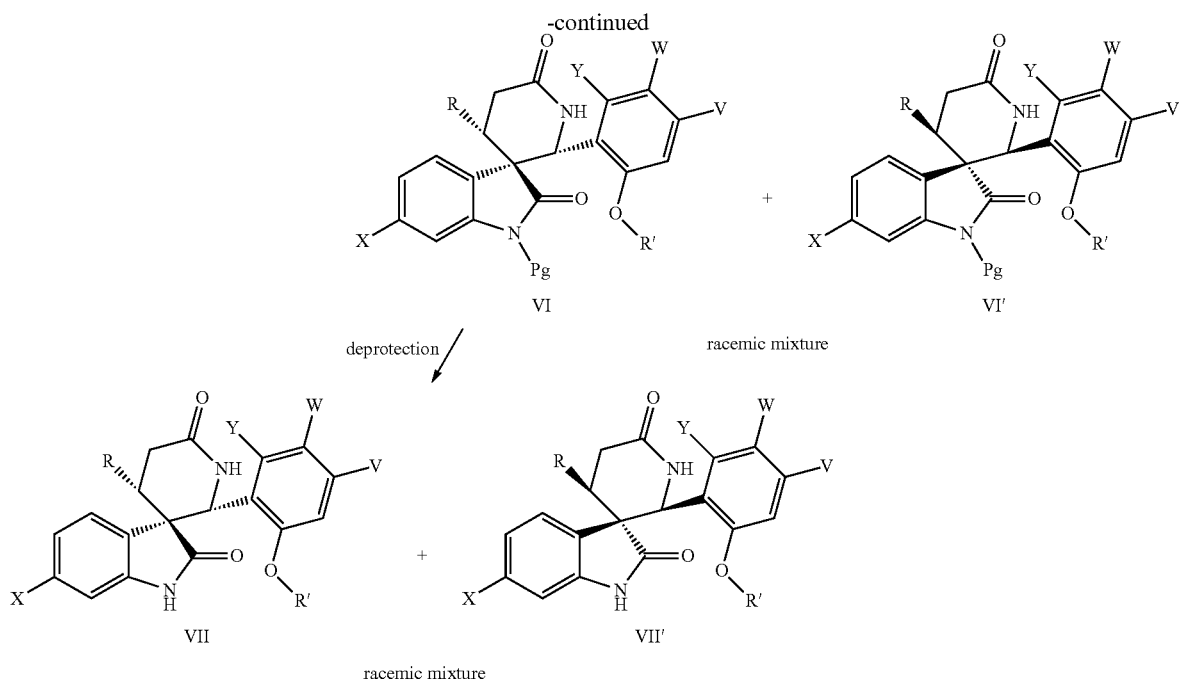

Intermediate V can be reacted with a selected 2-aza-butadiene II prepared in Scheme 1 in toluene or o-xylene under heating from 110° C. to 160° C. and anhydrous condition to form intermediate VI and VI' as the major products shown as a racemic mixture of two enantiomers. A subsequent reaction to remove protective group (Pg) leads to various $R_2$ derivatized compound VII and VII'. (Scheme 3). In the case Pg is Boc group, Boc group can be removed by either trifluoroacetic acid or prolonged heating at a temperature between 110 to 116° C. Racemic mixture of VI and VI' or VII and VII' can be readily resolved into two chiral enantiomers by chiral Super Fluid Chromatography (SFC) or chiral HPLC or chiral column chromatography.

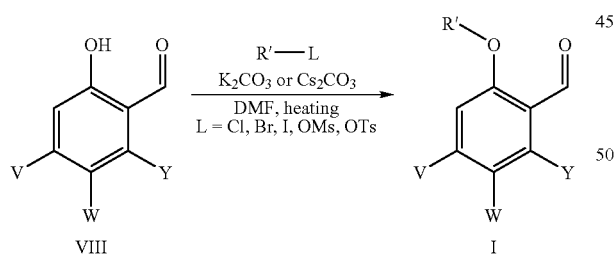

When R' is a heterocycle or substituted group, compound I can be prepared by reaction of reagent VIII, and compound R'-L, a base like $K_2CO_3$ or $Cs_2CO_3$ in anhydrous N,N-dimethylformamide or N,N-dimethylacetamide under heating conditions. L is a good leaving group like Cl, Br, I, OMs or OTs. Compound VIII is either commercially available or readily prepared according to well established literature procedure (Scheme 4). Alternatively, starting material IX can be reacted R'—OH under MItsunobu reaction condition to give intermediate X, which can be reduced by $LiAlH_4$ or DIBAL to alcohol, then oxidized by $MnO_2$ or under Swern oxidation conditions to give intermediate I (Scheme 5).

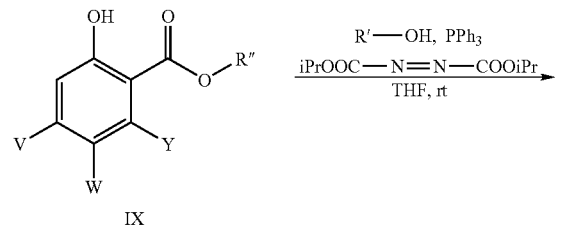

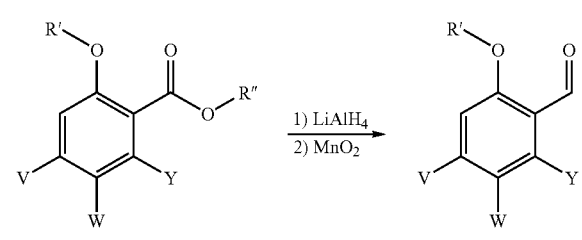

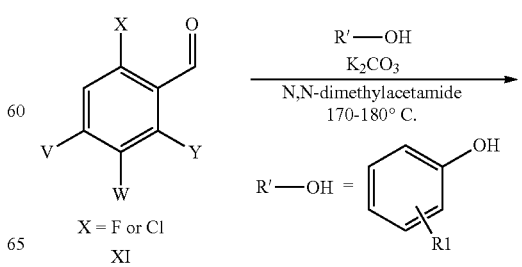

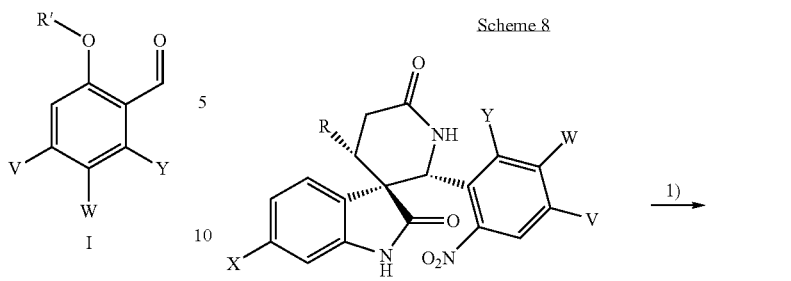

When R' is selected from aryl, substituted aryl, hetereoaryl, or substituted heteroaryl group, intermediate I can be prepared by a coupling reaction of compound XI and R'—OH under heated conditions (Scheme 6).

When W is ethynyl, 1-propynyl, isopropenyl, 1-propynyl, 3-methyl-1-butynyl, 3,3-dimethyl-1-butynyl, 3-trifluoroethynyl, alternative synthetic methods can be used to gain access to compounds or XII-a or XII-b. Typically, the analogues XII-a with corresponding Iodo- or bromo-substituted phenyl are prepared first according to the methods in Scheme 1-3, followed by a catalytic palladium mediated Sonogashira reaction to give those XII-b (Scheme 7).

Scheme 7

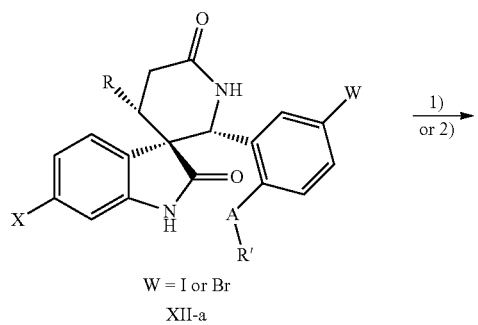

W = I or Br
XII-a

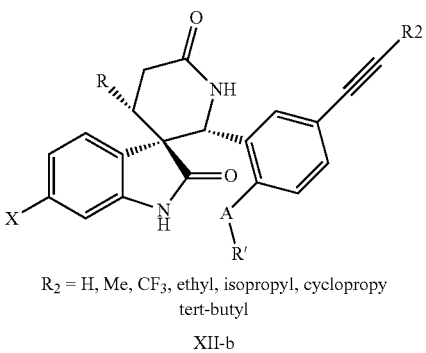

$R_2$ = H, Me, $CF_3$, ethyl, isopropyl, cyclopropy tert-butyl
XII-b

Reagents and conditions:
1) If $R_2$ = Me, Et, iPr, cyleopropyl, tBu, $CF_3$, CuI, $NEt_3$, $PdCl_2(PPh_3)_2$ (cat.), 100° C.
≡—R2
2) If $R_2$ = H: CuI, $NEt_3$, trimethylsilyl acetylene, $PdCl_2(PPh_3)_2$ (cat.), 100° C.; then NaOH/MeOH, rt, Analogues XIII-a are prepared first according to the methods in Scheme 1-3, followed by reduction of nitro group to amine group in XIII-b, then a reductive amination reaction to give XIII-c (Scheme 8). Analogue XIV-b can be prepared according to the procedure in Scheme 9.

Scheme 8

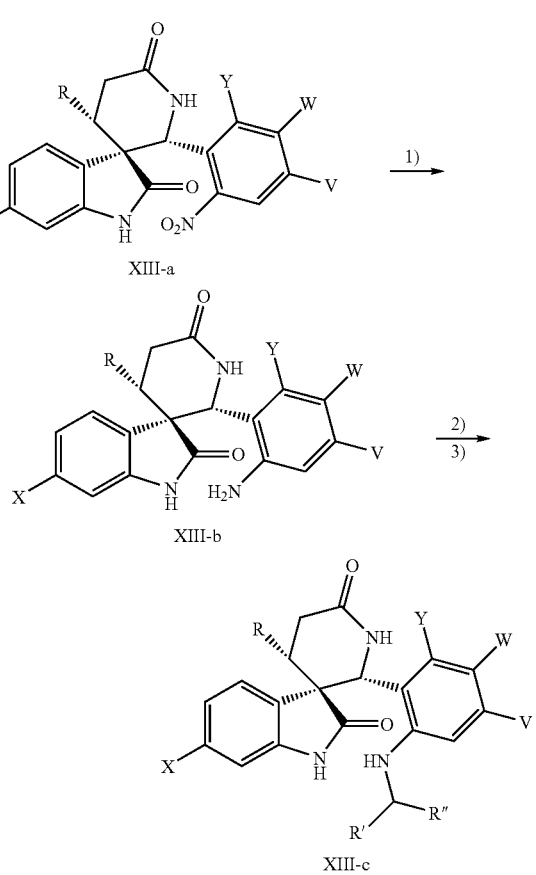

Reagents and conditions:
1) Zn, $NH_4Cl$, or Raney Ni, $NH_2NH_2$;
2) R'C(=O)R", cat p-toluensufonic acid, o-xylene, heating;
3) $NaCNBH_3$, MeOH Scheme 9

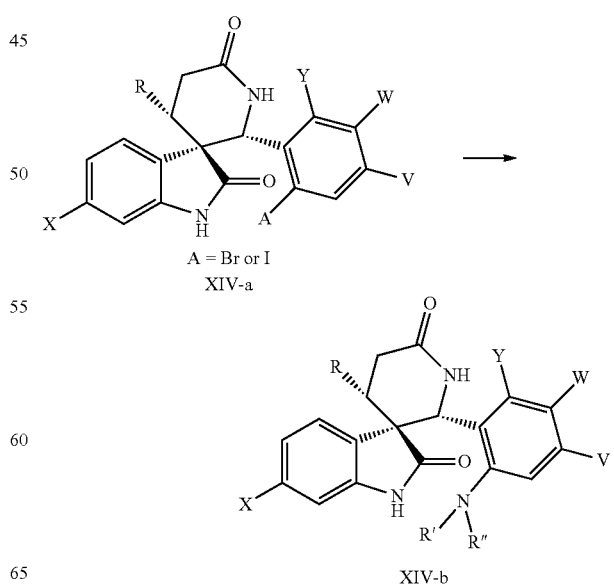

Reagents and conditions:

CuI, $Cs_2CO_3$, NHR'R", N,N,N',N'-tetramethyletheylenediamine, heating, DMF

The following examples and references are provided to aid the understanding of the present invention, the true scope of which is set forth in the appended claims.

EXAMPLE 1a

Preparation of intermediate E/Z-6-chloro-3-(3-chloro-benzylidene)-1,3-dihydro-indol-2-one

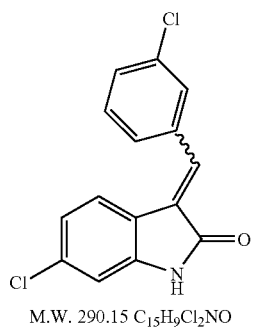

M.W. 290.15 $C_{15}H_9Cl_2NO$

To the mixture of 6-chlorooxindole (16.2 g, 92 mmol) (Crescent) and 3-chloro-benzaldehyde (12.9 g, 92 mmol) (Aldrich) in methanol (109 mL) was added pyrrolidine (6.55 g, 92 mmol) (Aldrich) dropwise. The mixture was then heated at 70° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 25.2 g, 95%).

EXAMPLE 1b

Preparation of intermediate E/Z-6-chloro-3-(3-chloro-benzylidene)-2-oxo-2,3-dihydro-indole-1-carboxylic acid tert-butyl ester

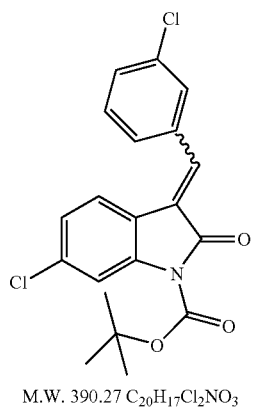

M.W. 390.27 $C_{20}H_{17}Cl_2NO_3$

To a solution of E/Z-6-chloro-3-(3-chloro-benzylidene)-1,3-dihydro-indol-2-one prepared in example 5a (1 g, 3.4 mmol) in dichloromethane (50 mL) at room temperature was added Di-tert-butyl-dicarbonate (1.5 g, 6.9 mmol) (Aldrich), followed by the addition of 4-dimethylaminopyridine (1 g, 8.2 mmol). The reaction mixture was stirred at room temperature for 1 h. The mixture was then concentrated and the residue was purified by chromatography to give E/Z-6-chloro-3-(3-chloro-benzylidene)-2-oxo-2,3-dihydro-indole -1-carboxylic acid tert-butyl ester as an orange solid (Yield 1.3 g, 96%).

EXAMPLE 1c

Preparation of intermediate 4-(2-formyl-4-iodo-phenoxymethyl)-piperidine-1-carboxylic acid tert-butyl ester

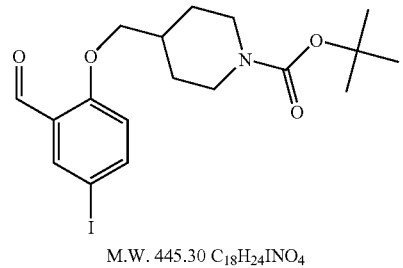

M.W. 445.30 $C_{18}H_{24}INO_4$

To a solution of 5-iodosalicylaldehyde (2 g, 8.2 mmol) (Aldrich) in N,N-dimethylformamide (20 mL) was added anhydrous $K_2CO_3$ (1.15 g, 8.2 mmol), and 4-bromomethyl-piperidine -1-carboxylic acid tert-butyl ester (2.3 g, 8.2 mmol, Pharmacore). The reaction mixture was heated at 60° C. for 18 h. The crude was cooled to room temperature, diluted with ethyl acetate, washed with water, brine. The organic layer was separated, dried over $MgSO_4$, concentrated to give 4-(2-formyl-4-iodo-phenoxymethyl)-piperidine-1-carboxylic acid tert-butyl ester (Yield 2.3 g, 63%).

EXAMPLE 1d

Preparation of intermediate 1-[2-(1-(tert-butoxycarbonyl)-4-piperidinylmethoxy)-5-iodo-phenyl]-3-trimethylsilyoxy-2-aza-1,3-butadiene

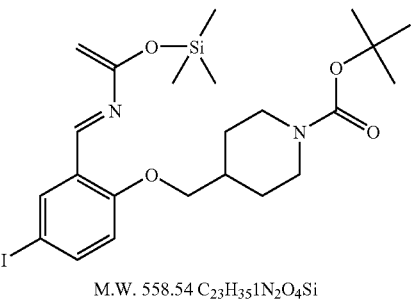

M.W. 558.54 $C_{23}H_{35}IN_2O_4Si$

To 1,1,1,3,3,3-hexamethyldisilazane (0.8 g, 5 mmol) (Aldrich) under nitrogen at room temperature was added n-butyl-lithium (2.5 M, 2 mL, 5 mmol) (Aldrich). The reaction mixture was stirred at room temperature for 10 minutes. Then dry tetrahydrofuran (20 mL) was added, followed by the addition of 4-(2-formyl-4-iodo-phenoxymethyl)-piperidine -1-carboxylic acid tert-butyl ester (2.3 g, 5 mmol) prepared in Example 1c. After the mixture was stirred at room temperature for 0.5 h, trimethylsilyl chloride (0.55 g, 5 mmol) (Aldrich) was added dropwise. Then the temperature of the mixture was lowered to 0° C. on a cooling ice bath. To this mixture was added triethylamine (0.7 g, 6.8 mmol) in one portion, followed by the dropwise addition of a solution of acetyl chloride (0.5 g, 6.8 mmol) in diethyl ether (40 mL). The cooling bath was removed, and the mixture was stirred at room temperature for 1 h. The mixture was quickly filtered on celite under nitrogen, and filtrate was concentrated under reduced pressure to give crude 1-[2-(1-(tert-butoxycarbonyl)-4-piperidinylmethoxy)-5-iodo-phenyl]-3-trimethylsilyoxy-2-aza-1,3-butadiene as a yellow oil and used for the next step without further purification.

EXAMPLE 1e

Preparation of racemic(2'R,3R,4'S)-2'-[2-(1-(tert-butoxycarbonyl)-4-piperidinylmethoxy) -5-iodo-phenyl]-6-chloro-4'-(3-chlorophenyl)spiro[3H-indole-3,3'-piperidine]-2,6'(1H)-dione

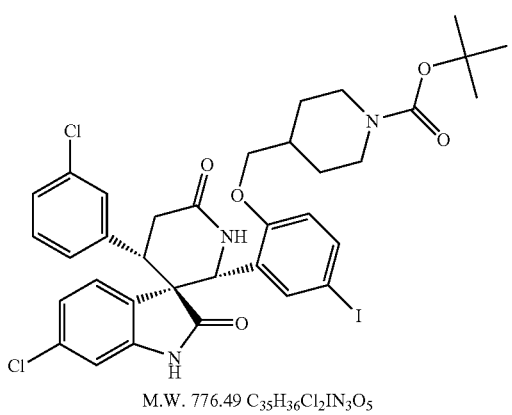

M.W. 776.49 $C_{35}H_{36}Cl_2IN_3O_5$

To a solution of 1-[2-(1-(tert-butoxycarbonyl)-4-piperidinylmethoxy)-5-iodo-phenyl]-3-trimethylsilyoxy-2-aza-1,3-butadiene prepared in example 1d (5 mmol) in toluene (20 mL) was added E/Z-6-chloro-3-(3-chlorobenzylidene)-2-oxo-2,3-dihydro-indole-1-carboxylic acid tert-butyl ester prepared in Example 1b (0.7 g, 1.8 mmol). The reaction mixture was heated under nitrogen at 150° C. for 5 h. After the solution was cooled to room temperature, methanol (10 mL) was added and the mixture was concentrated. The residue was purified by chromatography (EtOAc:CH$_2$Cl$_2$=1;1 then EtOAc) to give racemic(2'R,3R,4'S)-2'-[2-(1-(tert-butoxycarbonyl)-4-piperidinylmethoxy)-5-iodo-phenyl]-6-chloro-4'-(3-chlorophenyl)spiro[3H-indole-3,3'-piperidine]-2,6'(1H)-dione as a yellow solid (Yield 0.89 g, 64%).

HRMS(ES$^+$) m/z Calcd for $C_{35}H_{36}Cl_2IN_3O_5$+H [(M+H)$^+$]: 776.1150. Found: 776.1154.

EXAMPLE 2

Preparation of racemic(2'R,3R,4'S)-2'-[2-(1-(tert-butoxycarbonyl)-4-piperidinylmethoxy)-5-ethynyl-phenyl]-6-chloro-4'-(3-chlorophenyl)spiro[3H-indole-3,3'-piperidine]-2,6'(1H)-dione

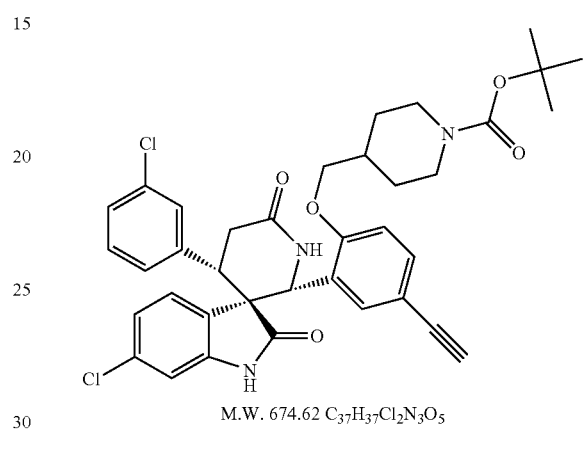

M.W. 674.62 $C_{37}H_{37}Cl_2N_3O_5$

A solution of racemic(2'R,3R,4'S)-2'-[2-(1-(tert-butoxycarbonyl)-4-piperidinylmethoxy) -5-iodo-phenyl]-6-chloro-4'-(3-chlorophenyl)spiro[3H-indole-3,3'-piperidine]-2,6' (1H)-dione (0.89 g, 1.15 mmol) prepared in example 1e in anhydrous tetrahydrofuran (30 mL) was added trimethylsilyl acetylene (0.23 g, 2.3 mmol) (Aldrich), CuI (0.44 g, 2.3 mmol) (Aldrich) and triethylamine (0.13 g, 2.3 mmol). The mixture was degassed under nitrogen for 5 min, then dichlorobis(triphenylphosphine)palladium(0) (160 mg, 0.23 mmol) (Strem) was added and the reaction mixture was heated at 80° C. under nitrogen for 2 h. The reaction mixture was cooled to room temperature and filtered through a short pad of silica gel, the silica gel was washed with ethyl acetate. The filtrate was concentrated. To the residue was added methanol (20 mL) and aqueous NaOH solution (1 N, 10 mL). The mixture was stirred at room temperature for 2 h, then partitioned between ethyl acetate and water. The organic layer was separated, and the aqueous layer was extracted with ethyl acetate. The organic layers were combined, dried over MgSO$_4$ and concentrated. The reidue was purified with chromatography (EtOAc: hexanes=2:1) to give racemic(2'R,3R,4'S)-2'-[2-(1-tert-butoxycarbonyl)-4-piperidinylmethoxy) -5-ethynyl-phenyl]-6-chloro-4'-(3-chlorophenyl)spiro[3H-indole -3,3'-piperidine]-2,6'(1H)-dione as a white solid (Yield 0.24 g, 31%).

HRMS(ES$^+$) m/z Calcd for $C_{37}H_{37}Cl_2N_3O_5$+H [(M+H)$^+$]: 674.2183. Found: 674.2185.

EXAMPLE 3a

Preparation of intermediate racemic(2'R,3R,4'S)-6-chloro-4'-(3-chlorophenyl)-2'-[5-ethynyl-2-(4-piperidinylmethoxy)-phenyl]spiro[3H-indole-3,3'-piperidine]-2,6'(1H)-dione

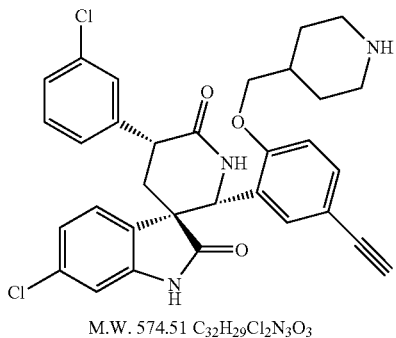

M.W. 574.51 C$_{32}$H$_{29}$Cl$_2$N$_3$O$_3$

Racemic(2'R,3R,4'S)-2'-[2-(1-(tert-butoxycarbonyl)-4-piperidinylmethoxy)-5-ethynyl-phenyl]-6-chloro-4'-(3-chlorophenyl)spiro[3H-indole-3,3'-piperidine]-2,6'(1H)-dione (0.22 g, 0.32 mmol) prepared in Example 2 was dissolved in formic acid (88%, Alfa). The reaction mixture was stirred at room temperature for 1 h, then poured into aqueous saturated NaHCO$_3$ solution. The mixture was extracted with ethyl acetate. The organic layer was separated, washed with water, brine, dried over MgSO$_4$ and concentrated to give crude racemic(2'R,3R,4'S)-6-chloro-4'-(3-chlorophenyl)-2'-[5-ethynyl-2-(4-piperidinylmethoxy)-phenyl]spiro[3H-indole-3,3'-piperidine]-2,6'(1H)-dione as a white solid (Yield: 0.19 g, 100%).

EXAMPLE 3b

Preparation of racemic(2'R,3R,4'S)-2'-[2-(1-acetyl-4-piperidinylmethoxy)-5-ethynyl-phenyl]-6-chloro-4'-(3-chlorophenyl)spiro[3H-indole-3,3'-piperidine]-2,6'(1H)-dione

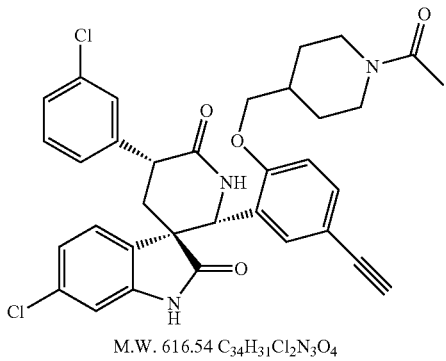

M.W. 616.54 C$_{34}$H$_{31}$Cl$_2$N$_3$O$_4$

To a solution of racemic(2'R,3R,4'S)-6-chloro-4'-(3-chlorophenyl)-2'-[5-ethynyl-2-(4-piperidinylmethoxy)-phenyl]spiro[3H-indole-3,3'-piperidine]-2,6'(1H)-dione (0.19 g, 0.32 mmol) prepared in Example 3a in dichloromethane (10 mL) was added anhydrous K$_2$CO$_3$ (0.2 g, 1.5 mmol), and acetic anhydride (50 mg, 0.49 mmol). The reaction mixture was stirred at room temperature for 1 h. The mixture was diluted with ethyl acetate, washed with water, brine. The organic layer was separated, dried over MgSO$_4$, concentrated. The residue was purified by chromatography (EtOAc:MeOH=92:8) to give racemic(2'R,3R,4'S)-2'-[2-(1-acetyl-4-piperidinylmethoxy)-5-ethynyl-phenyl]-6-chloro-4'-(3-chlorophenyl)spiro[3H-indole-3,3'-piperidine]-2,6'(1H)-dione as a white solid (Yield 0.12 g, 61%).

HRMS(ES$^+$) m/z Calcd for C$_{34}$H$_{31}$Cl$_2$N$_3$O$_4$+H [(M+H)$^+$]: 616.1765. Found: 616.1764.

EXAMPLE 4a

Preparation of intermediate 4-(2-formyl-4-iodo-phenoxy)-piperidine-1-carboxylic acid tert-butyl ester

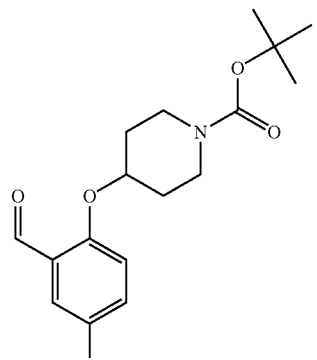

M.W. 431.21 C$_{17}$H$_{22}$INO$_4$

To a solution of 5-iodosalicylaldehyde (3 g, 12.1 mmol) (Aldrich) in N,N-dimethylformamide (20 mL) was added anhydrous K$_2$CO$_3$ (5 g, 36.3 mmol), and 4-(toluene-4-sulfonyloxy)-piperidine-1-carboxylic acid tert-butyl ester (5.4 g, 18.1 mmol, ASTATECH). The reaction mixture was heated at 60° C. for 18 h. The mixture was cooled to room temperature, diluted with ethyl acetate, washed with water. The organic layer was separated, the aqueous layer was extracted with ethyl acetate. The organic layers were combined, washed with water, brine, dried over MgSO$_4$, and concentrated to give crude 4-(2-formyl-4-iodo-phenoxy)-piperidine-1-carboxylic acid tert-butyl ester as a yellow oil (Yield 4.38 g, 84%).

EXAMPLE 4b

Preparation of intermediate 1-[2-(1-(tert-butoxycarbonyl)-4-piperidinyloxy)-5-iodo-phenyl]-3-trimethylsilyoxy-aza-1,3-butadiene

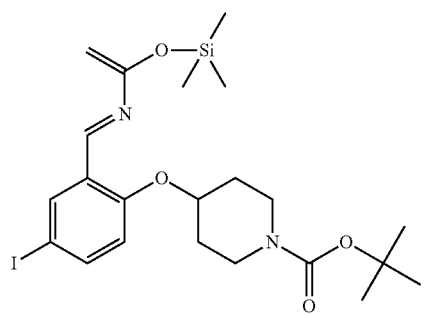

M.W. 544.51 C$_{22}$H$_{33}$IN$_2$O$_4$Si

In a manner similar to the method described in example 1d, 4-(2-formyl-4-iodo-phenoxy)-piperidine-1-carboxylic acid tert-butyl ester (22 g, 51 mmol) prepared in Example 4a was used as the starting material in place of 4-(2-formyl-4-iodo-phenoxymethyl)-piperidine-1-carboxylic acid tert-butyl ester to react with 1,1,3,3,3-hexamethyldisilazane (13.4 mL, 51 mmol), n-butyllithium (2.5 M, 25.7 mL, 51 mmol), trimethylsilyl chloride (8.09 mL, 51 mmol), triethylamine (11.7 mL, 66 mmol) and acetyl chloride (5.88 mL, 66 mmol) to give crude 1-[2-(1-(tert-butoxycarbonyl)-4-piperidinyloxy)-5-iodo-phenyl]-3-trimethylsilyoxy-2-aza-1,3-butadiene as a yellow gum and used for the next step without further purification.

EXAMPLE 4c

Preparation of racemic(2'R,3R,4'S)-2'-[2-(1-(tert-butoxycarbonyl)-4-piperidinyloxy)-5-iodo-phenyl]-6-chloro-4'-(3-chlorophenyl)spiro[3H-indole-3,3'-piperidine]-2,6'(1H)-dione

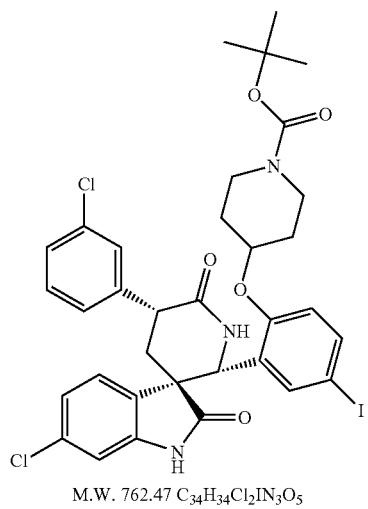

M.W. 762.47 $C_{34}H_{34}Cl_2IN_3O_5$

In a manner similar to the method described in example 1e, E/Z-6-chloro-3-(3-chloro-benzylidene)-2-oxo-2,3-dihydro-indole-1-carboxylic acid tert-butyl ester prepared in example 5b (14 g, 36 mmol) was reacted with 1-[2-(1-(tert-butoxycarbonyl)-4-piperidinyloxy)-5-iodo-phenyl]-3-trimethylsilyoxy-2-aza-1,3-butadiene prepared in example 4b (66 mmol) in toluene (200 mL) at 140° C. for 6 h to give racemic(2'R,3R,4'S)-2'-[2-(1-(tert-butoxycarbonyl)-4-piperidinyloxy)-5-iodo-phenyl]-6-chloro-4'-(3-chlorophenyl)spiro[3H-indole-3,3'-piperidine]-2,6'(1H)-dione as a white solid (Yield 4.1 g, 15%)

HRMS(ES$^+$) m/z Calcd for $C_{34}H_{34}Cl_2IN_3O_5$+H [(M+H)$^+$]: 762.0993. Found: 762.0993

EXAMPLE 5a

Preparation of intermediate racemic(2'R,3R,4'S)-6-chloro-4'-(3-chlorophenyl)-2'-[5-iodo-2-(4-piperidinyloxy)-phnyl]spiro[3H-indole-3,3'-piperidine]-2,6'(1H)-dione

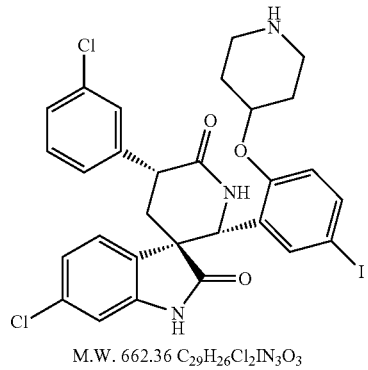

M.W. 662.36 $C_{29}H_{26}Cl_2IN_3O_3$

Trifluoroacetic acid (30 mL) was added to a solution of racemic(2'R,3R,4'S)-2'-[2-(1-(tert-butoxycarbonyl)-4-piperidinyloxy)-5-iodo-phenyl]-6-chloro-4'-(3-chlorophenyl)spiro[3H-indole-3,3'-piperidine]-2,6'(1H)-dione (2 g, 2.62 mmol) prepared in example 4c in dichloromethane (30 mL). The mixture was stirred at room temperature for 1 h. The solvent was evaporated in vacuo, then aqueous saturated NaHCO$_3$ solution was added. The mixture was extracted with ethyl acetate. The organic layers was separated, washed with water and brine, dried over MgSO$_4$, and concentrated to give racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione as a yellow solid (Yield: 1.7 g, 98%).

EXAMPLE 5b

Preparation of racemic(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione

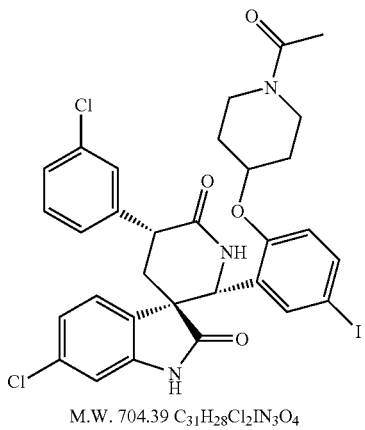

M.W. 704.39 $C_{31}H_{28}Cl_2IN_3O_4$

To a solution of racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (50 mg, 0.076 mmol) prepared in Example 5a in anhydrous tetrahydrofuran (2 mL) was added triethylamine (11.4 mg, 0.114 mmol), and acetyl chloride (6.5 mg, 0.083 mmol). The reaction mixture was stirred at room temperature for 0.5 h. The mixture was diluted with ethyl acetate, washed with water. The organic layer was separated, and aqueous layer was extracted with ethyl acetate. The organic layers were combined, washed with brine, dried over $MgSO_4$, concentrated. The residue was triturated with dichloromethane and hexanes to give racemic(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione as a white solid (Yield 43 mg, 81%).

HRMS(ES$^+$) m/z Calcd for $C_{31}H_{28}Cl_2IN_3O_4$+H [(M+H)$^+$]: 704.0575. Found: 704.0573.

EXAMPLE 5c

Preparation of chiral(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione

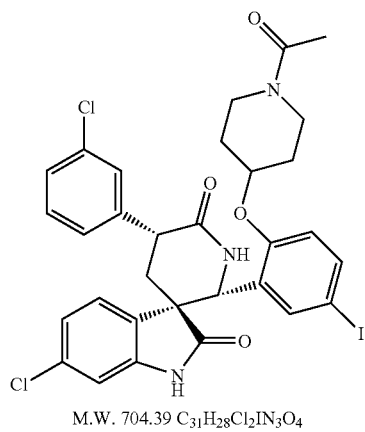

M.W. 704.39 $C_{31}H_{28}Cl_2IN_3O_4$

Separation of the two enantiomers from racemic(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione (64 mg) was conducted by chiral SFC to provide chiral (2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione as a white solid (20 mg, 31%) and chiral (2'S,3S,4'R)-2'-[2-(1-acetyl-4-piperidinyloxy)-5-iodo-phenyl]-6-chloro -4'-(3-chlorophenyl)spiro[3H-indole-3,3'-piperidine]-2,6'(1H)-dione as a white solid (17 mg, 27%).

EXAMPLE 6a

Preparation of racemic(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione

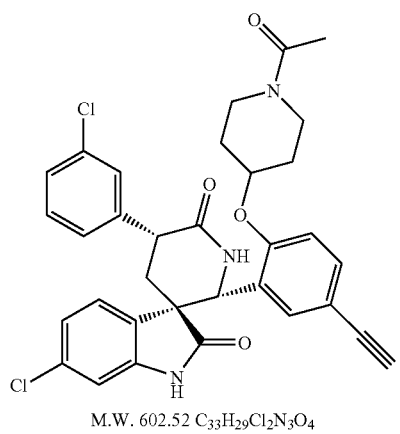

M.W. 602.52 $C_{33}H_{29}Cl_2N_3O_4$

A solution of racemic(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione (0.1 g, 0.14 mmol) prepared in example 5b in anhydrous N,N-dimethylformamide (1 mL) was added trimethylsilyl acetylene (0.2 mL, 1.4 mmol) (Aldrich), CuI (2 mg) (Aldrich) and triethylamine (0.59 mL, 4.2 mmol). The mixture was degassed under nitrogen for 5 min, then dichlorobis(triphenylphosphine)palladium(0) (10 mg, 0.014 mmol) (Strem) was added and the reaction mixture was heated under nitrogen at 90° C. for 2 h. The mixture was cooled to room temperature, partitioned between ethyl acetate and water. The organic layer was separated, and the aqueous layer was extracted with ethyl acetate. The organic layers were combined, washed with brine, dried over $MgSO_4$, and concentrated. The residue was purified by chromatography to give a yellow solid (50 mg). The sloid was dissolved into methanol (10 mL), and aqueous NaOH solution (1 N, 1.2 mL) was added. The mixture was stirred at room temperature for 2 h, then partitioned between ethyl acetate and water. The organic layer was separated, dried over $MgSO_4$ and concentrated. The reidue was purified with chromatography to give racemic(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione as a yellow solid (Yield 17 mg, 20%).

HRMS(ES$^+$) m/z Calcd for $C_{33}H_{29}Cl_2N_3O_4$+H [(M+H)$^+$]: 602.1608. Found: 602.1610.

EXAMPLE 6b

Preparation of chiral(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione

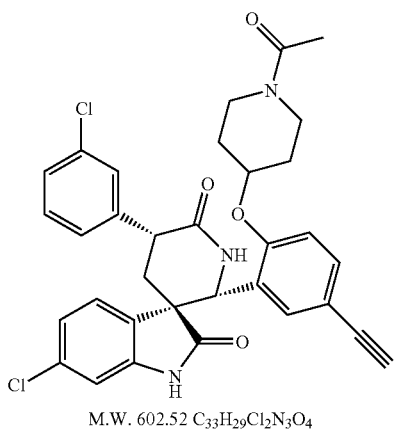

M.W. 602.52 $C_{33}H_{29}Cl_2N_3O_4$

Separation of the two enantiomers from racemic(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione prepared in Example 6a (70 mg) was conducted by chiral SFC to provide chiral (2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione as a white solid (15 mg, 22%) and chiral (2'S,3S,4'R)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione as a white solid (30 mg, 44%).

EXAMPLE 7

Preparation of racemic(2'R,3R,4'S)-6-chloro-4'-(3-chlorophenyl)-2'-[5-iodo-2-(1-methyl-4-piperidinyloxy)-phenyl]spiro[3H-indole-3,3'-piperidine]-2,6'(1H)-dione

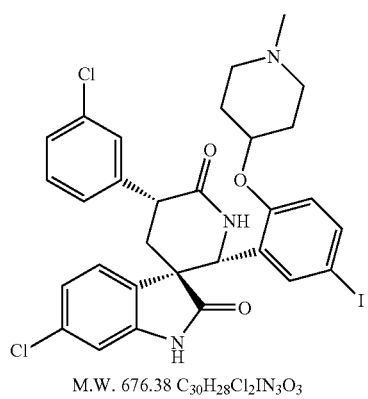

M.W. 676.38 $C_{30}H_{28}Cl_2IN_3O_3$

To a solution of racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.2 g, 0.3 mmol) prepared in example 5a in methanol (10 mL) was added an aqueous solution (37 wt %, Aldrich) of formaldehyde (0.045 mL, 0.6 mmol) and NaCNBH$_3$ (28 mg, 0.45 mmol). The reaction mixture was stirred at room temperature for 1 h, then concentrated. The residue was partitioned between ethyl acetate and water. The organic layer was separated, and the aqueous layer was extracted with ethyl acetate. The organic layers were combined, washed with brine, dried over MgSO$_4$, and concentrated. The residue was purified by chromatography (EtOAc:triethylamine=10:3.5) to give racemic(2'R,3R,4'S)-6-chloro-4'-(3-chlorophenyl)-2'-[5-iodo-2-(1-methyl-4-piperidinyloxy)-phenyl]spiro[3H-indole-3,3'-piperidine]-2,6'(1H)-dione as a white solid (Yield 70 mg, 35%).

HRMS(ES$^+$) m/z Calcd for $C_{30}H_{28}Cl_2IN_4O_4$+H [(M+H)$^+$]: 676.0625. Found: 676.0628.

EXAMPLE 8a

Preparation of racemic(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione

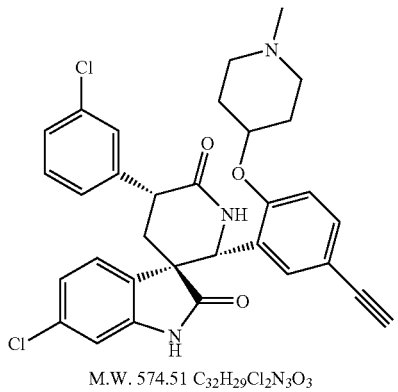

M.W. 574.51 $C_{32}H_{29}Cl_2N_3O_3$

In a manner similar to the method described in example 6a, racemic(2'R,3R,4'S)-6-chloro-4'-(3-chlorophenyl)-2'-[5-iodo-2-(1-methyl-4-piperidinyloxy)-phenyl]spiro[3H-indole-3,3'-piperidine]-2,6'(1H)-dione prepared in example 7 (0.35 g, 0.51 mmol) was reacted with trimethylsilyl acetylene (0.51 mL, 5.1 mmol), CuI (10 mg), triethylamine (1.56 g, 15.3 mmol), and dichlorobis(triphenylphosphine)palladium(0) (36 mg, 0.051 mmol) in anhydrous N,N-dimethylformamide, and then treated with aqueous NaOH in methanol to give racemic(2'R,3R,4'S)-6-chloro-4'-(3-chlorophenyl)-2'-(3-ethynyl-4-fluoro-phenyl)spiro[3H-indole-3,3'-piperidine]-2,6'(1H)-dione as a off white solid (Yield 0.115 g, 39%)

EXAMPLE 8b

Preparation of chiral(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione

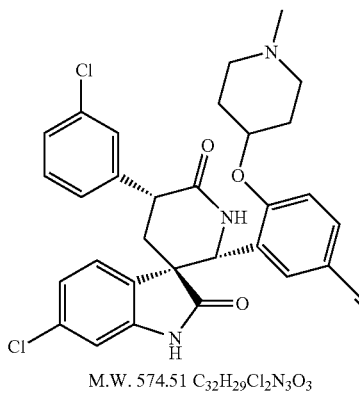

M.W. 574.51 C$_{32}$H$_{29}$Cl$_2$N$_3$O$_3$

Separation of the two enantiomers from racemic(2'R,3R,4'S)-6-chloro-4'-(3-chlorophenyl)-2'-[5-ethynyl-2-(1-methyl-4-piperidinyloxy)-phenyl]spiro[3H-indole -3,3'-piperidine]-2,6'(1H)-dione prepared in Example 8a (100 mg) was conducted by chiral SFC to provide chiral (2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6' (1H)-dione as a yellow solid (35 mg, 35%) and chiral (2'S, 3S,4'R)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione as a yellow solid (40 mg, 40%).

HRMS(ES$^+$) m/z Calcd for C$_{32}$H$_{29}$Cl$_2$N$_3$O$_3$+H [(M+H)$^+$]: 574.1659. Found: 574.1656.

EXAMPLE 9a

Preparation of intermediate 5-Iodo-2-nitro-benzaldehyde

M.W. 277.02 C$_7$H$_4$INO$_3$

To a solution of 5-iodo-2-nitrobenzoic acid (37 g, 126 mmol) (APIN) in anhydrous tetrahydrofuran (200 mL) at 0° C. was added borane tetrahydrofuran (1 M, 360 mL, 360 mmol) dropwise. The reaction mixture was then stirred at room temperature for 24 h. The mixture was concentrated and residue was partitioned between ethyl acetate and water. Organic layer was separated, washed with brine, dried over MgSO$_4$, concentrated, and triturated. The precipitate 5-Iodo-2-nitro-phenyl)-methanol was collected as a yellow solid (20 g, 57%).

The solid (5.5 g) was dissolved into dichloromethane (100 mL), and activated MnO$_2$ (15 g) was added. The mixture was then heated at reflux for 4 h, cooled to room temperature, and filtered through a short pad of celite. The filtrated was concentrated to give 5-Iodo-2-nitro-benzaldehyde as a yellow solid (Yield 4.2 g, 76%).

EXAMPLE 9b

Preparation of intermediate 1-(5-Iodo-2-nitrophenyl)-3trimethylsilyoxy-2-aza-1,3-butadiene

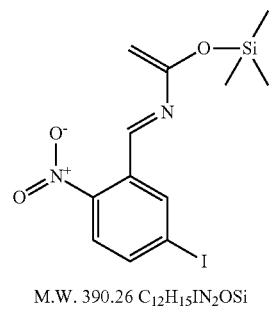

M.W. 390.26 C$_{12}$H$_{15}$IN$_2$OSi

In a manner similar to the method described in example 1d, 5-iodo-2-nitrobenzaldehyde prepared in Example 9a (4.2 g, 15 mmol) was used as the starting material in place of 2-[2-(tert-butyl-dimethyl-silanyloxy)-ethoxy]-5-iodo-benzaldehyde to react with 1,1,3,3,3-hexamethyldisilazane (2.4 g, 15 mmol), n-butyllithium (2.5 M, 6 mL, 15 mmol), trimethylsilyl chloride (1.6 g, 15 mmol), triethylamine (2.1 g, 20 mmol) and acetyl chloride (1.5 g, 20 mmol) to give crude 1-(5-Iodo-2-nitrophenyl)-3-trimethylsilyoxy -2-aza-1,3-butadiene as a yellow gum and used for the next step without further purification.

EXAMPLE 9c

Preparation of intermediate racemic(2'R,3R,4'S)-6-chloro-4'-(3-chlorophenyl)-2'-(5-iodo-2-nitrophenyl)spiro[3H-indole-3,3'-piperidine]-2,6'(1H)-dione

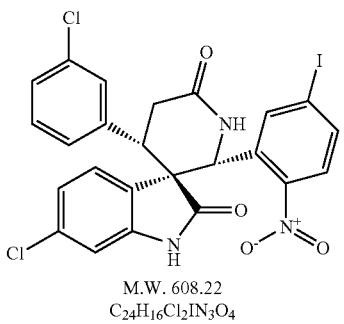

M.W. 608.22 C$_{24}$H$_{16}$Cl$_2$IN$_3$O$_4$

To a solution of 1-(5-Iodo-2-nitrophenyl)-3-trimethylsilyoxy-2-aza-1,3-butadiene prepared in example 9b (15 mmol) in toluene (40 mL) was added E/Z-6-chloro-3-(3-chlorobenzylidene) -2-oxo-2,3-dihydro-indole-1-carboxylic acid tert-butyl ester prepared in Example 1b (2 g, 5 mmol). The reaction mixture was stirred under nitrogen at 150° C. for 3 h. After the solution was cooled to room temperature and concentrated. The residue was dissolved in dichloromethane (20 mL) and trifluoroactic acid (10 mL) was added. After the reaction mixture was stirred at room temperature for 0.5 h, the mixture was concentrated. The residue was partitioned between saturated NaHCO$_3$ solution and ethyl acetae. The aqueous layer was extracted with ethyl acetate. The combined organic layer was dried over Na$_2$SO$_4$ and concentrated. The residue was purified by chromatography (EtOAc:CH$_2$Cl$_2$=1:4) to give racemic(2'R,3R,4'S)-6-chloro-4'-(3-chlorophenyl) 2'-(5-iodo-2-nitrophenyl)spiro[3H-indole-3,3'-piperidine]-2,6'(1H)-dione as a yellow solid (Yield 1.8 g, 59%)

HRMS(ES$^+$) m/z Calcd for C$_{24}$H$_{16}$Cl$_2$IN$_3$O$_4$+H [(M+H)$^+$]: 607.9636. Found: 607.9638.

EXAMPLE 9d

Preparation of intermediate racemic(2'R,3R,4'S)-2'-(2-amino-5-iodophenyl)-6-chloro -4'-(3-chlorophenyl)spiro[3H-indole-3,3'-piperidine]-2,6'(1H)-dione

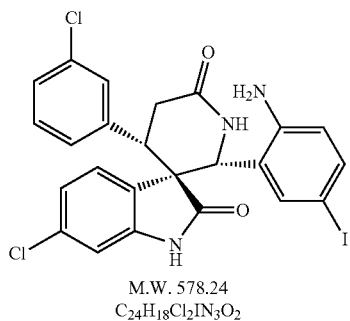

M.W. 578.24
C$_{24}$H$_{18}$Cl$_2$IN$_3$O$_2$

To a suspension of racemic(2'R,3R,4'S)-6-chloro-4'-(3-chlorophenyl)-2'-(5-iodo-2-nitrophenyl)spiro[3H-indole-3,3'-piperidine]-2,6'(1H)-dione prepared in Example 9c (0.7 g, 1.15 mmol) in methanol (50 mL) was added aqueous NH$_4$Cl solution (0.61 g, 11.5 mmol, 20 mL), followed by addition of Zn powder (0.75 g, 11.5 mmol). The reaction mixture was stirred at room temperature for 1 h, then filtered throught a short pad of celite. The filtrate was concentrated, extracted with ethyl acetate and dichloromethane. The organic layers were combined, dried over MgSO$_4$, and concentrated. The residue was purified by chromatography (EtOAc, then EtOAc:MeOH=19;1) to give racemic(2'R,3R,4'S)-2'-(2-amino-5-iodophenyl)-6-chloro -4'-(3-chlorophenyl)spiro[3H-indole-3,3'-piperidine]-2,6'(1H)-dione as a white solid (Yield 0.41 g, 61%)

HRMS(ES$^+$) m/z Calcd for C$_{24}$H$_{18}$Cl$_2$IN$_3$O$_2$+H [(M+H)$^+$]: 577.9894. Found: 577.9894.

EXAMPLE 9e

Preparation of racemic(2'R,3R,4'S)-2'-[2-(1-acetyl-4-piperidinylamino)-5-iodo-phenyl]-6-chloro-4'-(3-chlorophenyl)spiro[3H-indole-3,3'-piperidine]-2,6' (1H)-dione

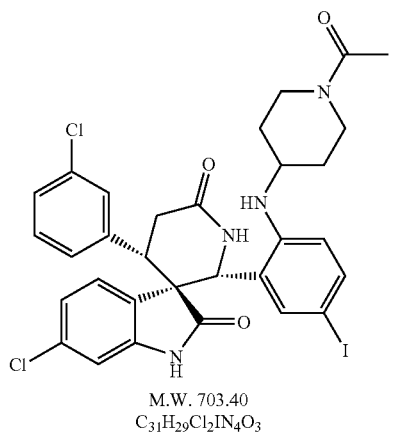

M.W. 703.40
C$_{31}$H$_{29}$Cl$_2$IN$_4$O$_3$

To a suspension of racemic(2'R,3R,4'S)-2'-(2-amino-5-iodophenyl)-6-chloro-4'-(3-chlorophenyl)spiro[3H-indole-3,3'-piperidine]-2,6'(1H)-dione prepared in Example 9d (0.16 g, 0.28 mmol) in o-xylene (50 mL) was added 1-acetyl-4-piperidinone (0.14 g, 1 mmol, Lancaster) and p-toluenesulfonic acid monohydrate (15 mg). The reaction mixture was heated at reflux (180° C.) for 8 h, then cooled to room temperature and concentrated. To the residue was added methanol (10 mL), acetic acid (1 mL), and NaCNBH$_3$ (0.1 g, 1.6 mmol). The reaction mixture was stirred at room temperature for 1 h, then concentrated. The residue was partitioned between ethyl acetate and water. The organic layer was separated, aqueous layer was extracted with ethyl acetate. The organic layers were combined, washed with brine, dried over MgSO$_4$, and concentrated. The residue was purified by chromatography (EtOAc:MeOH=9;1) to give racemic(2'R,3R,4'S)-2'-[2-(1-acetyl-4-piperidinylamino)-5-iodo-phenyl]-6-chloro-4'-(3-chlorophenyl)spiro[3H-indole-3,3'-piperidine]-2,6'(1H)-dione as a white solid (Yield 0.15 g, 76%)

HRMS(ES$^+$) m/z Calcd for C$_{31}$H$_{29}$Cl$_2$IN$_4$O$_3$+H [(M+H)$^+$]: 703.0734. Found: 703.0730.

EXAMPLE 10

Preparation of racemic(2'R,3R,4'S)-2'-[2-(1-acetyl-4-piperidinylamino)-5-ethynyl-phenyl]-6-chloro-4'-(3-chlorophenyl)spiro[3H-indole-3,3'-piperidine]-2,6' (1H)-dione

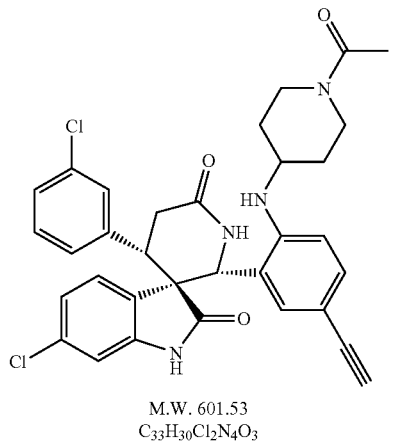

M.W. 601.53
C$_{33}$H$_{30}$Cl$_2$N$_4$O$_3$

In a manner similar to the method described in example 2, racemic(2'R,3R,4'S)-2'-[2-(1-acetyl-4-piperidinylamino)-5-iodo-phenyl]-6-chloro-4'-(3-chlorophenyl)spiro[3H-indole-3,3'-piperidine]-2,6'(1H)-dione prepared in example 9e (0.14 g, 0.2 mmol) was reacted with trimethylsilyl acetylene (39 mg, 0.4 mmol), CuI (76 mg, 0.4 mmol), triethylamine (40 mg, 0.4 mmol), and dichlorobis(triphenylphosphine)palladium (0) (30 mg, 0.04 mmol) in anhydrous tetrahydrofuran, and then treated with aqueous NaOH in methanol to give racemic (2'R,3R,4'S)-2'-[2-(1-acetyl-4-piperidinylamino)-5-ethynyl-phenyl]-6-chloro-4'-(3-chlorophenyl)spiro[3H-indole-3,3'-piperidine]-2,6'(1H)-dione as a off white solid (Yield 0.25 g, 84%)

HRMS(ES$^+$) m/z Calcd for $C_{33}H_{30}Cl_2N_4O_3$+H [(M+H)$^+$]: 601.1768. Found: 601.1767.

EXAMPLE 11a

Preparation of racemic(2'R,3R,4'S)-6-chloro-4'-(3-chlorophenyl)-2'-[5-iodo-2-(1-propionyl-4-piperidinyloxy)-phenyl]spiro[3H-indole-3,3'-piperidine]-2,6'(1H)-dione

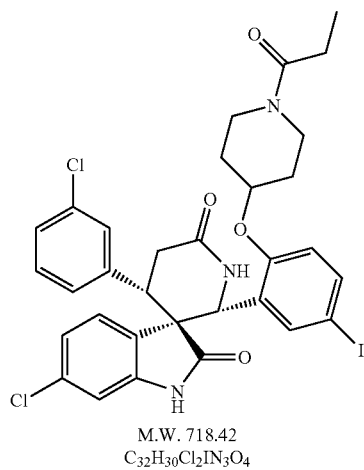

M.W. 718.42
$C_{32}H_{30}Cl_2IN_3O_4$

In a manner similar to the method described in example 5b, propionyl chloride (15.4 mg, 0.17 mmol) as the starting material in place of acetyl chloride to react with racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a and triethylamine in tetrahydrofuran to give racemic(2'R,3R,4'S)-6-chloro-4'-(3-chlorophenyl)-2'-[5-iodo-2-(1-propionyl-4-piperidinyloxy)-phenyl]spiro[3H-indole-3,3'-piperidine]-2,6'(1H)-dione as a yellow solid (Yield 0.11 g, 100%).

EXAMPLE 11b

Preparation of racemic(2'R,3R,4'S)-6-chloro-4'-(3-chlorophenyl)-2'-[5-ethynyl-2-(1-propionyl-4-piperidinyloxy)-phenyl]spiro[3H-indole-3,3'-piperidine]-2,6'(1H)-dione

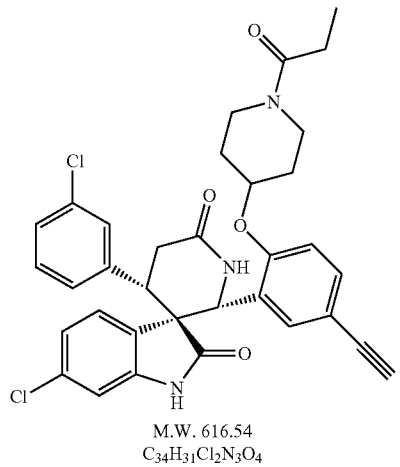

M.W. 616.54
$C_{34}H_{31}Cl_2N_3O_4$

In a manner similar to the method described in example 6a, racemic(2'R,3R,4'S)-6-chloro-4'-(3-chlorophenyl)-2'-[5-iodo-2-(1-propionyl-4-piperidinyloxy)-phenyl]spiro[3H-indole-3,3'-piperidine]-2,6'(1H)-dione prepared in example 11a (0.1 g, 0.14 mmol) was reacted with trimethylsilyl acetylene (0.14 g, 1.4 mmol), CuI (2 mg), triethylamine (0.42 g, 4.17 mmol), and ichlorobis(triphenylphosphine)palladium (0) (9.8 mg, 0.014 mmol) in anhydrous N,N-dimethylformamide, and then treated with aqueous NaOH in methanol to give racemic racemic(2'R,3R,4'S)-6-chloro-4'-(3-chlorophenyl)-2'-[5-ethynyl-2-(1-propionyl-4-piperidinyloxy)-phenyl]spiro[3H-indole-3,3'-piperidine]-2,6'(1H)-dione as a off white solid (Yield 10 mg)

HRMS(ES$^+$) m/z Calcd for $C_{34}H_{31}Cl_2N_3O_4$+H [(M+H)$^+$]: 616.1765. Found: 616.1760.

EXAMPLE 12a

Preparation of racemic(2'R,3R,4'S)-6-chloro-4'-(3-chlorophenyl)-2'-{5-iodo-2-[1-(3-methanesulfonyl-propyl)-4-piperidinyloxy]-phenyl}spiro[3H-indole-3,3'-piperidine]-2,6'(1H)-dione

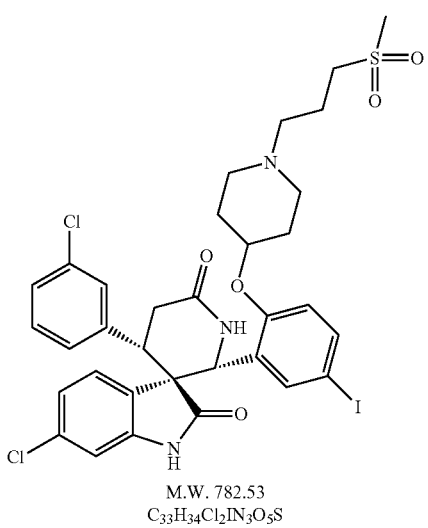

M.W. 782.53
$C_{33}H_{34}Cl_2IN_3O_5S$

To a solution of racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in example 5a in ethanol (2 mL) was methanesulfonic acid 3-methanesulfonyl-propyl ester (54 mg, 0.25 mmol) (WO2001062668) and triethylamine (0.031 mL, 0.225 mmol). The reaction mixture was heated at 68° C. for 18 h, then cooled to room temperature and concentrated. The residue was partitioned between ethyl acetate and water. The organic layer was separated, and the aqueous layer was extracted with ethyl acetate. The organic layers were combined, washed with brine, dried over MgSO$_4$, and concentrated to give crude racemic(2'R,3R,4'S)-6-chloro-4'-(3-chlorophenyl)-2'-{5-iodo-2-[1-(3-methanesulfonyl-propyl)-4-piperidinyloxy]-phenyl}spiro[3H-indole-3,3'-piperidine]-2,6'(1H)-dione as a light yellow solid (Yield 0.1 g)

EXAMPLE 12b

Preparation of racemic(2'R,3R,4'S)-6-chloro-4'-(3-chlorophenyl)-2'-{5-ethynyl-2-[1-(3-methanesulfonyl-propyl)-4-piperidinyloxy]-phenyl}spiro[3H-indole-3,3'-piperidine]-2,6'(1H)-dione

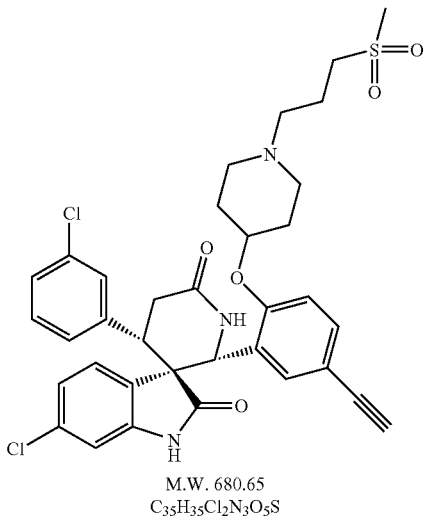

M.W. 680.65
C$_{35}$H$_{35}$Cl$_2$N$_3$O$_5$S

In a manner similar to the method described in example 6a, racemic(2'R,3R,4'S)-6-chloro-4'-(3-chlorophenyl)-2'-{5-iodo-2-[1-(3-methanesulfonyl-propyl)-4-piperidinyloxy]-phenyl}spiro[3H-indole-3,3'-piperidine]-2,6'(1H)-dione prepared in example 12a (0.1 g, 0.13 mmol) was reacted with trimethylsilyl acetylene (0.13 mL, 1.3 mmol), CuI (3 mg), triethylamine (0.39 g, 3.84 mmol), and dichlorobis(triphenylphosphine)palladium (0) (8.9 mg, 0.013 mmol) in anhydrous N,N-dimethylformamide, and then treated with aqueous NaOH in methanol to give racemic (2'R,3R,4'S)-6-chloro-4'-(3-chlorophenyl)-2'-{5-ethynyl-2-[1-(3-methanesulfonyl-propyl)-4-piperidinyloxy]-phenyl}spiro[3H-indole-3,3'-piperidine]-2,6'(1H)-dione as a brown solid (Yield 39 mg, 45%)

HRMS(ES$^+$) m/z Calcd for C$_{35}$H$_{35}$Cl$_2$N$_3$O$_5$S+H [(M+H)$^+$]: 680.1747. Found: 680.1746.

EXAMPLE 13a

Preparation of racemic(2'R,3R,4'S)-6-chloro-4'-(3-chlorophenyl)-2'-[5-iodo-2-(1-methanesulfonyl-4-piperidinyloxy)phenyl]spiro[3H-indole-3,3'-piperidine]-2,6'(1H)-dione

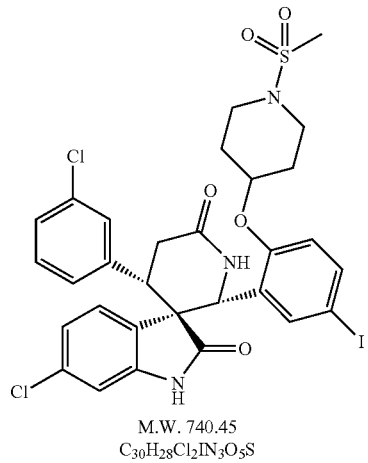

M.W. 740.45
C$_{30}$H$_{28}$Cl$_2$IN$_3$O$_5$S

To a solution of racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a in dichloromethane (2 mL) was added triethylamine (18.3 mg, 0.18 mmol), and methanesulfonyl chloride (19.1 mg, 0.165 mmol). The reaction mixture was stirred at room temperature for 0.5 h. The mixture was diluted with dichloromethane, washed with water. The organic layer was separated, washed with brine, dried over MgSO$_4$, concentrated to give racemic(2'R,3R,4'S)-6-chloro-4'-(3-chlorophenyl)-2'-[5-iodo-2-(1-methanesulfonyl-4-piperidinyloxy)phenyl]spiro[3H-indole-3,3'-piperidine]-2,6'(1H)-dione as a yellow solid (Yield 0.11 g, 99%).

EXAMPLE 13b

Preparation of racemic(2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione

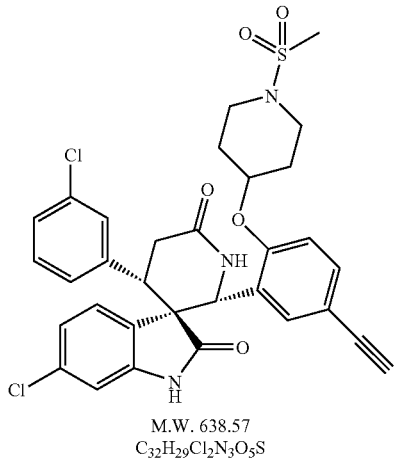

M.W. 638.57
C$_{32}$H$_{29}$Cl$_2$N$_3$O$_5$S

In a manner similar to the method described in example 6a, racemic(2'R,3R,4'S)-6-chloro-4'-(3-chlorophenyl)-2'-[5-iodo-2-(1-methanesulfonyl-4-piperidinyloxy)phenyl]spiro[3H-indole-3,3'-piperidine]-2,6'(1H)-dione prepared in example 13a (0.11 g, 0.15 mmol) was reacted with trimethylsilyl acetylene (0.15 mL, 1.49 mmol), CuI (3 mg), triethylamine (0.45 g, 4.46 mmol), and dichlorobis(triphenylphosphine)palladium (0) (10 mg, 0.015 mmol) in anhydrous N,N-dimethylformamide, and then treated with aqueous NaOH in methanol to give racemic (2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione as a light yellow solid (Yield 51 mg, 54%)

HRMS(ES+) m/z Calcd for $C_{32}H_{29}Cl_2N_3O_5S+H$ [(M+H)+]: 638.1278. Found: 638.1274.

EXAMPLE 13c

Preparation of chiral (2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione

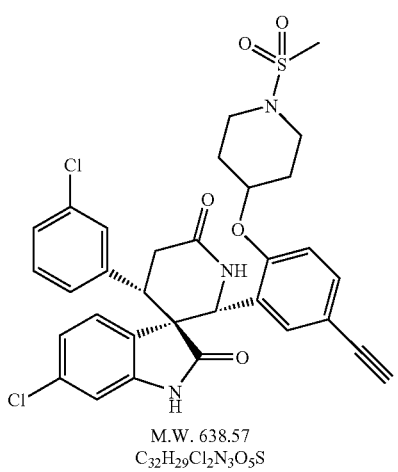

M.W. 638.57
$C_{32}H_{29}Cl_2N_3O_5S$

Separation of the two enantiomers from racemic(2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione prepared in Example 13b (100 mg) was conducted by chiral SFC to provide chiral (2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione as a white solid (31 mg, 31%) and chiral (2'S,3S,4'R)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione as a white solid (34 mg, 34%).

EXAMPLE 14a

Preparation of racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H)-dione

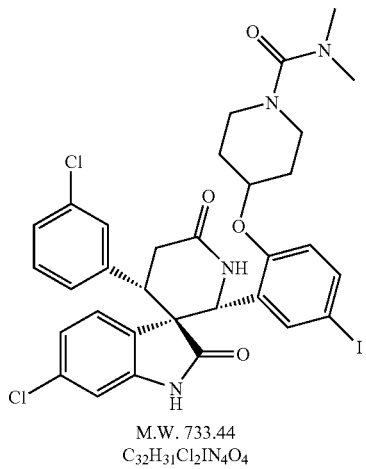

M.W. 733.44
$C_{32}H_{31}Cl_2IN_4O_4$

In a manner similar to the method described in example 5b, dimethylcarbamyl chloride (17.9 mg, 0.17 mmol) as the starting material in place of acetyl chloride to react with racemic (2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a and triethylamine in tetrahydrofuran to give racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H)-dione as a yellow solid (Yield 0.1 g, 91%).

EXAMPLE 14b

Preparation of racemic(2'R,3R,4'S)-6-chloro-4'-(3-chlorophenyl)-2'-[2-(1-dimethylcarbamoyl-4-piperidinyloxy)-5-ethynyl-phenyl]spiro[3H-indole-3,3'-piperidine]-2,6'(1H)-dione

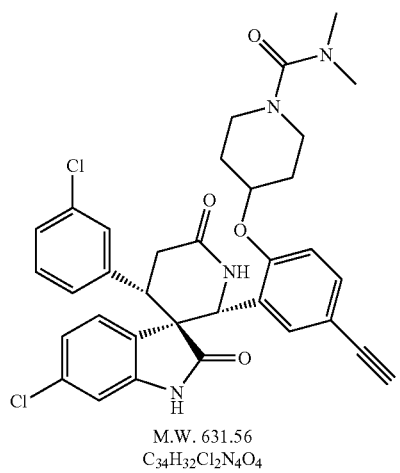

M.W. 631.56
$C_{34}H_{32}Cl_2N_4O_4$

In a manner similar to the method described in example 6a, racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H)-dione prepared in example 14a (0.1 g, 0.14 mmol) was reacted with trimethylsilyl acetylene (0.13 g, 1.4 mmol), CuI (3 mg), triethylamine (0.41 g, 4.08 mmol), and dichlorobis(triphenylphosphine) palladium (0) (9.5 mg, 0.014 mmol) in anhydrous N,N-dimethylformamide, and then treated with aqueous NaOH in methanol to give racemic(2'R,3R,4'S)-6-chloro-4'-(3-chlorophenyl)-2'-[2-(1-dimethylcarbamoyl-4-piperidinyloxy)-5-ethynyl-phenyl]spiro[3H-indole-3,3'-piperidine]-2,6'(1H)-dione as a yellow solid (Yield 35 mg, 41%)

HRMS(ES$^+$) m/z Calcd for $C_{34}H_{32}Cl_2N_4O_4$+H [(M+H)$^+$]: 631.1874. Found: 631.1873.

EXAMPLE 15a

Preparation of intermediate 4-(4-bromo-2-formyl-phenoxy)-piperidine-1-carboxylic acid tert-butyl ester

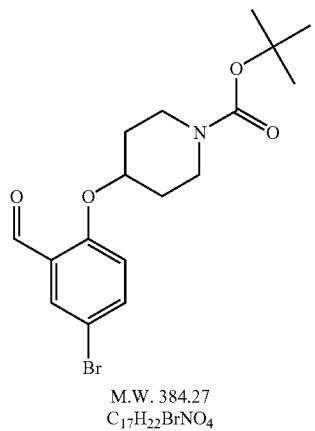

M.W. 384.27
$C_{17}H_{22}BrNO_4$

In a manner similar to the method described in example 4a, 5-bromosalicylaldehyde (5.65 g, 28 mmol) (Aldrich) reacted with 4-(toluene-4-sulfonyloxy)-piperidine-1-carboxylic acid tert-butyl ester (5 g, 14 mmol, ASTATECH) and $K_2CO_3$ in N,N-dimethylformamide to give 4-(4-bromo-2-formyl-phenoxy)-piperidine-1-carboxylic acid tert-butyl ester as a yellow gum (Yield 5.15 g, 51%).

EXAMPLE 15b

Preparation of intermediate 1-[5-bromo-2-(1-(tert-butoxycarbonyl)-4-piperidinyloxy)-phenyl]-3-trimethylsilyoxy-2-aza-1,3-butadiene

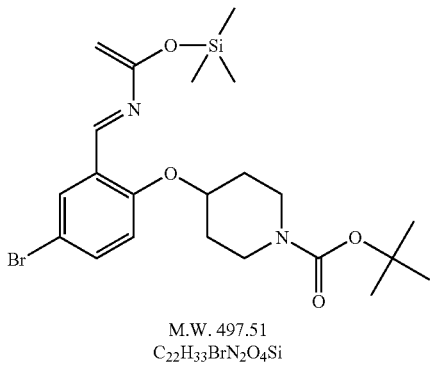

M.W. 497.51
$C_{22}H_{33}BrN_2O_4Si$

In a manner similar to the method described in example 1d, 4-(4-bromo-2-formyl-phenoxy)-piperidine-1-carboxylic acid tert-butyl ester (5.5 g, 14.3 mmol) prepared in Example 15a was used as the starting material in place of 4-(2-formyl-4-iodo-phenoxymethyl)-piperidine-1-carboxylic acid tert-butyl ester to react with 1,1,3,3,3-hexamethyldisilazane (3.97 mL, 14.3 mmol), n-butyllithium (2.5 M, 5.7 mL, 14.3 mmol), trimethylsilyl chloride (1.81 mL, 14.3 mmol), triethylamine (2.59 mL, 18.6 mmol) and acetyl chloride (1.31 mL, 18.6 mmol) to give crude 1-[5-bromo-2-(1-(tert-butoxycarbonyl)-4-piperidinyloxy)-phenyl]-3-trimethylsilyoxy-2-aza-1,3-butadiene as a yellow gum and used for the next step without further purification.

EXAMPLE 15c

Preparation of racemic(2'R,3R,4'S)-2'-[5-bromo-2-(1-(tert-butoxycarbonyl)-4-piperidinyloxy)-phenyl]-6-chloro-4'-(3-chlorophenyl)spiro[3H-indole-3,3'-piperidine]-2,6'(1H)-dione

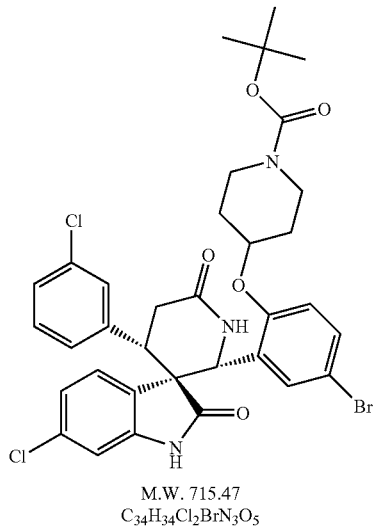

M.W. 715.47
$C_{34}H_{34}Cl_2BrN_3O_5$

In a manner similar to the method described in example 1e, E/Z-6-chloro-3-(3-chloro-benzylidene)-2-oxo-2,3-dihydro-indole-1-carboxylic acid tert-butyl ester prepared in example 5b (1.8 g, 4.62 mmol) was reacted with 1-[5-bromo-2-(1-(tert-butoxycarbonyl)-4-piperidinyloxy)-phenyl]-3-trimethylsilyoxy-2-aza-1,3-butadiene prepared in example 15b (14.3 mmol) in toluene (50 mL) at 140° C. for 6 h to give racemic (2'R,3R,4'S)-2'-[5-bromo-2-(1-(tert-butoxycarbonyl)-4-piperidinyloxy)-phenyl]-6-chloro-4'-(3-chlorophenyl)spiro[3H-indole-3,3'-piperidine]-2,6'(1H)-dione as a white solid (Yield 4.1 g, 15%)

HRMS(ES$^+$) m/z Calcd for $C_{34}H_{34}Cl_2BrN_3O_5$+H [(M+H)$^+$]: 714.1132. Found: 714.1134

EXAMPLE 16a

Preparation of intermediate racemic(2'R,3R,4'S)-2'-[5-bromo-2-(4-piperidinyloxy)-phenyl]-6-chloro-4'-(3-chlorophenyl)spiro[3H-indole-3,3'-piperidine]-2,6'(1H)-dione

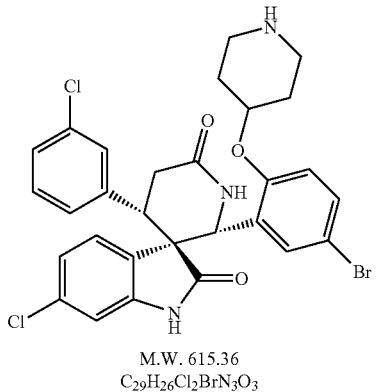

M.W. 615.36
$C_{29}H_{26}Cl_2BrN_3O_3$

In a manner similar to the method described in example 5a, racemic(2'R,3R,4'S)-2'-[5-bromo-2-(1-(tert-butoxycarbonyl)-4-piperidinyloxy)-phenyl]-6-chloro-4'-(3-chlorophenyl)spiro[3H-indole-3,3'-piperidine]-2,6'(1H)-dione (0.13 g, 0.18 mmol) reacted with trifluoroacetic acid in dichloromethane to give racemic(2'R,3R,4'S)-2'-[5-bromo-2-(4-piperidinyloxy)-phenyl]-6-chloro-4'-(3-chlorophenyl)spiro[3H-indole-3,3'-piperidine]-2,6'(1H)-dione as a white solid (Yield: 90 mg, 82%).

EXAMPLE 16b

Preparation of racemic(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione

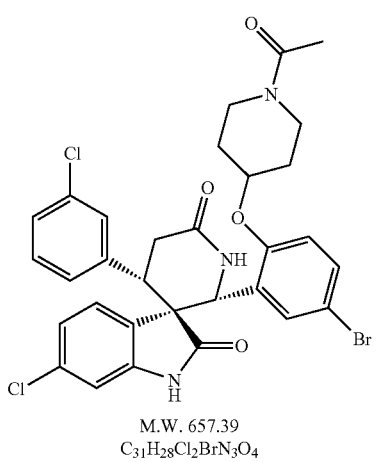

M.W. 657.39
$C_{31}H_{28}Cl_2BrN_3O_4$

In a manner similar to the method described in example 5a, racemic(2'R,3R,4'S)-2'-[5-bromo-2-(4-piperidinyloxy)-phenyl]-6-chloro-4'-(3-chlorophenyl)spiro[3H-indole-3,3'-piperidine]-2,6'(1H)-dione (90 mg, 0.146 mmol) reacted with acetyl chloride (13.8 mg, 0.175 mmol) and triethylamine in anhydrous tetrahydrofuran to give (2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione as a white solid (Yield 50 mg, 52%).

HRMS(ES$^+$) m/z Calcd for $C_{31}H_{28}Cl_2BrN_3O_4$+H [(M+H)$^+$]: 656.0713. Found: 656.0713.

EXAMPLE 16c

Preparation of chiral(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione

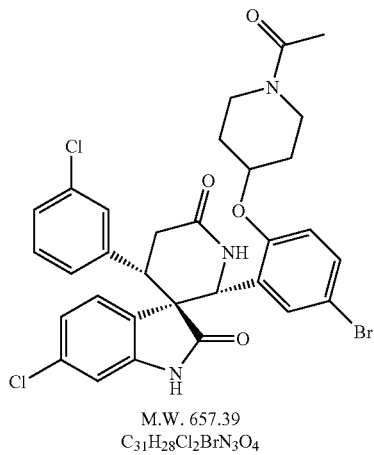

M.W. 657.39
$C_{31}H_{28}Cl_2BrN_3O_4$

Separation of the two enantiomers from racemic(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione (140 mg) was conducted by chiral SFC to provide chiral(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione as a white solid (49 mg, 35%) and chiral(2'S,3S,4'R)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione as a white solid (54 mg, 39%).

EXAMPLE 17a

Preparation of intermediate 3-bromo-2-fluoro-6-methoxy-benzaldehyde

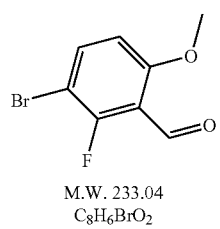

M.W. 233.04
$C_8H_6BrO_2$

To a solution of 4-bromo-3-fluoroanisole (10 g, 48.7 mmol, Matrix) in tetrahydrofuran (100 mL) at −78° C. was added lithium diisopropyl amine (32.5 mL, 1.8 M in THF, 58.4 mmol) dropwise during a period of 15 min. The mixture was stirred at −78° C. for another 20 mins. Then N,N-dimethylformamide (4.53 mL, 58.4 mmol) was added in one portion. The mixture was stirred at −78° C. for 10 min, then quenched with acetic acid (12 g, 194 mmol) and followed by the addition of water (61 mL). The mixture was partitioned between ethyl acetate and water. The organic layer was separated, concentrated. The residue was purified by chromatography (EtOAc:hexanes=1:4) to give 3-bromo-2-fluoro-6-methoxy-benzaldehyde as a yellow solid (Yield: 10 g, 89%)

EXAMPLE 17b

Preparation of intermediate 3-bromo-2-fluoro-6-hydroxy-benzaldehyde

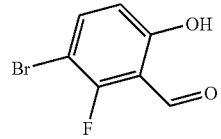

M.W. 219.01
$C_7H_4BrFO_2$

To a solution of 3-bromo-2-fluoro-6-methoxy-benzaldehyde (9.8 g, 42.06 mmol,) in dichloromethane (200 mL) at −50° C. was added a dichloromethane solution (1 M) of $BBr_3$ (126 mL, 126 mmol) dropwise. The mixture was gradually warmed to room temperature and stirred for 1 h, then quenched with water. The mixture was extracted with dichloromethane three times. The organic layer were combined, washed with brine, dried over $MgSO_4$, concentrated to give 3-bromo-2-fluoro-6-hydroxy-benzaldehyde as a off white solid (Yield: 9 g, 98%)

EXAMPLE 17c

Preparation of intermediate 4-(4-bromo-3-fluoro-2-formyl-phenoxy)-piperidine-1-carboxylic acid tert-butyl ester

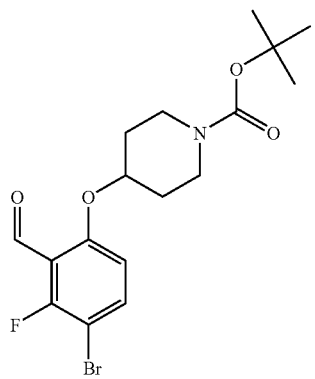

M.W. 402.26
$C_{17}H_{21}BrFNO_4$

In a manner similar to the method described in example 4a, 3-bromo-2-fluoro-6-hydroxy-benzaldehyde (3.69 g, 16.8 mmol) reacted with 4-(toluene-4-sulfonyloxy)-piperidine-1-carboxylic acid tert-butyl ester (4 g, 11.2 mmol, ASTATECH) and $K_2CO_3$ in N,N-dimethylformamide to give 4-(4-bromo-3-fluoro-2-formyl-phenoxy)-piperidine-1-carboxylic acid tert-butyl ester as a brown oil (Yield 4.23 g, 94%).

EXAMPLE 17d

Preparation of intermediate 1-[3-bromo-6-(1-(tert-butoxycarbonyl)-4-piperidinyloxy)-2-fluoro-phenyl]-3-trimethylsilyoxy-2-aza-1,3-butadiene

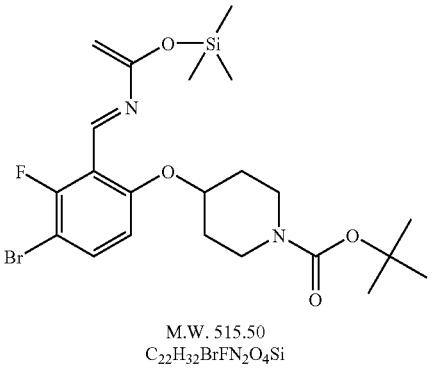

M.W. 515.50
$C_{22}H_{32}BrFN_2O_4Si$

In a manner similar to the method described in example 1d, 4-(4-bromo-3-fluoro-2-formyl-phenoxy)-piperidine-1-carboxylic acid tert-butyl ester (4.22 g, 10.5 mmol) was used as the starting material in place of 4-(2-formyl-4-iodo-phenoxymethyl)-piperidine-1-carboxylic acid tert-butyl ester to react with 1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give crude 1-[3-bromo-6-(1-(tert-butoxycarbonyl)-4-piperidinyloxy)-2-fluoro-phenyl]-3-trimethylsilyoxy-2-aza-1,3-butadiene as a yellow gum and used for the next step without further purification.

EXAMPLE 17e

Preparation of racemic(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione

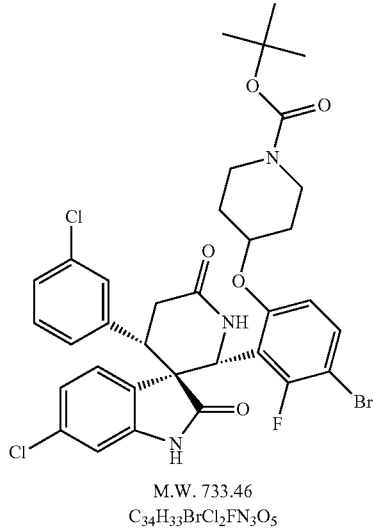

M.W. 733.46
$C_{34}H_{33}BrCl_2FN_3O_5$

In a manner similar to the method described in example 1e, E/Z-6-chloro-3-(3-chloro-benzylidene)-2-oxo-2,3-dihydro-indole-1-carboxylic acid tert-butyl ester prepared in example 5b (1.36 g, 3.5 mmol) was reacted with 1-[3-bromo-6-(1-(tert-butoxycarbonyl)-4-piperidinyloxy)-2-fluoro-phenyl]-3-trimethylsilyoxy-2-aza-1,3-butadiene (10.5 mmol) in toluene (30 mL) at 140° C. for 6 h to give racemic(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione as a light yellow solid (Yield 0.7 g, 28%)

HRMS(ES+) m/z Calcd for $C_{34}H_{33}BrCl_2FN_3O_5$+H [(M+H)+]: 732.1038. Found: 732.1035

EXAMPLE 17f

Preparation of chiral(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione

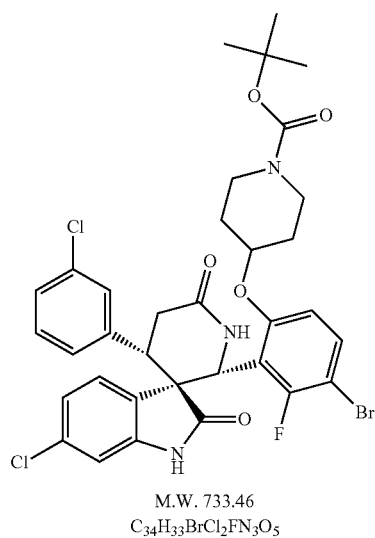

M.W. 733.46
$C_{34}H_{33}BrCl_2FN_3O_5$

Separation of the two enantiomers from racemic(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione (87 mg) was conducted by chiral SFC to provide chiral(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione as a light yellow solid (37 mg, 43%) and chiral(2'S,3S,4'R)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione as a light yellow solid (28 mg, 32%).

EXAMPLE 18a

Preparation of intermediate racemic(2'R,3R,4'S)-2'-[3-bromo-2-fluoro-6-(4-piperidinyloxy)-phenyl]-6-chloro-4'-(3-chlorophenyl)spiro[3H-indole-3,3'-piperidine]-2,6'(1H)-dione

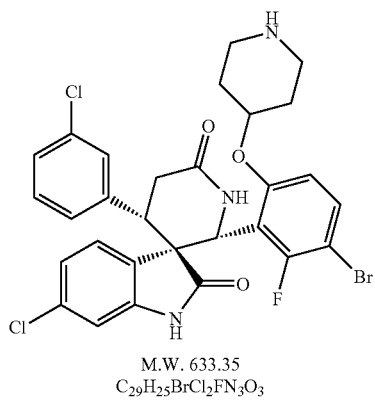

M.W. 633.35
$C_{29}H_{25}BrCl_2FN_3O_3$

In a manner similar to the method described in example 5a, racemic(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione (0.6 g, 0.818 mmol) reacted with trifluoroacetic acid in dichloromethane to give racemic(2'R,3R,4'S)-2'-[3-bromo-2-fluoro-6-(4-piperidinyloxy)-phenyl]-6-chloro-4'-(3-chlorophenyl)spiro[3H-indole-3,3'-piperidine]-2,6'(1H)-dione as a yellow solid (Yield: 0.5 g, 98%).

EXAMPLE 18b

Preparation of racemic(2'R,3R,4'S)-2'-[6-(1-acetyl-4-piperidinyloxy)-3-bromo-2-fluoro-phenyl]-6-chloro-4'-(3-chlorophenyl)spiro[3H-indole-3,3'-piperidine]-2,6'(1H)-dione

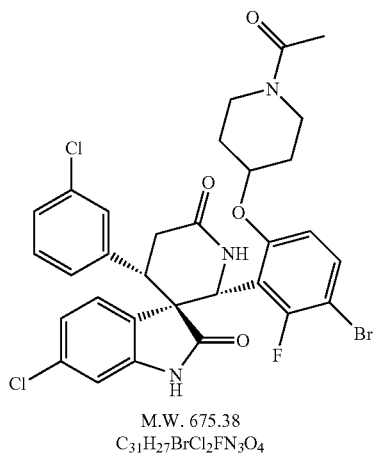

M.W. 675.38
$C_{31}H_{27}BrCl_2FN_3O_4$

In a manner similar to the method described in example 5a, racemic(2'R,3R,4'S)-2'-[3-bromo-2-fluoro-6-(4-piperidinyloxy)-phenyl]-6-chloro-4'-(3-chlorophenyl)spiro[3H-indole-3,3'-piperidine]-2,6'(1H)-dione (0.1 g, 0.158 mmol) reacted with acetyl chloride (14.9 mg, 0.189 mmol) and triethylamine in anhydrous tetrahydrofuran to give racemic (2'R,3R,4'S)-2'-[6-(1-acetyl-4-piperidinyloxy)-3-bromo-2-fluoro-phenyl]-6-chloro-4'-(3-chlorophenyl)spiro[3H-indole-3,3'-piperidine]-2,6'(1H)-dione as an off white solid (Yield 48 mg, 45%).

HRMS(ES$^+$) m/z Calcd for $C_{31}H_{27}BrCl_2FN_3O_4$+H [(M+H)$^+$]: 674.0619. Found: 674.0617.

EXAMPLE 19a

Preparation of racemic(2'R,3R,4'S)-6-chloro-4'-(3-chlorophenyl)-2'-[2-(1-ethyl-4-piperidinyloxy)-5-iodo-phenyl]spiro[3H-indole-3,3'-piperidine]-2,6'(1H)-dione

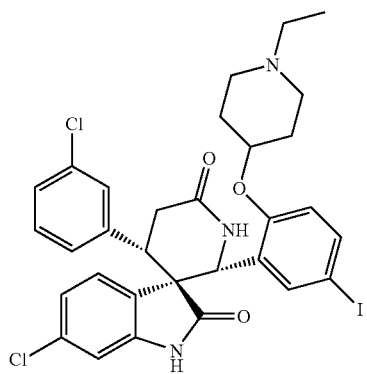

M.W. 690.41
$C_{31}H_{30}Cl_2IN_3O_3$

In a manner similar to the method described in example 7, racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.17 g, 0.257 mmol) prepared in example 5a was reacted with acetaldehyde (22 mg, 0.514 mmol) and NaCNBH$_3$ (22.5 mg, 0.39 mmol) in methanol to give racemic(2'R,3R,4'S)-6-chloro-4'-(3-chlorophenyl)-2'-[2-(1-ethyl-4-piperidinyloxy)-5-iodo-phenyl]spiro[3H-indole-3,3'-piperidine]-2,6'(1H)-dione as an off white solid (Yield 80 mg, 45%).

EXAMPLE 19b

Preparation of racemic(2'R,3R,4'S)-6-chloro-4'-(3-chlorophenyl)-2'-[2-(1-ethyl-4-piperidinyloxy)-5-ethynyl-phenyl]spiro[3H-indole-3,3'-piperidine]-2,6'(1H)-dione

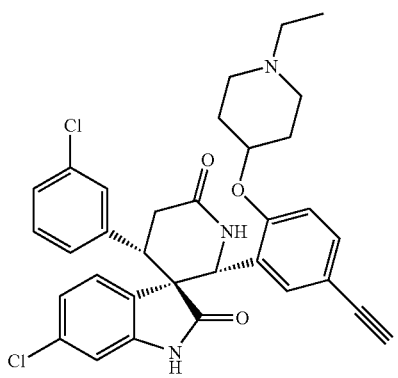

M.W. 588.53
$C_{33}H_{31}Cl_2N_3O_3$

In a manner similar to the method described in example 6a, racemic(2'R,3R,4'S)-6-chloro-4'-(3-chlorophenyl)-2'-[2-(1-ethyl-4-piperidinyloxy)-5-iodo-phenyl]spiro[3H-indole-3,3'-piperidine]-2,6'(1H)-dione (80 mg, 0.116 mmol) was reacted with trimethylsilyl acetylene (0.114 g, 1.16 mmol), CuI (5 mg), triethylamine (0.35 g, 3.46 mmol), and dichlorobis(triphenylphosphine)palladium (0) (8 mg, 0.012 mmol) in anhydrous N,N-dimethylformamide, and then treated with aqueous NaOH in methanol to give racemic(2'R,3R,4'S)-6-chloro-4'-(3-chlorophenyl)-2'-(3-ethynyl-4-fluoro-phenyl)spiro[3H-indole-3,3'-piperidine]-2,6'(1H)-dione as a off white solid (Yield 54 mg, 79%)

HRMS(ES$^+$) m/z Calcd for $C_{33}H_{31}Cl_2N_3O_3$+H [(M+H)$^+$]: 588.1815. Found: 588.1818.

EXAMPLE 20a

Preparation of racemic(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione

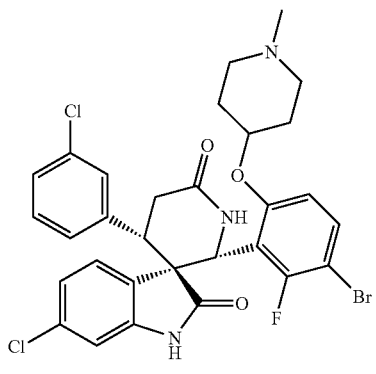

M.W. 647.37
$C_{30}H_{27}BrCl_2FN_3O_3$

In a manner similar to the method described in example 7, racemic(2'R,3R,4'S)-2'-[3-bromo-2-fluoro-6-(4-piperidinyloxy)-phenyl]-6-chloro-4'-(3-chlorophenyl)spiro[3H-indole-3,3'-piperidine]-2,6'(1H)-dione (0.12 g, 0.189 mmol) prepared in Example 18a was reacted with formaldehyde (37 wt %, Aldrich, 0.028 mL, 0.38 mmol) and NaCNBH$_3$ (18 mg, 0.28 mmol) in methanol to give racemic(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione as an off white solid (Yield 25 mg, 20%).

HRMS(ES$^+$) m/z Calcd for $C_{30}H_{27}BrCl_2FN_3O_3$+H [(M+H)$^+$]: 646.0670. Found: 646.0674.

EXAMPLE 20b

Preparation of chiral(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione

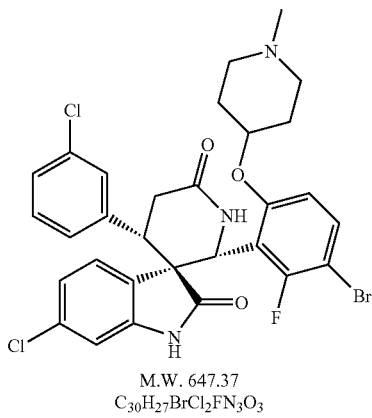

M.W. 647.37
$C_{30}H_{27}BrCl_2FN_3O_3$

Separation of the two enantiomers from racemic(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione (105 mg) was conducted by chiral SFC to provide chiral(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione as an off whitesolid (39 mg, 37%) and chiral(2'S,3S,4'R)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione as a light yellow solid (41 mg, 39%).

EXAMPLE 21a

Preparation of racemic(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione

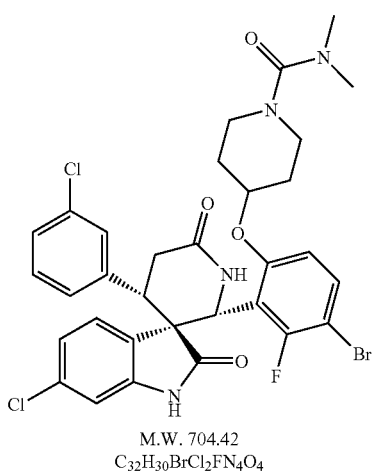

M.W. 704.42
$C_{32}H_{30}BrCl_2FN_4O_4$

In a manner similar to the method described in Example 5b, racemic(2'R,3R,4'S)-2'-[3-bromo-2-fluoro-6-(4-piperidinyloxy)-phenyl]-6-chloro-4'-(3-chlorophenyl)spiro[3H-indole-3,3'-piperidine]-2,6'(1H)-dione (42 mg, 0.066 mmol) prepared in Example 18a was reacted with dimethylcarbamyl chloride (8.54 mg, 0.079 mmol) and trimethylamine in tetrahydrofuran to give racemic(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione as an off white solid (Yield 27 mg, 58%).

HRMS(ES$^+$) m/z Calcd for $C_{32}H_{30}BrCl_2FN_4O_4$+H [(M+H)$^+$]: 703.0885. Found: 703.0882.

EXAMPLE 21b

Preparation of chiral(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione

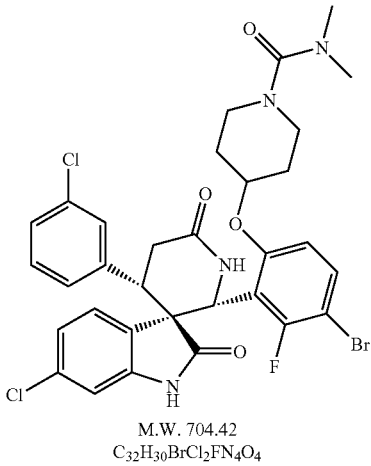

M.W. 704.42
$C_{32}H_{30}BrCl_2FN_4O_4$

Separation of the two enantiomers from racemic(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione (100 mg) was conducted by chiral SFC to provide chiral(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione as an off white solid (28 mg, 28%) and chiral(2'S,3S,4'R)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione as a light yellow solid (23 mg, 23%)

EXAMPLE 22a

Preparation of racemic(2'R,3R,4'S)-6-chloro-4'-(3-chlorophenyl)-2'-[2-(1-diethylcarbamoyl-4-piperidinyloxy)-5-iodo-phenyl]spiro[3H-indole-3,3'-piperidine]-2,6'(1H)-dione

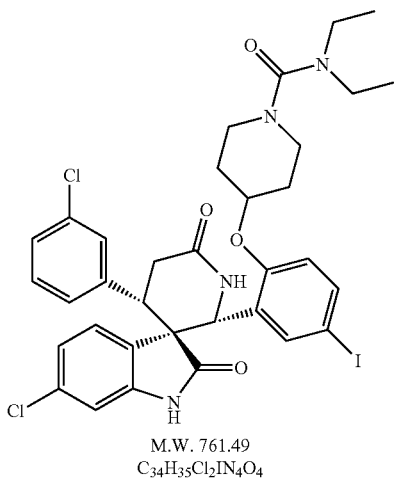

M.W. 761.49
$C_{34}H_{35}Cl_2IN_4O_4$

In a manner similar to the method described in example 5b, diethylcarbamyl chloride (24.6 mg, 0.18 mmol) as the starting material in place of acetyl chloride to react with racemic (2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a and triethylamine in tetrahydrofuran to give racemic(2'R,3R,4'S)-6-chloro-4'-(3-chlorophenyl)-2'-[2-(1-diethylcarbamoyl-4-piperidinyloxy)-5-iodo-phenyl]spiro[3H-indole-3,3'-piperidine]-2,6'(1H)-dione as a white solid (Yield 50 mg, 36%).

EXAMPLE 22b

Preparation of racemic(2'R,3R,4'S)-6-chloro-4'-(3-chlorophenyl)-2'-[2-(1-diethylcarbamoyl-4-piperidinyloxy)-5-ethynyl-phenyl]spiro[3H-indole-3,3'-piperidine]-2,6'(1H)-dione

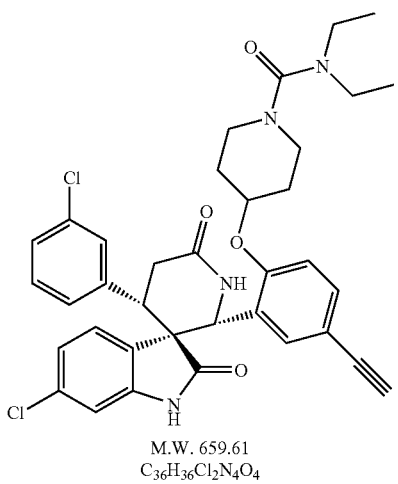

M.W. 659.61
$C_{36}H_{36}Cl_2N_4O_4$

In a manner similar to the method described in example 6a, racemic(2'R,3R,4'S)-6-chloro-4'-(3-chlorophenyl)-2'-[2-(1-diethylcarbamoyl-4-piperidinyloxy)-5-iodo-phenyl]spiro[3H-indole-3,3'-piperidine]-2,6'(1H)-dione (50 mg, 0.066 mmol) was reacted with trimethylsilyl acetylene (64.7 mg, 0.66 mmol), CuI (5 mg), triethylamine (0.2 g, 1.97 mmol), and dichlorobis(triphenylphosphine)palladium (0) (4.56 mg, 0.0066 mmol) in anhydrous N,N-dimethylformamide, and then treated with aqueous NaOH in methanol to give racemic (2'R,3R,4'S)-6-chloro-4'-(3-chlorophenyl)-2'-[2-(1-diethylcarbamoyl-4-piperidinyloxy)-5-ethynyl-phenyl]spiro[3H-indole-3,3'-piperidine]-2,6'(1H)-dione as a yellow solid (Yield 36 mg, 83%)

HRMS(ES$^+$) m/z Calcd for $C_{36}H_{36}Cl_2N_4O_4$+H [(M+H)$^+$]: 659.2187. Found: 659.2192.

EXAMPLE 23a

Preparation of racemic(2'R,3R,4'S)-6-chloro-4'-(3-chlorophenyl)-2'-{5-iodo-2-[1-(pyrrolidine-1-carbonyl)-4-piperidinyloxy]-phenyl}spiro[3H-indole-3,3'-piperidine]-2,6'(1H)-dione

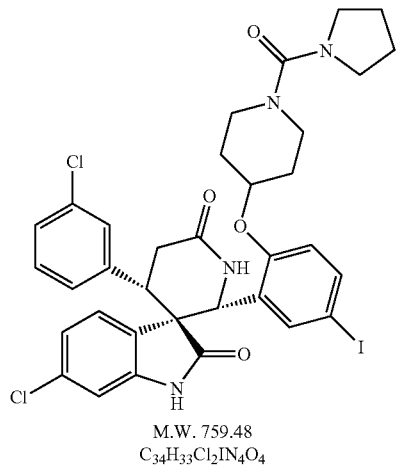

M.W. 759.48
$C_{34}H_{33}Cl_2IN_4O_4$

In a manner similar to the method described in example 5b, 1-pyrrolidinecarbonyl chloride (24.2 mg, 0.18 mmol) as the starting material in place of acetyl chloride to react with racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a and triethylamine in tetrahydrofuran to give racemic(2'R,3R,4'S)-6-chloro-4'-(3-chlorophenyl)-2'-{5-iodo-2-[1-(pyrrolidine-1-carbonyl)-4-piperidinyloxy]-phenyl}spiro[3H-indole-3,3'-piperidine]-2,6'(1H)-dione as a white solid (Yield 90 mg, 82%).

HRMS(ES$^+$) m/z Calcd for $C_{34}H_{33}Cl_2IN_4O_4$+H [(M+H)$^+$]: 759.0997. Found: 759.1002.

EXAMPLE 23b

Preparation of racemic(2'R,3R,4'S)-6-chloro-4'-(3-chlorophenyl)-2'-{5-ethynyl-2-[1-(pyrrolidine-1-carbonyl)-4-piperidinyloxy]-phenyl}spiro[3H-indole-3,3'-piperidine]-2,6'(1H)-dione

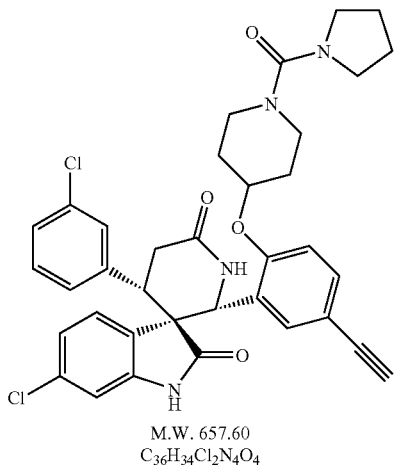

M.W. 657.60
$C_{36}H_{34}Cl_2N_4O_4$

In a manner similar to the method described in example 6a, racemic(2'R,3R,4'S)-6-chloro-4'-(3-chlorophenyl)-2'-{5-iodo-2-[1-(pyrrolidine-1-carbonyl)-4-piperidinyloxy]-phenyl}spiro[3H-indole-3,3'-piperidine]-2,6'(1H)-dione (90 mg, 0.118 mmol) was reacted with trimethylsilyl acetylene (0.117 g, 1.18 mmol), CuI (5 mg), triethylamine (0.36 g, 3.55 mmol), and dichlorobis(triphenylphosphine)palladium (0) (8.3 mg, 0.012 mmol) in anhydrous N,N-dimethylformamide, and then treated with aqueous NaOH in methanol to give racemic(2'R,3R,4'S)-6-chloro-4'-(3-chlorophenyl)-2'-{5-ethynyl-2-[1-(pyrrolidine-1-carbonyl)-4-piperidinyloxy]-phenyl}spiro[3H-indole-3,3'-piperidine]-2,6'(1H)-dione as a white white solid (Yield 8 mg, 10%)

HRMS(ES$^+$) m/z Calcd for $C_{36}H_{34}Cl_2N_4O_4$+H [(M+H)$^+$]: 657.2030. Found: 657.2034.

EXAMPLE 24a

Preparation of racemic(2'R,3R,4'S)-6-chloro-4'-(3-chlorophenyl)-2'-[5-iodo-2-(1-isopropyl-4-piperidinyloxy)-phenyl]spiro[3H-indole-3,3'-piperidine]-2,6'(1H)-dione

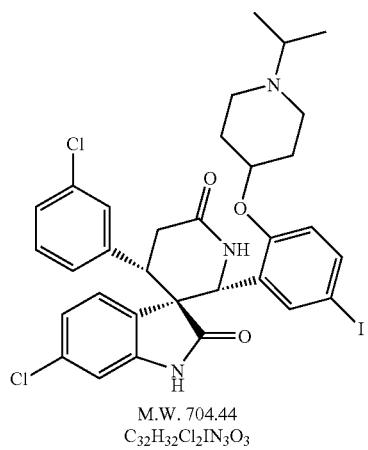

M.W. 704.44
$C_{32}H_{32}Cl_2IN_3O_3$

To a solution of racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in example 5a in N,N-dimethyformamide (2 mL) was added triethylamine (30.5 mg, 0.3 mmol) and 2-iodopropane (77 mg, 0.45 mmol). The reaction mixture was heated at 75° C. for 24 h. The mixture was cooled to room temperature, diluted with ethyl acetate, washed with water. The organic layer was separated, and aqueous layer was extracted with ethyl acetate. The organic layers were combined, washed with brine, dried over MgSO$_4$, concentrated to give crude racemic(2'R,3R,4'S)-6-chloro-4'-(3-chlorophenyl)-2'-[5-iodo-2-(1-isopropyl-4-piperidinyloxy)-phenyl]spiro[3H-indole-3,3'-piperidine]-2,6'(1H)-dione as a light yellow solid (Yield 80 mg, 73%).

EXAMPLE 24b

Preparation of racemic(2'R,3R,4'S)-6-chloro-4'-(3-chlorophenyl)-2'-[5-ethynyl-2-(1-isopropyl-4-piperidinyloxy)-phenyl]spiro[3H-indole-3,3'-piperidine]-2,6'(1H)-dione

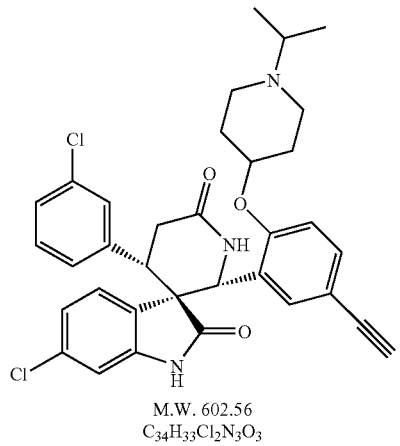

M.W. 602.56
$C_{34}H_{33}Cl_2N_3O_3$

In a manner similar to the method described in example 6a, racemic(2'R,3R,4'S)-6-chloro-4'-(3-chlorophenyl)-2'-[5-iodo-2-(1-isopropyl-4-piperidinyloxy)-phenyl]spiro[3H-indole-3,3'-piperidine]-2,6'(1H)-dione (80 mg, 0.11 mmol) was reacted with trimethylsilyl acetylene (0.11 g, 1.1 mmol), CuI (5 mg), triethylamine (0.34 g, 3.3 mmol), and dichlorobis (triphenylphosphine)palladium (0) (8 mg, 0.012 mmol) in anhydrous N,N-dimethylformamide, and then treated with aqueous NaOH in methanol to give racemic(2'R,3R,4'S)-6-chloro-4'-(3-chlorophenyl)-2'-[5-ethynyl-2-(1-isopropyl-4-piperidinyloxy)-phenyl]spiro[3H-indole-3,3'-piperidine]-2,6'(1H)-dione as an off white solid (Yield 10 mg, 15%)

HRMS(ES$^+$) m/z Calcd for $C_{34}H_{33}Cl_2N_3O_3$+H [(M+H)$^+$]: 602.1972. Found: 602.1977.

EXAMPLE 25a

Preparation of racemic(2'R,3R,4'S)-6-chloro-4'-(3-chlorophenyl)-2'-{5-iodo-2-[1-(2-oxo-imidazolidine-1-carbonyl)-4-piperidinyloxy]-phenyl}spiro[3H-indole-3,3'-piperidine]-2,6'(1H)-dione

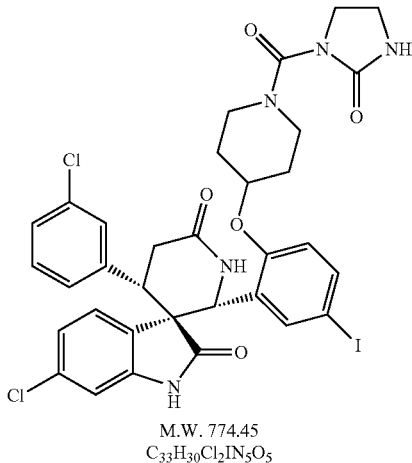

M.W. 774.45
$C_{33}H_{30}Cl_2IN_5O_5$

In a manner similar to the method described in example 5b, 1-chlorocarbonyl-2-imidazolidinone (40.4 mg, 0.27 mmol) (Aldrich) as the starting material in place of acetyl chloride to react with racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.15 g, 0.23 mmol) prepared in Example 5a and triethylamine in tetrahydrofuran to give racemic(2'R,3R,4'S)-6-chloro-4'-(3-chlorophenyl)-2'-{5-iodo-2-[1-(2-oxo-imidazolidine-1-carbonyl)-4-piperidinyloxy]-phenyl}spiro[3H-indole-3,3'-piperidine]-2,6'(1H)-dione as a white solid (Yield 0.12 g, 71%).

EXAMPLE 25b

Preparation of racemic(2'R,3R,4'S)-6-chloro-4'-(3-chlorophenyl)-2'-{5-ethynyl-2-[1-(2-oxo-imidazolidine-1-carbonyl)-4-piperidinyloxy]-phenyl}spiro[3H-indole-3,3'-piperidine]-2,6'(1H)-dione

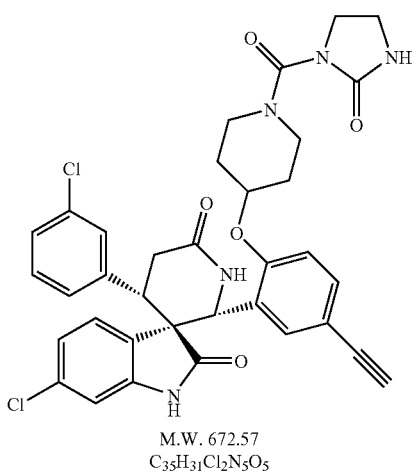

M.W. 672.57
$C_{35}H_{31}Cl_2N_5O_5$

In a manner similar to the method described in example 6a, racemic(2'R,3R,4'S)-6-chloro-4'-(3-chlorophenyl)-2'-{5-iodo-2-[1-(2-oxo-imidazolidine-1-carbonyl)-4-piperidinyloxy]-phenyl}spiro[3H-indole-3,3'-piperidine]-2,6'(1H)-dione (0.12 g, 0.15 mmol) was reacted with trimethylsilyl acetylene (0.15 g, 1.55 mmol), CuI (5 mg), triethylamine (0.47 g, 4.65 mmol), and dichlorobis(triphenylphosphine) palladium (0) (11 mg, 0.016 mmol) in anhydrous N,N-dimethylformamide, and then treated with aqueous NaOH in methanol to give racemic(2'R,3R,4'S)-6-chloro-4'-(3-chlorophenyl)-2'-{5-ethynyl-2-[1-(2-oxo-imidazolidine-1-carbonyl)-4-piperidinyloxy]-phenyl}spiro[3H-indole-3,3'-piperidine]-2,6'(1H)-dione as an off white solid (Yield 25 mg, 25%)

HRMS(ES$^+$) m/z Calcd for $C_{35}H_{31}Cl_2N_5O_5$+H [(M+H)$^+$]: 672.1775. Found: 672.1774.

EXAMPLE 26a

Preparation of intermediate 3-chloro-2-fluoro-6-methoxy-benzaldehyde

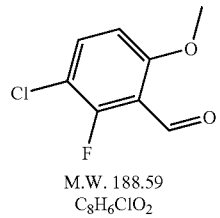

M.W. 188.59
$C_8H_6ClO_2$

To a solution of 4-chloro-3-fluoroanisole (10.2 g, 63.5 mmol, Oakwood) in tetrahydrofuran (100 mL) at -78° C. was added lithium diisopropyl amine (42.3 mL, 1.8 M in THF, 76.2 mmol) dropwise during a period of 15 min. The mixture was stirred at -78° C. for another 20 mins. Then N,N-dimethyl-formamide (5.9 mL, 76.2 mmol) was added in one portion. The mixture was stirred at -78° C. for 10 min, then quenched with acetic acid (15.6 g, 254 mmol) and followed by the addition of water (80 mL). The mixture was partitioned between ethyl acetate and water. The organic layer was separated, concentrated to give 3-chloro-2-fluoro-6-methoxy-benzaldehyde as a yellow solid (Yield: 10 g, 85%)

EXAMPLE 25b

Preparation of intermediate 3-chloro-2-fluoro-6-hydroxy-benzaldehyde

M.W. 174.56
$C_7H_4ClFO_2$

To a solution of 3-chloro-2-fluoro-6-methoxy-benzaldehyde (10 g, 53.2 mmol,) in dichloromethane (200 mL) at −78° C. was added a dichloromethane solution (1 M) of $BBr_3$ (159 mL, 159 mmol) dropwise. The mixture was gradually warmed to room temperature and stirred for 1 h, then quenched with water. The mixture was extracted with dichloromethane three times. The organic layer were combined, washed with brine, dried over $MgSO_4$, concentrated to give a residue. The reside was triturated with dichloromethane and hexanes to afford 3-chloro-2-fluoro-6-hydroxy-benzaldehyde as a brown solid (Yield: 2.07 g, 22%)

EXAMPLE 25c

Preparation of intermediate 4-(4-chloro-3-fluoro-2-formyl-phenoxy)-piperidine-1-carboxylic acid tert-butyl ester

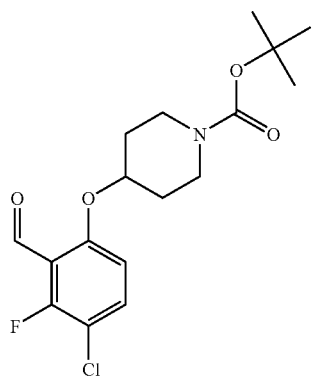

M.W. 357.81
$C_{17}H_{21}ClFNO_4$

In a manner similar to the method described in example 4a, 3-chloro-2-fluoro-6-hydroxy-benzaldehyde (2.07 g, 11.8 mmol) reacted with 4-(toluene-4-sulfonyloxy)-piperidine-1-carboxylic acid tert-butyl ester (3.51 g, 9.88 mmol, ASTATECH) and $K_2CO_3$ in N,N-dimethylformamide to give 4-(4-chloro-3-fluoro-2-formyl-phenoxy)-piperidine-1-carboxylic acid tert-butyl ester as a brown oil (Yield 3.75 g, 84%).

EXAMPLE 25d

Preparation of intermediate 1-[6-(1-(tert-butoxycarbonyl)-4-piperidinyloxy)-3-chloro-2-fluoro-phenyl]-3-trimethylsilyoxy-2-aza-1,3-butadiene

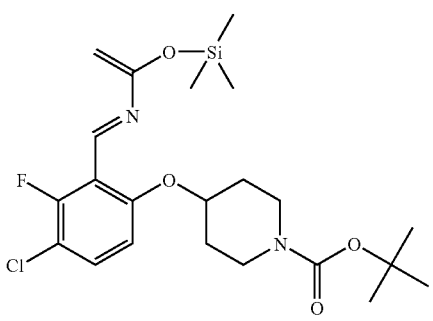

M.W. 471.05
$C_{22}H_{32}ClFN_2O_4Si$

In a manner similar to the method described in example 1d, 4-(4-chloro-3-fluoro-2-formyl-phenoxy)-piperidine-1-carboxylic acid tert-butyl ester (3.75 g, 10.5 mmol) was used as the starting material in place of 4-(2-formyl-4-iodo-phenoxymethyl)-piperidine-1-carboxylic acid tert-butyl ester to react with 1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give crude 1-[6-(1-(tert-butoxycarbonyl)-4-piperidinyloxy)-3-chloro-2-fluoro-phenyl]-3-trimethylsilyoxy-2-aza-1,3-butadiene as a yellow gum and used for the next step without further purification.

EXAMPLE 25e

Preparation of racemic(2'R,3R,4'S)-2'-[6-(1-(tert-butoxycarbonyl)-4-piperidinyloxy)-3-chloro-2-fluoro-phenyl]-6-chloro-4'-(3-chlorophenyl)spiro[3H-indole-3,3'-piperidine]-2,6'(1H)-dione

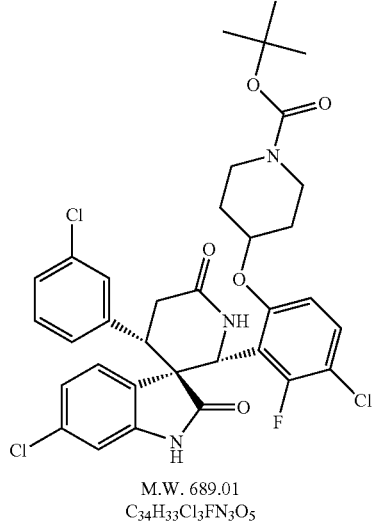

M.W. 689.01
$C_{34}H_{33}Cl_3FN_3O_5$

In a manner similar to the method described in example 1e, E/Z-6-chloro-3-(3-chloro-benzylidene)-2-oxo-2,3-dihydro-indole-1-carboxylic acid tert-butyl ester prepared in example 5b (1.63 g, 4.2 mmol) was reacted with 1-[6-(1-(tert-butoxycarbonyl)-4-piperidinyloxy)-3-chloro-2-fluoro-phenyl]-3-trimethylsilyoxy-2-aza-1,3-butadiene (10.5 mmol) in toluene (50 mL) at 140° C. for 6 h to give racemic(2'R,3R,4'S)-2'-[6-(1-(tert-butoxycarbonyl)-4-piperidinyloxy)-3-chloro-2-fluoro-phenyl]-6-chloro-4'-(3-chlorophenyl)spiro[3H-indole-3,3'-piperidine]-2,6'(1H)-dione as a light yellow solid (Yield 1.13 g, 39%)

HRMS(ES$^+$) m/z Calcd for C$_{34}$H$_{33}$Cl$_3$FN$_3$O$_5$+H [(M+H)$^+$]: 688.1543. Found: 688.1541.

EXAMPLE 26a

Preparation of intermediate racemic(2'R,3R,4'S)-6-chloro-2'-[3-chloro-2-fluoro-6-(4-piperidinyloxy)-phenyl]-4'-(3-chlorophenyl)spiro[3H-indole-3,3'-piperidine]-2,6'(1H)-dione

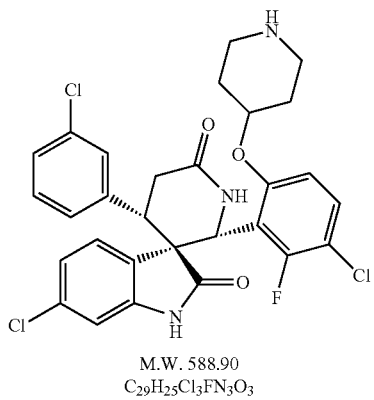

M.W. 588.90
C$_{29}$H$_{25}$Cl$_3$FN$_3$O$_3$

In a manner similar to the method described in example 5a, racemic(2'R,3R,4'S)-2'-[6-(1-(tert-butoxycarbonyl)-4-piperidinyloxy)-3-chloro-2-fluoro-phenyl]-6-chloro-4'-(3-chlorophenyl)spiro[3H-indole-3,3'-piperidine]-2,6'(1H)-dione (1.0 g, 1.45 mmol) reacted with trifluoroacetic acid in dichloromethane to give racemic(2'R,3R,4'S)-6-chloro-2'-[3-chloro-2-fluoro-6-(4-piperidinyloxy)-phenyl]-4'-(3-chlorophenyl)spiro[3H-indole-3,3'-piperidine]-2,6'(1H)-dione as a yellow solid (Yield: 0.85 g, 100%).

EXAMPLE 26b

Preparation of racemic(2'R,3R,4'S)-2'-[6-(1-acetyl-4-piperidinyloxy)-3-chloro-2-fluoro-phenyl]-6-chloro-4'-(3-chlorophenyl)spiro[3H-indole-3,3'-piperidine]-2,6'(1H)-dione

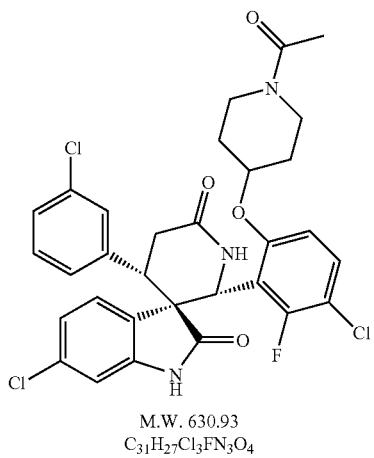

M.W. 630.93
C$_{31}$H$_{27}$Cl$_3$FN$_3$O$_4$

In a manner similar to the method described in example 5a, racemic(2'R,3R,4'S)-6-chloro-2'-[3-chloro-2-fluoro-6-(4-piperidinyloxy)-phenyl]-4'-(3-chlorophenyl)spiro[3H-indole-3,3'-piperidine]-2,6'(1H)-dione (72.5 mg, 0.123 mmol) reacted with acetyl chloride (11.6 mg, 0.148 mmol) and triethylamine in anhydrous tetrahydrofuran to give racemic(2'R,3R,4'S)-2'-[6-(1-acetyl-4-piperidinyloxy)-3-chloro-2-fluoro-phenyl]-6-chloro-4'-(3-chlorophenyl)spiro[3H-indole-3,3'-piperidine]-2,6'(1H)-dione as an off white solid (Yield 30 mg, 39%).

HRMS(ES$^+$) m/z Calcd for C$_{31}$H$_{27}$Cl$_3$FN$_3$O$_4$+H [(M+H)$^+$]: 630.1124. Found: 630.1128.

EXAMPLE 27

Preparation of racemic(2'R,3R,4'S)-6-chloro-2'-[3-chloro-6-(1-dimethylcarbamoyl-4-piperidinyloxy)-2-fluoro-phenyl]-4'-(3-chlorophenyl)spiro[3H-indole-3,3'-piperidine]-2,6'(1H)-dione

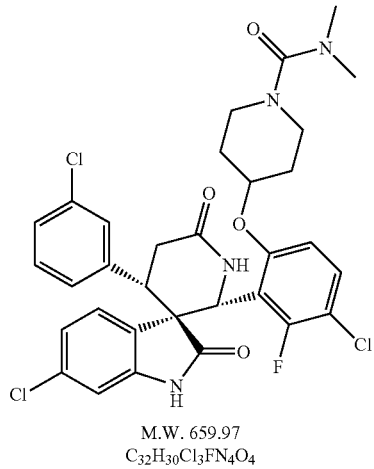

M.W. 659.97
C$_{32}$H$_{30}$Cl$_3$FN$_4$O$_4$

In a manner similar to the method described in Example 5b, racemic(2'R,3R,4'S)-6-chloro-2'-[3-chloro-2-fluoro-6-(4-piperidinyloxy)-phenyl]-4'-(3-chlorophenyl)spiro[3H-indole-3,3'-piperidine]-2,6'(1H)-dione (87.7 mg, 0.149 mmol) prepared in Example 26a was reacted with dimethylcarbamyl chloride (19.2 mg, 0.178 mmol) and trimethylamine in tetrahydrofuran to give racemic(2'R,3R,4'S)-6-chloro-2'-[3-chloro-6-(1-dimethylcarbamoyl-4-piperidinyloxy)-2-fluoro-phenyl]-4'-(3-chlorophenyl)spiro[3H-indole-3,3'-piperidine]-2,6'(1H)-dione as an off white solid (Yield 51 mg, 52%).

HRMS(ES$^+$) m/z Calcd for C$_{32}$H$_{30}$Cl$_3$FN$_4$O$_4$+H [(M+H)$^+$]: 659.1390. Found: 659.1392.

EXAMPLE 28

Preparation of racemic(2'R,3R,4'S)-6-chloro-2'-[3-chloro-6-(1-methylcarbamoyl-4-piperidinyloxy)-2-fluoro-phenyl]-4'-(3-chlorophenyl)spiro[3H-indole-3,3'-piperidine]-2,6'(1H)-dione

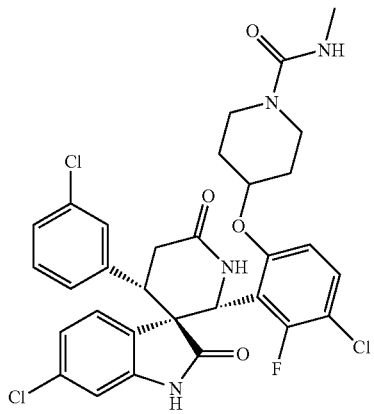

M.W. 645.94
$C_{32}H_{28}Cl_3FN_4O_4$

To a solution of racemic(2'R,3R,4'S)-6-chloro-2'-[3-chloro-2-fluoro-6-(4-piperidinyloxy)-phenyl]-4'-(3-chlorophenyl)spiro[3H-indole-3,3'-piperidine]-2,6'(1H)-dione (0.1 g, 0.17 mmol) prepared in Example 26a in dichloromethane (2 mL) was added triethylamine (34.3 mg, 0.34 mmol) and methy isocyanate (11.6 mg, 0.2 mmol). The reaction mixture was stirred at room temperature for 0.5 h. The mixture was diluted with dichloromethane, washed with water and brine, dried over MgSO$_4$, filtered and concentrated. The residue was tritruated with dichloromethane and hexanes to give racemic(2'R,3R,4'S)-6-chloro-2'-[3-chloro-6-(1-methylcarbamoyl-4-piperidinyloxy)-2-fluoro-phenyl]-4'-(3-chlorophenyl)spiro[3H-indole-3,3'-piperidine]-2,6'(1H)-dione as a light yellow solid (Yield 23 mg, 21%).

HRMS(ES$^+$) m/z Calcd for $C_{32}H_{28}Cl_3FN_4O_4$+H [(M+H)$^+$]: 645.1233. Found: 645.1232.

EXAMPLE 29

Preparation of racemic(2'R,3R,4'S)-2'-[3-bromo-6-(1-methylcarbamoyl-4-piperidinyloxy)-2-fluoro-phenyl]-6-chloro-4'-(3-chlorophenyl)spiro[3H-indole-3,3'-piperidine]-2,6'(1H)-dione

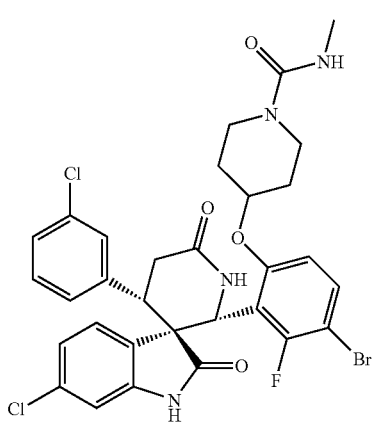

M.W. 690.39
$C_{32}H_{28}BrCl_2FN_4O_4$

In a manner similar to the method described in Example 28, racemic(2'R,3R,4'S)-2'-[3-bromo-2-fluoro-6-(4-piperidinyloxy)-phenyl]-6-chloro-4'-(3-chlorophenyl)spiro[3H-indole-3,3'-piperidine]-2,6'(1H)-dione (40 mg, 0.063 mmol) prepared in Example 18a was reacted with triethylamine and methy isocyanate (4.3 mg, 0.076 mmol) to give racemic(2'R,3R,4'S)-2'-[3-bromo-6-(1-methylcarbamoyl-4-piperidinyloxy)-2-fluoro-phenyl]-6-chloro-4'-(3-chlorophenyl)spiro[3H-indole-3,3'-piperidine]-2,6'(1H)-dione as a light yellow solid (Yield 37 mg, 85%).

HRMS(ES$^+$) m/z Calcd for $C_{32}H_{28}BrCl_2FN_4O_4$+H [(M+H)$^+$]: 689.0728. Found: 689.0732.

EXAMPLE 30

Preparation of racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H)-dione

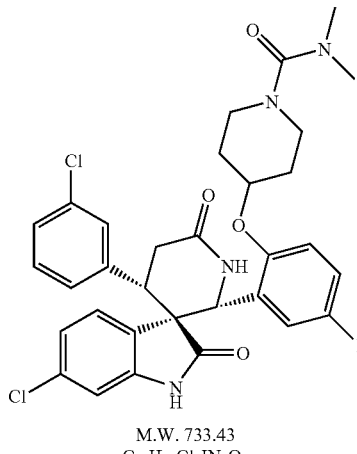

M.W. 733.43
$C_{32}H_{31}Cl_2IN_4O_4$

In a manner similar to the method described in Example 5b, racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a was reacted with dimethylcarbamyl chloride (19.5 mg, 0.18 mmol) and trimethylamine in tetrahydrofuran to give racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H)-dione as an off white solid (Yield 75 mg, 68%).

HRMS(ES⁺) m/z Calcd for $C_{32}H_{31}Cl_2IN_4O_4$+H [(M+H)⁺]: 733.0840. Found: 733.0841.

EXAMPLE 31a

Preparation of racemic(2'R,3R,4'S)-6-chloro-4'-(3-chlorophenyl)-2'-{5-iodo-2-[1-(4-methylpiperazine-1-carbonyl)-4-piperidinyloxy]-phenyl}spiro[3H-indole-3,3'-piperidine]-2,6'(1H)-dione

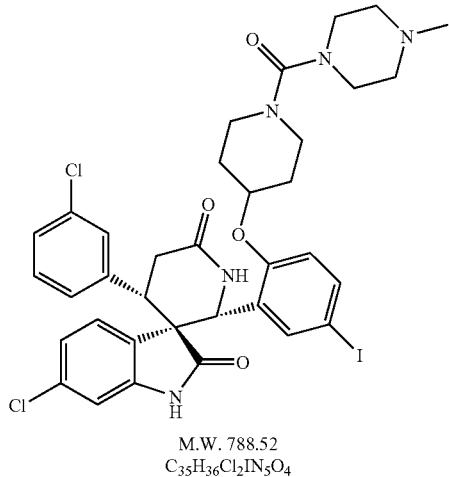

M.W. 788.52
$C_{35}H_{36}Cl_2IN_5O_4$

In a manner similar to the method described in Example 5b, racemic(2'R,3R,4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.15 g, 0.23 mmol) prepared in Example 5a was reacted with 4-methylpiperazine-1-carbonyl chloride (44.5 mg, 0.27 mmol) and trimethylamine in tetrahydrofuran to give racemic(2'R,3R,4'S)-6-chloro-4'-(3-chlorophenyl)-2'-{5-iodo-2-[1-(4-methylpiperazine-1-carbonyl)-4-piperidinyloxy]-phenyl}spiro[3H-indole-3,3'-piperidine]-2,6'(1H)-dione as a yellow gum (Yield 0.19 g, 99%).

EXAMPLE 31b

Preparation of racemic(2'R,3R,4'S)-6-chloro-4'-(3-chlorophenyl)-2'-{5-ethynyl-2-[1-(4-methylpiperazine-1-carbonyl)-4-piperidinyloxy]-phenyl}spiro[3H-indole-3,3'-piperidine]-2,6'(1H)-dione

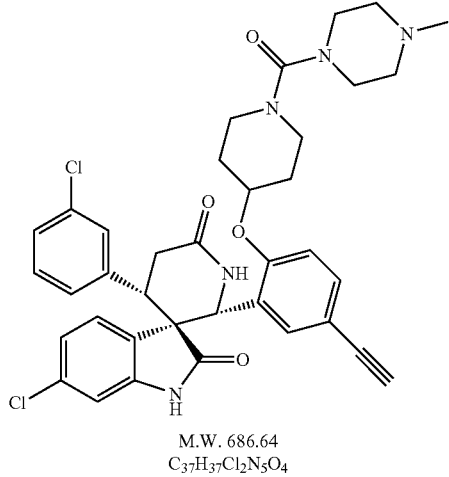

M.W. 686.64
$C_{37}H_{37}Cl_2N_5O_4$

In a manner similar to the method described in example 6a, racemic(2'R,3R,4'S)-6-chloro-4'-(3-chlorophenyl)-2'-{5-iodo-2-[1-(4-methylpiperazine-1-carbonyl)-4-piperidinyloxy]-phenyl}spiro[3H-indole-3,3'-piperidine]-2,6'(1H)-dione (0.18 g 0.23 mmol) was reacted with trimethylsilyl acetylene (0.23 g, 2.28 mmol), CuI (5 mg), triethylamine (0.69 g, 6.8 mmol), and dichlorobis(triphenylphosphine)palladium (0) (16 mg, 0.023 mmol) in anhydrous N,N-dimethylformamide, and then treated with aqueous NaOH in methanol to give racemic(2'R,3R,4'S)-6-chloro-4'-(3-chlorophenyl)-2'-{5-ethynyl-2-[1-(4-methylpiperazine-1-carbonyl)-4-piperidinyloxy]-phenyl}spiro[3H-indole-3,3'-piperidine]-2,6'(1H)-dione as a brown solid (Yield 0.12 g, 71%)

HRMS(ES⁺) m/z Calcd for $C_{37}H_{37}Cl_2N_5O_4$+H [(M+H)⁺]: 686.2296. Found: 686.2295.

EXAMPLE 32a

Preparation of intermediate methanesulfonic acid tetrahydropyran-4-yl ester

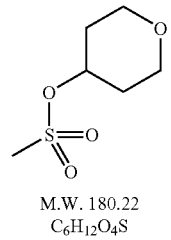

M.W. 180.22
$C_6H_{12}O_4S$

To a solution of 4-hydroxytetrahydropyran (4.5 g, 44 mmol) (Aldrich) in dichloromethane (90 mL) at 0° C. was added triethylamine (5.4 g, 53 mmol), and methanesulfonyl chloride (3.73 mL, 48 mmol, Aldrich). The reaction mixture was stirred at 0° C. for 1 h, then at room temperature for 1.5 h. The mixture was poured into water, extracted with dichloromethane. The organic layer was separated, washed with water, brine, dried over MgSO₄, and concentrated to give crude methanesulfonic acid tetrahydropyran-4-yl ester as a white solid (Yield 8 g, 100%).

Similar transformation has been described by Suto, M. J. et al in *J. Med. Chem,* 1991, 2484.

EXAMPLE 32b

Preparation of intermediate 5-Iodo-2-(tetrahydro-pyran-4-yloxy)-benzaldehyde

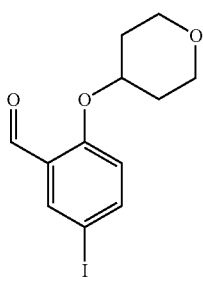

M.W. 332.14
$C_{12}H_{13}IO_3$

In a manner similar to the method described in example 4a, 5-iodosalicylaldehyde (3 g, 12.1 mmol) (Aldrich) reacted with methanesulfonic acid tetrahydropyran-4-yl ester (4 g, 22 mmol) and K$_2$CO$_3$ in N,N-dimethylformamide to give 5-Iodo-2-(tetrahydro-pyran-4-yloxy)-benzaldehyde as a yellow solid (Yield 3.4 g, 85%).

EXAMPLE 32c

Preparation of intermediate 1-[5-Iodo-2-(tetrahydro-pyran-4-yloxy)-phenyl]-3-trimethylsilyoxy-2-aza-1,3-butadiene

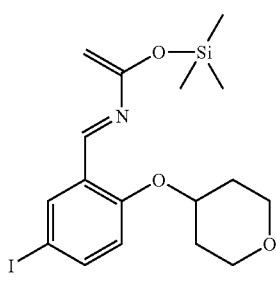

M.W. 445.38
C$_{17}$H$_{24}$INO$_3$Si

In a manner similar to the method described in example 1d, 5-Iodo-2-(tetrahydro-pyran-4-yloxy)-benzaldehyde (3.3 g, 10 mmol) was used as the starting material in place of 4-(2-formyl-4-iodo-phenoxymethyl)-piperidine-1-carboxylic acid tert-butyl ester to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1 g, 13.6 mmol) to give crude 1-[5-Iodo-2-(tetrahydro-pyran-4-yloxy)-phenyl]-3-trimethylsilyoxy-2-aza-1,3-butadiene as a yellow gum and used for the next step without further purification.

EXAMPLE 32d

Preparation of racemic(2'R,3R,4'S)-6-chloro-4'-(3-chlorophenyl)-2'-[5-Iodo-2-(tetrahydro-pyran-4-yloxy)-phenyl]spiro[3H-indole-3,3'-piperidine]-2,6'(1H)-dione

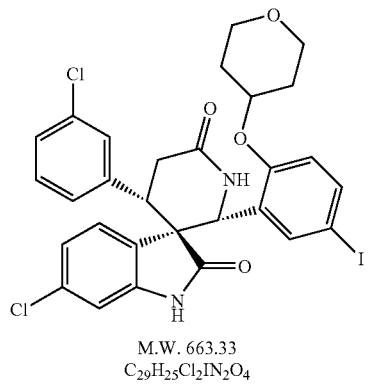

M.W. 663.33
C$_{29}$H$_{25}$Cl$_2$IN$_2$O$_4$

E/Z-6-chloro-3-(3-chloro-benzylidene)-2-oxo-2,3-dihydro-indole-1-carboxylic acid tert-butyl ester prepared in example 5b (1.2 g, 3 mmol) was added to the solution of 1-[5-Iodo-2-(tetrahydro-pyran-4-yloxy)-phenyl]-3-trimethylsilyoxy-2-aza-1,3-butadiene (10 mmol) in toluene (30 mL). The reaction mixture was heated under nitrogen at 140° C. for 2 h. The mixture was cooled to room temperature, concentrated. The residue was diluted with dichloromethane (10 mL), followed by the addition of trifuloroacetic acid (5 mL). The reaction mixture was stirred at room temperature for 1 h, then concentrated. The residue was neutralized to "pH" 7 by aqueous NaHCO$_3$ solution. The mixture was then extracted with ethyl acetate. The organic layer was separated, washed with brine, dried over MgSO$_4$, and concentrated. The residue was purified by chromatography (EtOAc:CH$_2$Cl$_2$=1:1) to give racemic(2'R,3R,4'S)-6-chloro-4'-(3chlorophenyl)-2'-[5-Iodo-2-(tetrahydro-pyran-4-yloxy)-phenyl]spiro[3H-indole-3,3'-piperidine]-2,6'(1H)-dione as a yellow solid (Yield 1.5 g, 75%)

HRMS(ES$^+$) m/z Calcd for C$_{29}$H$_{25}$Cl$_2$IN$_2$O$_4$+H [(M+H)$^+$]: 663.0309. Found: 663.0309

EXAMPLE 33a

Preparation of racemic(2'R,3R,4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione

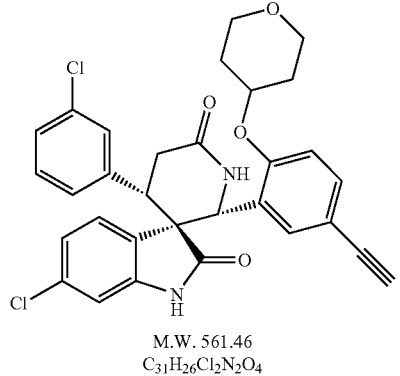

M.W. 561.46
C$_{31}$H$_{26}$Cl$_2$N$_2$O$_4$

In a manner similar to the method described in Example 2, racemic(2'R, 3R, 4'S)-6-chloro-4'-(3-chlorophenyl)-2'-[5-Iodo-2-(tetrahydro-pyran-4-yloxy)-phenyl]spiro[3H-indole-3,3'-piperidine]-2,6'(1H)-dione (1.3 g, 1.97 mmol) was reacted with trimethylsilyl acetylene (0.4 g, 3.94 mmol), CuI (0.75 g, 3.94 mmol), triethylamine (0.4 mL, 3.94 mmol) and dichlorobis(triphenylphosphine) palladium(0) (0.28 g, 0.39 mmol), then treated with aqueous NaOH solution in methanol to give racemic(2'R, 3R, 4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione as an off white solid (Yield 0.62 g, 56%).

HRMS(ES$^+$) m/z Calcd for C$_{31}$H$_{26}$Cl$_2$N$_2$O$_4$+H [(M+H)$^+$]: 561.1343. Found: 561.1342.

EXAMPLE 33b

Preparation of chiral(2'R, 3R, 4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione

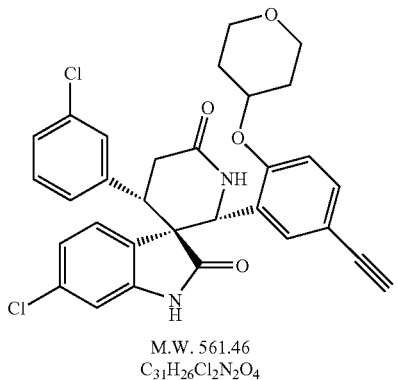

M.W. 561.46
$C_{31}H_{26}Cl_2N_2O_4$

Separation of the two enantiomers from racemic(2'R, 3R, 4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione (0.6 g) was conducted by chiral SFC to provide chiral(2'R, 3R, 4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione as an off white solid (0.177 g, 30%) and chiral(2'S, 3S, 4'R)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione as an off white solid (0.176 g, 29%).

EXAMPLE 34a

Preparation of intermediate 5-bromo-2-(tetrahydro-pyran-4-yloxy)-benzaldehyde

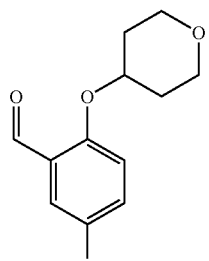

M.W. 285.14
$C_{12}H_{13}BrO_3$

In a manner similar to the method described in example 4a, 5-bromosalicylaldehyde (3 g, 15 mmol) (Aldrich) reacted with methanesulfonic acid tetrahydropyran-4-yl ester (4 g, 22 mmol) prepared in Example 32a and $K_2CO_3$ in N,N-dimethylformamide to give 5-bromo-2-(tetrahydro-pyran-4-yloxy)-benzaldehyde as a yellow solid (Yield 2.86 g, 67%).

EXAMPLE 34b

Preparation of intermediate 1-[5-bromo-2-(tetrahydro-pyran-4-yloxy)-phenyl]-3-trimethylsilyoxy-2-aza-1,3-butadiene

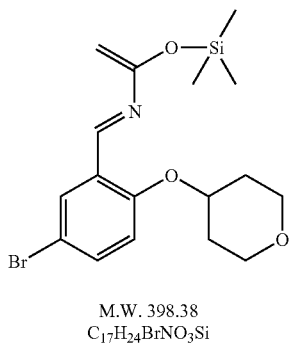

M.W. 398.38
$C_{17}H_{24}BrNO_3Si$

In a manner similar to the method described in example Id, 5-bromo-2-(tetrahydro-pyran-4-yloxy)-benzaldehyde (2.86 g, 10 mmol) was used as the starting material in place of 4-(2-formyl-4-iodo-phenoxymethyl)-piperidine-1-carboxylic acid tert-butyl ester to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1 g, 13.6 mmol) to give crude 1-[5-Iodo-2-(tetrahydro-pyran-4-yloxy)-phenyl]-3-trimethylsilyoxy-2-aza-1,3-butadiene as a yellow gum and used for the next step without further purification.

EXAMPLE 34c

Preparation of racemic(2'R, 3R, 4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione

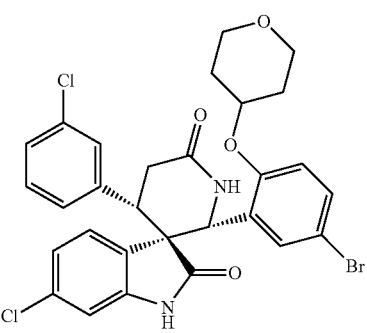

M.W. 616.34
$C_{29}H_{25}BrCl_2N_2O_4$

In a manner similar to the method described in example 32d, E/Z-6-chloro-3-(3-chloro-benzylidene)-2-oxo-2,3-dihydro-indole-1-carboxylic acid tert-butyl ester prepared in example 5b (1.0 g, 2.5 mmol) was reacted with 1-[5-bromo- 2-(tetrahydro-pyran-4-yloxy)-phenyl]-3-trimethylsilyoxy-2-aza-1,3-butadiene (4 g, 10 mmol) in toluene at 140° C., then treated with trifuloroacetic acid in dicloromethane to give racemic(2'R, 3R, 4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione as a yellow solid (Yield 0.76 g, 49%)

HRMS(ES$^+$) m/z Calcd for $C_{29}H_{25}BrCl_2N_2O_4$+H [(M+H)$^+$]: 615.0448. Found: 615.0444.

EXAMPLE 34d

Preparation of chiral(2'R, 3R, 4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione

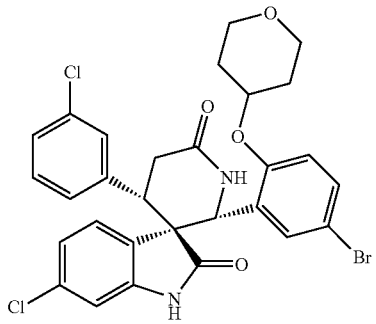

M.W. 616.34
$C_{29}H_{25}BrCl_2N_2O_4$

Separation of the two enantiomers from racemic(2'R, 3R, 4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione (0.7 g) was conducted by chiral SFC to provide chiral(2'R, 3R, 4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione as a yellow solid (0.208 g, 30%) and chiral(2'S, 3S, 4'R)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione as a yellow solid (0.21 g, 30%).

EXAMPLE 35a

Preparation of racemic(2'R, 3R, 4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione

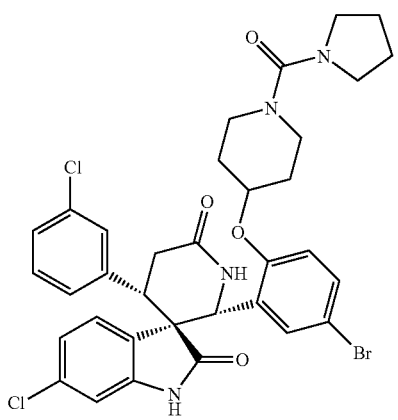

M.W. 712.47
$C_{34}H_{33}BrCl_2N_4O_4$

In a manner similar to the method described in example 5b, 1-pyrrolidinecarbonyl chloride (26 mg, 0.195 mmol) as the starting material in place of acetyl chloride to react with racemic(2'R, 3R, 4'S)-2'-[5-bromo-2-(4-piperidinyloxy)-phenyl]-6-chloro-4'-(3-chlorophenyl)spiro[3H-indole-3,3'-piperidine]-2,6'(1H)-dione (0.1 g, 0.16 mmol) prepared in Example 16a and triethylamine in tetrahydrofuran to give racemic(2'R, 3R, 4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione as a yellow solid (Yield 54 mg, 82%).

HRMS(ES$^+$) m/z Calcd for $C_{34}H_{33}BrCl_2N_4O_4$+H [(M+H)$^+$]: 711.1135. Found: 711.1133.

EXAMPLE 35b

Preparation of chiral(2'R, 3R, 4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione

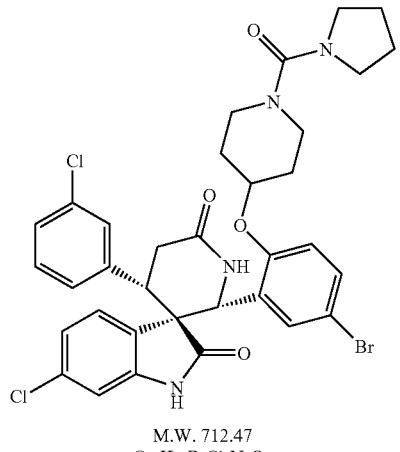

M.W. 712.47
$C_{34}H_{33}BrCl_2N_4O_4$

Separation of the two enantiomers from racemic(2'R, 3R, 4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione (140 mg) was conducted by chiral SFC to provide chiral(2'R, 3R, 4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione as a light yellow solid (38 mg, 27%) and chiral(2'S, 3S, 4'R)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione as a light yellow solid (37 mg, 26%).

EXAMPLE 36

Preparation of racemic(2'R, 3R, 4'S)-2'-[5-bromo-2-(1-dimethylcarbamoyl-4-piperidinyloxy)-phenyl]-6-chloro-4'-(3-chlorophenyl)spiro[3H-indole-3,3'-piperidine]-2,6'(1H)-dione

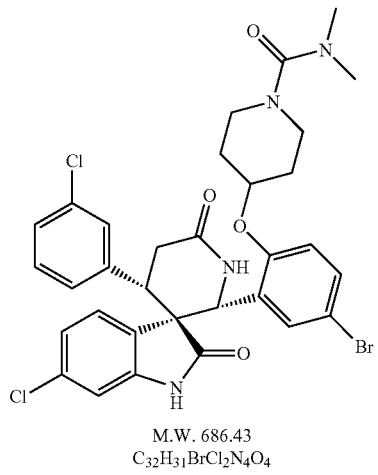

M.W. 686.43
$C_{32}H_{31}BrCl_2N_4O_4$

In a manner similar to the method described in example 5b, dimethylcarbamyl chloride (25 mg, 0.234 mmol) as the starting material in place of acetyl chloride to react with racemic (2'R, 3R, 4'S)-2'-[5-bromo-2-(4-piperidinyloxy)-phenyl]-6-chloro-4'-(3-chlorophenyl)spiro[3H-indole-3,3'-piperidine]-2,6'(1H)-dione (0.12 g, 0.195 mmol) prepared in Example 16a and triethylamine in tetrahydrofuran to give racemic(2'R, 3R, 4'S)-2'-[5-bromo-2-(1-dimethylcarbamoyl-4-piperidinyloxy)-phenyl]-6-chloro-4'-(3-chlorophenyl)spiro[3H-indole-3,3'-piperidine]-2,6'(1H)-dione as a light yellow solid (Yield 87 mg, 65%).

HRMS(ES⁺) m/z Calcd for $C_{32}H_{31}BrCl_2N_4O_4$+H [(M+H)⁺]:685.0979. Found: 685.0975.

EXAMPLE 37

Preparation of racemic(2', 3R, 4'S)-6-chloro-4'-(3-chlorophenyl)-2'-[2-(1-ethoxycarbonyl-4-piperidinyloxy)-5-iodo-phenyl]spiro[3H-indole-3,3'-piperidine]-2,6'(1H)-dione

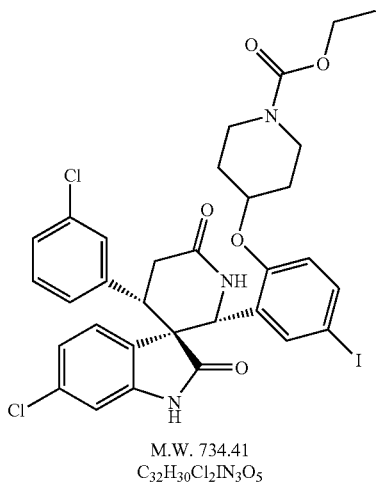

M.W. 734.41
$C_{32}H_{30}Cl_2IN_3O_5$

In a manner similar to the method described in Example 5b, racemic(2'R, 3R, 4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.15 g, 0.23 mmol) prepared in Example 5a was reacted with ethyl chloroformate (29.4 mg, 0.27 mmol) and trimethylamine in tetrahydrofuran to give racemic(2'R, 3R, 4'S)-6-chloro-4'-(3-chlorophenyl)-2'-[2-(1-ethoxycarbonyl-4-piperidinyloxy)-5-iodo-phenyl]spiro[3H-indole-3,3'-piperidine]-2,6'(1H)-dione as a light yellow solid (Yield 0.11 g, 65%).

HRMS(ES⁺) m/z Calcd for $C_{32}H_{30}Cl_2IN_3O_5$+H [(M+H)⁺]: 734.0680. Found: 734.0682.

EXAMPLE 38

Preparation of racemic(2'R, 3R, 4'S)-2'-[5-bromo-2-(1-ethoxycarbonyl-4-piperidinyloxy)-phenyl]-6-chloro-4'-(3-chlorophenyl)spiro[3H-indole-3,3'-piperidine]-2,6'(1H)-dione

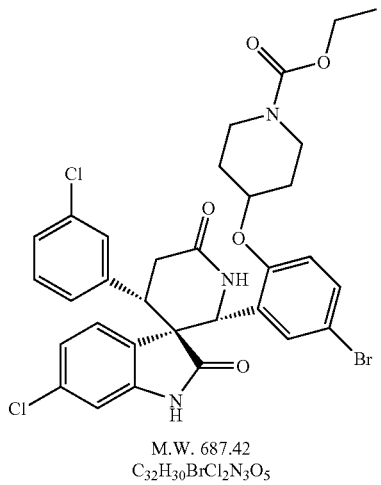

M.W. 687.42
$C_{32}H_{30}BrCl_2N_3O_5$

In a manner similar to the method described in example 5b, racemic(2'R, 3R, 4'S)-2'-[5-bromo-2-(4-piperidinyloxy)-phenyl]-6-chloro-4'-(3-chlorophenyl)spiro[3H-indole-3,3'-piperidine]-2,6'(1H)-dione (0.11 g, 0.179 mmol) prepared in Example 16a was reacted with ethyl chloroformate (23.3 mg, 0.214 mmol) and triethylamine in tetrahydrofuran to give racemic(2'R, 3R, 4'S)-2'-[5-bromo-2-(1-ethoxycarbonyl-4-piperidinyloxy)-phenyl]-6-chloro-4'-(3-chlorophenyl)spiro[3H-indole-3,3'-piperidine]-2,6'(1H)-dione as a white solid (Yield 17 mg, 14%).

HRMS(ES⁺) m/z Calcd for $C_{32}H_{30}BrCl_2N_3O_5$+H [(M+H)⁺]: 686.0819. Found: 686.0814.

EXAMPLE 39

Preparation of racemic(2'R, 3R, 4'S)-2'-[5-bromo-2-(1-isobutyryl-4-piperidinyloxy)-phenyl]-6-chloro-4'-(3-chlorophenyl)spiro[3H-indole-3,3'-piperidine]-2,6'(1H)-dione

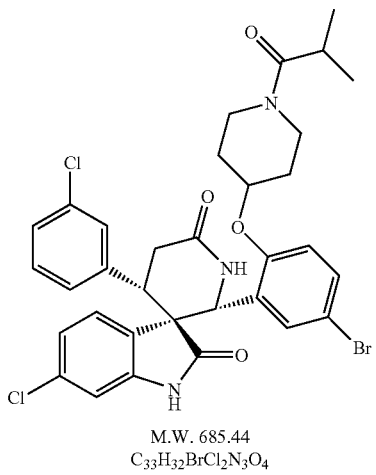

M.W. 685.44
$C_{33}H_{32}BrCl_2N_3O_4$

In a manner similar to the method described in example 5b, racemic(2'R, 3R, 4'S)-2'-[5-bromo-2-(4-piperidinyloxy)-phenyl]-6-chloro-4'-(3-chlorophenyl)spiro[3H-indole-3,3'-piperidine]-2,6'(1H)-dione (50 mg, 0.081 mmol) prepared in Example 16a was reacted with isobutyryl chloride (10 mg, 0.097 mmol) and triethylamine in tetrahydrofuran to give racemic(2'R, 3R, 4'S)-2'-[5-bromo-2-(1-isobutyryl-4-piperidinyloxy)-phenyl]-6-chloro-4'-(3-chlorophenyl)spiro[3H-indole-3,3'-piperidine]-2,6'(1H)-dione as a light yellow solid (Yield 42 mg, 76%).

HRMS(ES$^+$) m/z Calcd for $C_{33}H_{32}BrCl_2N_3O_4$+H [(M+H)$^+$]: 684.1026. Found: 684.1025.

EXAMPLE 40

Preparation of racemic(2'R, 3R, 4'S)-2'-[5-bromo-2-(1-isopropoxycarbonyl-4-piperidinyloxy)-phenyl]-6-chloro-4'-(3-chlorophenyl)spiro[3H-indole-3,3'-piperidine]-2,6'(1H)-dione

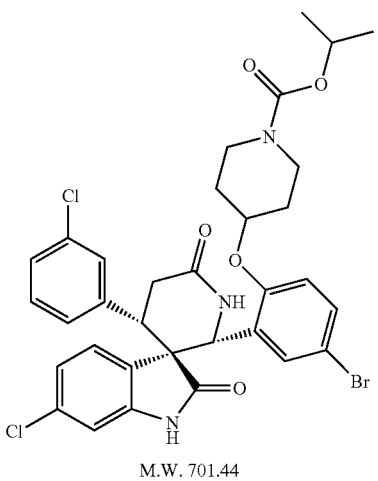

M.W. 701.44
$C_{33}H_{32}BrCl_2N_3O_5$

In a manner similar to the method described in example 5b, racemic(2'R, 3R, 4'S)-2'-[5-bromo-2-(4-piperidinyloxy)-phenyl]-6-chloro-4'-(3-chlorophenyl)spiro[3H indole-3,3'-piperidine]-2,6'(1H)-dione (0.1 g, 0.16 mmol) prepared in Example 16a was reacted with isopropyl chloroformate (0.19 mL, 0.196 mmol) and triethylamine in tetrahydrofuran to give racemic(2'R, 3R, 4'S)-2'-[5-bromo-2-(1-isopropoxycarbonyl-4-piperidinyloxy)-phenyl]-6-chloro-4'-(3-chlorophenyl)spiro[3H-indole-3,3'-piperidine]-2,6'(1H)-dione as a white solid (Yield 27 mg, 24%).

HRMS(ES$^+$) m/z Calcd for $C_{33}H_{32}BrCl_2N_3O_5$+H [(M+H)$^+$]: 700.0975. Found: 700.0972.

EXAMPLE 41

Preparation of racemic(2'R, 3R, 4'S)-6-chloro-4'-(3-chlorophenyl)-2'-[5-iodo-2-(1-isobutyryl-4-piperidinyloxy)-phenyl]spiro[3H-indole-3,3'-piperidine]-2,6'(1H)-dione

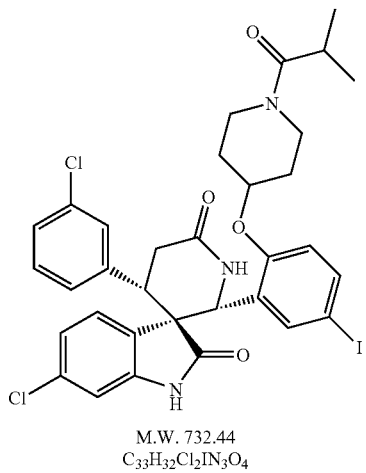

M.W. 732.44
$C_{33}H_{32}Cl_2IN_3O_4$

In a manner similar to the method described in Example 5b, racemic(2'R, 3R, 4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.15 g, 0.23 mmol) prepared in Example 5a was reacted with isobutyryl chloride (29 mg, 0.27 mmol) and trimethylamine in tetrahydrofuran to give racemic (2'R, 3R, 4'S)-6-chloro-4'-(3-chlorophenyl)-2'-[5-iodo-2-(1-isobutyryl-4-piperidinyloxy)-phenyl]spiro[3H-indole-3,3'-piperidine]-2,6'(1H)-dione as a light yellow solid (Yield 91 mg, 54%).

HRMS(ES$^+$) m/z Calcd for $C_{33}H_{32}Cl_2IN_3O_4$+H [(M+H)$^+$]: 732.0888. Found: 732.0892.

EXAMPLE 42

Preparation of racemic(2'R, 3R, 4'S)-6-chloro-4'-(3-chlorophenyl)-2'-[5-iodo-2-(1-isopropoxycarbonyl-4-piperidinyloxy)-phenyl]spiro[3H-indole-3,3'-piperidine]-2,6'(1H)-dione

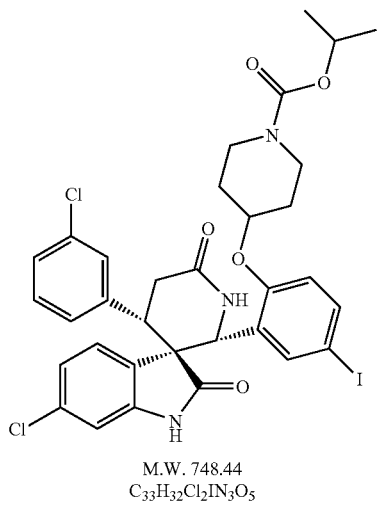

M.W. 748.44
$C_{33}H_{32}Cl_2IN_3O_5$

In a manner similar to the method described in Example 5b, racemic(2'R, 3R, 4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in Example 5a was reacted with isopropyl chloroformate (0.15 mL, 0.15 mmol) and trimethylamine in tetrahydrofuran to give racemic(2'R, 3R, 4'S)-6-chloro-4'-(3-chlorophenyl)-2'-[5-iodo-2-(1-isopropoxycarbonyl-4-piperidinyloxy)-phenyl]spiro[3H-indole-3,3'-piperidine]-2,6'(1H)-dione as a light yellow solid (Yield 54 mg, 48%).

HRMS(ES$^+$) m/z Calcd for $C_{33}H_{32}Cl_2IN_3O_5$+H [(M+H)$^+$]: 748.0837. Found: 748.0835.

EXAMPLE 43

Preparation of racemic(2'R, 3R, 4'S)-6-chloro-4'-(3-chlorophenyl)-2'-{2-[1-(2-hydroxy-ethyl)-4-piperidinyloxy]-5-iodo-phenyl}spiro[3H-indole-3,3'-piperidine]-2,6'(1H)-dione

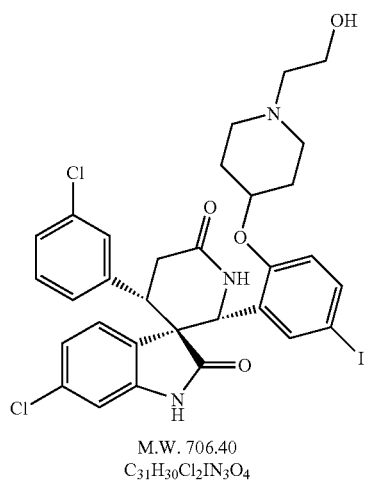

M.W. 706.40
$C_{31}H_{30}Cl_2IN_3O_4$

To a solution of racemic(2'R, 3R, 4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.1 g, 0.15 mmol) prepared in example 5a in ethanol (2 mL) was added triethylamine (45.7 mg, 0.46 mmol) and 2-bromoethanol (42.4 mg, 0.345 mmol) (Aldrich). The reaction mixture was heated at 80° C. for 18 h, then cooled to room temperature and concentrated. The residue was partitioned between ethyl acetate and water. The organic layer was separated, and the aqueous layer was extracted with ethyl acetate. The organic layers were combined, washed with brine, dried over MgSO$_4$, and concentrated. The residue was purified by chromatography (MeOH:EtOAc:NEt$_3$=12:88:5) to give racemic(2'R, 3R, 4'S)-6-chloro-4'-(3-chlorophenyl)-2'-{2-[1-(2-hydroxy-ethyl)-4-piperidinyloxy]-5-iodo-phenyl}spiro[3H-indole-3,3'-piperidine]-2,6'(1H)-dione as a white solid (Yield 36 mg, 34%)

HRMS(ES$^+$) m/z Calcd for $C_{31}H_{30}Cl_2IN_3O_4$+H [(M+H)$^+$]: 706.0731. Found: 706.0729.

EXAMPLE 44

Preparation of racemic(2'R, 3R, 4'S)-6-chloro-4'-(3-chlorophenyl)-2'-[5-iodo-2-(1-methoxycarbonylmethyl-4-piperidinyloxy)-phenyl]spiro[3H-indole-3,3'-piperidine]-2,6'(1H)-dione

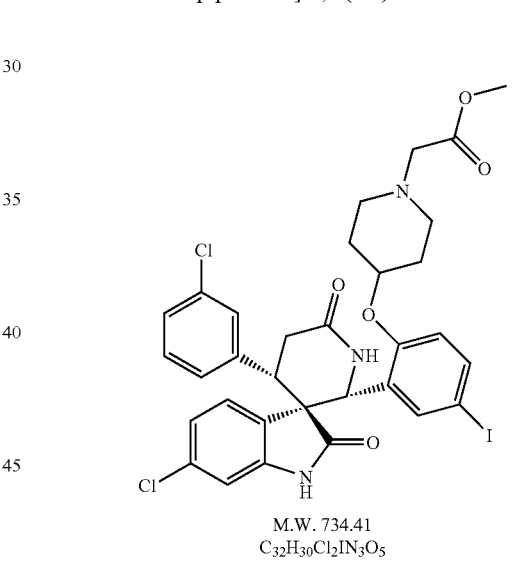

M.W. 734.41
$C_{32}H_{30}Cl_2IN_3O_5$

To a solution of racemic(2'R, 3R, 4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.36 g, 0.54 mmol) prepared in example 5a in ethanol (2 mL) was added triethylamine (0.15 mL, 1.08 mmol) and methyl bromoacetate (0.124 g, 0.81 mmol) (Aldrich). The reaction mixture was heated at 80° C. for 2 h, then cooled to room temperature. The mixture was partitioned between dichloromethane and water. The organic layer was separated, and the aqueous layer was extracted with dichloromethane. The organic layers were combined, washed with brine, dried over MgSO$_4$, and concentrated. The residue was purified by chromatography (MeOH:EtOAc=7:93) to give racemic(2'R, 3R, 4'S)-6-chloro-4'-(3-chlorophenyl)-2'-[5-iodo-2-(1-methoxycarbonylmethyl-4-piperidinyloxy)-phenyl]spiro[3H-indole-3,3'-piperidine]-2,6'(1H)-dione as a light yellow solid (Yield 0.21 g, 53%)

HRMS(ES$^+$) m/z Calcd for $C_{32}H_{30}Cl_2IN_3O_5$+H [(M+H)$^+$]: 734.0680. Found: 734.0683.

EXAMPLE 45

Preparation of racemic(2'R, 3R, 4'S)-2'-[2-(1-tert-butoxycarbonylmethyl-4-piperidinyloxy)-5-iodo-phenyl]-6-chloro-4'-(3-chlorophenyl)spiro[3H-indole-3,3'-piperidine]-2,6'(1H)-dione

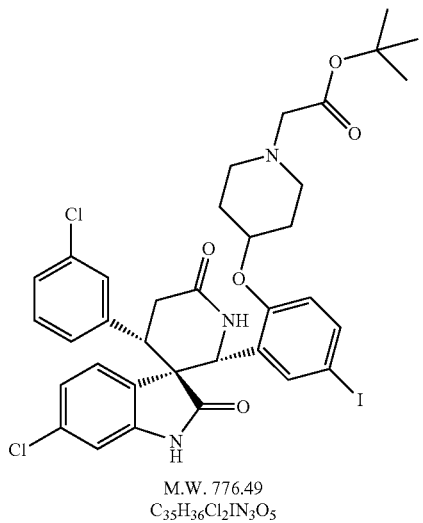

M.W. 776.49
$C_{35}H_{36}Cl_2IN_3O_5$

In a manner similar to the method described in Example 44, racemic(2'R, 3R, 4'S)-6-chloro-4'-(3-chlorophenyl)-2'-[5-iodo-2-(4-piperidinyloxy)-phenyl]spiro[3H-indole-3,3'-piperidine]-2,6'(1H)-dione (0.32 g, 0.48 mmol) prepared in example 5a was reacted with tert-butyl bromoacetate (0.14 g, 0.72 mmol) and triethylamine in ethanol to give racemic(2'R, 3R, 4'S)-2'-[2-(1-tert-butoxycarbonylmethyl-4-piperidinyloxy)-5-iodo-phenyl]-6-chloro-4'-(3-chlorophenyl)spiro[3H-indole-3,3'-piperidine]-2,6'(1H)-dione as a light yellow solid (Yield 0.25 g, 67%)

HRMS(ES$^+$) m/z Calcd for $C_{35}H_{36}Cl_2IN_3O_5$+H [(M+H)$^+$]: 776.1150. Found: 776.1147.

EXAMPLE 46

Preparation of racemic(2'R, 3R, 4'S)-6-chloro-4'-(3-chlorophenyl)-2'-[2-(1-hydroxycarbonylmethyl-4-piperidinyloxy)-5-iodo-phenyl]spiro[3H-indole-3,3'-piperidine]-2,6'(1H)-dione

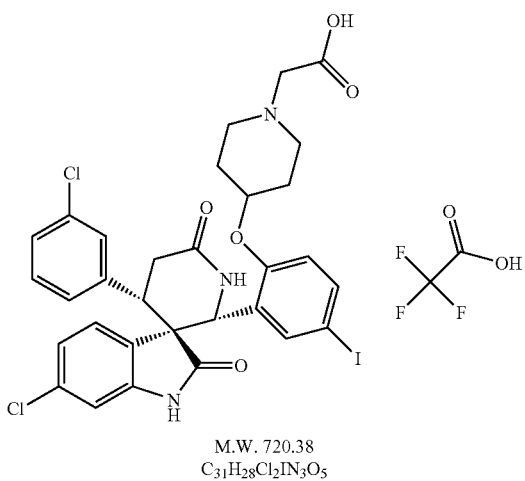

M.W. 720.38
$C_{31}H_{28}Cl_2IN_3O_5$

To a solution of racemic(2'R, 3R, 4'S)-2'-[2-(1-tert-butoxycarbonylmethyl-4-piperidinyloxy)-5-iodo-phenyl]-6-chloro-4'-(3-chlorophenyl)spiro[3H-indole-3,3'-piperidine]-2,6'(1H)-dione (0.22 g, 0.28 mmol) in dichloromethane (2 mL) was added trifluoroacetic acid (2 mL). The reaction mixture was stirred at room temperature for 18 h, then concentrated. The residue was triturated with dichlormethane and hexanes to give racemic(2'R, 3R, 4'S)-6-chloro-4'-(3-chlorophenyl)-2'-[2-(1-hydroxycarbonylmethyl-4-piperidinyloxy)-5-iodo-phenyl]spiro[3H-indole-3,3'-piperidine]-2,6'(1H)-dione as trifluoroacetic acid salt: yellow solid (Yield 0.18 g)

HRMS(ES$^+$) m/z Calcd for $C_{31}H_{28}Cl_2IN_3O_5$+H [(M+H)$^+$]: 720.0524. Found: 720.0525.

EXAMPLE 47a

Preparation of racemic(2'R, 3R, 4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dioe

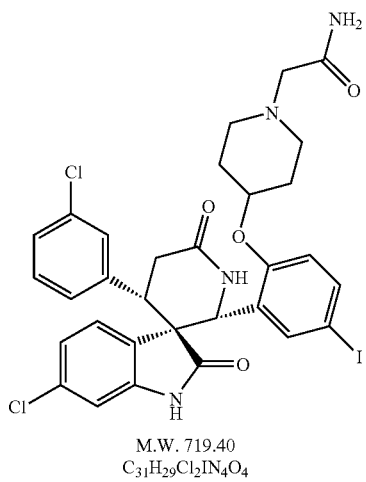

M.W. 719.40
$C_{31}H_{29}Cl_2IN_4O_4$

To a solution of racemic(2'R, 3R, 4'S)-6-chloro-4'-(3-chlorophenyl)-2'-[2-(1-hydroxycarbonylmethyl-4-piperidinyloxy)-5-iodo-phenyl]spiro[3H-indole-3,3'-piperidine]-2,6'(1H)-dione (50 mg, 0.069 mmol) in anhydrous N,N-dimethylformamide (2 mL) was added EDCI (26.5 mg, 0.139 mmol), HOBT (18.8 mg, 0.139 mmol), diisopropylethylamine (35.9 mg, 0.278 mmol), NH$_4$Cl (7.4 mg, 0.278 mmol). The reaction mixture was heated at 80° C. for 1 h, then cooled to room temperature. The mixture was partitioned between ethyl acetate and water. The organic layer was separated, and the aqueous layer was extracted with ethyl acetate. The organic layers were combined, washed with brine, dried over MgSO$_4$, and concentrated. The residue was purified by chromatography (MeOH:EtOAc=8:92) to give racemic(2'R, 3R, 4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione as an off white solid (Yield 25.6 mg, 51%)

HRMS(ES$^+$) m/z Calcd for $C_{31}H_{29}Cl_2IN_4O_4$+H [(M+H)$^+$]: 719.0684. Found: 719.0690.

EXAMPLE 47b

Preparation of chiral(2'R, 3R, 4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione

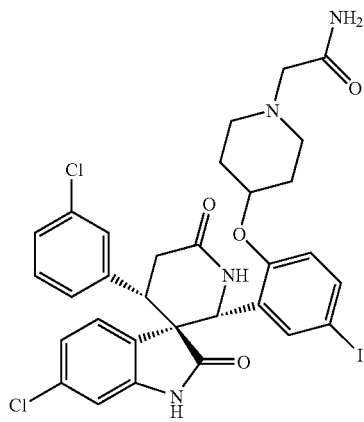

M.W. 719.40
$C_{31}H_{29}Cl_2IN_4O_4$

Separation of the two enantiomers from racemic(2'R, 3R, 4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione (0.3 g) was conducted by chiral SFC to provide chiral(2'R, 3R, 4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione as a light yellow solid (83 mg, 28%) and chiral(2'S, 3S, 4'R)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione as a light yellow solid (88 mg, 29%).

EXAMPLE 48a

Preparation of intermediate (S)-3-methanesulfonyloxy-pyrrolidine-1-carboxylic acid tert-butyl ester

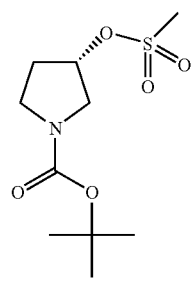

M.W. 265.33
$C_{10}H_{19}NO_5S$

To a solution of (S)-1-tert-butoxycarbonyl-3-hydroxypyrrolidine (7.7 g, 41 mmol) (Aldrich) in dichloromethane (130 mL) at 0° C. was added triethylamine (10.4 g, 103 mmol), and methanesulfonyl chloride (8 g, 70 mmol, Aldrich). The reaction mixture was stirred at 0° C. for 1 h, then at room temperature for 0.5 h. The mixture was poured into water, extracted with dichloromethane. The organic layer was separated, washed with water, brine, dried over MgSO$_4$, and concentrated to give crude (S)-3-methanesulfonyloxy-pyrrolidine-1-carboxylic acid tert-butyl ester as a yellow oil (Yield 11 g, 100%).

EXAMPLE 48b

Preparation of intermediate (R/S)-3-(4-bromo-2-formyl-phenoxy)-pyrrolidine-1-carboxylic acid tert-butyl ester

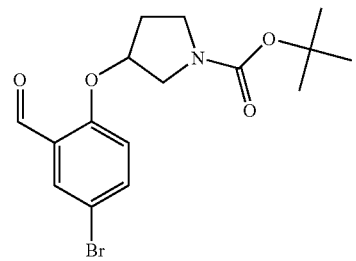

M.W. 370.25
$C_{16}H_{20}BrNO_4$

In a manner similar to the method described in example 4a, 5-bromosalicylaldehyde (3.6 g, 18 mmol) (Aldrich) reacted with (S)-3-methanesulfonyloxy-pyrrolidine-1-carboxylic acid tert-butyl ester (5.3 g, 20 mmol) and K$_2$CO$_3$ in N,N-dimethylformamide to give (R/S)-3-(4-bromo-2-formyl-phenoxy)-pyrrolidine-1-carboxylic acid tert-butyl ester as an orange oil (Yield 3.6 g, 54%).

EXAMPLE 48c

Preparation of intermediate (R/S)-1-[5-bromo-2-(1-tert-butoxycarbonyl-3-pyrrolidinyloxy)-phenyl]-3-trimethylsilyoxy-2-aza-1,3-butadiene

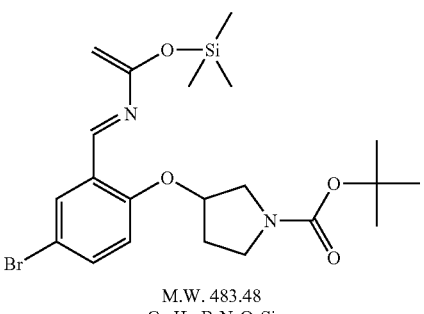

M.W. 483.48
$C_{21}H_{31}BrN_2O_3Si$

In a manner similar to the method described in example 1d, (R/S)-3-(4-bromo-2-formyl-phenoxy)-pyrrolidine-1-carboxylic acid tert-butyl ester (2.7 g, 7.4 mmol) was used as the starting material in place of 4-(2-formyl-4-iodo-phenoxymethyl)-piperidine-1-carboxylic acid tert-butyl ester to react with 1,1,3,3,3-hexamethyldisilazane (1.2 g, 7.4 mmol), n-butyllithium (2.5 M, 3 mL, 7.5 mmol), trimethylsilyl chloride (0.8 g, 7.4 mmol), triethylamine (1 g, 10 mmol) and acetyl chloride (0.79 g, 10 mmol) to give crude (R/S)-1-[5-bromo-2-(1-tert-butoxycarbonyl-3-pyrrolidinyloxy)-phenyl]-3-trimethylsilyoxy-2-aza-1,3-butadiene as a yellow gum and used for the next step without further purification.

EXAMPLE 48d

Preparation of racemic(2'R, 3R, 4'S)-2'-[5-bromo-2-(1-tert-butoxycarbonyl-3-pyrrolidinyloxy)-phenyl]-6-chloro-4'-(3-chlorophenyl)spiro[3H-indole-3,3'-piperidine]-2,6'(1H)-dione

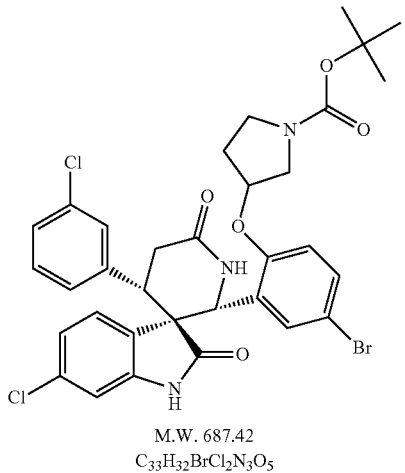

M.W. 687.42
$C_{33}H_{32}BrCl_2N_3O_5$

In a manner similar to the method described in example 1e, E/Z-6-chloro-3-(3-chloro-benzylidene)-2-oxo-2,3-dihydro-indole-1-carboxylic acid tert-butyl ester prepared in example 5b (0.6 g, 1.5 mmol) was reacted with (R/S)-1-[5-bromo-2-(1-tert-butoxycarbonyl-3-pyrrolidinyloxy)-phenyl]-3-trimethylsilyoxy-2-aza-1,3-butadiene (7.4 mmol) in toluene (30 mL) at 140° C. for 6 h to give racemic(2'R, 3R, 4'S)-2'-[5-bromo-2-(1-tert-butoxycarbonyl-3-pyrrolidinyloxy)-phenyl]-6-chloro-4'-(3-chlorophenyl)spiro[3H-indole-3,3'-piperidine]-2,6'(1H)-dione as an off white solid (Yield 0.5 g, 48%)

HRMS(ES$^+$) m/z Calcd for $C_{33}H_{32}BrCl_2N_3O_5$+H [(M+H)$^+$]: 700.0975. Found: 700.0973.

EXAMPLE 49a

Preparation of intermediate (R/S)-3-(2-formyl-4-iodo-phenoxy)-pyrrolidine-1-carboxylic acid tert-butyl ester

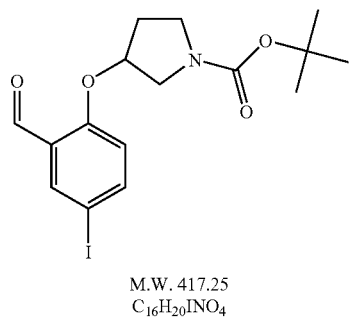

M.W. 417.25
$C_{16}H_{20}INO_4$

In a manner similar to the method described in example 4a, 5-iodosalicylaldehyde (5 g, 20 mmol) (Aldrich) reacted with (S)-3-methanesulfonyloxy-pyrrolidine-1-carboxylic acid tert-butyl ester (7 g, 26 mmol) prepared in Example 48a and $K_2CO_3$ in N,N-dimethylformamide to give (R/S)-3-(2-formyl-4-iodo-phenoxy)-pyrrolidine-1-carboxylic acid tert-butyl ester as a white foam (Yield 5 g, 60%).

EXAMPLE 49b

Preparation of intermediate (R/S)-1-[2-(1-tert-butoxycarbonyl-3-pyrrolidinyloxy)-5-iodo-phenyl]-3-trimethylsilyoxy-2-aza-1,3-butadiene

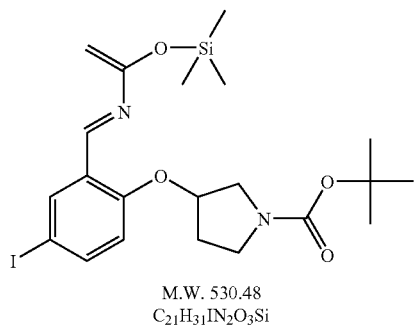

M.W. 530.48
$C_{21}H_{31}IN_2O_3Si$

In a manner similar to the method described in example 1d, (R/S)-3-(2-formyl-4-iodo-phenoxy)-pyrrolidine-1-carboxylic acid tert-butyl ester (4.2 g, 10 mmol) was used as the starting material in place of 4-(2-formyl-4-iodo-phenoxymethyl)-piperidine-1-carboxylic acid tert-butyl ester to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1 g, 13.6 mmol) to give crude (R/S)-1-[2-(1-tert-butoxycarbonyl-3-pyrrolidinyloxy)-5-iodo-phenyl]-3-trimethylsilyoxy-2-aza-1,3-butadiene as a yellow gum and used for the next step without further purification.

EXAMPLE 49c

Preparation of racemic(2'R, 3R, 4'S)-2'-[2-(1-tert-butoxycarbonyl-3-pyrrolidinyloxy)-5-iodo-phenyl]-6-chloro-4'-(3-chlorophenyl)spiro[3H-indole-3,3'-piperidine]-2,6'(1H)-dione

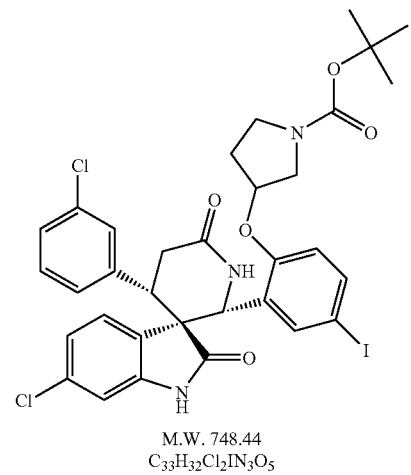

M.W. 748.44
$C_{33}H_{32}Cl_2IN_3O_5$

In a manner similar to the method described in example 1e, E/Z-6-chloro-3-(3-chloro-benzylidene)-2-oxo-2,3-dihydro-indole-1-carboxylic acid tert-butyl ester prepared in example 5b (1.1 g, 2.8 mmol) was reacted with (R/S)-1-[2-(1-tert-butoxycarbonyl-3-pyrrolidinyloxy)-5-iodo-phenyl]-3-trimethylsilyoxy-2-aza-1,3-butadiene (5.3 g, 10 mmol) in toluene (30 mL) at 140° C. for 4 h to give racemic(2'R, 3R, 4'S)-2'-[2-(1-tert-butoxycarbonyl-3-pyrrolidinyloxy)-5-iodo-phenyl]-6-chloro-4'-(3-chlorophenyl) spiro[3H-indole-3,3'-piperidine]-2,6'(1H)-dione as a yellow solid (Yield 0.5 g, 48%)

HRMS(ES$^+$) m/z Calcd for $C_{33}H_{32}Cl_2IN_3O_5+H$ [(M+H)$^+$]: 748.0837. Found: 748.0837

EXAMPLE 50a

Preparation of intermediate 4-(4-bromo-2-formyl-phenoxy)-benzoic acid methyl ester

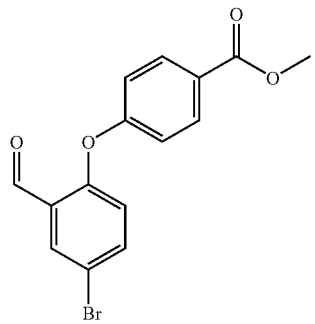

M.W. 335.16
$C_{15}H_{11}BrO_4$

To a solution of 5-bromo-2-fluorobenzaldehyde (4.04 g, 20 mmol) (Alfa) in N,N-dimethylacetamide (30 mL) was added anhydrous $K_2CO_3$ (2.76 g, 20 mmol), and methyl 4-hydroxybenzoate (3.1 g, 20 mmol, Aldrich). The reaction mixture was heated at 170° C. for 1 h. The mixture was cooled to room temperature, diluted with ethyl acetate, washed with water, brine. The organic layer was separated, aqueous layer was extracted with ethyl acetate. The combined organic layers were washed with water, dried over $MgSO_4$, concentrated. The residue was purified by chromatography (EtOAc: hexanes=1:8 then 1:4) to give 4-(4-bromo-2-formyl-phenoxy)-benzoic acid methyl ester as a white solid (Yield 6.4 g, 95%).

Similar transformations have been described by Marsh, G. et al in *Eur. J. Org. Chem.* 2003, 2566-2576. The procedures were used with little modification.

EXAMPLE 50b

Preparation of intermediate 1-[5-bromo-2-(4-methoxycarbonyl-phenoxy)-phenyl]-3-trimethylsilyoxy-2-aza-1,3-butadiene

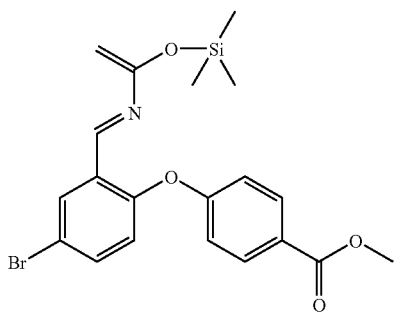

M.W. 448.39
$C_{20}H_{22}BrNO_4Si$

In a manner similar to the method described in example 1d, 4-(4-bromo-2-formyl-phenoxy)-benzoic acid methyl ester (5 g, 15 mmol) was reacted with 1,1,3,3,3-hexamethyldisilazane (2.4 g, 15 mmol), n-butyllithium (2.5 M, 6 mL, 15 mmol), trimethylsilyl chloride (1.6 g, 15 mmol), triethylamine (2 g, 20 mmol) and acetyl chloride (1.5 g, 15 mmol) to give crude 1-[5-bromo-2-(4-methoxycarbonyl-phenoxy)-phenyl]-3-trimethylsilyoxy-2-aza-1,3-butadiene as a yellow gum and used for the next step without further purification.

EXAMPLE 50c

Preparation of racemic(2'R, 3R, 4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione

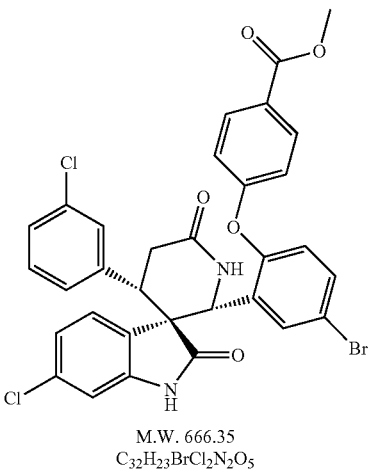

M.W. 666.35
$C_{32}H_{23}BrCl_2N_2O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.1 g, 2.8 mmol) was reacted with 1-[5-bromo-2-(4-methoxycarbonyl-phenoxy)-phenyl]-3-trimethylsilyoxy-2-aza-1,3-butadiene (6.6 g, 15 mmol) in toluene then trifluoroacetic acid in dichloromethane to give racemic(2'R, 3R, 4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione as an off white solid (Yield 1.2 g, 64%)

HRMS(ES$^+$) m/z Calcd for $C_{32}H_{23}BrCl_2N_2O_5+H$ [(M+H)$^+$]: 665.0240. Found: 665.0238.

EXAMPLE 50d

Preparation of chiral(2'R, 3R, 4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione

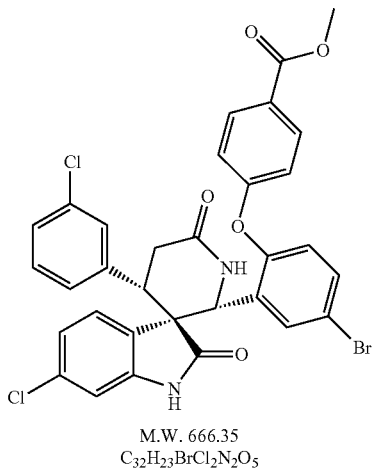

M.W. 666.35
$C_{32}H_{23}BrCl_2N_2O_5$

Separation of the two enantiomers from racemic(2'R, 3R, 4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione (79 mg) was conducted by chiral SFC to provide chiral(2'R, 3R, 4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione as a white solid (26 mg, 33%) and chiral(2'S, 3S, 4'R)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione as a white solid (27 mg, 34%).

EXAMPLE 51a

Preparation of intermediate 5-bromo-2-(4-methoxy-phenoxy)-benzaldehyde

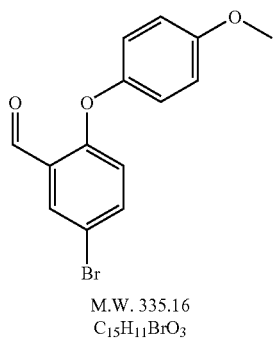

M.W. 335.16
$C_{15}H_{11}BrO_3$

In a manner similar to the method described in Example 50a, 5-bromo-2-fluorobenzaldehyde (2.1 g, 10 mmol) (Alfa) was reacted with 4-methoxyphenol (1.24 g, 10 mmol) and $K_2CO_3$ in N,N-dimethylacetamide to give 5-bromo-2-(4-methoxy-phenoxy)-benzaldehyde as a white solid (Yield 3.1 g, 92%).

EXAMPLE 51b

Preparation of intermediate 1-[5-bromo-2-(4-methoxy-phenoxy)-phenyl]-3-trimethylsilyoxy-2-aza-1,3-butadiene

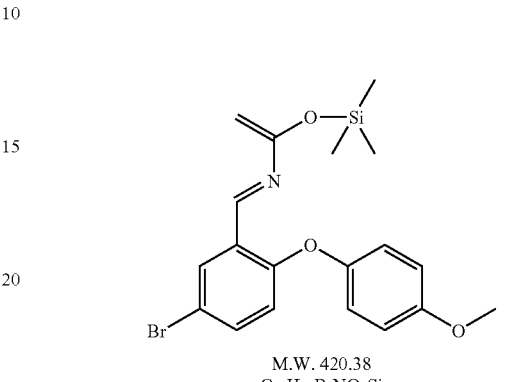

M.W. 420.38
$C_{19}H_{22}BrNO_3Si$

In a manner similar to the method described in example 1d, 5-bromo-2-(4-methoxy-phenoxy)-benzaldehyde (3.1 g, 10 mmol) was reacted with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1.0 g, 13.6 mmol) to give crude 1-[5-bromo-2-(4-methoxy-phenoxy)-phenyl]-3-trimethylsilyoxy-2-aza-1,3-butadiene as a yellow gum and used for the next step without further purification.

EXAMPLE 51c

Preparation of racemic(2'R, 3R, 4'S)-2'-[5-bromo-2-(4-methoxy-phenoxy)-phenyl]-6-chloro-4'-(3-chlorophenyl)spiro[3H-indole-3,3'-piperidine]-2,6'(1H)-dione

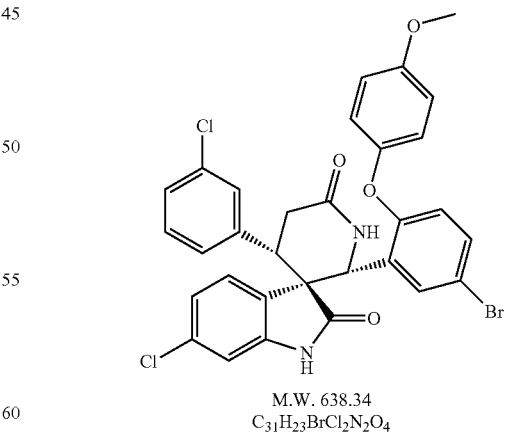

M.W. 638.34
$C_{31}H_{23}BrCl_2N_2O_4$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.6 g, 1.5 mmol) was reacted with 1-[5-bromo-2-(4-methoxy-phenoxy)-phenyl]-3-trimethylsilyoxy-2-aza- 1,3-butadiene (4.2 g, 10 mmol) in toluene then trifluoroacetic acid in dichloromethane to give racemic(2'R, 3R, 4'S)-2'-[5-bromo-2-(4-methoxy-phenoxy)-phenyl]-6-chloro-4'-(3-chlorophenyl)spiro[3H-indole-3,3'-piperidine]-2,6'(1H)-dione as an off white solid (Yield 0.61 g, 64%)

HRMS(ES+) m/z Calcd for $C_{31}H_{23}BrCl_2N_2O_4$+H [(M+H)+]: 637.0291. Found: 637.0289.

EXAMPLE 52a

Preparation of intermediate 5-bromo-2-(2,5-dimethyl-phenoxy)-benzaldehyde

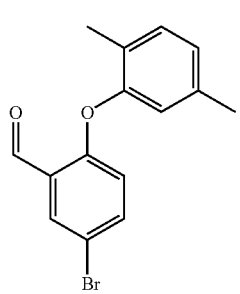

M.W. 305.17
$C_{15}H_{13}BrO_2$

In a manner similar to the method described in Example 50a, 5-bromo-2-fluorobenzaldehyde (2.1 g, 10 mmol) (Alfa) was reacted with 2,5-dimethylphenol (1.4 g, 11 mmol) and $K_2CO_3$ in N,N-dimethylacetamide to give 5-bromo-2-(2,5-dimethyl-phenoxy)-benzaldehyde as an orange oil (Yield 3 g, 98%).

EXAMPLE 52b

Preparation of intermediate 1-[5-bromo-2-(2,5-dimethyl-phenoxy)-phenyl]-3-trimethylsilyoxy-2-aza-1,3-butadiene

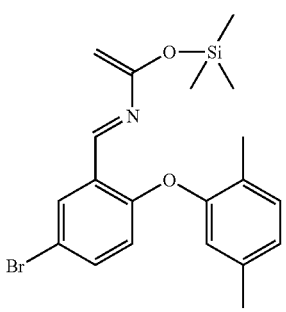

M.W. 418.41
$C_{20}H_{24}BrNO_2Si$

In a manner similar to the method described in example 1d, 5-bromo-2-(2,5-dimethyl-phenoxy)-benzaldehyde (1.6 g, 5 mmol) was reacted with 1,1,3,3,3-hexamethyldisilazane (0.8 g, 5 mmol), n-butyllithium (2.5 M, 2 mL, 5 mmol), trimethylsilyl chloride (0.55 g, 10 mmol), triethylamine (0.7 g, 7 mmol) and acetyl chloride (0.5 g, 7 mmol) to give crude 1-[5-bromo-2-(2,5-dimethyl-phenoxy)-phenyl]-3-trimethylsilyoxy-2-aza-1,3-butadiene as a yellow gum and used for the next step without further purification.

EXAMPLE 52c

Preparation of racemic(2'R, 3R, 4'S)-2'-[5-bromo-2-(2,5-dimethyl-phenoxy)-phenyl]-6-chloro-4'-(3-chlorophenyl)spiro[3H-indole-3,3'-piperidine]-2,6'(1H)-dione

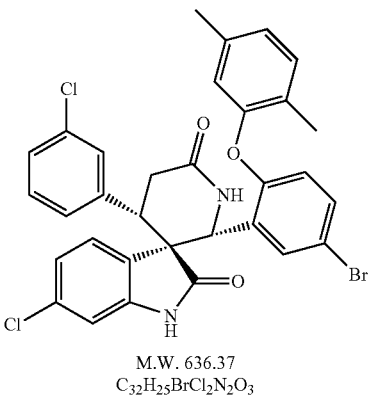

M.W. 636.37
$C_{32}H_{25}BrCl_2N_2O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.3 g, 0.77 mmol) was reacted with 1-[5-bromo-2-(2,5-dimethyl-phenoxy)-phenyl]-3-trimethylsilyoxy-2-aza-1,3-butadiene (2.2 g, 5 mmol) in toluene then trifluoroacetic acid in dichloromethane to give racemic(2'R, 3R, 4'S)-2'-[5-bromo-2-(2,5-dimethyl-phenoxy)-phenyl]-6-chloro-4'-(3-chlorophenyl)spiro[3H-indole-3,3'-piperidine]-2,6'(1H)-dione as an off white solid (Yield 0.38 g, 78%).

HRMS(ES+) m/z Calcd for $C_{32}H_{25}BrCl_2N_2O_3$+H [(M+H)+]: 635.0499. Found: 635.0498.

EXAMPLE 53a

Preparation of intermediate 4-(4-bromo-2-formyl-phenoxy)-3-methoxy-benzoic acid methyl ester

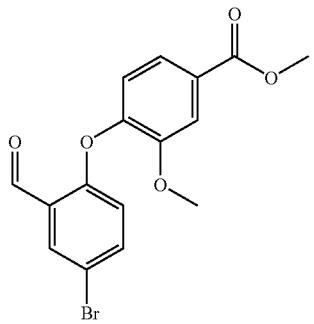

M.W. 365.18
$C_{16}H_{13}BrO_5$

In a manner similar to the method described in Example 50a, 5-bromo-2-fluorobenzaldehyde (4.1 g, 20 mmol) (Alfa)

was reacted with methyl vanillate (3.64 g, 20 mmol)(Aldrich) and $K_2CO_3$ in N,N-dimethylacetamide to give 4-(4-bromo-2-formyl-phenoxy)-3-methoxy-benzoic acid methyl ester as a white solid (Yield 3.1 g, 92%).

EXAMPLE 53b

Preparation of intermediate 1-[5-bromo-2-(2-methoxy-4-methoxycarbonyl-phenoxy)-phenyl]-3-trimethylsilyoxy-2-aza-1,3-butadiene

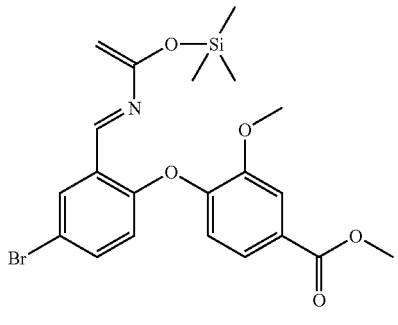

M.W. 478.42
$C_{21}H_{24}BrNO_5Si$

In a manner similar to the method described in example 1d, 4-(4-bromo-2-formyl-phenoxy)-3-methoxy-benzoic acid methyl ester (3.7 g, 10 mmol) was reacted with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1.0 g, 10 mmol) to give crude 1-[5-bromo-2-(2-methoxy-4-methoxycarbonyl-phenoxy)-phenyl]-3-trimethylsilyoxy-2-aza-1,3-butadiene as a yellow gum and used for the next step without further purification.

EXAMPLE 53c

Preparation of racemic(2'R, 3R, 4'S)-2'-[5-bromo-2-(2-methoxy-4-methoxycarbonyl-phenoxy)-phenyl]-6-chloro-4'-(3-chlorophenyl)spiro[3H-indole-3,3'-piperidine]-2,6'(1H)-dione

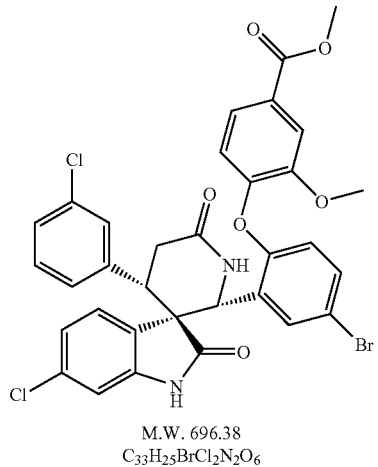

M.W. 696.38
$C_{33}H_{25}BrCl_2N_2O_6$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.0 g, 2.56 mmol) was reacted with 1-[5-bromo-2-(2-methoxy-4-methoxycarbonyl-phenoxy)-phenyl]-3-trimethylsilyoxy-2-aza-1,3-butadiene (4.8 g, 10 mmol) in toluene then trifluoroacetic acid in dichloromethane to give racemic(2'R, 3R, 4'S)-2'-[5-bromo-2-(2-methoxy-4-methoxycarbonyl-phenoxy)-phenyl]-6-chloro-4'-(3-chlorophenyl)spiro[3H-indole-3,3'-piperidine]-2,6'(1H)-dione as an off white solid (Yield 0.65 g, 36%).

HRMS(ES$^+$) m/z Calcd for $C_{33}H_{25}BrCl_2N_2O_6$+H [(M+H)$^+$]: 695.0346. Found: 695.0346.

EXAMPLE 54

Preparation of racemic(2'R, 3R, 4'S)-2'-[5-bromo-2-(4-hydroxycarbonyl-phenoxy)-phenyl]-6-chloro-4'-(3-chlorophenyl)spiro[3H-indole-3,3'-piperidine]-2,6'(1H)-dione

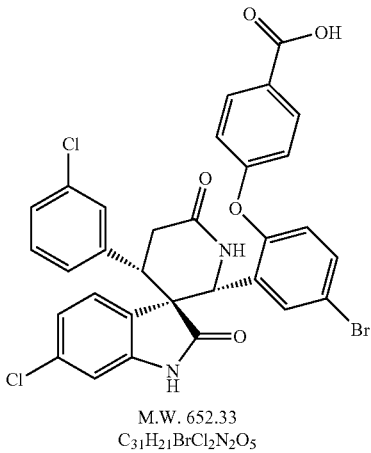

M.W. 652.33
$C_{31}H_{21}BrCl_2N_2O_5$

To a solution of racemic(2'R, 3R, 4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione prepared in Example 50c(0.8 g, 1.2 mmol) in tetrahydrofuran (20 mL) was added an aqueous solution (1 M) of NaOH (10 mL, 10 mmol) and methanol (10 mL). The reaction mixture was stirred at room temperature for 18 h, then acidified to "pH" 2 with concentrated aqueous HCl solution. The mixture was concentrated, partitioned between ethyl acetate and water. The organic layer was separated, washed with water, brine, dried over $MgSO_4$, and concentrated to give racemic (2'R, 3R, 4'S)-2'-[5-bromo-2-(4-hydroxycarbonyl-phenoxy)-phenyl]-6-chloro-4'-(3-chlorophenyl)spiro[3H-indole-3,3'-piperidine]-2,6'(1H)-dione as a white solid (Yield 0.6 g, 74%).

HRMS(ES$^+$) m/z Calcd for $C_{31}H_{21}BrCl_2N_2O_5$+H [(M+H)$^+$]: 651.0084. Found: 651.0083.

EXAMPLE 55a

Preparation of racemic(2'R, 3R, 4'S)-2'-[5-bromo-2-(4-fluorocarbonyl-phenyl)-phenyl]-6-chloro-4'-(3-chlorophenyl)spiro[3H-indole-3,3'-piperidine]-2,6'(1H)-dione

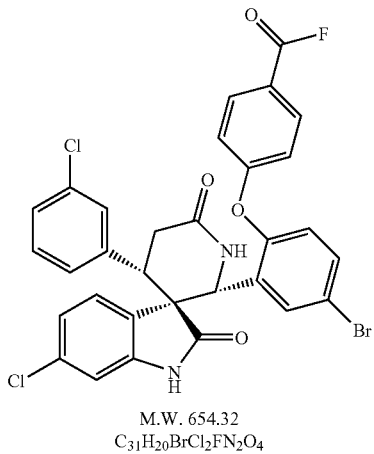

M.W. 654.32
$C_{31}H_{20}BrCl_2FN_2O_4$

To the solution of racemic(2'R, 3R, 4'S)-2'-[5-bromo-2-(4-hydroxycarbonyl-phenyl)-phenyl]-6-chloro-4'-(3-chlorophenyl)spiro[3H-indole-3,3'-piperidine]-2,6'(1H)-dione (0.18 g, 0.28 mmol) in dichloromethane (50 mL) at 0° C. was added cyanuric fluoride (120 mg, 0.88 mmol) (Alfa) and pyridine (100 mg, 1.3 mmol). After the mixture was stirred at 0° C. for 2 h, the mixture was partitioned between H₂O and dichloromethane. The organic layer was separated and the aqueous layer was extracted with dichloromethane. The organic layers were combined, dried over MgSO₄, concentrated to give racemic(2'R, 3R, 4'S)-2'-[5-bromo-2-(4-fluorocarbonyl-phenoxy)-phenyl]-6-chloro-4'-(3-chlorophenyl)spiro[3H-indole-3,3'-piperidine]-2,6'(1H)-dione as a yellow foam and used for the next step without further purification (Yield: 0. 18 g, 98%).

EXAMPLE 55b

Preparation of racemic(2'R, 3R, 4'S)-2'-{5-Bromo-2-[4-(2-hydroxy-1,1-dimethyl-ethylcarbamoyl)-phenoxy]-phenyl}-6-chloro-4'-(3-chlorophenyl)spiro[3H-indole-3,3'-piperidine]-2,6'(1H)-dione

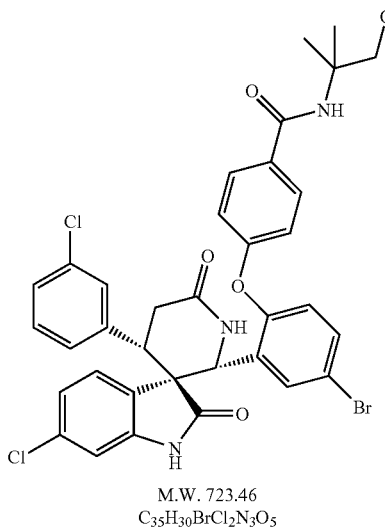

M.W. 723.46
$C_{35}H_{30}BrCl_2N_3O_5$

To a solution of racemic(2'R, 3R, 4'S)-2'-[5-bromo-2-(4-fluorocarbonyl-phenoxy)-phenyl]-6-chloro-4'-(3-chlorophenyl)spiro[3H-indole-3,3'-piperidine]-2,6'(1H)-dione (0.18 g, 0.28 mmol) in tetrahydrofuran (20 mL) was added 2-amino-2-methyl-propan-1-ol (0.2 g, 2.24 mmol), N-methylmorpholine (0.2 g, 2 mmol) and 4-dimethylaminopyridine (3 mg, 0.025 mmol). The reaction mixture was heated under nitrogen at 100° C. for 1 h, then cooled to room temperature. The mixture was diluted with ethyl acetate, washed with 1N HCl aqueous solution and H₂O. The organic layer was separated, dried over Na₂SO₄ and concentrated. The residue was purified by chromatography (MeOH:EtOAc=1:19) to give racemic(2'R, 3R, 4'S)-2'-{5-Bromo-2-[4-(2-hydroxy-1,1-dimethyl-ethylcarbamoyl)-phenoxy]-phenyl}-6-chloro-4'-(3-chlorophenyl)spiro[3H-indole-3,3'-piperidine]-2,6'(1H)-dione as a white solid (Yield: 84 mg, 42%).

HRMS(ES⁺) m/z Calcd for $C_{35}H_{30}BrCl_2N_3O_5$+H [(M+H)⁺]: 722.0819. Found: 722.0815.

EXAMPLE 56

Preparation of racemic(2'R, 3R, 4'S)-2'-{5-bromo-2-[4-(2-pyrrolidin-1-yl-ethylcarbamoyl)-phenoxy]-phenyl}-6-chloro-4'-(3-chlorophenyl)spiro[3H-indole-3,3'-piperidine]-2,6'(1H)-dione

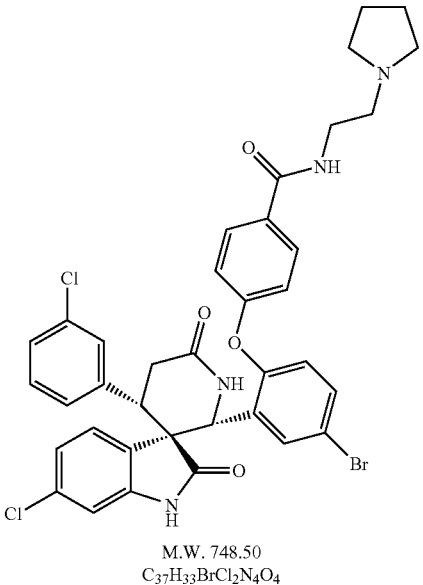

M.W. 748.50
$C_{37}H_{33}BrCl_2N_4O_4$

In a manner similar to the method described in example 55b, racemic(2'R, 3R, 4'S)-2'-[5-bromo-2-(4-fluorocarbonyl-phenoxy)-phenyl]-6-chloro-4'-(3-chlorophenyl)spiro[3H-indole-3,3'-piperidine]-2,6'(1H)-dione (0.18 g, 0.28 mmol) was reacted with N-(2-aminoethyl)pyrrolidine (0.4 g, 3.5 mmol), N-methylmorpholine and 4-dimethylaminopyridine in tetrahydrofuran to give racemic(2'R, 3R, 4'S)-2'-{5-bromo-2-[4-(2-pyrrolidin-1-yl-ethylcarbamoyl)-phenoxy]-phenyl}-6-chloro-4'-(3-chlorophenyl)spiro[3H-indole-3,3'-piperidine]-2,6'(1H)-dione as a white solid (Yield 0.17 g, 83%).

HRMS(ES⁺) m/z Calcd for $C_{37}H_{33}BrCl_2N_4O_4$+H [(M+H)⁺]: 747.1135. Found: 747.1133.

EXAMPLE 57

Preparation of racemic(2'R, 3R, 4'S)-2'-[5-bromo-2-(4-carbamoyl-phenoxy)-phenyl]-6-chloro-4'-(3-chlorophenyl)spiro[3H-indole-3,3'-piperidine]-2,6'(1H)-dione

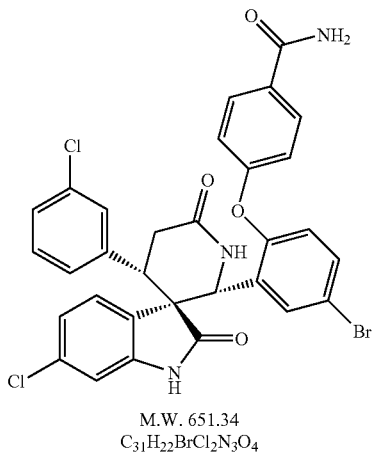

M.W. 651.34
$C_{31}H_{22}BrCl_2N_3O_4$

Racemic(2'R, 3R, 4'S)-2'-[5-bromo-2-(4-fluorocarbonyl-phenoxy)-phenyl]-6-chloro-4'-(3-chlorophenyl)spiro[3H-indole-3,3'-piperidine]-2,6'(1H)-dione (0.14 g, 0.21 mmol) prepared in example 55a was stirred in a methanolic ammonia solution (7 N, 10 mL) at room temperature for 18 h. The reaction mixture was concentrated, and the residue was purified by chromatography (EtOAc: MeOH=19: 1) to give racemic(2'R, 3R, 4'S)-2'-[5-bromo-2-(4-carbamoyl-phenoxy)-phenyl]-6-chloro-4'-(3-chlorophenyl)spiro[3H-indole-3,3'-piperidine]-2,6'(1H)-dione as a yellow solid (Yield 0.11 g, 80%).

HRMS(ES⁺) m/z Calcd for $C_{31}H_{22}BrCl_2N_3O_4$+H [(M+H)⁺]: 650.0244, Found: 650.0246.

EXAMPLE 58a

Preparation of intermediate 4-(4-bromo-2-formyl-phenoxy)-3-chloro-benzoic acid methyl ester

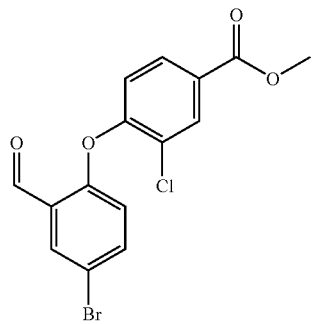

M.W. 369.60
$C_{15}H_{10}BrClO_4$

In a manner similar to the method described in Example 50a, 5-bromo-2-fluorobenzaldehyde (4.1 g, 20 mmol) (Alfa) was reacted with methyl 3-chloro-4-hydroxybenzoate (4 g, 21 mmol)(Lancaster) and $K_2CO_3$ in N,N-dimethylacetamide to give 4-(4-bromo-2-formyl-phenoxy)-3-chloro-benzoic acid methyl ester as an off white solid (Yield 3.7 g, 50%).

EXAMPLE 58b

Preparation of intermediate 1-[5-bromo-2-(2-chloro-4-methoxycarbonyl-phenoxy)-phenyl]-3-trimethylsilyoxy-2-aza-1,3-butadiene

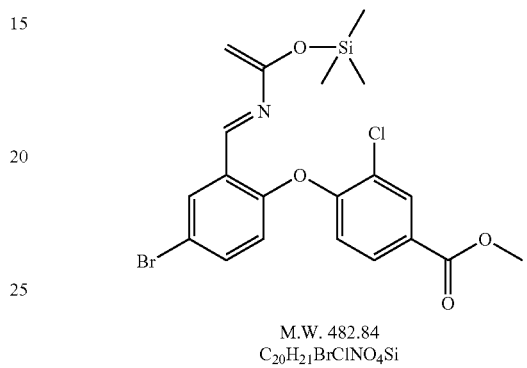

M.W. 482.84
$C_{20}H_{21}BrClNO_4Si$

In a manner similar to the method described in example 1d, 4-(4-bromo-2-formyl-phenoxy)-3-chloro-benzoic acid methyl ester (3.7 g, 10 mmol) was reacted with 1,1,1, 3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1.0 g, 13.6 mmol) to give crude 1-[5-bromo-2-(2-chloro-4-methoxycarbonyl-phenoxy)-phenyl]-3-trimethylsilyoxy-2-aza-1, 3-butadiene as a yellow gum and used for the next step without further purification.

EXAMPLE 58c

Preparation of racemic(2'R, 3R, 4'S)-2'-[5-bromo-2-(2-chloro-4-methoxycarbonyl-phenoxy)-phenyl]-6-chloro-4'-(3-chlorophenyl)spiro[3H-indole-3,3'-piperidine]-2,6'(1H)-dione

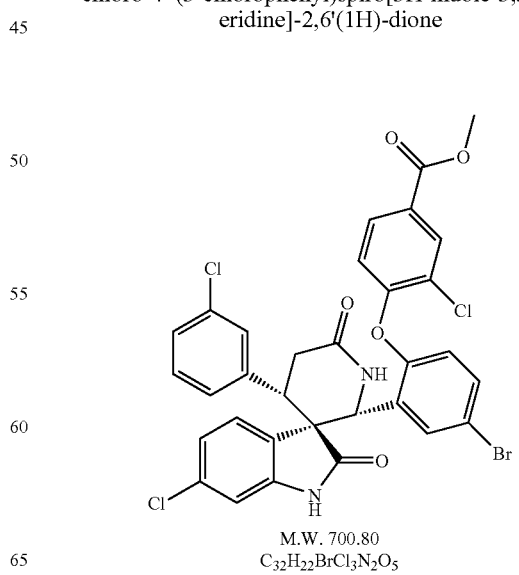

M.W. 700.80
$C_{32}H_{22}BrCl_3N_2O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.6 g, 1.53 mmol) was reacted with 1-[5-bromo-2-(2-methoxy-4-methoxycarbonyl-phenoxy)-phenyl]-3-trimethylsilyoxy-2-aza-1,3-butadiene (4.6 g, 9.5 mmol) in toluene then trifluoroacetic acid in dichloromethane to give racemic(2'R, 3R, 4'S)-2'-[5-bromo-2-(2-chloro-4-methoxycarbonyl-phenoxy)-phenyl]-6-chloro-4'-(3-chlorophenyl)spiro[3H-indole-3,3'-piperidine]-2,6'(1H)-dione as a yellow solid (Yield 0.6 g, 56%)

HRMS(ES$^+$) m/z Calcd for $C_{32}H_{22}BrCl_3N_2O_5$+H [(M+H)$^+$]: 698.9851. Found: 698.9845.

EXAMPLE 59a

Preparation of intermediate 4-(4-chloro-2-formyl-phenoxy)-benzoic acid methyl ester

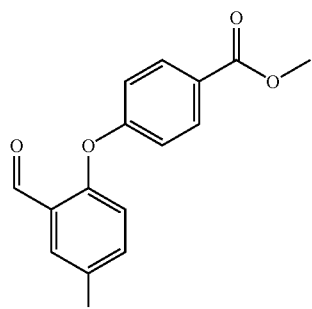

M.W. 290.71
$C_{15}H_{11}ClO_4$

In a manner similar to the method described in Example 50a, 5-chloro-2-fluorobenzaldehyde (4.2 g, 26 mmol) (Alfa) was reacted with methyl 4-hydroxybenzoate (4 g, 28 mmol) (Aldrich) and $K_2CO_3$ in N,N-dimethylacetamide to give 4-(4-chloro-2-formyl-phenoxy)-benzoic acid methyl ester as a white solid (Yield 6.1 g, 80%).

EXAMPLE 59b

Preparation of intermediate 1-[5-chloro-2-(4-methoxycarbonyl-phenoxy)-phenyl]-3-trimethylsilyoxy-2-aza-1,3-butadiene

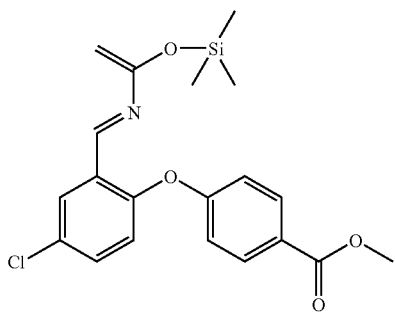

M.W. 403.94
$C_{20}H_{22}ClNO_4Si$

In a manner similar to the method described in example 1d, 4-(4-chloro-2-formyl-phenoxy)-benzoic acid methyl ester (2.9 g, 10 mmol) was reacted with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1.0 g, 10 mmol) to give crude 1-[5-chloro-2-(4-methoxycarbonyl-phenoxy)-phenyl]-3-trimethylsilyoxy-2-aza-1,3-butadiene as a yellow gum and used for the next step without further purification.

EXAMPLE 59c

Preparation of racemic(2'R, 3R, 4'S)-6-chloro-2'-[5-chloro-2-(4-methoxycarbonyl-phenoxy)-phenyl]-4'-(3-chlorophenyl)spiro[3H-indole-3,3'-piperidine]-2,6'(1H)-dione

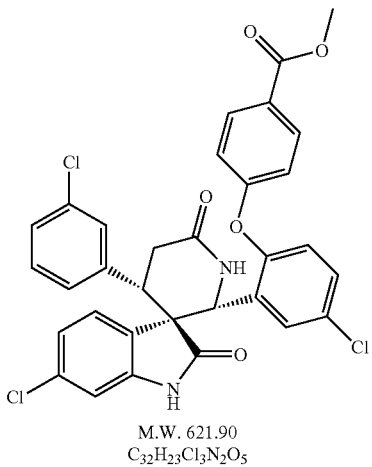

M.W. 621.90
$C_{32}H_{23}Cl_3N_2O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.0 g, 2.56 mmol) was reacted with 1-[5-chloro-2-(4-methoxycarbonyl-phenoxy)-phenyl]-3-trimethylsilyoxy-2-aza-1,3-butadiene (4 g, 9.9 mmol) in toluene then trifluoroacetic acid in dichloromethane to give racemic(2'R, 3R, 4'S)-6-chloro-2'-[5-chloro-2-(4-methoxycarbonyl-phenoxy)-phenyl]-4'-(3-chlorophenyl)spiro[3H-indole-3,3'-piperidine]-2,6'(1H)-dione as an off white solid (Yield 1.2 g, 75%)

HRMS(ES$^+$) m/z Calcd for $C_{32}H_{23}Cl_3N_2O_5$+H [(M+H)$^+$]: 621.0746. Found: 621.0744.

EXAMPLE 60a

Preparation of intermediate 4-(2-hydroxy-ethoxy)-phenol

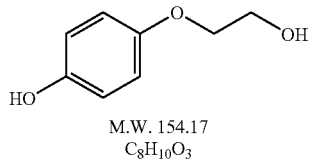

M.W. 154.17
$C_8H_{10}O_3$

To a solution of 4-hydroxyphenoxyacetic acid (4.9 g, 29 mmol) (Aldrich) in anhydrous tetrahydrofuran (30 mL) at 0° C. was added borane tetrahydrofuran (1 M, 90 mL, 90 mmol) dropwise. The reaction mixture was then stirred at room temperature for 2 h. The mixture was concentrated and residue was partitioned between ethyl acetate and water. Organic layer was separated, washed with brine, dried over MgSO$_4$, and concentrated to give title compound as a yellow oil (4.2 g, 94%)

EXAMPLE 60b

Preparation of intermediate 4-[2-(tert-butyl-dimethyl-silanyloxy)-ethoxy]-phenol

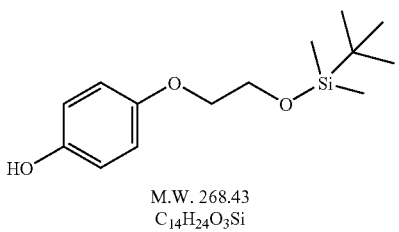

M.W. 268.43
C$_{14}$H$_{24}$O$_3$Si

To a solution of 4-(2-hydroxy-ethoxy)-phenol (4.2 g, 27 mmol) in anhydrous N,N-dimethylformamide (30 mL) at 0° C. was added imidazole (2.1 g, 31 mmol) and tert-butyldimethylchlorosilane (4 g, 27 mmol). The reaction mixture was then stirred at 0° C. for 1 h. The mixture was partitioned between ethyl acetate and water. Organic layer was separated, aqueous layer was extracted with ethyl acetate. The combined organic layers were washed with water and brine, dried over MgSO$_4$, and concentrated. The residue was purified by chromatography (EtOAc:hexanes=1;4) to give 4-[2-(tert-butyl-dimethyl-silanyloxy)-ethoxy]-phenol as a colorless oil (5.1 g, 70%)

EXAMPLE 60c

Preparation of intermediate 2-[4-(2-hydroxy-ethoxy)-phenoxy]-5-iodo-benzaldehyde

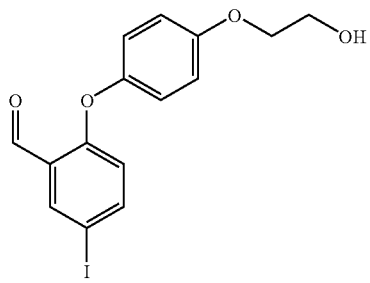

M.W. 384.17
C$_{15}$H$_{13}$IO$_4$

In a manner similar to the method described in Example 50a, 2-fluoro-5-iodobenzaldehyde (2.5 g, 10 mmol) (Aldrich) was reacted with 4-[2-(tert-butyl-dimethyl-silanyloxy)-ethoxy]-phenol (2.7 g, 10 mmol) and K$_2$CO$_3$ in N,N-dimethylacetamide at 170° C. for 0.5 h to give 2-[4-(2-hydroxy-ethoxy)-phenoxy]-5-iodo-benzaldehyde as a yellow solid (Yield 3.8 g, 98%).

EXAMPLE 60d

Preparation of intermediate 2-{4-[2-(tert-butyl-dimethyl-silanyloxy)-ethoxy]-phenoxy}-5-iodo-benzaldehyde

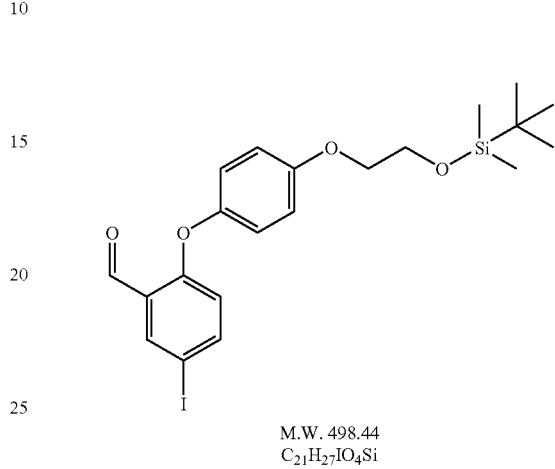

M.W. 498.44
C$_{21}$H$_{27}$IO$_4$Si

In a manner similar to the method described in Example 60b, 2-[4-(2-hydroxy-ethoxy)-phenoxy]-5-iodo-benzaldehyde (3.8 g, 9.8 mmol) was reacted with tert-butyldimethylchlorosilane (1.8 g, 12 mmol) and imidazole in N,N-dimethylformamide to give 2-{4-[2-(tert-butyl-dimethyl-silanyloxy)-ethoxy]-phenoxy}-5-iodo-benzaldehyde as a white solid (Yield 4.7 g, 95%).

EXAMPLE 60e

Preparation of intermediate 1-{2-{4-[2-(tert-butyl-dimethyl-silanyloxy)-ethoxy]-phenoxy}-5-iodo-phenyl}-3-trimethylsilyoxy-2-aza-1,3-butadiene

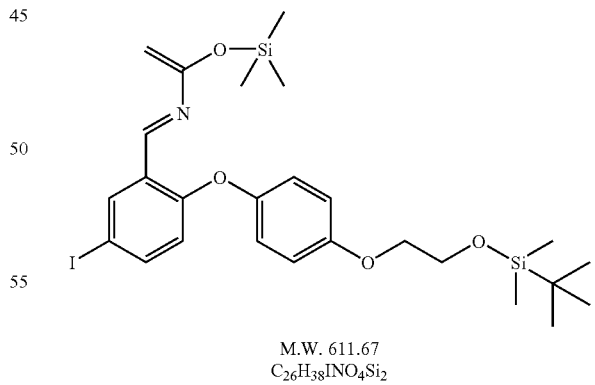

M.W. 611.67
C$_{26}$H$_{38}$INO$_4$Si$_2$

In a manner similar to the method described in example 1d, 2-{4-[2-(tert-butyl-dimethyl-silanyloxy)-ethoxy]-phenoxy}-5-iodo-benzaldehyde (4.7 g, 9.4 mmol) was reacted with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1.0 g, 10 mmol) to give crude 1-{2-{4-[2-

(tert-butyl-dimethyl-silanyloxy)-ethoxy]-phenoxy}-5-iodo-phenyl}-3-trimethylsilyoxy-2-aza-1,3-butadiene as a yellow gum and used for the next step without further purification.

EXAMPLE 60f

Preparation of racemic(2'R, 3R, 4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)dione

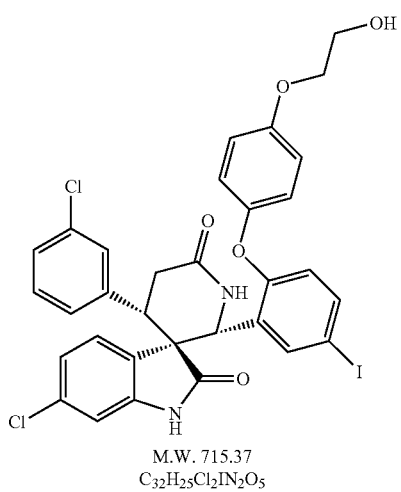

M.W. 715.37
$C_{32}H_{25}Cl_2IN_2O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.0 g, 2.56 mmol) was reacted with 1-{2-{4-[2-(tert-butyl-dimethyl-silanyloxy)-ethoxy]-phenoxy}-5-iodo-phenyl}-3-trimethylsilyoxy-2-aza-1,3-butadiene (5 g, 8.2 mmol) in toluene then trifluoroacetic acid in dichloromethane to give racemic(2'R, 3R, 4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione as a light yellow solid (Yield 0.9 g, 49%)

HRMS(ES$^+$) m/z Calcd for $C_{32}H_{25}Cl_2IN_2O_5$+H [(M+H)$^+$]: 715.0258. Found: 715.0258.

EXAMPLE 60g

Preparation of chiral(2'R, 3R, 4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione

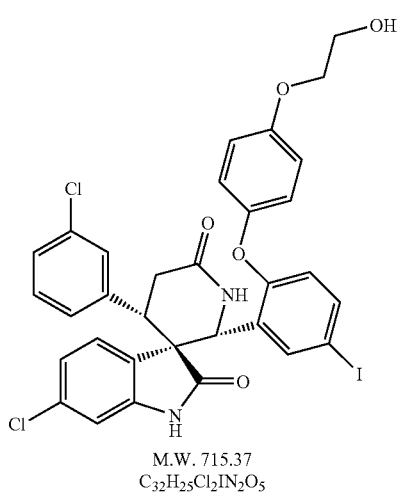

M.W. 715.37
$C_{32}H_{25}Cl_2IN_2O_5$

Separation of the two enantiomers from racemic(2'R, 3R, 4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione (220 mg) was conducted by chiral SFC to provide chiral (2'R, 3R, 4'S)-6-chloro-4'-(3-chlorophenyl)-2'-{2-[4-(2-hydroxy-ethoy)-phenoxy]-5-iodo-phenyl}spiro[3H-indole-3,3'-piperidine]-2,6'(1H)-dione as a yellow solid (93 mg, 42%) and chiral(2'S, 3S, 4'R)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione as a yellow solid (87 mg, 40%)

EXAMPLE 61a

Preparation of racemic(2'R, 3R, 4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione

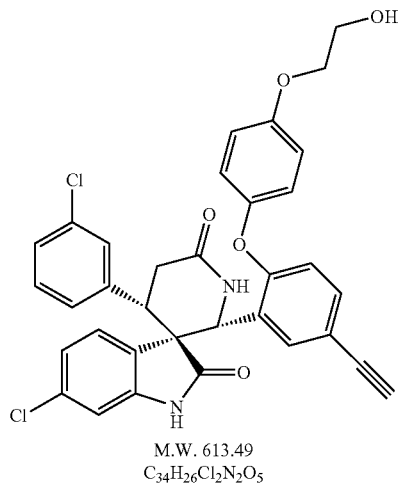

M.W. 613.49
$C_{34}H_{26}Cl_2N_2O_5$

In a manner similar to the method described in Example 2, racemic(2'R, 3R, 4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione (0.9 g, 1.26 mmol) was reacted with trimethylsilyl acetylene (0.25 g, 2.5 mmol), CuI (0.48 g, 2.5 mmol), triethylamine (0.25 g, 2.5 mmol) and dichlorobis(triphenylphosphine) palladium(0) (0.18 g, 0.025 mmol) in tetrahydrofuran, then treated with aqueous NaOH solution in methanol to give racemic(2'R, 3R, 4'S)-6-chloro-4'-(3-chlorophenyl)-2'-{5-ethynyl-2-[4-(2-ethoxy)-phenoxy]-phenyl}spiro[3H-indole-3,3'-piperidine]-2,6'(1H)-dione as an off white solid (Yield 0.58 g, 75%).

HRMS(ES$^+$) m/z Calcd for $C_{34}H_{26}Cl_2N_2O_5$+H [(M+H)$^+$]: 613.1292. Found: 613.1289.

EXAMPLE 61b

Preparation of chiral(2'R, 3R, 4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione

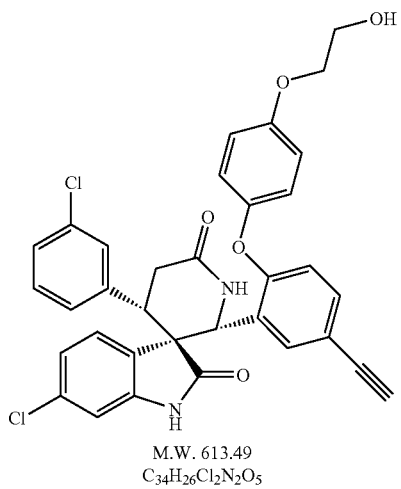

M.W. 613.49
$C_{34}H_{26}Cl_2N_2O_5$

Separation of the two enantiomers from racemic(2'R, 3R, 4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione (550 mg) was conducted by chiral SFC to provide chiral(2'R, 3R, 4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione as na off white solid (195 mg, 36%) and chiral(2'S, 3S, 4'R)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione as na off white solid (183 mg, 30%).

EXAMPLE 62a

Preparation of intermediate 5-chloro-2-[4-(2-hydroxy-ethoxy)-phenoxy]-benzaldehyde

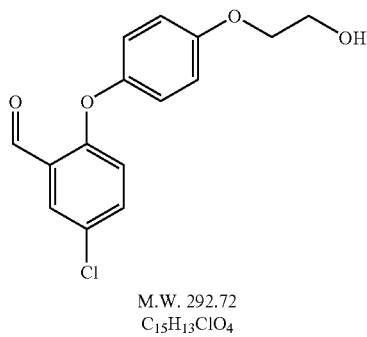

M.W. 292.72
$C_{15}H_{13}ClO_4$

In a manner similar to the method described in Example 50a, 5-chloro-2-fluorobenzaldehyde (1.2 g, 7.6 mmol) (Aldrich) was reacted with 4-[2-(tert-butyl-dimethyl-silanyloxy)-ethoxy]-phenol (2.1 g, 7.8 mmol) prepared in Example 60b and $K_2CO_3$ in N,N-dimethylacetamide at 170° C. for 0.5 h to give 5-chloro-2-[4-(2-hydroxy-ethoxy)-phenoxy]-benzaldehyde as a colorless oil (Yield 1.68 g, 75%).

EXAMPLE 62b

Preparation of intermediate 2-{4-[2-(tert-butyl-dimethyl-silanyloxy)-ethoxy]-phenoxy}-5-chloro-benzaldehyde

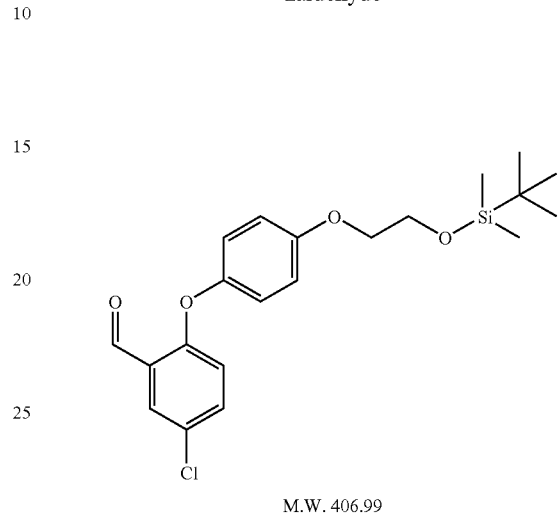

M.W. 406.99
$C_{21}H_{27}ClO_4Si$

In a manner similar to the method described in Example 60b, 5-chloro-2-[4-(2-hydroxy-ethoxy)-phenoxy]-benzaldehyde (1.68 g, 5.7 mmol) was reacted with tert-butyldimethylchlorosilane (1.3 g, 8.6 mmol) and imidazole in N,N-dimethylformamide to give 2-{4-[2-(tert-butyl-dimethyl-silanyloxy)-ethoxy]-phenoxy}-5-chloro-benzaldehyde as a white solid (Yield 2.1 g, 90%).

EXAMPLE 62c

Preparation of intermediate 1-{2-{4-[2-(tert-butyl-dimethyl-silanyloxy)-ethoxy]-phenoxy}-5-chloro-phenyl}-3-trimethylsilyoxy-2-aza-1,3-butadiene

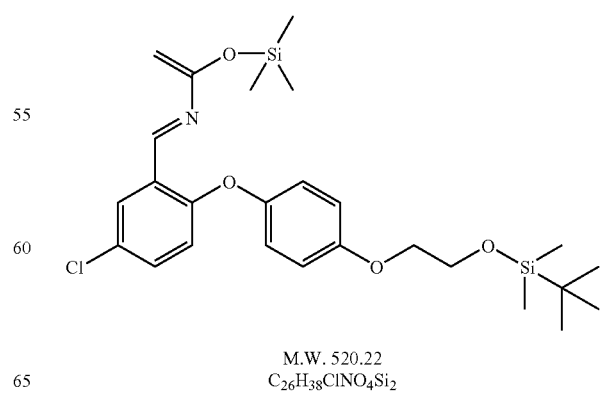

M.W. 520.22
$C_{26}H_{38}ClNO_4Si_2$

In a manner similar to the method described in example 1d, 2-{4-[2-(tert-butyl-dimethyl-silanyloxy)-ethoxy]-phenoxy}-5-chloro-benzaldehyde (2.1 g, 5.1 mmol) was reacted with 1,1,3,3,3-hexamethyldisilazane (0.8 g, 5 mmol), n-butyllithium (2.5 M, 2 mL, 5 mmol), trimethylsilyl chloride (0.55 g, 5 mmol), triethylamine (0.68 g, 6.8 mmol) and acetyl chloride (0.5 g, 6.8 mmol) to give crude 1-{2-{4-[2-(tert-butyl-dimethyl-silanyloxy)-ethoxy]-phenoxy}-5-chloro-phenyl}-3-trimethylsilyoxy-2-aza-1,3-butadiene as a yellow gum and used for the next step without further purification.

EXAMPLE 62d

Preparation of racemic(2'R, 3R, 4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione

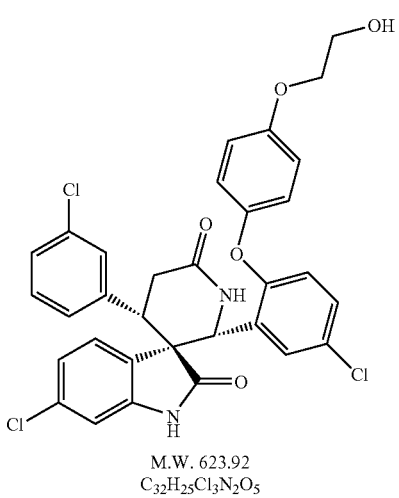

M.W. 623.92
$C_{32}H_{25}Cl_3N_2O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.4 g, 1.03 mmol) was reacted with 1-{2-{4-[2-(tert-butyl-dimethyl-silanyloxy)-ethoxy]-phenoxy}-5-chloro-phenyl}-3-trimethylsilyoxy-2-aza-1,3-butadiene (2.5 g, 4.8 mmol) in toluene then trifluoroacetic acid in dichloromethane to give racemic (2'R, 3R, 4'S)-6-chloro-2'-{5-chloro-2-[4-(2-hydroxy-ethoxy)-phenoxy]-phenyl}4'-(3-chlorophenyl)spiro[3H-indole-3,3'-piperidine]-2,6'(1H)-dione as a light yellow solid (Yield 0.36 g, 57%)

HRMS(ES⁺) m/z Calcd for $C_{32}H_{25}Cl_3N_2O_5$+H [(M+H)⁺]: 623.0902. Found: 623.0900.

EXAMPLE 62e

Preparation of chiral(2'R, 3R, 4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione

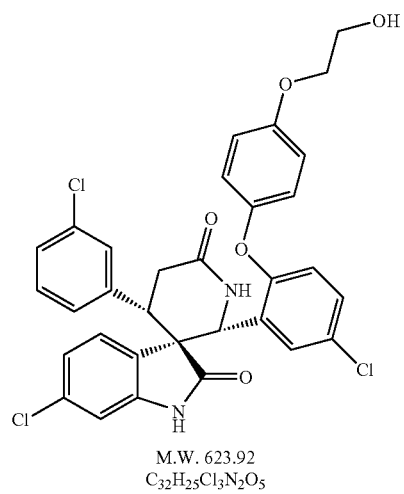

M.W. 623.92
$C_{32}H_{25}Cl_3N_2O_5$

Separation of the two enantiomers from racemic(2'R, 3R, 4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione (200 mg) was conducted by chiral SFC to provide chiral (2'R, 3R, 4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione as a yellow solid (84 mg, 42%) and chiral(2'S, 3S, 4'R)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione as a yellow solid (77 mg, 39%).

EXAMPLE 63a

Preparation of intermediate 5-bromo-2-(2,6-dimethyl-pyridin-4-yloxy)-benzaldehyde

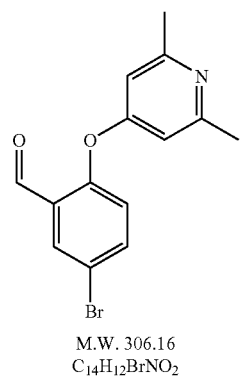

M.W. 306.16
$C_{14}H_{12}BrNO_2$

In a manner similar to the method described in Example 50a, 5-bromo-2-fluorobenzaldehyde (4.1 g, 20 mmol) (Alfa) was reacted with 2,6-dimethyl-4-hydroxypyridine (2.5 g, 20 mmol) and K₂CO₃ in N,N-dimethylacetamide to give 5-bromo-2-(2,6-dimethyl-pyridin-4-yloxy)-benzaldehyde as an off white solid (Yield 6 g, 98%).

EXAMPLE 63b

Preparation of intermediate 1-[5-bromo-2-(2,6-dimethyl-pyridin-4-yloxy)-phenyl]-3-trimethylsilyoxy-2-aza-1,3-butadiene

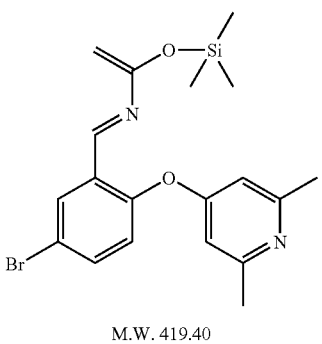

M.W. 419.40
$C_{19}H_{23}BrN_2O_2Si$

In a manner similar to the method described in example 1d, 5-bromo-2-(2,6-dimethyl-pyridin-4-yloxy)-benzaldehyde (3.1 g, 10 mmol) was reacted with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1.0 g, 13.6 mmol) to give crude 1-[5-bromo-2-(2,6-dimethyl-pyridin-4-yloxy)-phenyl]-3-trimethylsilyoxy-2-aza-1,3-butadiene as a yellow gum and used for the next step without further purification.

EXAMPLE 63c

Preparation of racemic(2'R, 3R, 4'S)-2'-[5-bromo-2-(2,6-dimethyl-4-pyridinyloxy)-phenyl]-6-chloro-4'-(3-chlorophenyl)spiro[3H-indole-3,3'-piperidine]-2,6'(1H)-dione

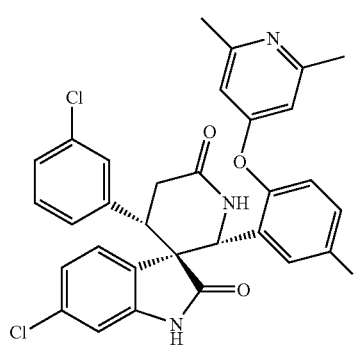

M.W. 637.36
$C_{31}H_{24}BrCl_2N_3O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.0 g, 2.56 mmol) was reacted with 1-[5-bromo-2-(2,6-dimethyl-pyridin-4-yloxy)-phenyl]-3-trimethylsilyoxy-2-aza-1,3-butadiene (4.2 g, 10 mmol) in toluene then trifluoroacetic acid in dichloromethane to give racemic(2'R, 3R, 4'S)-2'-[5-bromo-2-(2,6-dimethyl-4-pyridinyloxy)-phenyl]-6-chloro-4'-(3-chlorophenyl)spiro[3H-indole-3,3'-piperidine]-2,6'(1H)-dione as a white solid (Yield 0.99 g, 61%)
HRMS(ES⁺) m/z Calcd for $C_{31}H_{24}BrCl_2N_3O_3$+H [(M+H)⁺]: 636.0451. Found: 636.0454.

EXAMPLE 64a

Preparation of intermediate 5-chloro-2-Iodo-benzaldehyde

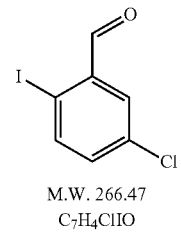

M.W. 266.47
$C_7H_4ClIO$

To a solution of 5-chloro-2-iodo benzoic acid (4.92 g, 17 mmol) (TRANS) in anhydrous tetrahydrofuran (100 mL) at 0° C. was added borane tetrahydrofuran (1 M, 34 mL, 34 mmol) dropwise. The reaction mixture was then stirred at room temperature for 18 h. The mixture was concentrated and residue was partitioned between ethyl acetate and water. Organic layer was separated, washed with brine, dried over MgSO₄, and concentrated to give a colorless oil. The oil was dissolved into 1,2-dichloroethane (50 mL), and activated MnO₂ (15 g) was added. The mixture was then heated at reflux for 2 h, cooled to room temperature, and filtered through a short pad of celite. The filtrated was concentrated and purified by chromatography (EtOAc:hexanes=1;8) to give 5-chloro-2-Iodo-benzaldehyde as a white solid (Yield 5.5 g, 25%).

EXAMPLE 64b

Preparation of intermediate 1-(5-chloro-2-iodophenyl)-3-trimethylsilyoxy-2-aza-1,3-butadiene

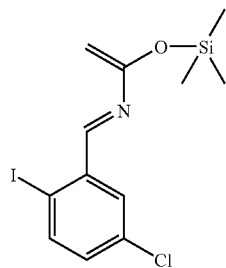

M.W. 379.70
$C_{12}H_{15}ClINOSi$

In a manner similar to the method described in example 5d, 5-chloro-2-iodobenzaldehyde prepared in example 23a (3.97 g, 15 mmol) was used as the starting material in place of 2-[2-(tert-butyl-dimethyl-silanyloxy)-ethoxy]-5-iodo-benzaldehyde to react with 1,1,3,3,3-hexamethyldisilazane (2.4 g, 15 mmol), n-butyllithium (2.5 M, 6 mL, 15 mmol), trimethylsilyl chloride (1.6 g, 15 mmol), triethylamine (2 g, 20 mmol) and acetyl chloride (1.5 g, 20 mmol) to give crude 1-(5-chloro-2-iodophenyl)-3-trimethylsilyoxy-2-aza-1,3-butadiene as a yellow gum and used for the next step without further purification.

EXAMPLE 64c

Preparation of intermediate racemic(2'R, 3R, 4'S)-6-chloro-4'-(3-chlorophenyl)-2'-(5-chloro-2-iodophenyl)spiro[3H-indole-3,3'-piperidine]-2,6'(1H)-dione

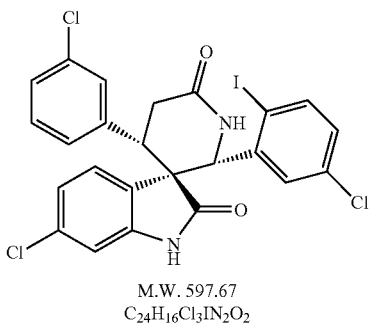

M.W. 597.67
$C_{24}H_{16}Cl_3IN_2O_2$

In a manner similar to the method described in example 7b, E/Z-6-chloro-3-(3-chloro-benzylidene)-2-oxo-2,3-dihydro-indole-1-carboxylic acid tert-butyl ester prepared in example 1b (2 g, 5.6 mmol) was reacted with crude 1-(5-chloro-2-iodophenyl)-3-trimethylsilyoxy-2-aza-1,3-butadiene prepared in example 23b (5.6 g, 15 mmol) in toluene and then trifluoroacetic acid in dichloromethane to give racemic(2'R, 3R, 4'S)-6-chloro-4'-(3-chlorophenyl)-2'-(5-chloro-2-iodophenyl)spiro[3H-indole-3,3'-piperidine]-2,6'(1H)-dione as a yellow solid (Yield 2.1 g, 63%)

HRMS(ES$^+$) m/z Calcd for $C_{24}H_{16}Cl_3IN_2O_2$+H [(M+H)$^+$]: 596.9395. Found: 596.9393.

EXAMPLE 64d

Preparation of racemic(2'R, 3R, 4'S)-6-chloro-2'-(5-chloro-2-imidazol-1-yl-phenyl)-4'-(3-chlorophenyl)spiro[3H-indole-3,3'-piperidine]-2,6'(1H)-dione

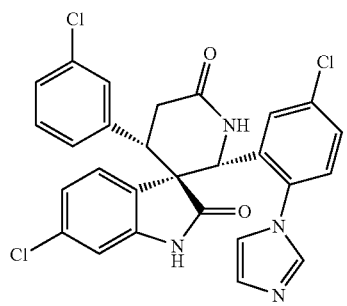

M.W. 537.83
$C_{27}H_{19}Cl_3N_4O_2$

A solution of racemic(2'R, 3R, 4'S)-6-chloro-4'-(3-chlorophenyl)-2'-(5-chloro-2-iodophenyl)spiro[3H-indole-3,3'-piperidine]-2,6'(1H)-dione (0.3 g, 0.5 mmol) in anhydrous N,N-dimethylformamide (10 mL) was added $Cs_2CO_3$ (1.2 g, 4 mmol) (Aldrich), CuI (95 mg, 0.5 mmol) (Aldrich), N,N,N',N'-tetramethylethylenediamine (0.2 mL, 2 mmol), and imidazole (80 mg, 1 mmol). The mixture was heated under nitrogen at 170° C. for 0.5 h. The mixture was cooled to room temperature, partitioned between ethyl acetate and water. The organic layer was separated, and the aqueous layer was extracted with ethyl acetate. The organic layers were combined, washed with brine, dried over $MgSO_4$, and concentrated. The residue was purified by chromatography (EtOAc: MeOH=9: 1) to give a crude product 997 mg), which was further purified by RP-HPLC to give racemic(2'R, 3R, 4'S)-6-chloro-2'-(5-chloro-2-imidazol-1-yl-phenyl)-4'-(3-chlorophenyl)spiro[3H-indole-3,3'-piperidine]-2,6'(1H)-dione as a white solid (Yield 16 mg).

HRMS(ES$^+$) m/z Calcd for $C_{27}H_{19}Cl_3N_4O_2$+H [(M+H)$^+$]: 537.0647. Found: 537.0646.

EXAMPLE 65a

Preparation of intermediate 4-(2-formyl-4-iodo-phenoxy)-benzonitrile

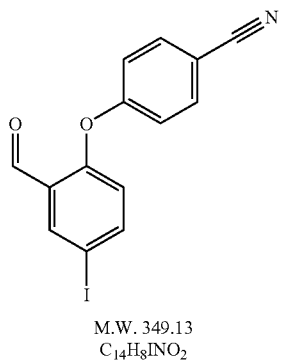

M.W. 349.13
$C_{14}H_8INO_2$

In a manner similar to the method described in Example 50a, 2-fluoro-5-iodobenzaldehyde (2 g, 8 mmol) (Aldrich) was reacted with 4-cyanophenol (1.43 g, 12 mmol) and $K_2CO_3$ in N,N-dimethylacetamide to give 4-(2-formyl-4-iodo-phenoxy)-benzonitrile as a light yellow solid (Yield 1.9 g, 70.4%).

EXAMPLE 65b

Preparation of intermediate 1-[2-(4-cyano-phenoxy)-5-iodo-phenyl]-3-trimethylsilyoxy-2-aza-1,3-butadiene

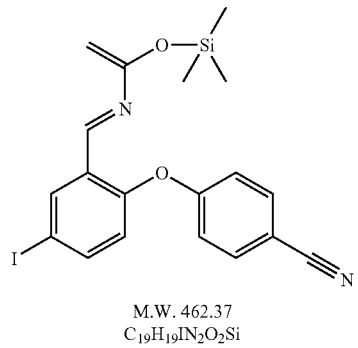

M.W. 462.37
$C_{19}H_{19}IN_2O_2Si$

In a manner similar to the method described in example 1d, 4-(2-formyl-4-iodo-phenoxy)-benzonitrile (1.9 g, 5.44 mmol) was reacted with 1,1,1,3,3,3-hexamethyldisilazane (1.13 mL, 5.44 mmol), n-butyllithium (2.5 M, 2.18 mL, 5.45 mmol), trimethylsilyl chloride (0.69 mL, 5.44 mmol), triethylamine (0.98 mL, 7.07 mmol) and acetyl chloride (0.66 mL, 7.07 mmol) to give crude 1-[2-(4-cyano-phenoxy)-5-iodo-phenyl]-3-trimethylsilyoxy-2-aza-1,3-butadiene as a yellow gum and used for the next step without further purification.

EXAMPLE 65c

Preparation of racemic(2'R, 3R, 4'S)-6-chloro-4'-(3-chlorophenyl)-2'-[2-(4-cyano-phenoxy)-5-iodo-phenyl]spiro[3H-indole-3,3'-piperidine]-2,6'(1H)-dione

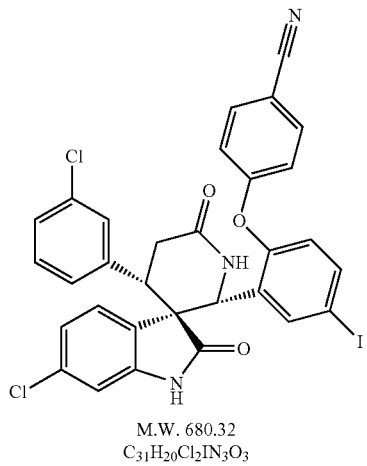

M.W. 680.32
$C_{31}H_{20}Cl_2IN_3O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.85 g, 2.18 mmol) was reacted with 1-[2-(4-cyano-phenoxy)-5-iodo-phenyl]-3-trimethylsilyoxy-2-aza-1,3-butadiene (5.44 mmol) in toluene then trifluoroacetic acid in dichloromethane to give racemic(2'R, 3R, 4'S)-6-chloro-4'-(3-chlorophenyl)-2'-[2-(4-cyano-phenoxy)-5-iodo-phenyl]spiro[3H-indole-3,3'-piperidine]-2,6'(1H)-dione as a white solid (Yield 0.8 g, 54%)

HRMS(ES$^+$) m/z Calcd for $C_{31}H_{20}Cl_2IN_3O_3$+H [(M+H)$^+$]: 679.9999. Found: 679.9999.

EXAMPLE 65d

Preparation of chiral(2'R, 3R, 4'S)-6-chloro-4'-(3-chlorophenyl)-2'-[2-(4-cyano-phenoxy)-5-iodo-phenyl]spiro[3H-indole-3,3'-piperidine]-2,6'(1H)-dione

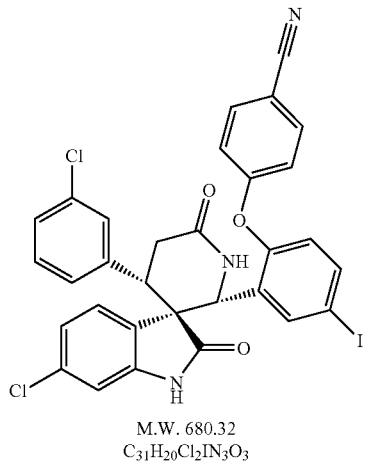

M.W. 680.32
$C_{31}H_{20}Cl_2IN_3O_3$

Separation of the two enantiomers from racemic(2'R, 3R, 4'S)-6-chloro-4'-(3-chlorophenyl)-2'-[2-(4-cyano-phenoxy)-5-iodo-phenyl]spiro[3H-indole-3,3'-piperidine]-2,6'(1H)-dione (500 mg) was conducted by chiral SFC to provide chiral (2'R, 3R, 4'S)-6-chloro-4'-(3-chlorophenyl)-2'-[2-(4-cyano-phenoxy)-5-iodo-phenyl]spiro[3H-indole-3,3'-piperidine]-2,6'(1H)-dione as a white solid (0.23 g, 46%) and chiral(2'S, 3S, 4'R)-6-chloro-4'-(3-chlorophenyl)-2'-[2-(4-cyano-phenoxy)-5-iodo-phenyl]spiro[3H-indole-3,3'-piperidine]-2,6'(1H)-dione as a white solid (0.21 g, 42%).

EXAMPLE 66a

Preparation of racemic(2'R, 3R, 4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione

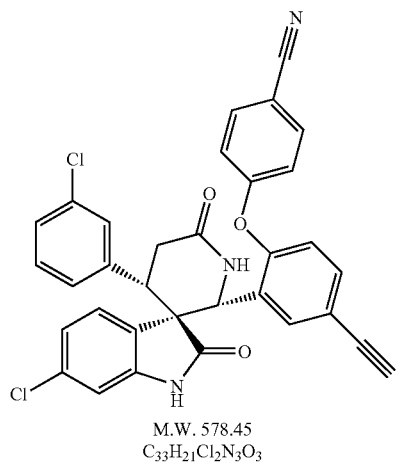

M.W. 578.45
$C_{33}H_{21}Cl_2N_3O_3$

In a manner similar to the method described in example 6a, racemic(2'R, 3R, 4'S)-6-chloro-4'-(3-chlorophenyl)-2'-[2-(4-cyano-phenoxy)-5-iodo-phenyl]spiro[3H-indole-3,3'-piperidine]-2,6'(1H)-dione (0.65 g, 0.96 mmol) was reacted with trimethylsilyl acetylene (0.94 g, 9.6 mmol), CuI (10 mg), triethylamine (2.89 g, 28.7 mmol), and dichlorobis(triphenylphosphine) palladium (0) (53.6 mg, 0.077 mmol) in anhydrous N,N-dimethylformamide, and then treated with aqueous NaOH in methanol to give racemic(2'R, 3R, 4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione as an off white solid (Yield 0.285 g, 51%)

HRMS(ES$^+$) m/z Calcd for $C_{33}H_{21}Cl_2N_3O_3$+H [(M+H)$^+$]: 578.1033. Found: 578.1030.

EXAMPLE 66b

Preparation of chiral(2'R, 3R, 4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione

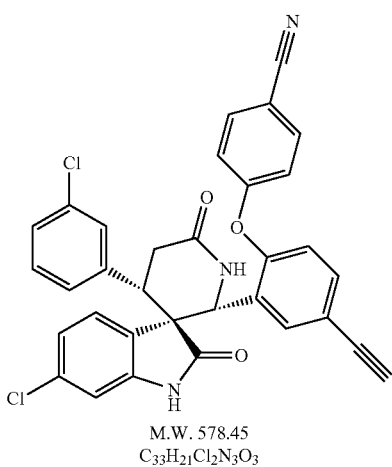

M.W. 578.45
C₃₃H₂₁Cl₂N₃O₃

Separation of the two enantiomers from racemic(2'R, 3R, 4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione (260 mg) was conducted by chiral SFC to provide chiral(2'R, 3R, 4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione as a white solid (98 mg, 38%) and chiral (2'S, 3S, 4'R)-6-chloro-4'-(3-chlorophenyl)-2'-[2-(4-cyano-phenoxy)-5-ethynyl-phenyl]spiro[3H-indole-3,3'-piperidine]-2,6'(1H)-dione as a white solid (102 mg, 39%).

EXAMPLE 67a

Preparation of intermediate 5-iodo-2-(4-methoxy-phenoxy)-benzaldehyde

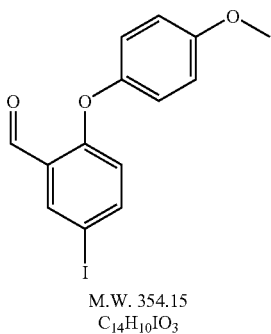

M.W. 354.15
C₁₄H₁₀IO₃

In a manner similar to the method described in Example 50a, 2-fluoro-5-iodobenzaldehyde (1.2 g, 4.8 mmol) (Aldrich) was reacted with 4-methoxyphenol (0.71 g, 5.76 mmol) and K₂CO₃ in N,N-dimethylacetamide to give 5-iodo-2-(4-methoxy-phenoxy)-benzaldehyde as a yellow oil (Yield 1.12 g, 66%).

EXAMPLE 67b

Preparation of intermediate 1-[5-iodo-2-(4-methoxy-phenoxy)-phenyl]-3-trimethylsilyoxy-2-aza-1,3-butadiene

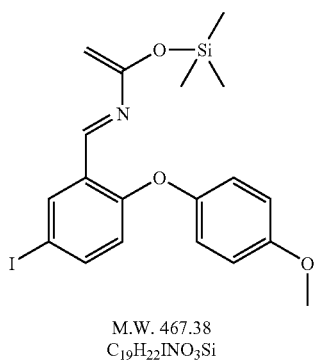

M.W. 467.38
C₁₉H₂₂INO₃Si

In a manner similar to the method described in example 1d, 5-iodo-2-(4-methoxy-phenoxy)-benzaldehyde (1.12 g, 3.16 mmol) was reacted with 1,1,1,3,3,3-hexamethyldisilazane (0.66 mL, 3.16 mmol), n-butyllithium (2.5 M, 1.26 mL, 3.16 mmol), trimethylsilyl chloride (0.4 mL, 3.16 mmol), triethylamine (0.57 mL, 4.1 mmol) and acetyl chloride (0.39 mL, 4.1 mmol) to give crude 1-[5-iodo-2-(4-methoxy-phenoxy)-phenyl]-3-trimethylsilyoxy-2-aza-1,3-butadiene as a yellow gum and used for the next step without further purification.

EXAMPLE 67c

Preparation of racemic(2'R, 3R, 4'S)-6-chloro-4'-(3-chlorophenyl)-2'-[5-iodo-2-(4-methoxy-phenoxy)-phenyl]spiro[3H-indole-3,3'-piperidine]-2,6'(1H)-dione

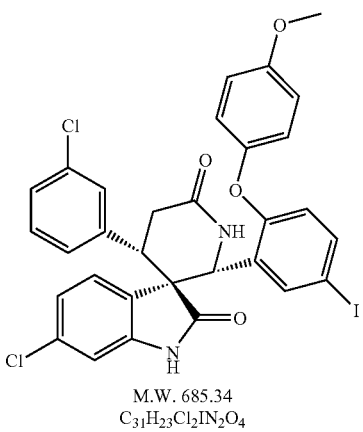

M.W. 685.34
C₃₁H₂₃Cl₂IN₂O₄

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.49 g, 1.26 mmol) was reacted with 1-[5-iodo- 2-(4-methoxy-phenoxy)-phenyl]-3-trimethylsilyoxy-2-aza-1,3-butadiene (3.16 mmol) in toluene then trifluoroacetic acid in dichloromethane to give racemic(2'R, 3R, 4'S)-6-chloro-4'-(3-chlorophenyl)-2'-[5-iodo-2-(4-methoxy-phenoxy)-phenyl]spiro[3H-indole-3,3'-piperidine]-2,6'(1H)-dione as a white solid (Yield 0.35 g, 41%)

HRMS(ES$^+$) m/z Calcd for $C_{31}H_{23}Cl_2IN_2O_4$+H [(M+H)$^+$]: 685.0153. Found: 685.0155.

EXAMPLE 68a

Preparation of racemic(2'R, 3R, 4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione

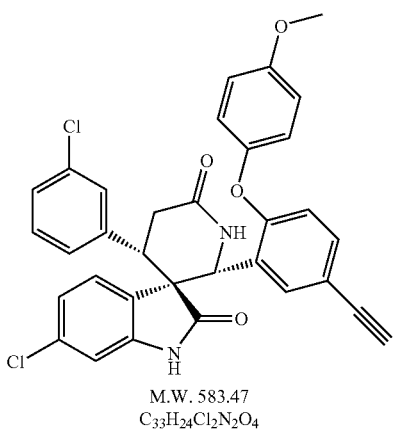

M.W. 583.47
$C_{33}H_{24}Cl_2N_2O_4$

In a manner similar to the method described in example 6a, racemic(2'R, 3R, 4'S)-6-chloro-4'-(3-chlorophenyl)-2'-[5-iodo-2-(4-methoxy-phenoxy)-phenyl]spiro[3H-indole-3,3'-piperidine]-2,6'(1H)-dione (0.29 g, 0.42 mmol) was reacted with trimethylsilyl acetylene (0.41 g, 4.2 mmol), CuI (5 mg), triethylamine (1.76 mL, 12.7 mmol), and dichlorobis(triphenylphosphine) palladium (0) (23.4 mg, 0.034 mmol) in anhydrous N,N-dimethylformamide, and then treated with aqueous NaOH in methanol to give racemic(2'R, 3R, 4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione as a white solid (Yield 0.15 g, 61%)

HRMS(ES$^+$) m/z Calcd for $C_{33}H_{24}Cl_2N_2O_4$+H [(M+H)$^+$]: 583.1186. Found: 583.1187.

EXAMPLE 68b

Preparation of chiral(2'R, 3R, 4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione

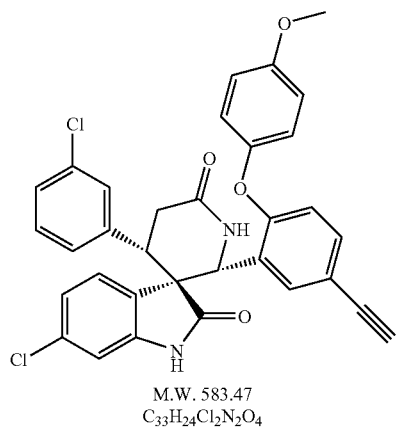

M.W. 583.47
$C_{33}H_{24}Cl_2N_2O_4$

Separation of the two enantiomers from racemic(2'R, 3R, 4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione (500 mg) was conducted by chiral SFC to provide chiral(2'R, 3R, 4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione as a light yellow solid (0.24 g, 48%) and chiral(2'S, 3S, 4'R)-6-chloro-4'-(3-chlorophenyl)-2'-[5-ethynyl-2-(4-methoxy-phenoxy)-phenyl]spiro[3H-indole-3,3'-piperidine]-2,6'(1H)-dione as a light yellow solid (0.24 g, 48%).

EXAMPLE 69a

Preparation of intermediate 4-(2-formyl-4-iodo-phenoxy)-benzoic acid methyl ester

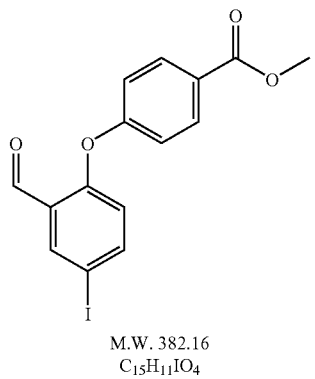

M.W. 382.16
$C_{15}H_{11}IO_4$

In a manner similar to the method described in Example 50a, 2-fluoro-5-iodobenzaldehyde (3.6 g, 14.4 mmol) (Aldrich) was reacted with methyl 4-hydroxybenzoate (2.62 g, 17.3 mmol) and $K_2CO_3$ in N,N-dimethylacetamide to give 4-(2-formyl-4-iodo-phenoxy)-benzoic acid methyl ester as a yellow oil (Yield 3.8 g, 69%).

EXAMPLE 69b

Preparation of intermediate 1-[5-iodo-2-(4-methoxycarbonyl-phenoxy)-phenyl]-3-trimethylsilyoxy-2-aza-1,3-butadiene

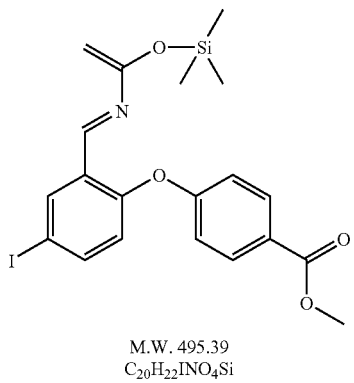

M.W. 495.39
$C_{20}H_{22}INO_4Si$

In a manner similar to the method described in example 1d, 4-(2-formyl-4-iodo-phenoxy)-benzoic acid methyl ester (3.8 g, 9.94 mmol) was reacted with 1,1,1,3,3,3-hexamethyldisilazane (2.06 mL, 9.94 mmol), n-butyllithium (2.5 M, 3.97 mL, 9.94 mmol), trimethylsilyl chloride (1.26 mL, 9.94 mmol), triethylamine (1.79 mL, 12.9 mmol) and acetyl chloride (1.22 mL, 12.9 mmol) to give crude 1-[5-iodo-2-(4methoxycarbonyl-phenoxy)-phenyl]-3-trimethylsilyoxy-2-aza-1,3-butadiene as a yellow gum and used for the next step without further purification.

EXAMPLE 69c

Preparation of racemic(2'R, 3R, 4'S)-6-chloro-4'-(3-chlorophenyl)-2'-[5-iodo-2-(4-methoxycarbonyl-phenoxy)-phenyl]spiro[3H-indole-3,3'-piperidine]-2,6'(1H)-dione

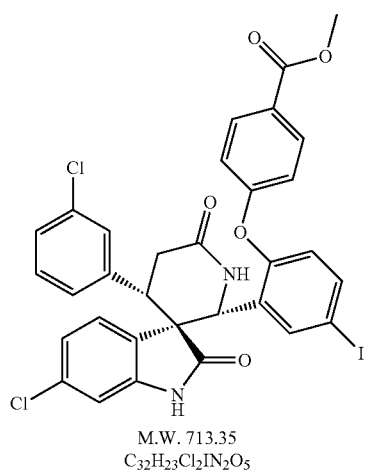

M.W. 713.35
$C_{32}H_{23}Cl_2IN_2O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.55 g, 3.98 mmol) was reacted with 1-[5-iodo-2-(4-methoxycarbonyl-phenoxy)-phenyl]-3-trimethylsilyoxy-2-aza-1,3-butadiene (9.94 mmol) in toluene then trifluoroacetic acid in dichloromethane to give racemic(2'R, 3R, 4'S)-6-chloro-4'-(3-chlorophenyl)-2'-[5-iodo-2-(4-methoxycarbonyl-phenoxy)-phenyl]spiro[3H-indole-3,3'-piperidine]-2,6'(1H)-dione as a white solid (Yield 1.5 g, 53%)

HRMS(ES+) m/z Calcd for $C_{32}H_{23}Cl_2IN_2O_5$+H [(M+H)+]: 713.0102. Found: 713.0102.

EXAMPLE 70

Preparation of racemic(2'R, 3R, 4'S)-6-chloro-4'-(3-chlorophenyl)-2'-[5-ethynyl-2-(4-methoxycarbonyl-phenoxy)-phenyl]spiro[3H-indole-3,3'-piperidine]-2,6'(1H)-dio

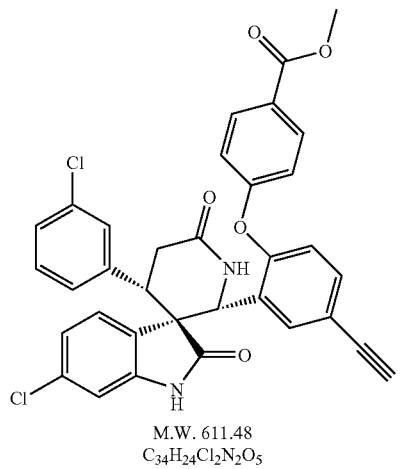

M.W. 611.48
$C_{34}H_{24}Cl_2N_2O_5$

In a manner similar to the method described in example 6a, racemic(2'R, 3R, 4'S)-6-chloro-4'-(3-chlorophenyl)-2'-[5-iodo-2-(4-methoxycarbonyl-phenoxy)-phenyl]spiro[3H-indole-3,3'-piperidine]-2,6'(1H)-dione (0.45 g, 0.63 mmol) was reacted with trimethylsilyl acetylene (0.45 g, 6.3 mmol), CuI (3 mg), triethylamine (2.63 mL, 18.9 mmol), and dichlorobis (triphenylphosphine) palladium (0) (35.3 mg, 0.05 mmol) in anhydrous N,N-dimethylformamide, and then treated with aqueous NaOH in methanol to give racemic(2'R, 3R, 4'S)-6-chloro-4'-(3-chlorophenyl)-2'-[5-ethynyl-2-(4-methoxycarbonyl-phenoxy)-phenyl]spiro[3H-indole-3,3'-piperidine]-2,6'(1H)-dione as a white solid (Yield 0.28 g, 73%)

HRMS(ES+) m/z Calcd for $C_{34}H_{24}Cl_2N_2O_5$+H [(M+H)+]: 611.1135. Found: 611.1134.

EXAMPLE 71

Preparation of racemic(2'R, 3R, 4'S)-6-chloro-4'-(3-chlorophenyl)-2'-[2-(4-hydroxycarbonyl-phenoxy)-5-iodo-phenyl]spiro[3H-indole-3,3'-piperidine]-2,6'(1H)-dione

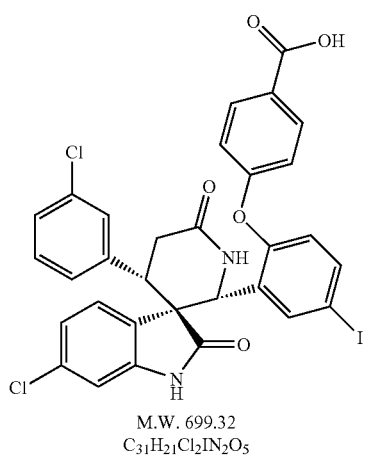

M.W. 699.32
$C_{31}H_{21}Cl_2IN_2O_5$

In a manner similar to the method described in Example 54, racemic(2'R, 3R, 4'S)-6-chloro-4'-(3-chlorophenyl)-2'-[5-ethynyl-2-(4-methoxycarbonyl-phenoxy)-phenyl]spiro[3H-indole-3,3'-piperidine]-2,6'(1H)-dione (0.68 g, 0.95 mmol) was reacted with an aqueous solution of LiOH (0.41 g, 9.5 mmol) in tetrahydrofuran and methanol to give racemic(2'R, 3R, 4'S)-6-chloro-4'-(3-chlorophenyl)-2'-[2-(4-hydroxycarbonyl-phenoxy)-5-iodo-phenyl]spiro[3H-indole-3,3'-piperidine]-2,6'(1H)-dione as a white solid (Yield 0.5 g, 75%).

HRMS(ES$^+$) m/z Calcd for $C_{31}H_{21}Cl_2IN_2O_5$+H [(M+H)$^+$]: 698.9945. Found: 698.9941.

EXAMPLE 72a

Preparation of racemic(2'R, 3R, 4'S)-2'-[2-(4-carbamoyl-phenoxy)-5-iodo-phenyl]-6-chloro-4'-(3-chlorophenyl)spiro[3H-indole-3,3'-piperidine]-2,6'(1H)-dione

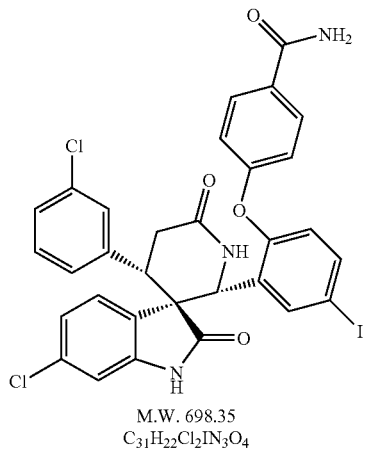

M.W. 698.35
$C_{31}H_{22}Cl_2IN_3O_4$

In a manner similar to the method described in Example 47a, racemic(2'R, 3R, 4'S)-6-chloro-4'-(3-chlorophenyl)-2'-[2-(4-hydroxycarbonyl-phenoxy)-5-iodo-phenyl]spiro[3H-indole-3,3'-piperidine]-2,6'(1H)-dione (0.4 g, 0.57 mmol) was reacted with EDCI (0.22 g, 1.14 mmol), HOBT (0.154 g, 1.14 mmol), diisopropylethylamine (0.29 g, 2.28 mmol), NH$_4$Cl (60 mg, 1.14 mmol) in N,N-dimethylformamide to give racemic(2'R, 3R, 4'S)-2'-[2-(4-carbamoyl-phenoxy)-5-iodo-phenyl]-6-chloro-4'-(3-chlorophenyl)spiro[3H-indole-3,3'-piperidine]-2,6'(1H)-dione as a white solid (Yield 0.35 g, 88%)

EXAMPLE 72b

Preparation of racemic(2'R, 3R, 4'S)-2'-[2-(4-carbamoyl-phenoxy)-5-ethynyl-phenyl]-6-chloro-4'-(3-chlorophenyl)spiro[3H-indole-3,3'-pieridine]-2,6'(1H)-dione

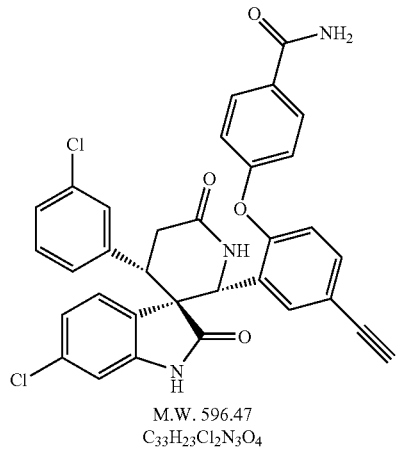

M.W. 596.47
$C_{33}H_{23}Cl_2N_3O_4$

In a manner similar to the method described in example 6a, racemic(2'R, 3R, 4'S)-2'-[2-(4-carbamoyl-phenoxy)-5-iodo-phenyl]-6-chloro-4'-(3-chlorophenyl)spiro[3H-indole-3,3'-piperidine]-2,6'(1H)-dione (0.35 g, 0.5 mmol) was reacted with trimethylsilyl acetylene (0.49 g, 5 mmol), CuI (3 mg), triethylamine (1.52 mL, 15 mmol), and dichlorobis(triphenylphosphine) palladium (0) (28 mg, 0.04 mmol) in anhydrous N,N-dimethylformamide, and then treated with aqueous NaOH in methanol to give racemic(2'R, 3R, 4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione as an off white solid (Yield 0.25 g, 84%)

HRMS(ES$^+$) m/z Calcd for $C_{33}H_{23}Cl_2N_3O_4$+H [(M+H)$^+$]: 596.1139. Found: 596.1135.

EXAMPLE 72c

Preparation of chiral(2'R, 3R, 4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione

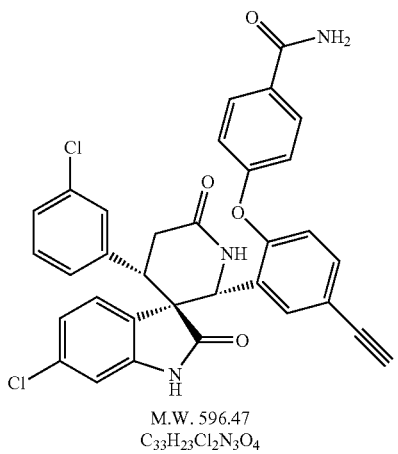

M.W. 596.47
C$_{33}$H$_{23}$Cl$_2$N$_3$O$_4$

Separation of the two enantiomers from racemic(2'R, 3R, 4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione (300 mg) was conducted by chiral SFC to provide chiral (2'R, 3R, 4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione as an off white solid (111 mg, 37%) and chiral(2'S, 3S, 4'R)-2'-[2-(4-carbamoyl-phenoxy)-5-ethynyl-phenyl]-6-chloro-4'-(3-chlorophenyl) spiro[3H-indole-3,3'-piperidine]-2,6'(1H)-dione as an off white solid (112 mg, 37%)

EXAMPLE 73a

Preparation of intermediate 2-(2,6-dimethyl-pyridin-4-yloxy)-5-iodo-benzaldehyde

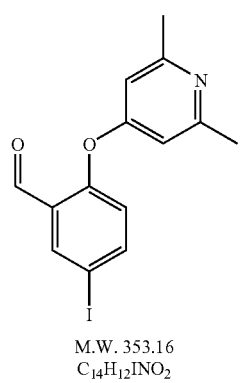

M.W. 353.16
C$_{14}$H$_{12}$INO$_2$

In a manner similar to the method described in Example 50a, 2-fluoro-5-iodobenzaldehyde (2 g, 8 mmol) (Aldrich) was reacted with 2,6-dimethyl-4-hydroxypyridine (1.08 g, 8.8 mmol) and K$_2$CO$_3$ in N,N-dimethylacetamide to give 2-(2,6-dimethyl-pyridin-4-yloxy)-5-iodo-benzaldehyde as a yellow solid (Yield 2.63 g, 92%).

EXAMPLE 73b

Preparation of intermediate 1-[2-(2,6-dimethyl-pyridin-4-yloxy)-5-iodo-phenyl]-3-trimethylsilyoxy-2-aza-1,3-butadiene

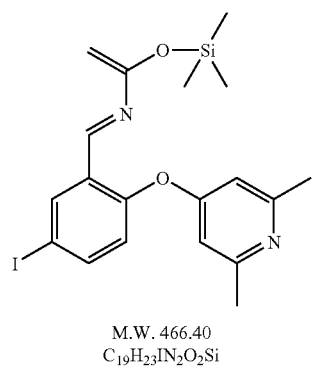

M.W. 466.40
C$_{19}$H$_{23}$IN$_2$O$_2$Si

In a manner similar to the method described in example 1d, 2-(2,6-dimethyl-pyridin-4-yloxy)-5-iodo-benzaldehyde (2.63 g, 7.4 mmol) was reacted with 1,1,1,3,3,3-hexamethyl-disilazane (1.55 mL, 7.4 mmol), n-butyllithium (2.5 M, 2.98 mL, 7.4 mmol), trimethylsilyl chloride (0.945 mL, 7.4 mmol), triethylamine (1.34 mL, 9.7 mmol) and acetyl chloride (0.68 mL, 9.7 mmol) to give crude 1-[2-(2,6-dimethyl-pyridin-4-yloxy)-5-iodo-phenyl]-3-trimethylsilyoxy-2-aza-1,3-butadiene as a yellow gum and used for the next step without further purification.

EXAMPLE 73c

Preparation of racemic(2'R, 3R, 4'S)-6-chloro-4'-(3-chlorophenyl)-2'-[2-(2,6-dimethyl-4-pyridinyloxy)-5-iodo-phenyl]spiro[3H-indole-3,3'-piperidine]-2,6'(1H)-dione

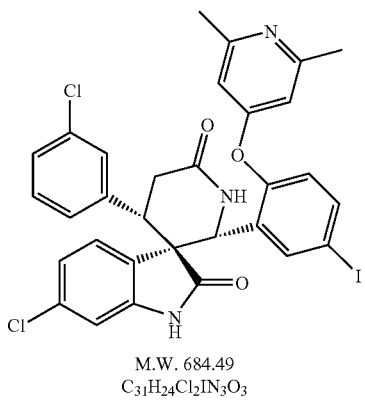

M.W. 684.49
C$_{31}$H$_{24}$Cl$_2$IN$_3$O$_3$

In a manner similar to the method described in example 32d, E/Z-6-chloro-3-(3-chloro-benzylidene)-2-oxo-2,3-di-hydro-indole-1-carboxylic acid tert-butyl ester prepared in example 1b (1.15 g, 2.96 mmol) was reacted with 1-[2-(2,6- dimethyl-pyridin-4-yloxy)-5-iodo-phenyl]-3-trimethylsilyoxy-2-aza-1,3-butadiene (7.4 mmol) in toluene then trifluoroacetic acid in dichloromethane to give racemic(2'R, 3R, 4'S)-6-chloro-4'-(3-chlorophenyl)-2'-[2-(2,6-dimethyl-4-pyridinyloxy)-5-iodo-phenyl]spiro[3H-indole-3,3'-piperidine]-2,6'(1H)-dione as a white solid (Yield 0.8 g, 39%)

HRMS(ES⁺) m/z Calcd for $C_{31}H_{24}Cl_2IN_3O_3$+H [(M+H)⁺]: 684.0312. Found: 684.0315.

EXAMPLE 74

Preparation of racemic(2'R, 3R, 4'S)-6-chloro-4'-(3-chlorophenyl)-2'-[2-(2,6-dimethyl-4-pyridinyloxy)-5-ethynyl-phenyl]spiro[3H-indole-3,3'-piperidine]-2,6'(1H)-dione

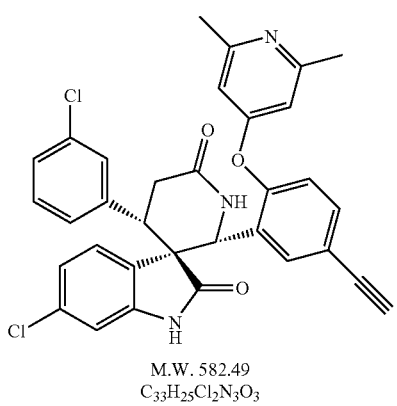

M.W. 582.49
$C_{33}H_{25}Cl_2N_3O_3$

In a manner similar to the method described in example 6a, racemic(2'R, 3R, 4'S)-6-chloro-4'-(3-chlorophenyl)-2'-[2-(2,6-dimethyl-4-pyridinyloxy)-5-iodo-phenyl]spiro[3H-indole-3,3'-piperidine]-2,6'(1H)-dione (0.62 g, 0.9 mmol) was reacted with trimethylsilyl acetylene (0.89 g, 9 mmol), CuI (5 mg), triethylamine (2.74 g, 27 mmol), and dichlorobis(triphenylphosphine) palladium (0) (50.7 mg, 0.07 mmol) in anhydrous N,N-dimethylformamide, and then treated with aqueous NaOH in methanol to give racemic(2'R, 3R, 4'S)-6-chloro-4'-(3-chlorophenyl)-2'-[2-(2,6-dimethyl-4-pyridinyloxy)-5-ethynyl-phenyl]spiro[3H-indole-3,3'-piperidine]-2,6'(1H)-dione as a pale yellow solid (Yield 0.28 g, 53%)

HRMS(ES⁺) m/z Calcd for $C_{33}H_{25}Cl_2N_3O_3$+H [(M+H)⁺]: 582.1346. Found: 582.1346.

EXAMPLE 75a

Preparation of intermediate 5-bromo-2-(4-fluoro-phenoxy)-benzaldehyde

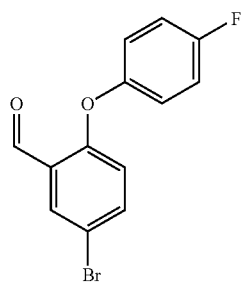

M.W. 295.11
$C_{13}H_8BrFO_2$

In a manner similar to the method described in Example 50a, 5-bromo-2-fluorobenzaldehyde (4.1 g, 20 mmol) (Alfa) was reacted with 4-fluorophenol (2.5 g, 22 mmol)(Aldrich) and $K_2CO_3$ in N,N-dimethylacetamide to give 5-bromo-2-(4-fluoro-phenoxy)-benzaldehyde as a yellow solid (Yield 5.8 g, 97%).

EXAMPLE 75b

Preparation of intermediate 1-[5-bromo-2-(4-fluoro-phenoxy)-phenyl]-3-trimethylsilyoxy-2-aza-1,3-butadiene

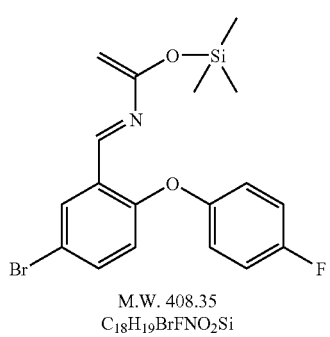

M.W. 408.35
$C_{18}H_{19}BrFNO_2Si$

In a manner similar to the method described in example 1d, 5-bromo-2-(4-fluoro-phenoxy)-benzaldehyde (5.8 g, 20 mmol) was reacted with 1,1,1,3,3,3-hexamethyldisilazane (4.1 mL, 20 mmol), n-butyllithium (2.5 M, 8 mL, 20 mmol), trimethylsilyl chloride (2.5 mL, 20 mmol), triethylamine (3.55 mL, 25 mmol) and acetyl chloride (1.8 mL, 25.5 mmol) to give crude 1-[5-bromo-2-(4-fluoro-phenoxy)-phenyl]-3-trimethylsilyoxy-2-aza-1,3-butadiene as a yellow gum and used for the next step without further purification.

EXAMPLE 75c

Preparation of racemic(2'R, 3R, 4'S)-2'-[5-bromo-2-(4-fluoro-phenoxy)-phenyl]-6-chloro-4'-(3-chlorophenyl)spiro[3H-indole-3,3'-piperidine]-2,6'(1H)-dione

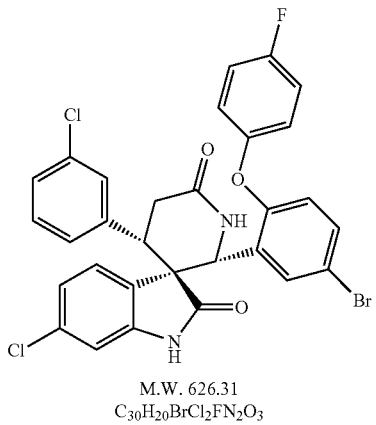

M.W. 626.31
$C_{30}H_{20}BrCl_2FN_2O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (3.1 g, 7.8 mmol) was reacted with 1-[5-bromo-2-(4-fluoro-phenoxy)-phenyl]-3-trimethylsilyoxy-2-aza-1,3-butadiene (20 mmol) in toluene then trifluoroacetic acid in dichloromethane to give racemic(2'R, 3R, 4'S)-2'-[5-bromo-2-(4-fluoro-phenoxy)-phenyl]-6-chloro-4'-(3-chlorophenyl)spiro[3H-indole-3,3'-piperidine]-2,6'(1H)-dione as a white solid (Yield 0.67 g, 14%)

HRMS(ES$^+$) m/z Calcd for $C_{30}H_{20}BrCl_2FN_2O_3$+H [(M+H)$^+$]: 625.0091. Found: 625.0094.

EXAMPLE 76a

Preparation of intermediate 5-bromo-2-(4-trifluoromethyl-phenoxy)-benzaldehyde

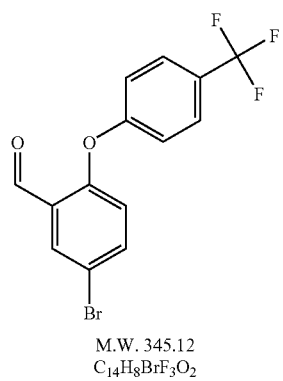

M.W. 345.12
$C_{14}H_8BrF_3O_2$

In a manner similar to the method described in Example 50a, 5-bromo-2-fluorobenzaldehyde (2.1 g, 11 mmol) (Alfa) was reacted with 4-trifluoromethylphenol (1.9 g, 12 mmol) (Aldrich) and $K_2CO_3$ in N,N-dimethylacetamide to give 5-bromo-2-(4-trifluoromethyl-phenoxy)-benzaldehyde as a yellow solid (Yield 2.47 g, 68%).

EXAMPLE 76b

Preparation of intermediate 1-[5-bromo-2-(4-trifluoromethyl-phenoxy)-phenyl]-3-trimethylsilyoxy-2-aza-1,3-butadiene

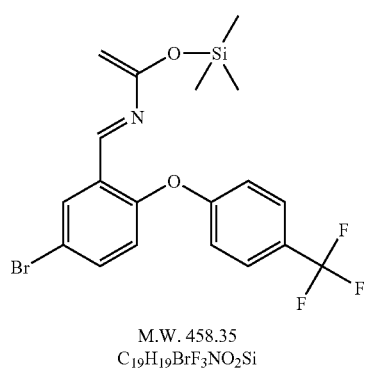

M.W. 458.35
$C_{19}H_{19}BrF_3NO_2Si$

In a manner similar to the method described in example 1d, 5-bromo-2-(4-trifluoromethyl-phenoxy)-benzaldehyde (2.47 g, 7 mmol) was reacted with 1,1,1,3,3,3-hexamethyldisilazane (1.5 mL, 7 mmol), n-butyllithium (2.5 M, 2.9 mL, 7 mmol), trimethylsilyl chloride (0.9 mL, 7 mmol), triethylamine (1.3 mL, 9 mmol) and acetyl chloride (0.5 mL, 9 mmol) to give crude 1-[5-bromo-2-(4-trifluoromethyl-phenoxy)-phenyl]-3-trimethylsilyoxy-2-aza-1,3-butadiene as a yellow gum and used for the next step without further purification.

EXAMPLE 76c

Preparation of racemic(2'R, 3R, 4'S)-2'-[5-bromo-2-(4-trifluoromethyl-phenoxy)-phenyl]-6-chloro-4'-(3-chlorophenyl)spiro[3H-indole-3,3'-piperidine]-2,6'(1H)-dione

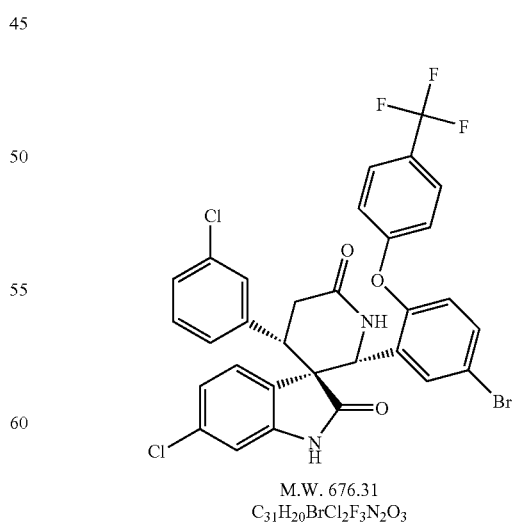

M.W. 676.31
$C_{31}H_{20}BrCl_2F_3N_2O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.1 g, 2.8 mmol) was reacted with 1-[5-bromo-2-(4-trifluoromethyl-phenoxy)-phenyl]-3-trimethylsilyoxy-2-aza-1,3-butadiene (7 mmol) in toluene then trifluoroacetic acid in dichloromethane to give racemic(2'R, 3R, 4'S)-2'-[5-bromo-2-(4-trifluoromethyl-phenoxy)-phenyl]-6-chloro-4'-(3-chlorophenyl)spiro[3H-indole-3,3'-piperidine]-2,6'(1H)-dione as a white solid (Yield 0.3 g, 16%)

HRMS(ES$^+$) m/z Calcd for $C_{31}H_{20}BrCl_2F_3N_2O_3$+H [(M+H)$^+$]: 675.0059. Found: 675.0060.

EXAMPLE 77a

Preparation of intermediate 5-chloro-2-(4-trifluoromethyl-phenoxy)-benzaldehyde

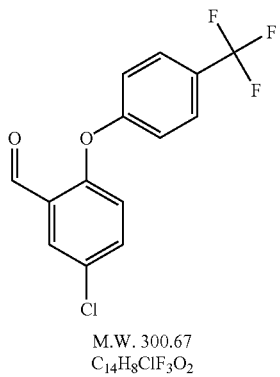

M.W. 300.67
$C_{14}H_8ClF_3O_2$

In a manner similar to the method described in Example 50a, 5-chloro-2-fluorobenzaldehyde (0.88 g, 5.6 mmol) (Beta Pharma) was reacted with 4-trifluoromethylphenol (1 g, 6.6 mmol)(Aldrich) and $K_2CO_3$ in N,N-dimethylacetamide to give 5-chloro-2-(4-trifluoromethyl-phenoxy)-benzaldehyde as a yellow solid (Yield 0.98 g, 58%).

EXAMPLE 77b

Preparation of intermediate 1-[5-chloro-2-(4-trifluoromethyl-phenoxy)-phenyl]-3-trimethylsilyoxy-2-aza-1,3-butadiene

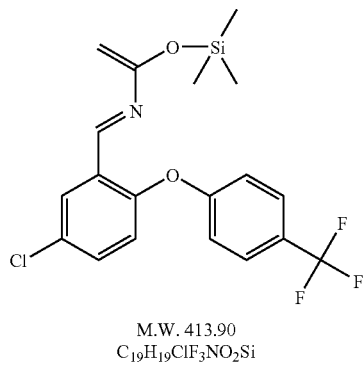

M.W. 413.90
$C_{19}H_{19}ClF_3NO_2Si$

In a manner similar to the method described in example 1d, 5-chloro-2-(4-trifluoromethyl-phenoxy)-benzaldehyde (0.98 g, 3.3 mmol) was reacted with 1,1,1,3,3,3-hexamethyldisilazane (0.67 mL, 3.3 mmol), n-butyllithium (2.5 M, 1.3 mL, 3.3 mmol), trimethylsilyl chloride (0.41 mL, 3.3 mmol), triethylamine (0.59 mL, 4.2 mmol) and acetyl chloride (0.3 mL, 4.2 mmol) to give crude 1-[5-chloro-2-(4-trifluoromethyl-phenoxy)-phenyl]-3-trimethylsilyoxy-2-aza-1,3-butadiene as a yellow gum and used for the next step without further purification.

EXAMPLE 77c

Preparation of racemic(2'R, 3R, 4'S)-6-chloro-4'-(3-chlorophenyl)-2'-[5-chloro-2-(4-trifluoromethyl-phenoxy)-phenyl]spiro[3H-indole-3,3'-piperidine]-2,6'(1H)-dione

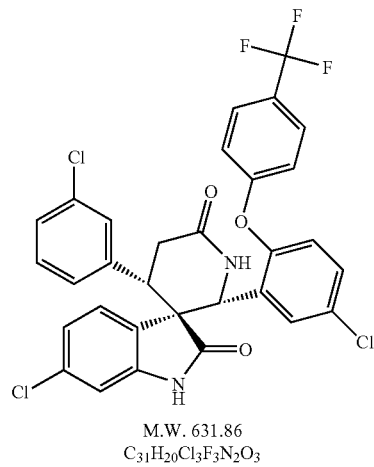

M.W. 631.86
$C_{31}H_{20}Cl_3F_3N_2O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.5 g, 1.3 mmol) was reacted with 1-[5-chloro-2-(4-trifluoromethyl-phenoxy)-phenyl]-3-trimethylsilyoxy-2-aza-1,3-butadiene (3.3 mmol) in toluene then trifluoroacetic acid in dichloromethane to give racemic(2'R, 3R, 4'S)-6-chloro-4'-(3-chlorophenyl)-2'-[5-chloro-2-(4-trifluoromethyl-phenoxy)-phenyl]spiro[3H-indole-3,3'-piperidine]-2,6'(1H)-dione as a white solid (Yield 0.22 g, 27%)

HRMS(ES$^+$) m/z Calcd for $C_{31}H_{20}Cl_3F_3N_2O_3$+H [(M+H)$^+$]: 631.0565. Found: 631.0568.

EXAMPLE 78a

Preparation of intermediate 3-(4-bromo-2-formyl-phenoxy)-benzonitrile

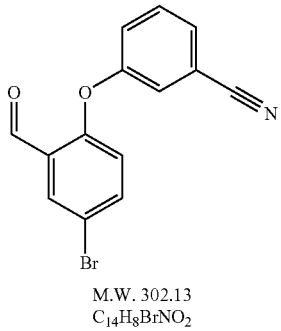

M.W. 302.13
$C_{14}H_8BrNO_2$

In a manner similar to the method described in Example 50a, 5-bromo-2-fluorobenzaldehyde (2.2 g, 11 mmol) (Alfa) was reacted with 3-cyanophenol (1.4 g, 12 mmol)(Aldrich) and $K_2CO_3$ in N,N-dimethylacetamide to give 3-(4-bromo-2-formyl-phenoxy)-benzonitrile as a brown solid (Yield 3 g, 100%).

EXAMPLE 78b

Preparation of intermediate 1-[5-bromo-2-(3-cyano-phenoxy)-phenyl]-3-trimethylsilyoxy-2-aza-1,3-butadiene

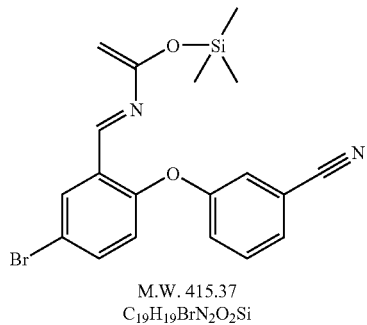

M.W. 415.37
$C_{19}H_{19}BrN_2O_2Si$

In a manner similar to the method described in example 1d, 3-(4-bromo-2-formyl-phenoxy)-benzonitrile (3 g, 10 mmol) was reacted with 1,1,1,3,3,3-hexamethyldisilazane (2.1 mL, 10 mmol), n-butyllithium (2.5 M, 4 mL, 10 mmol), trimethylsilyl chloride (1.3 mL, 10 mmol), triethylamine (1.8 mL, 13 mmol) and acetyl chloride (0.92 mL, 13 mmol) to give crude 1-[5-bromo-2-(3-cyano-phenoxy)-phenyl]-3-trimethylsilyoxy-2-aza-1,3-butadiene as a yellow gum and used for the next step without further purification.

EXAMPLE 78c

Preparation of racemic(2'R, 3R, 4'S)-2'-[5-bromo-2-(3-cyano-phenoxy)-phenyl]-6-chloro-4'-(3-chlorophenyl)spiro[3H-indole-3,3'-piperidine]-2,6'(1H)-dione

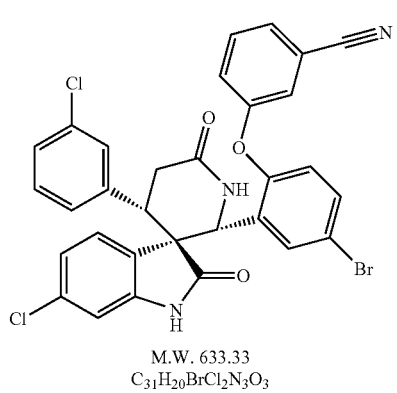

M.W. 633.33
$C_{31}H_{20}BrCl_2N_3O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.55 g, 4 mmol) was reacted with 1-[5-bromo-2-(3-cyano-phenoxy)-phenyl]-3-trimethylsilyoxy-2-aza-1,3-butadiene (10 mmol) in toluene then trifluoroacetic acid in dichloromethane to give racemic(2'R, 3R, 4'S)-2'-[5-bromo-2-(3-cyano-phenoxy)-phenyl]-6-chloro-4'-(3-chlorophenyl)spiro[3H-indole-3,3'-piperidine]-2,6'(1H)-dione as a white solid (Yield 0.4 g, 16%)

HRMS(ES$^+$) m/z Calcd for $C_{31}H_{20}BrCl_2N_3O_3$+H [(M+H)$^+$]: 632.0138. Found: 632.0140.

EXAMPLE 79a

Preparation of intermediate 5-bromo-2-[4-(3-hydroxy-propyl)-phenoxy]-benzaldehyde

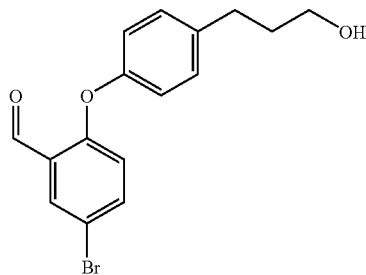

M.W. 335.20
$C_{16}H_{15}BrO_3$

In a manner similar to the method described in Example 50a, 5-bromo-2-fluorobenzaldehyde (5.5 g, 27 mmol) (Alfa) was reacted with 3-(4-hydroxyphenyl)-1-propanol (4.5 g, 30 mmol)(Aldrich) and $K_2CO_3$ in N,N-dimethylacetamide to give 5-bromo-2-[4-(3-hydroxy-propyl)-phenoxy]-benzaldehyde as a brown oil (Yield 9 g, 99%).

EXAMPLE 79b

Preparation of intermediate 5-bromo-2-{4-[3-(tert-butyl-dimethyl-silanyloxy)-propyl]-phenoxy}-benzaldehyde

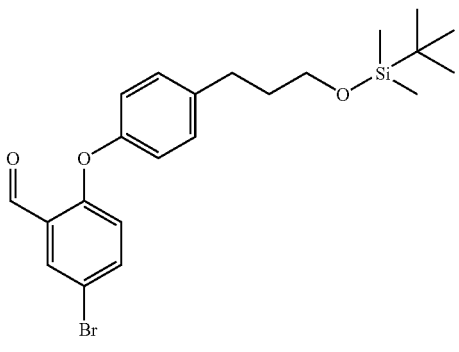

M.W. 449.46
$C_{22}H_{29}BrO_3Si$

In a manner similar to the method described in Example 60b, 5-bromo-2-[4-(3-hydroxy-propyl)-phenoxy]-benzaldehyde (9 g, 27 mmol) was reacted with tert-butyldimethylchlorosilane (4.45 g, 30 mmol) and imidazole in N,N-dimethylformamide to give 5-bromo-2-{4-[3-(tert-butyl-dimethyl-silanyloxy)-propyl]-phenoxy}-benzaldehyde as a brown oil (Yield 12 g, 100%).

EXAMPLE 79c

Preparation of intermediate 1-{5-bromo-2-{4-[3-(tert-butyl-dimethyl-silanyloxy)-propyl]-phenoxy}-phenyl}-3-trimethylsilyoxy-2-aza-1,3-butadiene

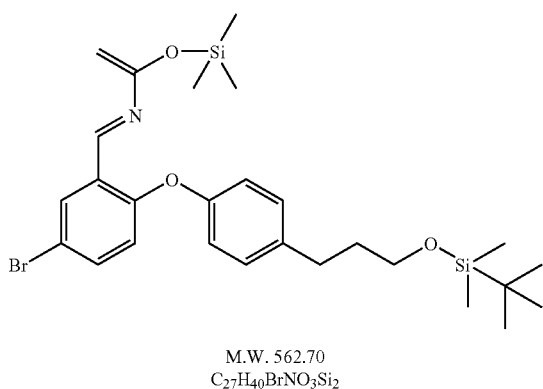

M.W. 562.70
$C_{27}H_{40}BrNO_3Si_2$

In a manner similar to the method described in example 1d, 5-bromo-2-{4-[3-(tert-butyl-dimethyl-silanyloxy)-propyl]-phenoxy}-benzaldehyde (4.72 g, 10.5 mmol) was reacted with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.89 mL, 13.6 mmol) and acetyl chloride (0.97mL, 13.6 mmol) to give crude 1-{5-bromo-2-{4-[3-(tert-butyl-dimethyl-silanyloxy)-propyl]-phenoxy}-phenyl}-3-trimethylsilyoxy-2-aza-1,3-butadiene as a yellow gum and used for the next step without further purification.

EXAMPLE 79d

Preparation of racemic(2'R, 3R, 4'S)-2'-{5-bromo-2-[4-(3-hydroxy-propyl)-phenoxy]-phenyl}-6-chloro-4'-(3-chlorophenyl)spiro[3H-indole-3,3'-piperidine]-2,6'(1H)-dione

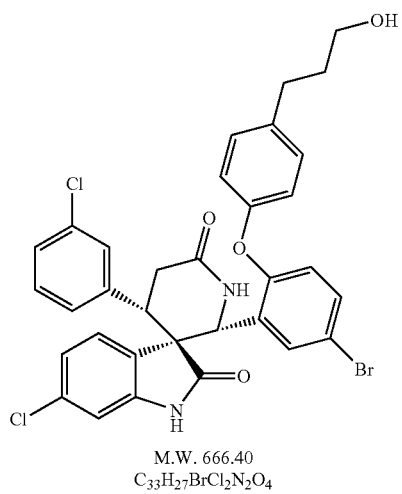

M.W. 666.40
$C_{33}H_{27}BrCl_2N_2O_4$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.64 g, 4.2 mmol) was reacted with 1-{5-bromo-2-{4-[3-(tert-butyl-dimethyl-silanyloxy)-propyl]-phenoxy}-phenyl}-3-trimethylsilyoxy-2-aza-1,3-butadiene (10.5 mmol) in toluene then trifluoroacetic acid in dichloromethane to give racemic(2'R, 3R, 4'S)-2'-{5-bromo-2-[4-(3-hydroxy-propyl)-phenoxy]-phenyl}-6-chloro-4'-(3-chlorophenyl) spiro[3H-indole-3,3'-piperidine]-2,6'(1H)-dione as a white solid (Yield 0.4 g, 14%)

HRMS(ES$^+$) m/z Calcd for $C_{33}H_{27}BrCl_2N_2O_4$+H [(M+H)$^+$]: 665.0604. Found: 665.0600.

EXAMPLE 80a

Preparation of intermediate 4-(4-chloro-2-formyl-phenoxy)-benzonitrile

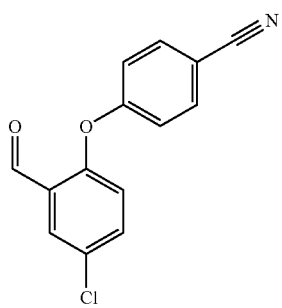

M.W. 257.68
C$_{14}$H$_8$ClNO$_2$

In a manner similar to the method described in Example 50a, 5-chloro-2-fluoro-benzaldehyde (2 g, 12.8 mmol) (Beta Pharma) was reacted with 4-cyanophenol (1.67 g, 14 mmol) and K$_2$CO$_3$ in N,N-dimethylacetamide to give 4-(4-chloro-2-formyl-phenoxy)-benzonitrile as a light yellow solid (Yield 2.81 g, 85%).

EXAMPLE 80b

Preparation of intermediate 1-[5-chloro-2-(4-cyano-phenoxy)-phenyl]-3-trimethylsilyoxy-2-aza-1,3-butadiene

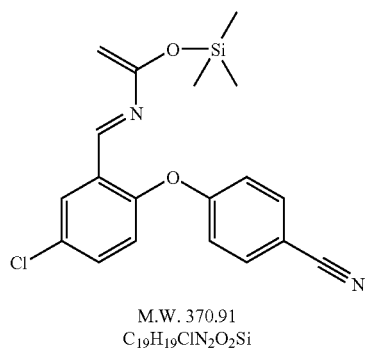

M.W. 370.91
C$_{19}$H$_{19}$ClN$_2$O$_2$Si

In a manner similar to the method described in example 1d, 4-(4-chloro-2-formyl-phenoxy)-benzonitrile (2.8 g, 11 mmol) was reacted with 1,1,1,3,3,3-hexamethyldisilazane (2.3 mL, 11 mmol), n-butyllithium (2.5 M, 4.4 mL, 11 mmol), trimethylsilyl chloride (1.4 mL, 11 mmol), triethylamine (2 mL, 14 mmol) and acetyl chloride (1 mL, 14 mmol) to give crude 1-[5-chloro-2-(4-cyano-phenoxy)-phenyl]-3-trimethylsilyoxy-2-aza-1,3-butadiene as a yellow gum and used for the next step without further purification.

EXAMPLE 80c

Preparation of racemic(2'R, 3R, 4'S)-6-chloro-2'-[5-chloro-2-(4-cyano-phenoxy)-phenyl]-4'-(3-chlorophenyl)spiro[3H-indole-3,3'-piperidine]-2,6'(1H)-dione

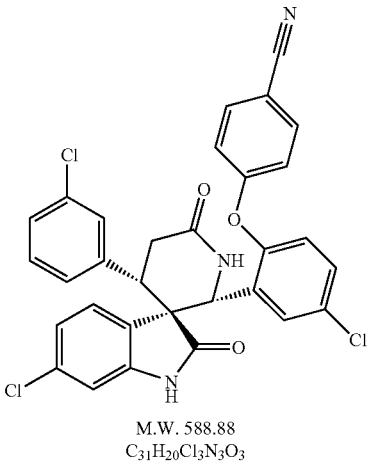

M.W. 588.88
C$_{31}$H$_{20}$Cl$_3$N$_3$O$_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.7 g, 4.4 mmol) was reacted with 1-[5-chloro-2-(4-cyano-phenoxy)-phenyl]-3-trimethylsilyoxy-2-aza-1,3-butadiene (11 mmol) in toluene then trifluoroacetic acid in dichloromethane to give racemic(2'R, 3R, 4'S)-6-chloro-2'-[5-chloro-2-(4-cyano-phenoxy)-phenyl]-4'-(3-chlorophenyl)spiro[3H-indole-3,3'-piperidine]-2,6'(1H)-dione as a white solid (Yield 0.6 g, 23%)

HRMS(ES$^+$) m/z Calcd for C$_{31}$H$_{20}$Cl$_3$N$_3$O$_3$+H [(M+H)$^+$]: 588.0643. Found: 588.0643.

EXAMPLE 80d

Preparation of chiral(2'R, 3R, 4'S)-6-chloro-2'-[5-chloro-2-(4-cyano-phenoxy)-phenyl]-4'-(3-chlorophenyl)spiro[3H-indole-3,3'-piperidine]-2,6'(1H)-dione

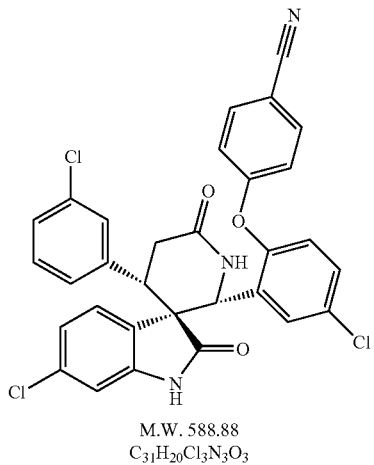

M.W. 588.88
C31H20Cl3N3O3

Separation of the two enantiomers from racemic(2'R, 3R, 4'S)-6-chloro-2'-[5-chloro-2-(4-cyano-phenoxy)-phenyl]-4'-(3-chlorophenyl)spiro[3H-indole-3,3'-piperidine]-2,6'(1H)-dione (500 mg) was conducted by chiral SFC to provide chiral(2'R, 3R, 4'S)-6-chloro-2'-[5-chloro-2-(4-cyano-phenoxy)-phenyl]-4'-(3-chlorophenyl)spiro[3H-indole-3,3'-piperidine]-2,6'(1H)-dione as a white solid (0.19 g, 38%) and chiral (2'S, 3S, 4'R)-6-chloro-2'-[5-chloro-2-(4-cyano-phenoxy)-phenyl]-4'-(3-chlorophenyl)spiro[3H-indole-3,3'-piperidine]-2,6'(1H)-dione as a white solid (0.19 g, 38%).

EXAMPLE 81a

Preparation of intermediate 5-chloro-2-(4-methylsulfanyl-phenoxy)-benzaldehyde

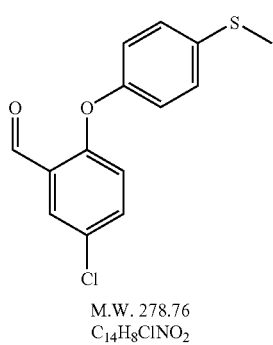

M.W. 278.76
C14H8ClNO2

In a manner similar to the method described in Example 50a, 5-chloro-2-fluoro-benzaldehyde (2 g, 12.8 mmol) (Beta Pharma) was reacted with 4-(methylthio)phenol (1.97 g, 14 mmol) (Aldrich) and K2CO3 in N,N-dimethylacetamide to give 5-chloro-2-(4-methylsulfanyl-phenoxy)-benzaldehyde as a brown oil (Yield 3.5 g, 98%).

EXAMPLE 81b

Preparation of intermediate 1-[5-chloro-2-(4-methylsulfanyl-phenoxy)-phenyl]-3-trimethylsilyoxy-2-aza-13-butadiene

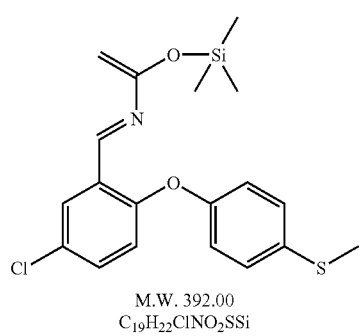

M.W. 392.00
C19H22ClNO2SSi

In a manner similar to the method described in example 1d, 5-chloro-2-(4-methylsulfanyl-phenoxy)-benzaldehyde (3.5 g, 12.6 mmol) was reacted with 1,1,1,3,3,3-hexamethyldisilazane (2.6 mL, 12.6 mmol), n-butyllithium (2.5 M, 5 mL, 12.6 mmol), trimethylsilyl chloride (1.6 mL, 12.6 mmol), triethylamine (2.3 mL, 16 mmol) and acetyl chloride (1.2 mL, 16 mmol) to give crude 1-[5-chloro-2-(4-methylsulfanyl-phenoxy)-phenyl]-3-trimethylsilyoxy-2-aza-1,3-butadiene as a yellow gum and used for the next step without further purification.

EXAMPLE 81c

Preparation of racemic(2'R, 3R, 4'S)-6-chloro-2'-[5-chloro-2-(4-methylsulfanyl-phenoxy)-phenyl]-4'-(3-chlorophenyl)spiro[3H-indole-3,3'-piperidine]-2,6'(1H)-dione

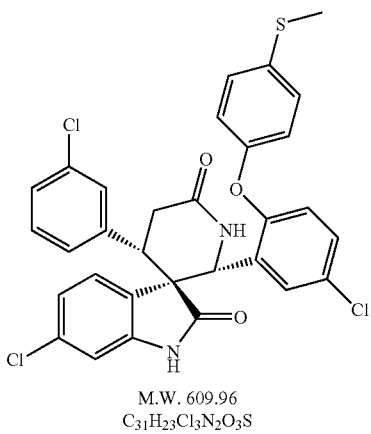

M.W. 609.96
C31H23Cl3N2O3S

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.96 g, 5 mmol) was reacted with 1-[5-chloro-2-(4-methylsulfanyl-phenoxy)-phenyl]-3-trimethylsilyoxy- 2-aza-1,3-butadiene (12.6 mmol) in toluene then trifluoroacetic acid in dichloromethane to give racemic(2'R, 3R, 4'S)-6-chloro-2'-[5-chloro-2-(4-methylsulfanyl-phenoxy)-phenyl]-4'-(3-chlorophenyl)spiro[3H-indole-3,3'-piperidine]-2,6'(1H)-dione as a white solid (Yield 0.6 g, 20%)

HRMS(ES$^+$) m/z Calcd for $C_{31}H_{23}Cl_3N_2O_3S$+H [(M+H)$^-$]: 609.0568. Found: 609.0568.

EXAMPLE 82

Preparation of racemic(2'R, 3R, 4'S)-6-chloro-2'-[5-chloro-2-(4-methylsulfonyl-phenoxy)-phenyl]-4'-(3-chlorophenyl)spiro[3H-indole-3,3'-piperidin]-2,6'(1H)-dione

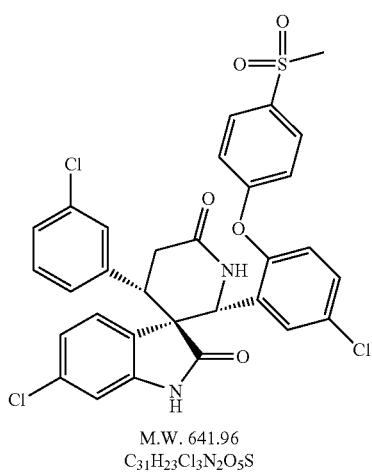

M.W. 641.96
$C_{31}H_{23}Cl_3N_2O_5S$

To a solution of racemic(2'R, 3R, 4'S)-6-chloro-2'-[5-chloro-2-(4-methylsulfanyl-phenoxy)-phenyl]-4'-(3-chlorophenyl)spiro[3H-indole-3,3'-piperidine]-2,6'(1H)-dione (0.36 g, 0.59 mmol) was added MCPBA (67%, 0.145 g, 0.87 mmol). The reaction mixture was stirred at room temperature for 0.5 h, then washed with saturated aqueous solution of Na$_2$S$_2$O$_3$, and aqueous solution of NaHCO3 sequentially. The organic layer was separated, concentrated. The residue was purified by chromatography (EtOAc:CH$_2$Cl$_2$=1:1) to give racemic(2'R, 3R, 4'S)-6-chloro-2'-[5-chloro-2-(4-methylsulfonyl-phenoxy)-phenyl]-4'-(3-chlorophenyl)spiro[3H-indole-3,3'-piperidine]-2,6'(1H)-dione as a light yellow solid (Yield 0.16 g, 42%).

HRMS(ES$^+$) m/z Calcd for $C_{31}H_{23}Cl_3N_2O_5S$+H [(M+H)$^-$]: 641.0466. Found: 641.0464.

EXAMPLE 83

Preparation of racemic(2'R, 3R, 4'S)-6-chloro-2'-[5-chloro-2-(4-methylsulfinyl-phenoxy)-phenyl]-4'-(3-chlorophenyl)spiro[3H-indole-3,3'-piperidine]-2,6'(1H)-dione

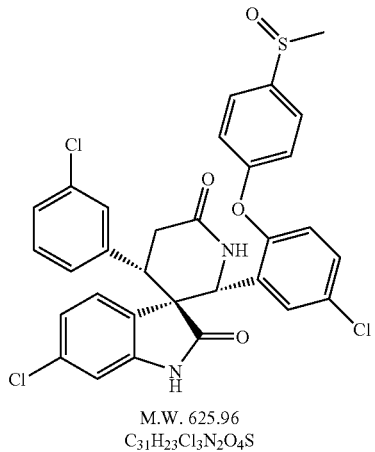

M.W. 625.96
$C_{31}H_{23}Cl_3N_2O_4S$

Purifcation by chromatography (MeOH:EtOAc=6:94) in Example 82 led to the other minor product racemic(2'R, 3R, 4'S)-6-chloro-2'-[5-chloro-2-(4-methylsulfinyl-phenoxy)-phenyl]-4'-(3-chlorophenyl)spiro[3H-indole-3,3'-piperidine]-2,6'(1H)-dione as a white solid (Yield 0.07 g, 19%).

HRMS(ES$^+$) m/z Calcd for $C_{31}H_{23}Cl_3N_2O_4S$+H [(M+H)$^-$]: 625.0517. Found: 625.0515.

EXAMPLE 84a

Preparation of intermediate 5-chloro-2-(4-nitro-phenoxy)-benzaldehyde

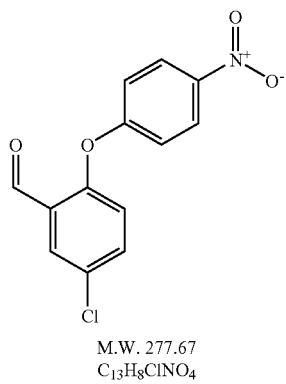

M.W. 277.67
$C_{13}H_8ClNO_4$

In a manner similar to the method described in Example 50a, 5-chloro-2-fluoro-benzaldehyde (1.71 g, 10.9 mmol) (Beta Pharma) was reacted with 4-nitrophenol (1.67 g, 12 mmol) (Aldrich) and K$_2$CO$_3$ in N,N-dimethylacetamide to give 5-chloro-2-(4-nitro-phenoxy)-benzaldehyde as a brown oil (Yield 2.23 g, 73%).

EXAMPLE 84b

Preparation of intermediate 1-[5-chloro-2-(4-nitro-phenoxy)-phenyl]-3-trimethylsilyoxy-2-aza-1,3-butadiene

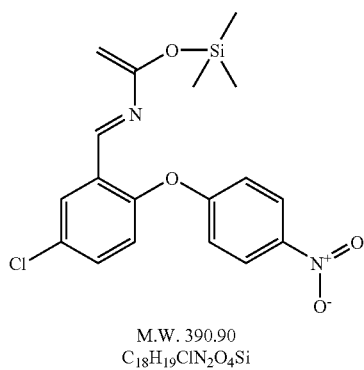

M.W. 390.90
$C_{18}H_{19}ClN_2O_4Si$

In a manner similar to the method described in example 1d, 5-chloro-2-(4-nitro-phenoxy)-benzaldehyde (2.23 g, 8 mmol) was reacted with 1,1,1,3,3,3-hexamethyldisilazane (1.67 mL, 8 mmol), n-butyllithium (2.5 M, 3.2 mL, 8 mmol), trimethylsilyl chloride (1.0 mL, 8 mmol), triethylamine (1.45 mL, 10 mmol) and acetyl chloride (0.74 mL, 10 mmol) to give crude 1-[5-chloro-2-(4-nitro-phenoxy)-phenyl]-3-trimethylsilyoxy-2-aza-1,3-butadiene as a yellow gum and used for the next step without further purification.

EXAMPLE 85c

Preparation of racemic(2'R, 3R, 4'S)-6-chloro-2'-[5-chloro-2-(4-nitro-phenoxy)-phenyl]-4'-(3-chlorophenyl)spiro[3H-indole-3,3'-piperidine]-2,6'(1H)-dione

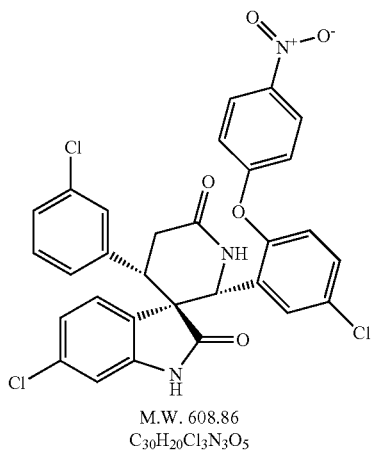

M.W. 608.86
$C_{30}H_{20}Cl_3N_3O_5$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.25 g, 3.2 mmol) was reacted with 1-[5-chloro-2-(4-nitro-phenoxy)-phenyl]-3-trimethylsilyoxy-2-aza-1,3-butadiene (8 mmol) in toluene then trifluoroacetic acid in dichloromethane to give racemic(2'R, 3R, 4'S)-6-chloro-2'-[5-chloro-2-(4-nitro-phenoxy)-phenyl]-4'-(3-chlorophenyl)spiro[3H-indole-3,3'-piperidine]-2,6'(1H)-dione as a light yellow solid (Yield 0.4 g, 21%)

HRMS(ES$^+$) m/z Calcd for $C_{30}H_{20}Cl_3N_3O_5$+H [(M+H)$^+$]: 608.0542. Found: 608.0543.

EXAMPLE 86a

Preparation of racemic(2'R, 3R, 4'S)-2'-[2-(4-amino-phenoxy)-5-chloro-phenyl]-6-chloro-4'-(3-chlorophenyl)spiro[3H-indole-3,3'-piperidine]-2,6'(1H)-dione

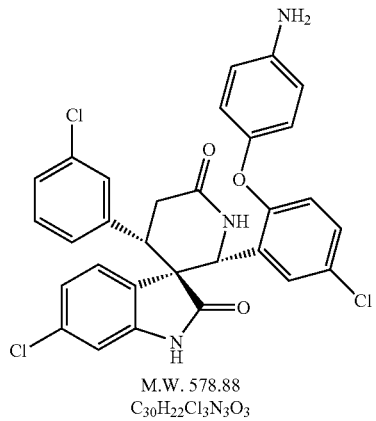

M.W. 578.88
$C_{30}H_{22}Cl_3N_3O_3$

To a solution of racemic(2'R, 3R, 4'S)-6-chloro-2'-[5-chloro-2-(4-nitro-phenoxy)-phenyl]-4'-(3-chlorophenyl)spiro[3H-indole-3,3'-piperidine]-2,6'(1H)-dione (0.31 g, 0.51 mmol) in anhydrous ethanol (20 mL) was added Raney-Ni (0.6 g) and anhydrous hydrazine (0.118 g, 2.54 mmol). The reaction mixture was stirred at room temperature for 0.5 h, then filtered through a short pad of celite. The filtrate was concentrated. The residue was partitioned between ethyl acetate and water. The organic layer was separated, and the aqueous layer was extracted with ethyl acetate three times. The organic layers were combined, washed with water, brine, and dried over MgSO$_4$, and concentrated to give racemic(2'R, 3R, 4'S)-2'-[2-(4-amino-phenoxy)-5-chloro-phenyl]-6-chloro-4'-(3-chlorophenyl)spiro[3H-indole-3,3'-piperidine]-2,6'(1H)-dione as a white solid (Yield 0.28 g, 95%).

HRMS(ES$^+$) m/z Calcd for $C_{30}H_{22}Cl_3N_3O_3$+H [(M+H)$^+$]: 578.0800. Found: 578.0797.

EXAMPLE 86b

Preparation of chiral(2'R, 3R, 4'S)-2'-[2-(4-amino-phenoxy)-5-chloro-phenyl]-6-chloro-4'-(3-chlorophenyl)spiro[3H-indole-3,3'-piperidine]-2,6'(1H)-dione

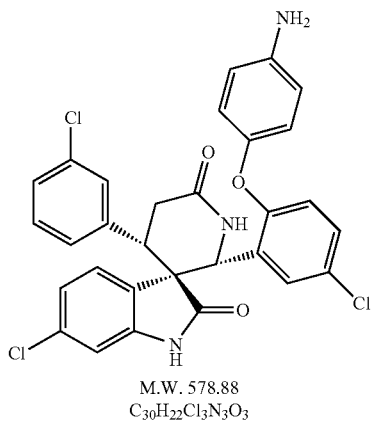

M.W. 578.88
C30H22Cl3N3O3

Separation of the two enantiomers from racemic(2'R, 3R, 4'S)-2'-[2-(4-amino-phenoxy)-5-chloro-phenyl]-6-chloro-4'-(3-chlorophenyl)spiro[3H-indole-3,3'-piperidine]-2,6'(1H)-dione (60 mg) was conducted by chiral SFC to provide chiral(2'R, 3R, 4'S)-2'-[2-(4-amino-phenoxy)-5-chloro-phenyl]-6-chloro-4'-(3-chlorophenyl)spiro[3H-indole-3,3+-piperidine]-2,6'(1H)-dione as a off white solid (24 mg, 40%) and chiral(2'S, 3S, 4'R)-2'-[2-(4-amino-phenoxy)-5-chloro-phenyl]-6-chloro-4'-chlorophenyl)spiro[3H-indole-3,3'-piperidine]-2,6'(1H)-dione as a off white solid (24 mg, 40%).

EXAMPLE 87

Preparation of racemic(2'R, 3R, 4'S)-2'-[2-(4-acetylamino-phenoxy)-5-chloro-phenyl]-6-chloro-4'-(3-chlorophenyl)spiro[3H-indole-3,3'-piperidine]-2,6'(1H)-dione

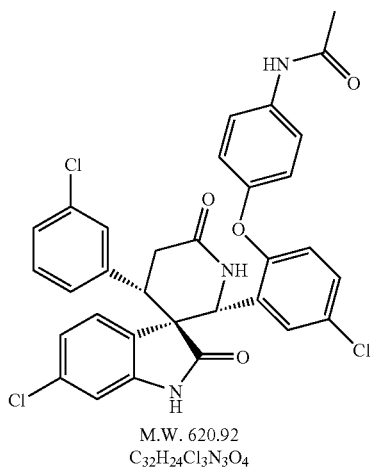

M.W. 620.92
C32H24Cl3N3O4

In a manner similar to the method described in example 5b, racemic(2'S, 3S, 4'R)-2'-[2-(4-amino-phenoxy)-5-chlorophenyl]-6-chloro-4'-(3-chlorophenyl)spiro[3H-indole-3,3'-piperidine]-2,6'(1H)-dione (0.18 g, 0.32 mmol) prepared in Example 86a was reacted with acetyl chloride (28 mg, 0.352 mmol) and triethylamine in tetrahydrofuran to give racemic (2'S, 3S, 4'R)-2'-[2-(4-acetylamino-phenoxy)-5-chloro-phenyl]-6-chloro-4'-(3-chlorophenyl)spiro[3H-indole-3,3'-piperidine]-2,6'(1H)-dione as a yellow solid (Yield 0.13 g, 65%).
HRMS(ES$^+$) m/z Calcd for $C_{32}H_{24}Cl_3N_3O_4$+H [(M+H)$^+$]: 620.0905. Found: 620.0905.

EXAMPLE 88a

Preparation of intermediate 5-iodo-2-(1,3,5-trimethyl-1H-pyrazol-4-yloxy)-benzaldehyde

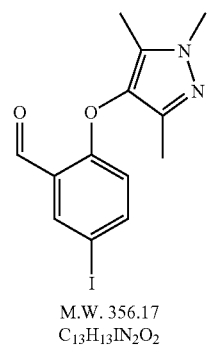

M.W. 356.17
C13H13IN2O2

In a manner similar to the method described in Example 50a, 2-fluoro-5-iodobenzaldehyde (5.84 g, 23.4 mmol) (Aldrich) was reacted with 1,3,5-trimethyl-1H-pyrazol-4-ol (3.24 g, 25.7 mmol) and K$_2$CO$_3$ in N,N-dimethylacetamide to give 5-iodo-2-(1,3,5-trimethyl-1H-pyrazol-4-yloxy)-benzaldehyde as a yellow solid (Yield 8.1 g, 97%).

1,3,5-Trimethyl-1H-pyrazol-4-ol was prepared according to the procedures described by Fagan, P. J., et al in *Can. J. Chem.* 1979, vol 57, 904-912

EXAMPLE 88b

Preparation of intermediate 1-[5-iodo-2-(1,3,5-trimethyl-1H-pyrazol-4-yloxy)-phenyl]-3-trimethylsilyoxy-2-aza-1,3-butadiene

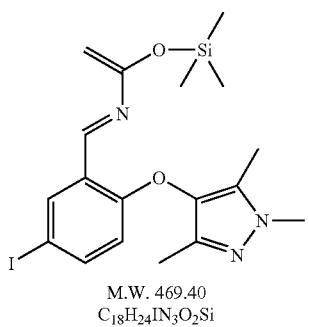

M.W. 469.40
C18H24IN3O2Si

In a manner similar to the method described in example 1d, 5-iodo-2-(1,3,5-trimethyl-1H-pyrazol-4-yloxy)-benzaldehyde (8.1 g, 23 mmol) was reacted with 1,1,1,3,3,3-hexamethyldisilazane (4.7 mL, 23 mmol), n-butyllithium (2.5 M, 9.1 mL, 23 mmol), trimethylsilyl chloride (2.9 mL, 23 mmol), triethylamine (4.1 mL, 30 mmol) and acetyl chloride (2.1 mL, 30 mmol) to give crude 1-[5-iodo-2-(1,3,5-trimethyl-1H-pyrazol-4-yloxy)-phenyl]-3-trimethylsilyoxy-2-aza-1,3-butadiene as a yellow gum and used for the next step without further purification.

EXAMPLE 88c

Preparation of racemic(2'R, 3R, 4'S)-6-chloro-4'-(3-chlorophenyl)-2'-[5-iodo-2-(1,3,5-trimethyl-1H-pyrazol-4-yloxy)-phenyl]spiro[3H-indole-3,3'-piperidine]-2,6'(1H)-dione

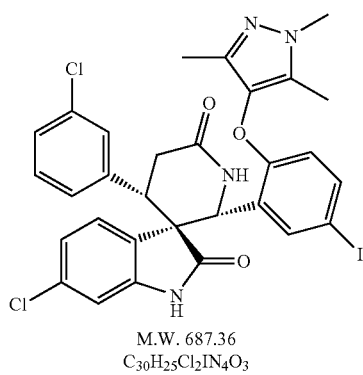

M.W. 687.36
$C_{30}H_{25}Cl_2IN_4O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (3.5 g, 9 mmol) was reacted with 1-[5-iodo-2-(1,3,5-trimethyl-1H-pyrazol-4-yloxy)-phenyl]-3-trimethylsilyoxy-2-aza-1,3-butadiene (23 mmol) in toluene then trifluoroacetic acid in dichloromethane to give racemic(2'R, 3R, 4'S)-6-chloro-4'-(3-chlorophenyl)-2'-[5-iodo-2-(1,3,5-trimethyl-1H-pyrazol-4-yloxy)-phenyl]spiro[3H-indole-3,3'-piperidine]-2,6'(1H)-dione as a pale yellow solid (Yield 0.64 g, 10%)

HRMS(ES$^+$) m/z Calcd for $C_{30}H_{25}Cl_2IN_4O_3$+H [(M+H)$^+$]: 687.0421. Found: 687.0425.

EXAMPLE 89a

Preparation of racemic(2'R, 3R, 4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione

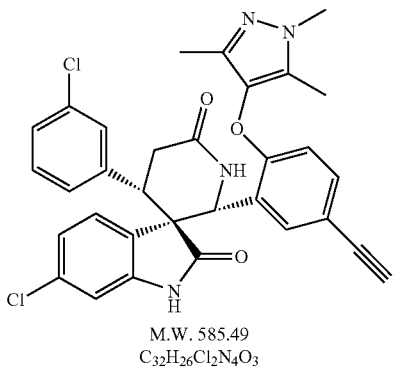

M.W. 585.49
$C_{32}H_{26}Cl_2N_4O_3$

In a manner similar to the method described in example 6a, racemic(2'R, 3R, 4'S)-6-chloro-4'-(3-chlorophenyl)-2'-[5-iodo-2-(1,3,5-trimethyl-1H-pyrazol-4-yloxy)-phenyl]spiro[3H-indole-3,3'-piperidine]-2,6'(1H)-dione (0.62 g, 0.9 mmol) was reacted with trimethylsilyl acetylene (0.88 g, 9 mmol), CuI (10 mg), triethylamine (2.71 g, 27 mmol), and dichlorobis(triphenylphosphine)palladium (0) (50.5 mg, 0.07 mmol) in anhydrous N,N-dimethylformamide, and then treated with aqueous NaOH in methanol to give racemic(2'R, 3R, 4'S)-6-chloro-4'-(3-chlorophenyl)-2'-[5-ethynyl-2-(1,3, 5-trimethyl-1H-pyrazol-4-yloxy)-phenyl]spiro[3H-indole-3,3'-piperidine]-2,6'(1H)-dione as a white solid (Yield 0.47 g, 90%)

HRMS(ES$^+$) m/z Calcd for $C_{32}H_{26}Cl_2N_4O_3$+H [(M+H)$^+$]: 584.1455. Found: 584.1457.

EXAMPLE 89b

Preparation of chiral(2'R, 3R, 4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione

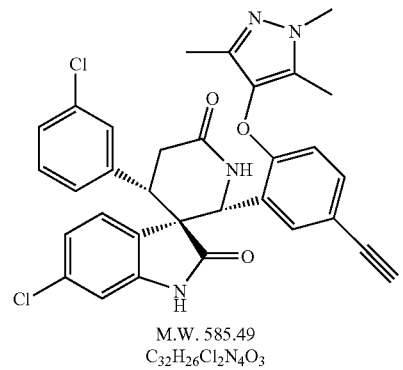

M.W. 585.49
$C_{32}H_{26}Cl_2N_4O_3$

Separation of the two enantiomers from racemic(2'R, 3R, 4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione (0.4 g) was conducted by chiral SFC to provide chiral(2'R, 3R, 4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione as a off white solid (0.18 g, 45%) and chiral(2'S, 3S, 4'R)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione as a off white solid (0.17 g, 44%)

EXAMPLE 90a

Preparation of intermediate 5-bromo-2-(1,3,5-trimethyl-1H-pyrazol-4-yloxy)-benzaldehyde

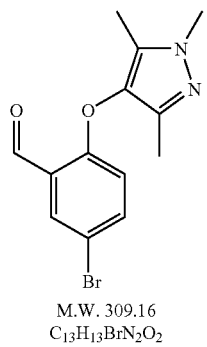

M.W. 309.16
$C_{13}H_{13}BrN_2O_2$

In a manner similar to the method described in Example 50a, 5-bromo-2-fluoro-benzaldehyde (2 g, 10 mmol) (Acros) was reacted with 1,3,5-trimethyl-1H-pyrazol-4-ol (1.3 g, 10 mmol) and $K_2CO_3$ in N,N-dimethylacetamide to give 5-bromo-2-(1,3,5-trimethyl-1H-pyrazol-4-yloxy)-benzaldehyde as a white solid (Yield 3.1 g, 100%).

EXAMPLE 90b

Preparation of intermediate 1-[5-bromo-2-(1,3,5-trimethyl-1H-pyrazol4-yloxy)-phenyl]-3-trimethylsilyoxy-2-aza-1,3-butadiene

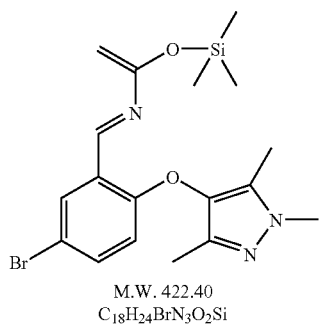

M.W. 422.40
$C_{18}H_{24}BrN_3O_2Si$

In a manner similar to the method described in example 1d, 5-bromo-2-(1,3,5-trimethyl-1H-pyrazol-4-yloxy)-benzaldehyde (3.1 g, 10 mmol) was reacted with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13 mmol) and acetyl chloride (1 g, 13 mmol) to give crude 1-[5-bromo-2-(1,3,5-trimethyl-1H-pyrazol-4-yloxy)-phenyl]-3-trimethylsilyoxy-2-aza-1,3-butadiene as a yellow gum and used for the next step without further purification.

EXAMPLE 90c

Preparation of racemic(2'R, 3R, 4'S)-2'-[5-bromo-2-(1,3,5-trimethyl-1H-pyrazol-4-yloxy)-phenyl]-6-chloro-4'-(3-chlorophenyl)spiro[3H-indole-3,3'-piperidine]-2,6'(1H)-dione

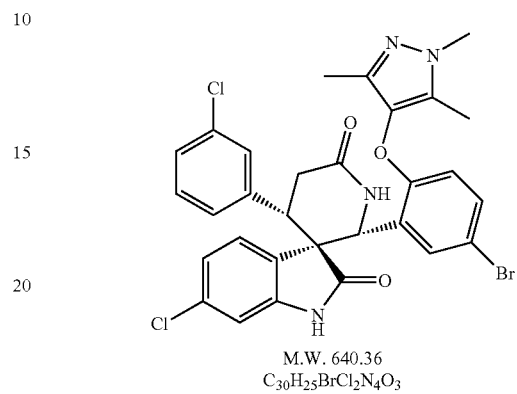

M.W. 640.36
$C_{30}H_{25}BrCl_2N_4O_3$

In a manner similar to the method described in example 32d, E/Z-6-chloro-3-(3-chloro-benzylidene)-2-oxo-2,3-dihydro-indole-1-carboxylic acid tert-butyl ester prepared in example 1b (1.2 g, 3 mmol) was reacted with 1-[5-bromo-2-(1,3,5-trimethyl-1H-pyrazol-4-yloxy)-phenyl]-3-trimethylsilyoxy-2-aza-1,3-butadiene (4.2 g, 10 mmol) in toluene then trifluoroacetic acid in dichloromethane to give racemic(2'R, 3R, 4'S)-2'-[5-bromo-2-(1,3,5-trimethyl-1H-pyrazol-4-yloxy)-phenyl]-6-chloro-4'-(3-chlorophenyl)spiro[3H-indole-3,3'-piperidine]-2,6'(1H)-dione as a pale yellow solid (Yield 0.2 g, 10%)

HRMS(ES$^+$) m/z Calcd for $C_{30}H_{25}BrCl_2N_4O_3$+H [(M+H)$^+$]: 639.0560. Found: 639.0561.

EXAMPLE 91a

Preparation of intermediate methanesulfonic acid 1,4-dioxa-spiro[4.5]dec-8-yl ester

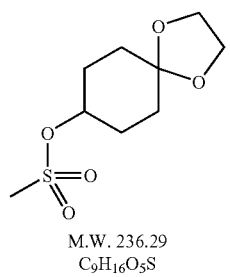

M.W. 236.29
$C_9H_{16}O_5S$

In a manner similar to the method described in example 32a, 1,4-dioxa-spiro[4.5]decan-8-ol (5.1 g, 32 mmol) (Alfa) was reacted with methanesulfonyl chloride (3.7 g, 32 mmol, Aldrich) and triethylamine in dichloromethane to give methanesulfonic acid 1,4-dioxa-spiro[4.5]dec-8-yl ester as a light yellow oil (Yield 6.8 g, 90%).

EXAMPLE 91b

Preparation of intermediate 5-chloro-2-(1,4-dioxa-spiro[4.5]dec-8-yloxy)-benzaldehyde

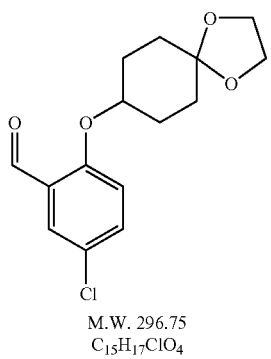

M.W. 296.75
$C_{15}H_{17}ClO_4$

In a manner similar to the method described in example 4a, 5-chlorosalicylaldehyde (2.32 g, 14.8 mmol) (Aldrich) reacted with methanesulfonic acid 1,4-dioxa-spiro[4.5]dec-8-yl ester (3.5 g, 14.8 mmol) and $K_2CO_3$ in N,N-dimethylformamide to give 5-chloro-2-(1,4-dioxa-spiro[4.5]dec-8-yloxy)-benzaldehyde as a colorless oil (Yield 1.5 g, 34%).

EXAMPLE 91c

Preparation of intermediate 1-[5-chloro-2-(1,4-dioxa-spiro[4.5]dec-8-yloxy)-phenyl]-3-trimethylsilyoxy-2-aza-1,3-butadiene

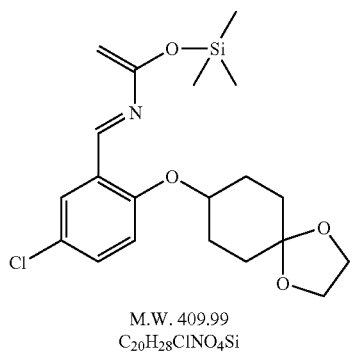

M.W. 409.99
$C_{20}H_{28}ClNO_4Si$

In a manner similar to the method described in example 1d, 5-chloro-2-(1,4-dioxa-spiro[4.5]dec-8-yloxy)-benzaldehyde (1.5 g, 5 mmol) was used as the starting material in place of 4-(2-formyl-4-iodo-phenoxymethyl)-piperidine-1-carboxylic acid tert-butyl ester to react with 1,1,3,3,3-hexamethyldisilazane (0.8 g, 5 mmol), n-butyllithium (2.5 M, 2 mL, 5 mmol), trimethylsilyl chloride (0.55 g, 5 mmol), triethylamine (0.7 g, 6.8 mmol) and acetyl chloride (0.5 g, 6.8 mmol) to give crude 1-[5-chloro-2-(1,4-dioxa-spiro[4.5]dec-8-yloxy)-phenyl]-3-trimethylsilyoxy-2-aza-1,3-butadiene as a yellow gum and used for the next step without further purification.

EXAMPLE 91d

Preparation of racemic(2'R, 3R, 4'S)-6-chloro-2'-[5-chloro-2-(1,4-dioxa-spiro[4.5]dec-8-yloxy)-phenyl]-4'-(3-chlorophenyl)spiro[3H-indole-3,3'-piperidine]-2,6'(1H)-dione

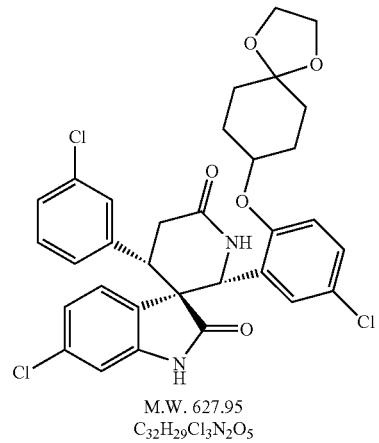

M.W. 627.95
$C_{32}H_{29}Cl_3N_2O_5$

In a manner similar to the method described in example 1e, E/Z-6-chloro-3-(3-chloro-benzylidene)-2-oxo-2,3-dihydro-indole-1-carboxylic acid tert-butyl ester prepared in example 1b (0.4 g, 1 mmol) was reacted 1-[5-chloro-2-(1,4-dioxa-spiro[4.5]dec-8-yloxy)-phenyl]-3-trimethylsilyoxy-2-aza-1,3-butadiene (1.5 g, 5 mmol) in toluene to give racemic(2'R, 3R, 4'S)-6-chloro-2'-[5-chloro-2-(1,4-dioxa-spiro[4.5]dec-8-yloxy)-phenyl]-4'-(3-chlorophenyl)spiro[3H-indole-3,3'-piperidine]-2,6'(1H)-dione as a off white solid (Yield 0.23 g, 37%)

HRMS($ES^+$) m/z Calcd for $C_{32}H_{29}Cl_3N_2O_5$+H [(M+H)$^+$]: 627.1215. Found: 627.1217.

EXAMPLE 92

Preparation of racemic(2'R, 3R, 4'S)-6-chloro-2'-[5-chloro-2-(4-oxo-cyclohexyloxy)-phenyl]-4'-(3-chlorophenyl)spiro[3H-indole-3,3'-piperidine]-2,6'(1H)-dione

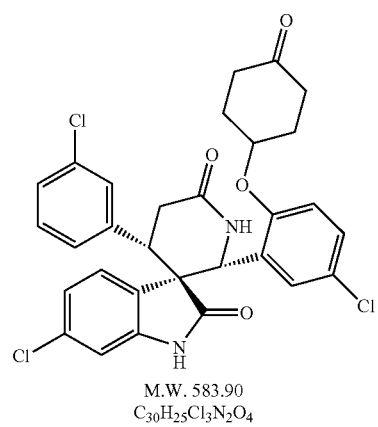

M.W. 583.90
$C_{30}H_{25}Cl_3N_2O_4$

To a solution of racemic(2'R, 3R, 4'S)-6-chloro-2'-[5-chloro-2-(1,4-dioxa-spiro[4.5]dec-8-yloxy)-phenyl]-4'-(3-chlorophenyl)spiro[3H-indole-3,3'-piperidine]-2,6'(1H)-dione (0.2 g, 0.32 mmol) in tetrahydrofuran (15 mL) and water (1 mL) was added aqueous HCl (2 N, 1 mL). The reaction mixture was stirred at room temperature for 1 h, then neutralized to "pH" 7 by aqueous NaHCO$_3$ solution. The mixture was then extracted with ethyl acetate. The organic layer was separated, washed with brine, dried over MgSO$_4$, and concentrated. The residue was purified by chromatography (EtOAc:CH$_2$Cl$_2$=1:1) to give racemic(2'R, 3R, 4'S)-6-chloro-2'-[5-chloro-2-cyclohexyloxy)-phenyl]-4'-(3-chlorophenyl) spiro[3H-indole-3,3'-piperidine]-2,6'(1H)-dione as a white solid (Yield 0.1 g, 54%)

HRMS(ES$^+$) m/z Calcd for C$_{30}$H$_{25}$Cl$_3$N$_2$O$_4$+H [(M+H)$^+$]: 583.0953. Found: 583.0953.

EXAMPLE 93a

Preparation of intermediate 2-chloro-6-(4-methoxy-phenoxy)-benzaldehyde

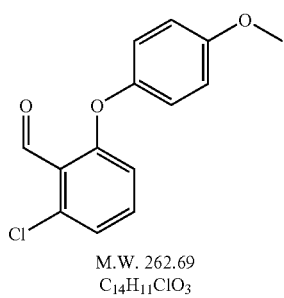

M.W. 262.69
C$_{14}$H$_{11}$ClO$_3$

In a manner similar to the method described in Example 50a, 2,6-dichlorobenzaldehyde (2.7 g, 15 mmol) (Aldrich) was reacted with 4-methoxyphenol (1.8 g, 15 mmol) and K$_2$CO$_3$ in N,N-dimethylacetamide to give 2-chloro-6-(4-methoxy-phenoxy)-benzaldehyde as a yellow oil (Yield 3.2 g, 80%).

EXAMPLE 93b

Preparation of intermediate 1-[2-chloro-6-(4-methoxy-phenoxy)-phenyl]-3-trimethylsilyoxy-2-aza-1,3-butadiene

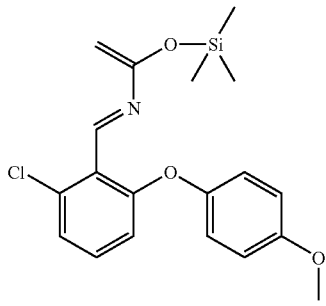

M.W. 375.93
C$_{19}$H$_{22}$ClNO$_3$Si

In a manner similar to the method described in example 1d, 2-chloro-6-(4-methoxy-phenoxy)benzaldehyde (2.8 g, 10 mmol) was reacted with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13 mmol) and acetyl chloride (1 g, 10 mmol) to give crude 1-[2-chloro-6-(4-methoxy-phenoxy)-phenyl]-3-trimethylsilyoxy-2-aza-1,3-butadiene as a yellow gum and used for the next step without further purification.

EXAMPLE 93c

Preparation of racemic(2'S, 3R, 4'S)-6-chloro-2'-[2-chloro-6-(4-methoxy-phenoxy)-phenyl]-4'-(3-chlorophenyl)spiro[3H-indole-3,3'-piperidine]-2,6'(1H)-dione

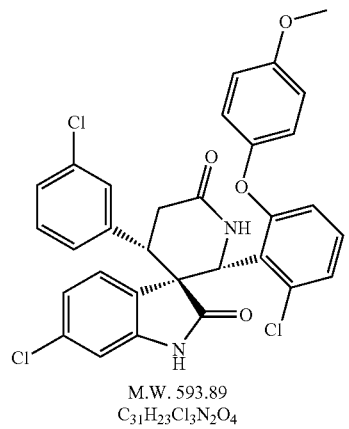

M.W. 593.89
C$_{31}$H$_{23}$Cl$_3$N$_2$O$_4$

In a manner similar to the method described in example 32d, E/Z-6-chloro-3-(3-chloro-benzylidene)-2-oxo-2,3-dihydro-indole-1-carboxylic acid tert-butyl ester prepared in example 1b (0.56 g, 1.4 mmol) was reacted with 1-[2-chloro-6-(4-methoxy-phenoxy)-phenyl]-3-trimethylsilyoxy-2-aza-1,3-butadiene (10 mmol) in toluene then trifluoroacetic acid in dichloromethane to give racemic(2'S, 3R, 4'S)-6-chloro-2'-[2-chloro-6-(4-methoxy-phenoxy)-phenyl]-4'-(3-chlorophenyl)spiro[3H-indole-3,3'-piperidine]-2,6'(1H)-dione as a light yellow solid (Yield 0.52 g, 60%)

HRMS(ES$^+$) m/z Calcd for C$_{31}$H$_{23}$Cl$_3$N$_2$O$_4$+H [(M+H)$^+$]: 593.0796. Found: 593.0797.

EXAMPLE 94a

Preparation of intermediate trans-4-(tert-buyl-dimethyl-silanyloxy)-cyclohexanol

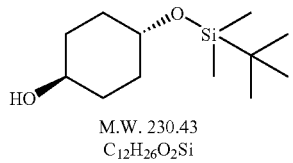

M.W. 230.43
C$_{12}$H$_{26}$O$_2$Si

To a solution of trans-1,4-cyclohexanediol (3 g, 26 mmol) in anhydrous N,N-dimethylformamide (30 mL) at 0° C. was added imidazole (1.7 g, 26 mmol) and tert-butyldimethylchlorosilane (3.87 g, 26 mmol). The reaction mixture was then stirred at 0° C. for 1 h. The mixture was partitioned between ethyl acetate and water. Organic layer was separated, aqueous layer was extracted with ethyl acetate. The combined organic layers were washed with water and brine, dried over MgSO$_4$, and concentrated. The residue was purified by chromatography (EtOAc:hexanes=1;2) to give trans-4-(tert-buyl-dimethyl-silanyloxy)-cyclohexanol as a white solid (3.9 g, 65%).

The starting material trans-1,4-cyclohexanediol was prepared by crystallization from 1:1 mixture of cis-/trans-1,4-cyclohexanediol according to procedures described by Doyle, M. P. et al in *Org. Lett.* 2005, Vol 7, No. 22, 5035-5038 supplimental materials without modification.

EXAMPLE 94b

Preparation of intermediate cis-2-[4-(tert-butyl-dimethyl-silanyloxy)-cyclohexyloxy]-5-chloro-benzoic acid methyl ester

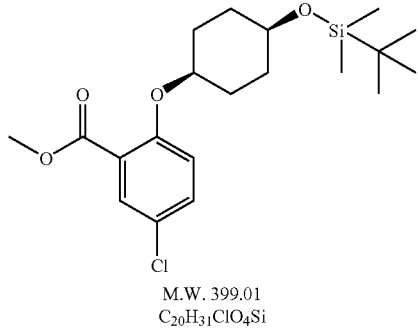

M.W. 399.01
C$_{20}$H$_{31}$ClO$_4$Si

To a solution of methyl 5-chloro-2-hydroxybenzoate (2.07 g, 11 mmol) and diisopropyl azodicarboxylate (2.98 g, 14 mmol) (Aldrich) in anhydrous tetrahydrofuran (10 mL) at 0° C. was added a mixture of trans-4-(tert-buyl-dimethyl-silanyloxy)-cyclohexanol (3.2 g, 14 mmol) and triphenylphosphine (3.64 g, 14 mmol) in tetrahydrofuran (40 mL). The reaction mixture was stirred at room temperature for 18 h. The mixture was poured into water, extracted with ethyl acetate (3×). The organic layers were combined, washed with water, brine, dried over MgSO$_4$, and concentrated. The residue was purified by chromatography (5% EtOAc;hexanes) to give cis-2-[4-(tert-butyl-dimethyl-silanyloxy)-cyclohexyloxy]-5-chloro-benzoic acid methyl ester as a yellow oil (Yield 4.0 g, 90%).

EXAMPLE 94c

Preparation of intermediate cis-2-[4-(tert-butyl-dimethyl-silanyloxy)-cyclohexyloxy]-5-chloro-benzaldehyde

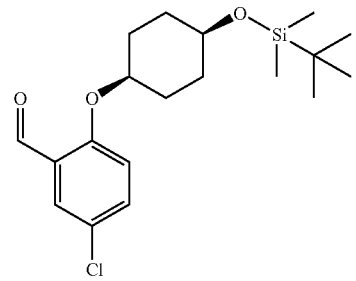

M.W. 368.98
C$_{19}$H$_{29}$ClO$_3$Si

To a solution of cis-2-[4-(tert-butyl-dimethyl-silanyloxy)-cyclohexyloxy]-5-chloro-benzoic acid methyl ester (4 g, 10 mmol) in anhydrous ethyl ether (30 mL) at 0° C. was added an ethyl ether (1 M) solution of LiAlH$_4$ (10 mL, 10 mmol) dropwise. The reaction mixture was warmed to room temperature and stirred for 0.5 h. The mixture was quenched by sequential dropwise addition of water (0.38 mL), aqueous NaOH solution (15%, 0.38 mL), and water (1.14 mL). The mixture was filtered, the granular precipitate was wahed with ethyl acetate (3×). The filtrate were combined, washed with water, brine, separated, dried over MgSO$_4$, and concentrated to give a colorless oil (3.6 g). The oil was dissolved into 1,2-dichloroethane, and activated MnO$_2$ (8.34 g, 97 mmol) was added. The reaction mixture was heated at 80° C. for 1 h. The mixture was cooled to room temperature, filtered through a short pad of celite. The filtrate was concentrated to give cis-2-[4-(tert-butyl-dimethyl-silanyloxy)-cyclohexyloxy]-5-chloro-benzaldehyde as a yellow solid (Yield 3.6 g, 97%).

EXAMPLE 94d

Preparation of intermediate 1-[2-[cis-4-(tert-butyl-dimethyl-silanyloxy)-cyclohexyloxy]-5-chloro-phenyl]-3-trimethylsilyoxy-2-aza-1,3-butadiene

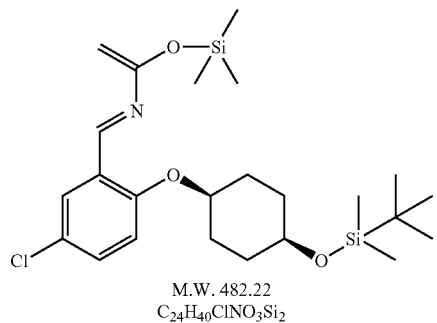

M.W. 482.22
C$_{24}$H$_{40}$ClNO$_3$Si$_2$

In a manner similar to the method described in example 1d, cis-2-[4-(tert-butyl-dimethyl-silanyloxy)-cyclohexyloxy]-5-chloro-benzaldehyde (3.6 g, 9.8 mmol) was reacted with 1,1,1,3,3,3-hexamethyldisilazane (1.6 g, 10 mmol), n-butyl-lithium (2.5 M, 4 mL, 10 mmol), trimethylsilyl chloride (1.1 g, 10 mmol), triethylamine (1.36 g, 13 mmol) and acetyl chloride (1 g, 13 mmol) to give crude 1-[2-[cis-4-(tert-butyl-dimethyl-silanyloxy)-cyclohexyloxy]-5-chloro-phenyl]-3-trimethylsilyoxy-2-aza-1,3-butadiene as a yellow gum and used for the next step without further purification.

EXAMPLE 94d

Preparation of racemic(2'R, 3R, 4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione

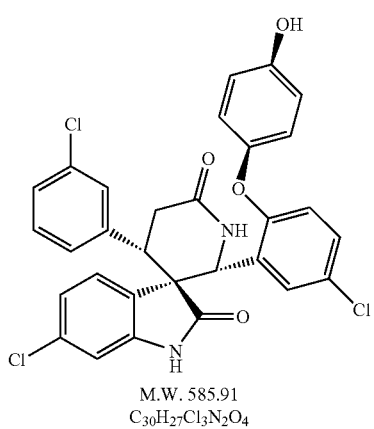

M.W. 585.91
$C_{30}H_{27}Cl_3N_2O_4$

In a manner similar to the method described in example 1e, E/Z-6-chloro-3-(3-chloro-benzylidene)-2-oxo-2,3-dihydro-indole-1-carboxylic acid tert-butyl ester prepared in example 1b (1.52 g, 3.8 mmol) was reacted 1-[2-[cis-4-(tert-butyl-dimethyl-silanyloxy)-cyclohexyloxy]-5-chloro-phenyl]-3-trimethylsilyoxy-2-aza-1,3-butadiene (9.8 mmol) in toluene to give racemic(2'R, 3R, 4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione as a white solid (Yield 0.4 g, 18%)

HRMS(ES$^+$) m/z Calcd for $C_{30}H_{27}Cl_3N_2O_4$+H [(M+H)$^+$]: 585.1109. Found: 585.1111.

EXAMPLE 94e

Preparation of chiral(2'R, 3R, 4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione

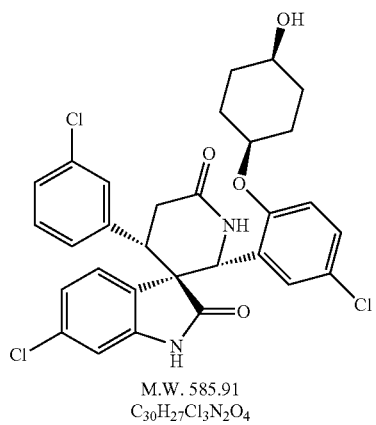

M.W. 585.91
$C_{30}H_{27}Cl_3N_2O_4$

Separation of the two enantiomers from racemic(2'R, 3R, 4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione (350 mg) was conducted by chiral SFC to provide chiral (2'R, 3R, 4'S)-6-chloro-2'-[5-chloro-2-(cis-4-hydroxy-cyclohexyloxy)-phenyl]-4'-(3-chlorophenyl) spiro[3H-indole-3,3'-piperidine]-2,6'(1H)-dione as a white solid (0.15 g, 43%) and chiral(2'S, 3S, 4'R)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione as a white solid (0.15 g, 43%).

EXAMPLE 95a

Preparation of intermediate cis-4-(tert-buyl-dimethyl-silanyloxy)-cyclohexanol

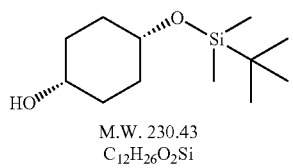

M.W. 230.43
$C_{12}H_{26}O_2Si$

In a manner similar to the method described in example 94a, cis-1,4-cyclohexanediol (3.8 g, 33 mmol) was reacted with tert-butyldimethylchlorosilane (5 g, 34 mmol) and imidazole in N,N-dimethylformamide to give cis-4-(tert-buyl-dimethyl-silanyloxy)-cyclohexanol as a colorless oil (2.4 g, 31%).

The starting material cis-1,4-cyclohexanediol was prepared from 1:1 mixture of cis-/trans-1,4-cyclohexanediol according to the procedures described in EP218433 without modification.

EXAMPLE 95b

Preparation of intermediate trans-2-[4-(tert-butyl-dimethyl-silanyloxy)-cyclohexyloxy]-5-chloro-benzoic acid methyl ester

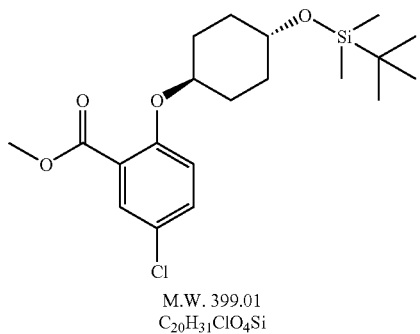

M.W. 399.01
C$_{20}$H$_{31}$ClO$_4$Si

In a manner similar to the method described in example 94b, cis-4-(tert-buyl-dimethyl-silanyloxy)-cyclohexanol (2.7 g, 12 mmol) was reacted with methyl 5-chloro-2-hydroxy-benzoate (1.77 g, 9.5 mmol) and diisopropyl azodicarboxy-late, triphenylphosphine in tetrahydrofuran to give trans-2-[4-(tert-butyl-dimethyl-silanyloxy)-cyclohexyloxy]-5-chloro-benzoic acid methyl ester as a yellow oil (Yield 2.7 g, 71%).

EXAMPLE 95c

Preparation of intermediate trans-2-[4-(tert-butyl-dimethyl-silanyloxy)-cyclohexyloxy]-5-chloro-benzaldehyde

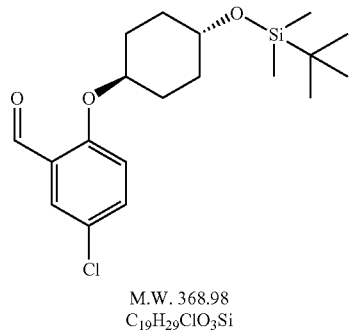

M.W. 368.98
C$_{19}$H$_{29}$ClO$_3$Si

In a manner similar to the method described in example 94c, trans-2-[4-(tert-butyl-dimethyl-silanyloxy)-cyclohexyloxy]-5-chloro-benzoic acid methyl ester (2.7 g, 6.76 mmol) was reacted with LiAlH$_4$ (1 M, 6.76 mL, 6.76 mmol) in ethyl ether, then oxidized with activated MnO$_2$ (4.64 g, 54 mmol) in dichloromethane to give trans-2-[4-(tert-butyl-dimethyl-silanyloxy)-cyclohexyloxy]-5-chloro-benzaldehyde as a white solid (Yield 1.12 g, 44%).

EXAMPLE 95d

Preparation of intermediate 1-[2-[trans-4-(tert-butyl-dimethyl-silanyloxy)-cyclohexyloxy]-5-chloro-phenyl]-3-trimethylsilyoxy-2-aza-1,3-butadiene

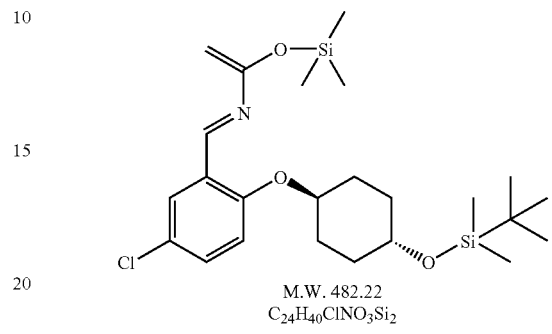

M.W. 482.22
C$_{24}$H$_{40}$ClNO$_3$Si$_2$

In a manner similar to the method described in example 1d, trans-2-[4-(tert-butyl-dimethyl-silanyloxy)-cyclohexyloxy]-5-chloro-benzaldehyde (1.12 g, 3 mmol) was reacted with 1,1,1,3,3,3-hexamethyldisilazane (0.63 mL, 3 mmol), n-butyllithium (2.5 M, 1.2 mL, 3 mmol), trimethylsilyl chloride (0.39 mL, 3 mmol), triethylamine (0.55 mL, 4 mmol) and acetyl chloride (0.28 mL, 4 mmol) to give crude 1-[2-[trans-4-(tert-butyl-dimethyl-silanyloxy)-cyclohexyloxy]-5-chloro-phenyl]-3-trimethylsilyoxy-2-aza-1,3-butadiene as a yellow gum and used for the next step without further purification.

EXAMPLE 95d

Preparation of racemic(2'R, 3R, 4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione

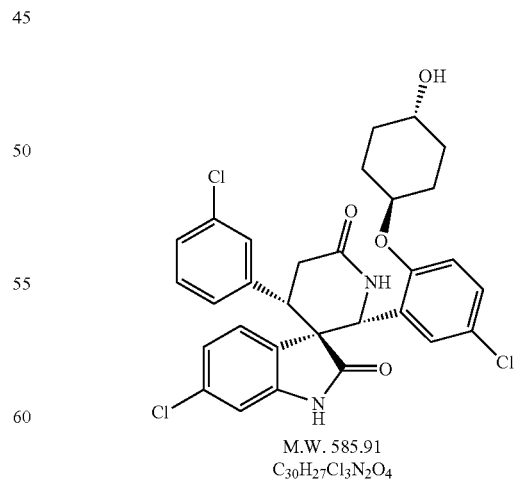

M.W. 585.91
C$_{30}$H$_{27}$Cl$_3$N$_2$O$_4$

In a manner similar to the method described in example 1e, E/Z-6-chloro-3-(3-chloro-benzylidene)-2-oxo-2,3-dihydro-indole-1-carboxylic acid tert-butyl ester prepared in example 1b (0.47 g, 1.2 mmol) was reacted 1-[2-[trans-4-(tert-butyl-dimethyl-silanyloxy)-cyclohexyloxy]-5-chloro-phenyl]-3-trimethylsilyoxy-2-aza-1,3-butadiene (3 mmol) in toluene to give racemic(2'R, 3R, 4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione as a pale yellow solid (Yield 0.3 g, 42%)

HRMS(ES$^+$) m/z Calcd for $C_{30}H_{27}Cl_3N_2O_4$+H [(M+H)$^+$]: 585.1109. Found: 585.1111.

EXAMPLE 95e

Preparation of chiral(2'R, 3R, 4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione

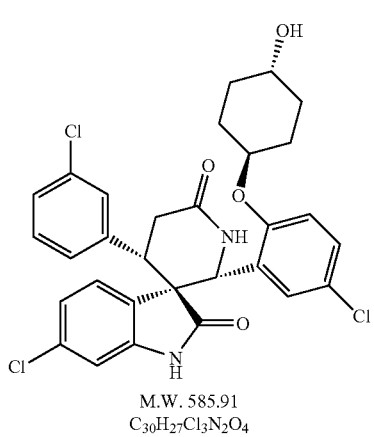

M.W. 585.91
$C_{30}H_{27}Cl_3N_2O_4$

Separation of the two enantiomers from racemic(2'R, 3R, 4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione (250 mg) was conducted by chiral SFC to provide chiral (2'R, 3R, 4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione as a light yellow solid (88 mg, 35%).

EXAMPLE 96a

Preparation of intermediate 5-chloro-4-fluoro-2-(tetrahydro-pyran-4-yloxy)-benzaldehyde

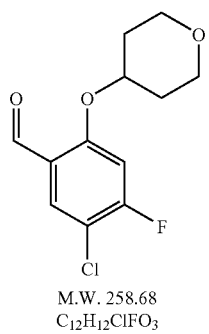

M.W. 258.68
$C_{12}H_{12}ClFO_3$

In a manner similar to the method described in example 4a, 5-chloro-4-fluoro-2-benzaldehyde (2 g, 11.5 mmol) was reacted with methanesulfonic acid tetrahydropyran-4-yl ester (3.72 g, 17 mmol) prepared in Example 32a and $K_2CO_3$ in N,N-dimethylformamide to give 5-chloro-4-fluoro-2-(tetrahydro-pyran-4-yloxy)-benzaldehyde as a yellow solid (Yield 1.32 g, 44%).

The starting material 5-chloro-4-fluoro-2-benzaldehyde was prepared according to the procedures described by Carter, J. S., et al in U.S. Pat. No. 6,077,850 without modification.

EXAMPLE 96b

Preparation of intermediate 1-[5-chloro-4-fluoro-2-(tetrahydro-pyran-4-yloxy)-phenyl]-3-trimethylsilyoxy-2-aza-1,3-butadiene

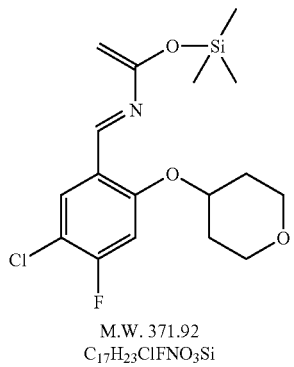

M.W. 371.92
$C_{17}H_{23}ClFNO_3Si$

In a manner similar to the method described in example 1d, 5-chloro-4-fluoro-2-(tetrahydro-pyran-4-yloxy)-benzaldehyde (1.32 g, 5 mmol) was reacted with 1,1,1,3,3,3-hexamethyldisilazane (0.8 g, 10 mmol), n-butyllithium (2.5 M, 2 mL, 5 mmol), trimethylsilyl chloride (0.55 g, 5 mmol), triethylamine (0.7 g, 7 mmol) and acetyl chloride (0.5 g, 7 mmol) to give crude 1-[5-chloro-4-fluoro-2-(tetrahydro-pyran-4-yloxy)-phenyl]-3-trimethylsilyoxy-2-aza-1,3-butadiene as a yellow gum and used for the next step without further purification.

EXAMPLE 96c

Preparation of racemic(2'R, 3R, 4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione

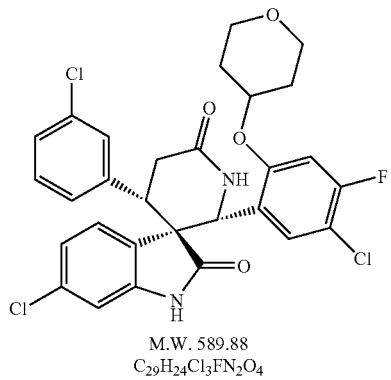

M.W. 589.88
$C_{29}H_{24}Cl_3FN_2O_4$

In a manner similar to the method described in example 32d, E/Z-6-chloro-3-(3-chloro-benzylidene)-2-oxo-2,3-dihydro-indole-1-carboxylic acid tert-butyl ester prepared in example 5b (0.79 g, 2 mmol) was reacted with 1-[5-chloro-4-fluoro-2-(tetrahydro-pyran-4-yloxy)-phenyl]-3-trimethylsilyoxy-2-aza-1,3-butadiene (5 mmol) in toluene, then treated with trifluoroacetic acid in dicloromethane to give racemic(2'R, 3R, 4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione as a white solid (Yield 0.59 g, 50%)

HRMS(ES+) m/z Calcd for $C_{29}H_{24}Cl_3FN_2O_4$+H [(M+H)+]: 589.0859. Found: 589.0858.

EXAMPLE 96c

Preparation of racemic(2'R, 3R, 4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione

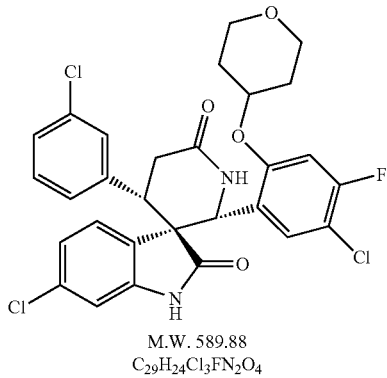

M.W. 589.88
$C_{29}H_{24}Cl_3FN_2O_4$

Separation of the two enantiomers from racemic(2'R, 3R, 4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione (0.3 g) was conducted by chiral SFC to provide chiral(2'R, 3R, 4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione as a white solid (0.099 g, 33%) and chiral(2'S, 3S, 4'R)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione as a white solid (0.128 g, 43%).

EXAMPLE 97a

Preparation of intermediate 5-chloro-4-methyl-2-(tetrahydro-pyran-4-yloxy)-benzaldehyde

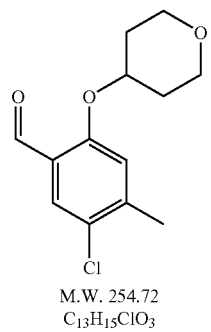

M.W. 254.72
$C_{13}H_{15}ClO_3$

In a manner similar to the method described in example 4a, 5-chloro-4-methyl-2-benzaldehyde (2 g, 11.7 mmol) (Asta tech) was reacted with methanesulfonic acid tetrahydropyran-4-yl ester (3.8 g, 17.6 mmol) prepared in Example 32a and $K_2CO_3$ in N,N-dimethylformamide to give 5-chloro-4-methyl-2-(tetrahydro-pyran-4-yloxy)-benzaldehyde as a yellow solid (Yield 2 g, 67%).

EXAMPLE 97b

Preparation of intermediate 1-[5-chloro-4-methyl-2-(tetrahydro-pyran-4-yloxy)-phenyl]-3-trimethylsilyoxy-2-aza-1,3-butadiene

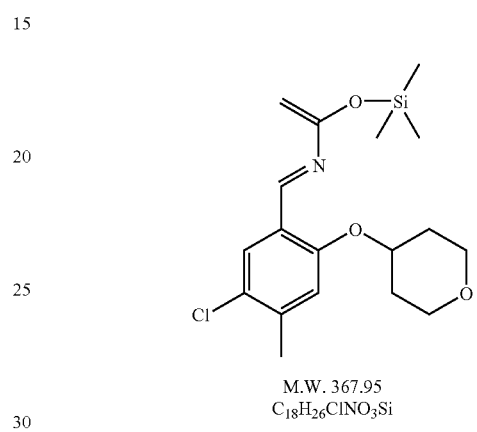

M.W. 367.95
$C_{18}H_{26}ClNO_3Si$

In a manner similar to the method described in example 1d, 5-chloro-4-methyl-2-(tetrahydro-pyran-4-yloxy)-benzaldehyde (2 g, 7.9 mmol) was reacted with 1,1,1,3,3,3-hexamethyldisilazane (1.6 mL, 7.9 mmol), n-butyllithium (2.5 M, 3.1 mL, 7.9 mmol), trimethylsilyl chloride (0.99 mL, 7.9 mmol), triethylamine (1.42 mL, 10 mmol) and acetyl chloride (0.73 mL, 10 mmol) to give crude 1-[5-chloro-4-methyl-2-(tetrahydro-pyran-4-yloxy)-phenyl]-3-trimethylsilyoxy-2-aza-1,3-butadiene as a yellow gum and used for the next step without further purification.

EXAMPLE 97c

Preparation of racemic(2'R, 3R, 4'S)-6-chloro-2'-[5-chloro-4-methyl-2-(tetrahydro-pyran-4-yloxy)-phenyl]]-4'-(3-chlorophenyl)spiro[3H-indole-3,3'-piperidine]-2,6'(1H)-dione

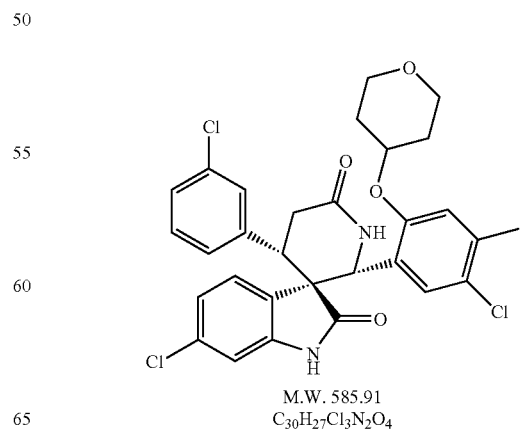

M.W. 585.91
$C_{30}H_{27}Cl_3N_2O_4$

163

In a manner similar to the method described in example 32d, E/Z-6-chloro-3-(3-chloro-benzylidene)-2-oxo-2,3-dihydro-indole-1-carboxylic acid tert-butyl ester prepared in example 5b (1.22 g, 3.14 mmol) was reacted with 1-[5-chloro-4-methy-2-(tetrahydro-pyran-4-yloxy)-phenyl]-3-trimethylsilyoxy-2-aza-1,3-butadiene (7.8 mmol) in toluene, then treated with trifluoroacetic acid in dicloromethane to give racemic(2'R, 3R, 4'S)-6-chloro-2'-[5-chloro-4-methyl-2-(tetrahydro-pyran-4-yloxy)-phenyl]]-4'-(3-chlorophenyl)spiro[3H-indole-3,3'-piperidine]-2,6'(1H)-dione as a white solid (Yield 0.59 g, 33%)

HRMS(ES$^+$) m/z Calcd for $C_{30}H_{27}Cl_3N_2O_4$+H [(M+H)$^+$]: 585.1109. Found: 585.1109.

EXAMPLE 98a

Preparation of intermediate methanesulfonic acid 2,2,6,6-tetramethyl-tetrahydro-pyran-4-yl ester

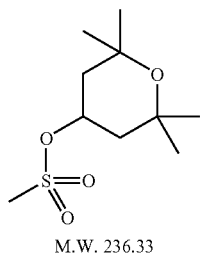

M.W. 236.33
$C_{10}H_{20}O_4S$

In a manner similar to the method described in example 32a, 2,2,6,6-Tetramethyl-tetrahydro-pyran-4-ol (5.5 g, 35 mmol) was reacted with methanesulfonyl chloride (6 g, 52 mmol, Aldrich) and triethylamine in dichloromethane to give methanesulfonic acid 2,2,6,6-tetramethyl-tetrahydro-pyran-4-yl ester as a yellow oil (Yield 8.5 g, 100%). The starting material 2,2,6,6-Tetramethyl-tetrahydro-pyran-4-ol was prepared according to the procedures described by Nemeroff, N. et al in *J. Org. Chem.* 1978, 43(2), 331-334 with slight modification.

EXAMPLE 98b

Preparation of intermediate 5-chloro-2-(2,2,6,6-tetramethyl-tetrahydro-pyran-4-yloxy)-benzaldehyde

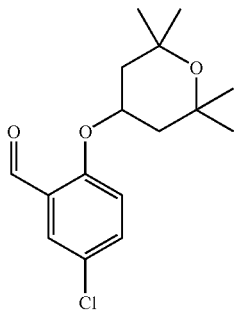

M.W. 296.80
$C_{16}H_{21}ClO_3$

164

In a manner similar to the method described in example 4a, 5-chlorosalicylaldehyde (4.6 g, 30 mmol) (Aldrich) reacted with methanesulfonic acid 2,2,6,6-tetramethyl-tetrahydro-pyran-4-yl ester (8 g, 34 mmol) and $K_2CO_3$ in N,N-dimethylformamide to give 5-chloro-2-(2,2,6,6-tetramethyl-tetrahydro-pyran-4-yloxy)-benzaldehyde as a off white solid (Yield 0.94 g, 10%).

EXAMPLE 98c

Preparation of intermediate 1-[5-chloro-2-(2,2,6,6-tetramethyl-tetrahydro-pyran-4-yloxy)-phenyl]-3-trimethylsilyoxy-2-aza-1,3-butadiene

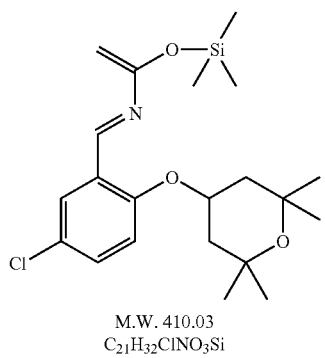

M.W. 410.03
$C_{21}H_{32}ClNO_3Si$

In a manner similar to the method described in example 1d, 5-chloro-2-(2,2,6,6-tetramethyl-tetrahydro-pyran-4-yloxy)-benzaldehyde (0.94 g, 3 mmol) was reacted with 1,1,1,3,3,3-hexamethyldisilazane (0.66 mL, 3 mmol), n-butyllithium (2.5 M, 1.3 mL, 3 mmol), trimethylsilyl chloride (.0.4 mL, 3 mmol), triethylamine (0.57 mL, 4 mmol) and acetyl chloride (0.29 mL, 4 mmol) to give crude 1-[5-chloro-2-(2,2,6,6-tetramethyl-tetrahydro-pyran-4-yloxy)-phenyl]-3-trimethylsilyoxy-2-aza-1,3-butadiene as a yellow gum and used for the next step without further purification.

EXAMPLE 98d

Preparation of racemic(2'R, 3R, 4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione

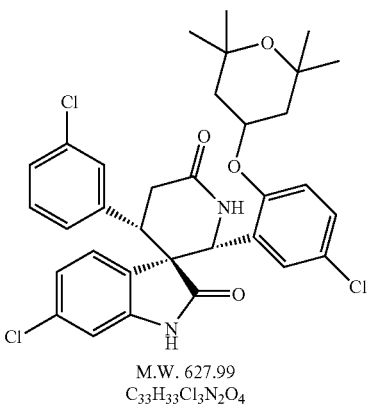

M.W. 627.99
$C_{33}H_{33}Cl_3N_2O_4$

In a manner similar to the method described in 1e, E/Z-6-chloro-3-(3-chloro-benzylidene)-2-oxo-2,3-dihydro-indole-1-carboxylic acid tert-butyl ester prepared in example 1b (0.49 g, 1.3 mmol) was reacted 1-[5-chloro-2-(2,2,6,6-tetramethyl-tetrahydro-pyran-4-yloxy)-phenyl]-3-trimethylsilyoxy-2-aza-1,3-butadiene (3 mmol) in toluene to give racemic(2'R, 3R, 4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione as a white solid (Yield 0.3 g, 37%)

HRMS(ES$^+$) m/z Calcd for $C_{33}H_{33}Cl_3N_2O_4$+H [(M+H)$^+$]: 627.1579. Found: 627.1576.

EXAMPLE 98e

Preparation of chiral(2'R, 3R, 4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione

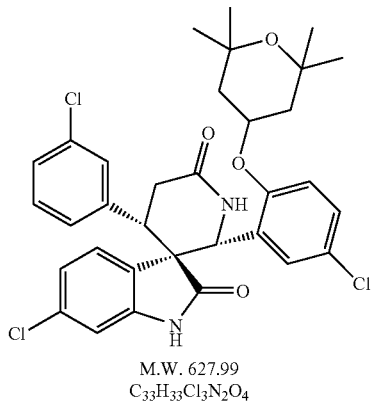

M.W. 627.99
$C_{33}H_{33}Cl_3N_2O_4$

Separation of the two enantiomers from racemic(2'R, 3R, 4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione (0.1 g) was conducted by chiral SFC to provide chiral(2'R, 3R, 4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione as a white solid (33 mg, 33%) and chiral (2'S, 3S, 4'R)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione as a white solid (33 mg, 33%).

EXAMPLE 99a

Preparation of intermediate 5-chloro-2-(tetrahydro-pyran-4-yloxy)-benzaldehyde

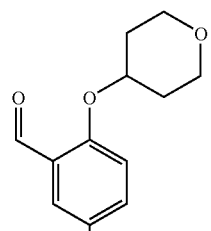

M.W. 240.69
$C_{12}H_{13}ClO_3$

In a manner similar to the method described in example 4a, 5-chlorosalicylaldehyde (6 g, 39 mmol) (Aldrich) was reacted with methanesulfonic acid tetrahydropyran-4-yl ester (10 g, 46 mmol) prepared in Example 32a and $K_2CO_3$ in N,N-dimethylformamide to give 5-chloro-2-(tetrahydro-pyran-4-yloxy)-benzaldehyde as a yellow solid (Yield 2 g, 64%).

EXAMPLE 99b

Preparation of intermediate 1-[5-chloro-2-(tetrahydro-pyran-4-yloxy)-phenyl]-3-trimethylsilyoxy-2-aza-1,3-butadiene

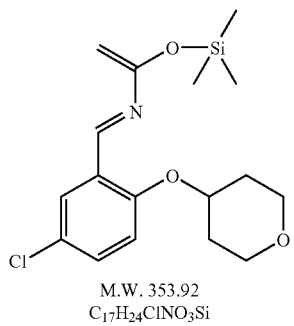

M.W. 353.92
$C_{17}H_{24}ClNO_3Si$

In a manner similar to the method described in example 1d, 5-chloro-2-(tetrahydro-pyran-4-yloxy)-benzaldehyde (2 g, 8.3 mmol) was reacted with 1,1,1,3,3,3-hexamethyldisilazane (1.7 mL, 8.3 mmol), n-butyllithium (2.5 M, 3.3 mL, 8.3 mmol), trimethylsilyl chloride (1.06 mL, 8.3 mmol), triethylamine (1.5 mL, 11 mmol) and acetyl chloride (0.77 mL, 11 mmol) to give crude 1-[5-chloro-4-2-(tetrahydro-pyran-4-yloxy)-phenyl]-3-trimethylsilyoxy-2-aza-1,3-butadiene as a yellow gum and used for the next step without further purification.

EXAMPLE 99c

Preparation of racemic(2'R, 3R, 4'S)-6-chloro-2'-[5-chloro-2-(tetrahydro-pyran-4-yloxy)-phenyl]]-4'-(3-chlorophenyl)spiro[3H-indole-3,3'-piperidine]-2,6'(1H)-dione

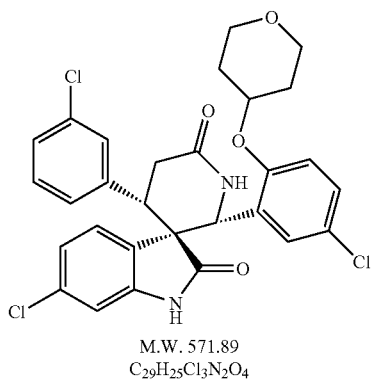

M.W. 571.89
$C_{29}H_{25}Cl_3N_2O_4$

In a manner similar to the method described in example 32d, E/Z-6-chloro-3-(3-chloro-benzylidene)-2-oxo-2,3-dihydro-indole-1-carboxylic acid tert-butyl ester prepared in example 5b (1.3 g, 3.3 mmol) was reacted with 1-[5-chloro-2-(tetrahydro-pyran-4-yloxy)-phenyl]-3-trimethylsilyoxy-2-aza-1,3-butadiene (8.3 mmol) in toluene, then treated with trifluoroacetic acid in dicloromethane to give racemic(2'R, 3R, 4'S)-6-chloro-2'-[5-chloro-2-(tetrahydro-pyran-4-yloxy)-phenyl]]-4'-(3-chlorophenyl)spiro[3H-indole-3,3'-piperidine]-2,6'(1H)-dione as a white solid (Yield 1.2 g, 64%)

HRMS(ES$^+$) m/z Calcd for $C_{29}H_{25}Cl_3N_2O_4$+H [(M+H)$^+$]: 571.0953. Found: 571.0951.

EXAMPLE 100a

Preparation of intermediate E/Z-6-chloro-3-(3-chloro-2-fluoro-benzylidene)-2-oxo-2,3-dihydro-indole-1-carboxylic acid tert-butyl ester

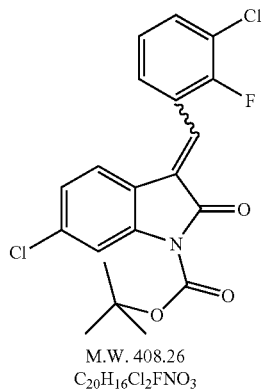

M.W. 408.26
$C_{20}H_{16}Cl_2FNO_3$

In a manner similar to the method describeds in Example 1a and Example 1b, 3-chloro-2-fluorobenzaldehyde (3.1 g, 20 mmol) was reacted with 6-chlorooxindole (3.3 g, 20 mmol) and pyrrolidine in methanol, then di-tert-butyl-dicarbonate (6.5 g, 30 mmol) (Aldrich), triethylamine and 4-dimethylaminopyridine in dichloromethane to give E/Z-6-chloro-3-(3-chloro-2-fluoro-benzylidene)-2-oxo-2,3-dihydro-indole-1-carboxylic acid tert-butyl ester as a yellow solid (Yield: 6.1 g, 75%).

EXAMPLE 100b

Preparation of racemic(2'R, 3R, 4'R)-6-chloro-4'-(3-chloro-2-fluoro-phenyl)-2'-[5-chloro-2-(tetrahydro-pyran-4-yloxy)-phenyl]]spiro[3H-indole-3,3'-piperidine]-2,6'(1H)-dione

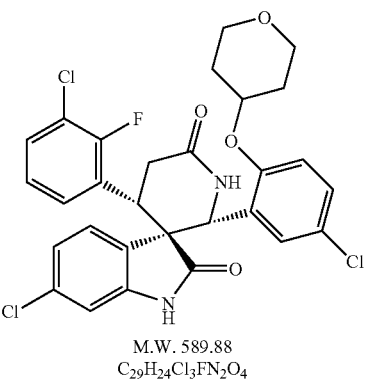

M.W. 589.88
$C_{29}H_{24}Cl_3FN_2O_4$

In a manner similar to the method described in example 32d, E/Z-6-chloro-3-(3-chloro-2-fluoro-benzylidene)-2-oxo-2,3-dihydro-indole-1-carboxylic acid tert-butyl ester (0.68 g, 1.66 mmol) was reacted with 1-[5-chloro-2-(tetrahydro-pyran-4-yloxy)-phenyl]-3-trimethylsilyoxy-2-aza-1,3-butadiene (4 mmol) in toluene, then treated with trifluoroacetic acid in dicloromethane to give racemic(2'R, 3R, 4'R)-6-chloro-4'-(3-chloro-2-fluoro-phenyl)-2'-[5-chloro-2-(tetrahydro-pyran-4-yloxy)-phenyl]]spiro[3H-indole-3,3'-piperidine]-2,6'(1H)-dione as a white solid (Yield 0.12 g, 12%)

HRMS(ES$^+$) m/z Calcd for $C_{29}H_{24}Cl_3FN_2O_4$+H [(M+H)$^+$]: 589.0859. Found: 589.0856.

EXAMPLE 101a

Preparation of intermediate E/Z-6-chloro-3-(3-chloro-4-fluoro-benzylidene)-2-oxo-2,3-dihydro-indole-1-carboxylic acid tert-butyl ester

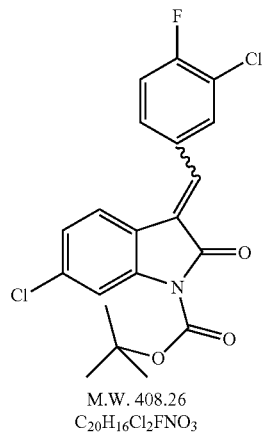

M.W. 408.26
$C_{20}H_{16}Cl_2FNO_3$

In a manner similar to the method describeds in Example 1a and Example 1b, 3-chloro-4-fluorobenzaldehyde (3.5 g, 23 mmol) was reacted with 6-chlorooxindole (4.7 g, 28 mmol) and pyrrolidine in methanol, then di-tert-butyl-dicarbonate (5 g, 23 mmol) (Aldrich), triethylamine and 4-dimethylaminopyridine in dichloromethane to give E/Z-6-chloro-3-(3-chloro-4-fluoro-benzylidene)-2-oxo-2,3-dihydro-indole-1-carboxylic acid tert-butyl ester as a yellow solid (Yield: 4.5 g, 48% ).

EXAMPLE 101b

Preparation of racemic(2'R, 3R, 4'R)-6-chloro-4'-(3-chloro-4-fluoro-phenyl)-2'-[5-chloro-2-(tetrahydro-pyran-4-yloxy)-phenyl]]spiro[3H-indole-3,3'-piperidine]-2,6'(1H)-dione

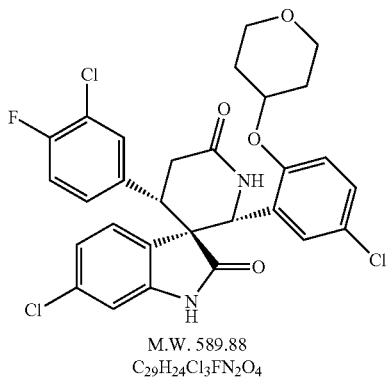

M.W. 589.88
$C_{29}H_{24}Cl_3FN_2O_4$

In a manner similar to the method described in example 32d, E/Z-6-chloro-3-(3-chloro-4-fluoro-benzylidene)-2-oxo-2,3-dihydro-indole-1-carboxylic acid tert-butyl ester (0.68 g, 1.66 mmol) was reacted with 1-[5-chloro-2-(tetrahydro-pyran-4-yloxy)-phenyl]-3-trimethylsilyoxy-2-aza-1,3-butadiene (4 mmol) in toluene, then treated with trifluoroacetic acid in dicloromethane to give racemic(2'R, 3R, 4'R)-6-chloro-4'-(3-chloro-4-fluoro-phenyl)-2'-[5-chloro-2-(tetrahydro-pyran-4-yloxy)-phenyl]]spiro[3H-indole-3,3'-piperidine]-2,6'(1H)-dione as a white solid (Yield 0.14 g, 14%)

HRMS(ES⁺) m/z Calcd for $C_{29}H_{24}Cl_3FN_2O_4$+H [(M+H)⁺]: 589.0859. Found: 589.0856.

EXAMPLE 102a

Preparation of intermediate 2-(4-bromo-2-formyl-phenoxy)-2-methyl-propionic acid ethyl ester

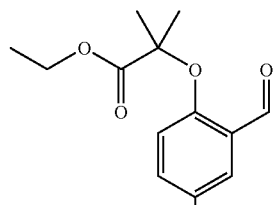

M.W. 315.17
$C_{13}H_{15}BrO_4$

To a mixture of 5-bromo-2-hydroxy-benzaldehyde (14 g, 70 mmol), KI (5 g) and $K_2CO_3$ (19 g, 140 mmol) in DMF (100 mL) was added 2-bromo-2-methyl-propionic acid ethyl ester (17.6 g, 90 mmol). The mixture was heated at 140° C. for 2 h, and then cooled to room temperature, partitioned between water and ethyl acetate. The organic layer was washed with water, dried over anhydrous $Na_2SO_4$ and concentrated. The residue was purified by column chromatography to give the title compound (15 g).

EXAMPLE 102b

Preparation of intermediate 1-[5-bromo-2-(1-ethoxy-carbonyl-1-methyl-ethoxy)-phenyl]-3-trimethylsily-oxy-2-aza-1,3-butadiene

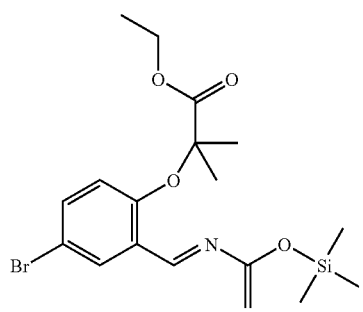

M.W. 428.40
$C_{18}H_{26}BrNO_4Si$

To a mixture of 2-(4-bromo-2-formyl-phenoxy)-2-methyl-propionic acid ethyl ester (6 g, 19 mmol) in THF (80 mL) at 0° C. was added a solution of lithium bis(trimethylsilyl)amide in THF (1 M, 19 mL, 19 mmol). The mixture was stirred under argon at 0° C. for 1h. Then trimethylsilyl chloride (2.4 ML, 19 mmol) was added dropwise, followed by addition of triethylamine (3.44 mL, 24.6 mmol) in one portion and a solution of acetyl chloride (1.75 mL, 24.6 mmol) in diethyl ether (80 mL) dropwise. The cooling bath was removed, and the mixture was stirred at room temperature for 1 h. The mixture was quickly filtered on celite under argon, and the filtrate was concentrated under reduced pressure. The residue was dissolved in toluene (19 mL) to give a solution (1 M) of the title compound.

EXAMPLE 102c

Preparation of intermediate racemic(2'R, 3R, 4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione

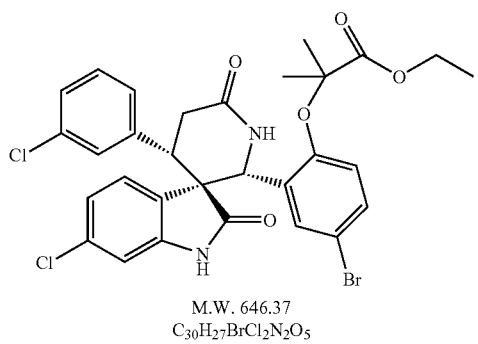

M.W. 646.37
$C_{30}H_{27}BrCl_2N_2O_5$

To a solution of 1-[5-bromo-2-(1-ethoxycarbonyl-1-methyl-ethoxy)-phenyl]-3-trimethylsilyoxy-2-aza-1,3-butadiene in toluene (1 M, 12 mL, 12 mmol) was added E/Z-6-chloro-3-(3-chloro-benzylidene)-1-(carboxylic acid tert-butyl ester)-1,3-dihydro-indole-2-one(1.5 g, 3.8 mmol). The reaction mixture was irradiated by microwave at 135° C. for 40 min, then purified by column chromatography to give the title compound as a white solid (800 mg).

EXAMPLE 102d

Preparation of intermediate racemic(2'R, 3R, 4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione

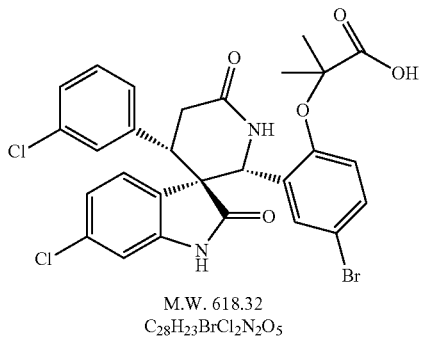

M.W. 618.32
$C_{28}H_{23}BrCl_2N_2O_5$

To a mixture of racemic(2'R, 3R, 4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione (700 mg, 1.08 mmol) in methanol (20 mL) was added a solution of NaOH (120 mg, 3 mmol) in water (10 mL). The mixture was heated at 60° C. for 1.5 h, evaporated to remove methanol, cooled to room temperature, and acidified to "pH" 2 with HCl aq. The precipitate was collected, washed with water and dried to give the title compound as a white solid (610 mg).

EXAMPLE 102e

Preparation of racemic(2'R, 3R, 4'S)-2'-{5-bromo-2-[2-(4-acetyl-piperazin-1,1-dimethyl-2-oxo-ethoxy]-phenyl}-6-chloro-4'-(3-chlorophenyl)spiro[3H-indole-3,3'-piperidine]-2,6'(1H)-dione

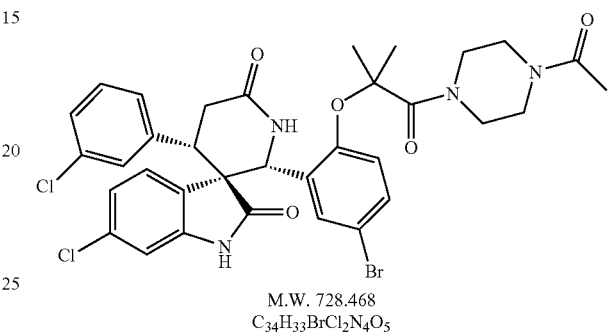

M.W. 728.468
$C_{34}H_{33}BrCl_2N_4O_5$

To a mixture of racemic(2'R, 3R, 4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione (40 mg, 0.065 mmol), EDCI (18.7 mg, 0.098 mmol), HOBt (15 mg, 0.098 mmol) and DIPEA (25 mg, 0.2 mmol) in THF (2 mL) was added 1-piperazin-1-yl-ethanone (25 mg, 0.195 mmol). The mixture was stirred at room temperature overnight, purified by prep-HPLC to give the title compound as a white solid (11 mg).
m/z (M+H)$^+$: 727

EXAMPLE 103

Preparation of racemic(2'R, 3R, 4'S)-2'-{5-bromo-2-[2-(4,4-difluoro-piperidin-1-yl)-1,1-dimethyl-2-oxo-ethoxy]-phenyl}-6-chloro-4'-(3-chlorophenyl)spiro[3H-indole-3,3'-piperidine]-2,6'(1H)-dione M.W. 721.423
$C_{33}H_{30}BrCl_2F_2N_3O_4$ To a mixture of racemic(2'R, 3R, 4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione (40 mg, 0.065 mmol), EDCI (18.7 mg, 0.098 mmol), HOBt (15 mg, 0.098 mmol) and DIPEA (75 mg, 0.6 mmol) in THF (2 mL) was added 4,4-difluoropiperidine hydrochloride (30 mg, 0.195 mmol). The mixture was stirred at room temperature overnight, purified by prep-HPLC to give the title compound as a white solid (19mg).

m/z (M+H)$^+$: 720

EXAMPLE 104

Preparation of racemic(2'R, 3R, 4'S)-2'-{5-bromo-2-[1-methyl-1-(2,2,2-trifluoro-ethylcarbamoyl)-ethoxy]-phenyl}-6-chloro-4'-(3-chlorophenyl)spiro[3H-indole-3,3'-piperidine]-2,6'(1H)-dione

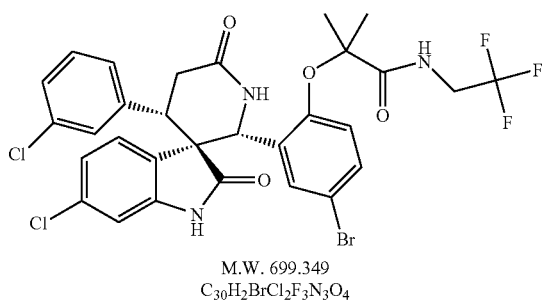

M.W. 699.349
$C_{30}H_2BrCl_2F_3N_3O_4$

To a mixture of racemic(2'R, 3R, 4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione (40 mg, 0.065 mmol), EDCI (18.7 mg, 0.098 mmol), HOBt (15 mg, 0.098 mmol) and DIPEA (75 mg, 0.6 mmol) in THF (2 mL) was added 2,2,2-trifluoroethylamine hydrochloride (25 mg, 0.185 mmol). The mixture was stirred at room temperature overnight, purified by prep-HPLC to give the title compound as a white solid (19 mg).

m/z (M+H)$^+$: 698

EXAMPLE 105

Preparation of racemic(2'R, 3R, 4'S)-2'-[5-bromo-2-(1-dimethylcarbamoyl-1-methyl-ethoxy)-phenyl]-6-chloro-4'-(3-chlorophenyl)spiro[3H-indole-3,3'-piperidine]-2,6'(1H)-dione

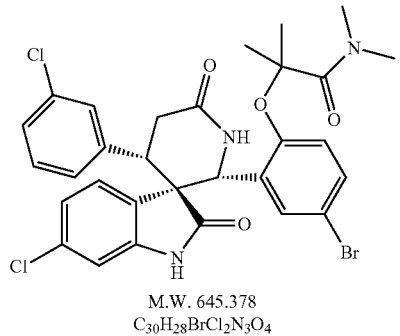

M.W. 645.378
$C_{30}H_{28}BrCl_2N_3O_4$

To a mixture of racemic(2'R, 3R, 4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione (40 mg, 0.065 mmol), EDCI (18.7 mg, 0.098 mmol), HOBt (15 mg, 0.098 mmol) and DIPEA (75 mg, 0.6 mmol) in THF (2 mL) was added dimethylamine hydrochloride (20 mg, 0.25 mmol). The mixture was stirred at room temperature overnight, purified by prep-HPLC to give the title compound as a white solid (26 mg).

m/z (M+H)$^+$: 644

EXAMPLE 106a

Preparation of intermediate 2,2-dimethyl-3-(toluene-4-sulfonyloxy)-propionic acid methyl ester

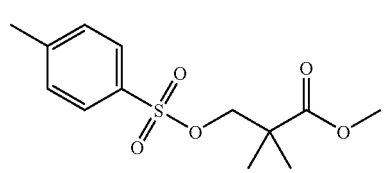

M.W. 286.35 $C_{13}H_{18}O_5S$

To a mixture of 3-hydroxy-2,2-dimethyl-propionic acid methyl ester (13.2 g, 0.1 mol), $K_2CO_3$ (20 g, 0.14 mol) and DMAP (6.2 g, 0.05 mol) in DCM (100 mL) was added p-toluenesulfonyl chloride (19 g, 0.1 mol). The mixture was stirred at room temperature overnight, then filtered. The filtrate was washed with HCl aq. (1 M) and water, dried over anhydrous $Na_2SO_4$ and concentrated to give the title compound (15 g).

EXAMPLE 106b

Preparation of intermediate 3-(4-bromo-2-formyl-phenoxy)-2,2-dimethyl-propionic acid methyl ester

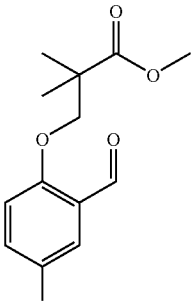

M.W. 315.17 $C_{13}H_{15}BrO_4$

To a mixture of 5-bromo-2-hydroxy-benzaldehyde (4 g, 20 mmol), KI (1 g) and $K_2CO_3$ (4 g, 29 mmol) in DMF (10 mL) was added 2,2-dimethyl-3-(toluene-4-sulfonyloxy)-propionic acid methyl ester (6.9 g, 24 mmol). The mixture was heated at 140° C. for 2 h, and then cooled to room temperature, partitioned between water and ethyl acetate. The organic layer was washed with water (3×), dried over anhydrous Na₂SO₄ and concentrated. The residue was purified by column chromatography to give the title compound (5.4 g).

EXAMPLE 106c

Preparation of intermediate 1-[5-bromo-2-(2-methoxycarbonyl-2-methyl-propoxy)phenyl]-3-trimethylsilyoxy-2-aza-1,3-butadiene

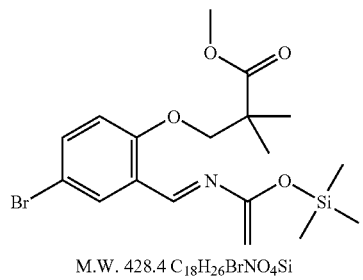

M.W. 428.4 C$_{18}$H$_{26}$BrNO$_4$Si

To a mixture of 3-(4-bromo-2-formyl-phenoxy)-2,2-dimethyl-propionic acid methyl ester (5 g, 16 mmol) in THF (80 mL) at 0° C. was added a solution of lithium bis(trimethylsilyl) amide in THF (1 M, 16 mL, 16 mmol). The mixture was stirred at same temperature for 1.5 h under argon. Then trimethylsilyl chloride (2 mL, 16 mmol) was added dropwise, followed by addition of triethylamine (2.87 mL, 20.8 mmol) in one portion and a solution of acetyl chloride (1.46 mL, 20.8 mmol) in diethyl ether (80 mL) dropwise. The cooling bath was removed, and the mixture was stirred at room temperature for 1 h. The mixture was quickly filtered on celite under nitrogen, and filtrate was concentrated under reduced pressure. The residue was dissolved in toluene (16 mL) to give a solution (1 M) of the title compound.

EXAMPLE 106d

Preparation of intermediate racemic(2'R, 3R, 4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione

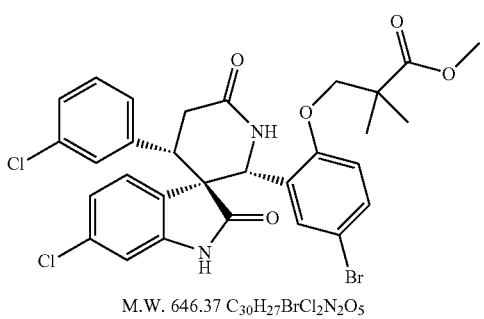

M.W. 646.37 C$_{30}$H$_{27}$BrCl$_2$N$_2$O$_5$

To a solution of 1-[5-bromo-2-(2-methoxycarbonyl-2-methyl-propoxy) phenyl]-3-trimethylsilyoxy-2-aza-1,3-butadiene in toluene (1 M, 12 mL, 12 mmol) was added E/Z-6-chloro-3-(3-chloro-benzylidene)-1-(carboxylic acid tert-butyl ester)-1,3-dihydro-indole-2-one(1.5 g, 3.8 mmol). The reaction mixture was irradiated by microwave at 135° C. for 40 min, then purified by column chromatography to give the title compound as a white solid (300 mg).

EXAMPLE 106e

Preparation of intermediate racemic(2'R, 3R, 4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione

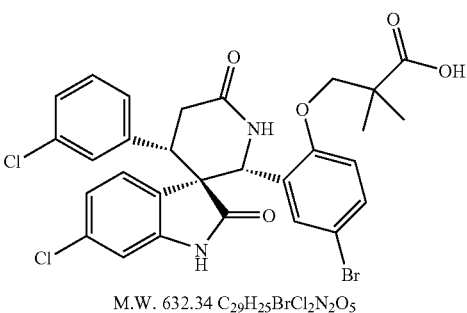

M.W. 632.34 C$_{29}$H$_{25}$BrCl$_2$N$_2$O$_5$

To a mixture of racemic(2'R, 3R, 4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione (106 mg, 0.16 mmol) in methanol (6 mL) was added a solution of NaOH (30 mg, 0.75 mmol) in water (3 mL). The mixture was heated at 60° C. for 5 h, evaporated to remove methanol, cooled to room temperature, and acidified to "pH" 2 with HCl aq. The precipitate was collected and dried to give the title compound as a white solid (70 mg). m/z (M+H)$^+$: 617

EXAMPLE 106f

Preparation of racemic(2'R,3R,4'S)-2'-[5-bromo-2-(2-dimethylcarbamoyl-2-methyl-propoxy)-phenyl]-6-chloro-4'-(3-chlorophenyl)spiro[3H-indole-3,3'-piperidine]-2,6'(1H)-dione

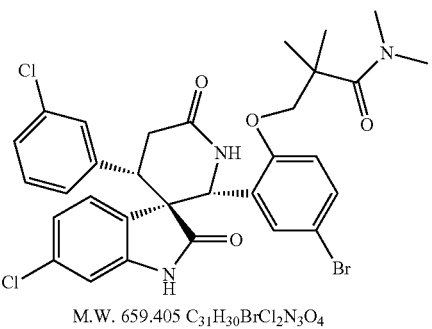

M.W. 659.405 C$_{31}$H$_{30}$BrCl$_2$N$_3$O$_4$

To a mixture of racemic (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione (50 mg, 0.08 mmol), EDCI (23 mg, 0.12 mmol), HOBt (18.4 mg, 0.12 mmol) and DIPEA (62 mg, 0.48 mmol) in THF (2 mL) was added dimethylamine hydrochloride (20 mg, 0.25 mmol). The mixture was stirred at room temperature overnight, purified by prep-HPLC to give the title compound as a white solid (20 mg)

m/z (M+H)$^+$: 658.

EXAMPLE 107

Preparation of racemic(2'R,3R,4'S)-2'-[5-bromo-2-(2,2-dimethyl-3-oxo-3-pyrrolidin-1-yl-propoxy)-phenyl]-6-chloro-4'-(3-chlorophenyl)spiro[3H-indole-3,3'-piperidine]-2,6'(1H)-dione

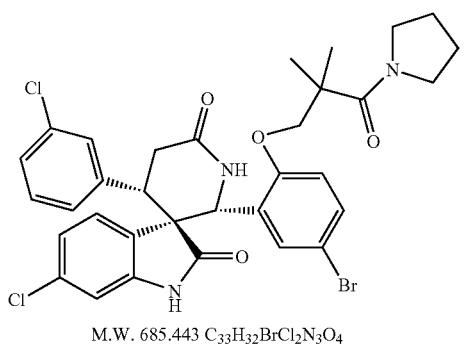

M.W. 685.443 C$_{33}$H$_{32}$BrCl$_2$N$_3$O$_4$

To a mixture of racemic(2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione (50 mg, 0.08 mmol), EDCI (23 mg, 0.12 mmol), HOBt (18.4 mg, 0.12 mmol) and DIPEA (62 mg, 0.48 mmol) in THF (2 mL) was added pyrrolidine (17 mg, 0.24 mmol). The mixture was stirred at room temperature overnight, purified by prep-HPLC to give the title compound as a white solid (33 mg).

m/z (M+H)$^+$: 684

EXAMPLE 108a

Preparation of intermediate toluene-4-sulfonic acid 3-methyl-oxetan-3-ylmethyl ester

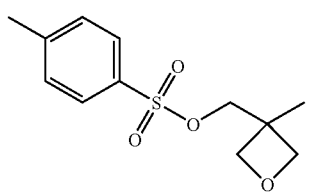

M.W. 256.32 C$_{12}$H$_{16}$O$_4$S

To a mixture of (3-methyl-oxetan-3-yl)-methanol (10.2 g, 0.1 mol) and DMAP (18.3 g, 0.15 mol) in DCM (100 mL) was added 4-methyl-benzenesulfonyl chloride (19 g, 0.1 mol). The mixture was stirred at room temperature for 1 h, then filtered. The filtrate was washed with HCl aq. (1 M) and water, dried over anhydrous Na$_2$SO$_4$ and concentrated to give the title compound (18 g).

EXAMPLE 108b

Preparation of Intermediate 5-bromo-2-(3-methyl-oxetan-3-ylmethoxy)-benzaldehyde

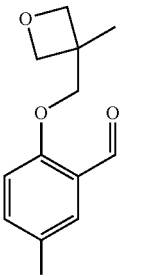

M.W. 285.14 C$_{12}$H$_{13}$BrO$_3$

To a mixture of 5-bromo-2-hydroxy-benzaldehyde (14 g, 70 mmol), KI (5 g) and K$_2$CO$_3$ (19 g, 140 mmol) in DMF (100 mL) was added toluene-4-sulfonic acid 3-methyl-oxetan-3-ylmethyl ester (18 g, 70 mmol). The mixture was heated at 140° C. for 2 h, and then cooled to room temperature, partitioned between water and ethyl acetate. The organic layer was washed with water for 3 times, dried over anhydrous Na$_2$SO$_4$ and concentrated. The residue was purified by column chromatography to give the title compound (10 g).

EXAMPLE 108c

Preparation of intermediate 1-[5-bromo-2-(3-methyl-oxetan-3-ylmethoxy)phenyl]-3-trimethylsilyoxy-2-aza-1,3-butadiene

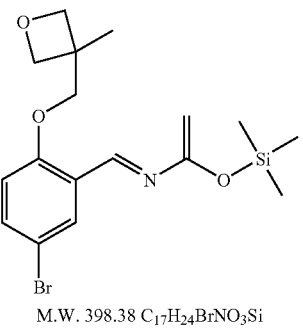

M.W. 398.38 C$_{17}$H$_{24}$BrNO$_3$Si

To a mixture of 5-bromo-2-(3-methyl-oxetan-3-ylmethoxy)-benzaldehyde (4.5 g, 16 mmol) in THF (80 mL) at 0° C. was added a solution of lithium bis(trimethylsilyl)amide in THF (1 M, 16 mL, 16 mmol). The mixture was stirred at same temperature for 1 h under argon. Then trimethylsilyl chloride (2 mL, 16 mmol) (Aldrich) was added dropwise, followed by addition of triethylamine (2.87 mL, 20.9 mmol) in one portion and a solution of acetyl chloride (1.46 mL, 20.9 mmol) in diethyl ether (80 mL) dropwise. The cooling bath was removed, and the mixture was stirred at room temperature for 1 h. The mixture was quickly filtered on celite under nitrogen, and filtrate was concentrated under reduced pressure. The residue was dissolved in toluene (16 mL) to give a solution (1 M) of the title compound.

EXAMPLE 108d

Preparation of racemic(2'R,3R,4'S)-2'-[5-bromo-2-(3-methyl-oxetan-3-ylmethoxy)-phenyl]-6-chloro-4'-(3-chlorophenyl)spiro[3H-indole-3,3'-piperidine]-2,6'(1H)-dione

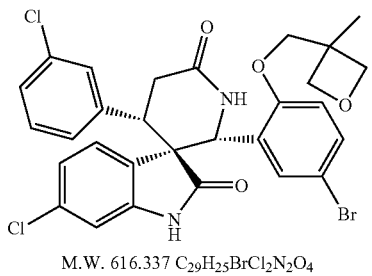

M.W. 616.337 C29H25BrCl2N2O4

To a solution of 1-[5-bromo-2-(3-methyl-oxetan-3-ylmethoxy)phenyl]-3-trimethylsilyoxy-2-aza-1,3-butadiene in toluene (1 M, 12 mL, 12 mmol) was added E/Z-6-chloro-3-(3-chloro-benzylidene)-1-(carboxylic acid tert-butyl ester)-1,3-dihydro-indole-2-one (1.5 g, 3.8 mmol). The reaction mixture was irradiated by microwave at 135° C. for 40 min, then purified by column chromatography to give the title compound as a white solid (300 mg).
m/z (M+H)+: 616

EXAMPLE 108e

Preparation of chiral(2'R,3R,4'S)-6-chloro-4'-(3-chlorophenyl)-2'-[5-bromo-2-(3-methyl-oxetan-3-ylmethoxy)phenyl]spiro[3H-indole-3,3'-piperidine]-2,6'(1H)-dione

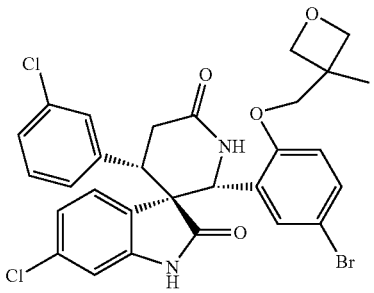

M.W. 616.337 C29H25BrCl2N2O4

Separation of the two enantiomers from racemic(2'R,3R,4'S)-6-chloro-4'-(3-chlorophenyl)-2'-[5-bromo-2-(3-methyl-oxetan-3-ylmethoxy)phenyl]spiro[3H-indole-3,3'-piperidine]-2,6'(1H)-dione (40 mg) was conducted by chiral Prep-HPLC to provide chiral(2'R,3R,4'S)-6-chloro-4'-(3-chlorophenyl)-2'-[5-bromo-2-(3-methyl-oxetan-3-ylmethoxy)phenyl]spiro[3H-indole-3,3'-piperidine]-2,6'(1H)-dione (15 mg) and chiral(2'S,3S,4'R)-6-chloro-4'-(3-chlorophenyl)-2'-[5-bromo-2-(3-methyl-oxetan-3-ylmethoxy)phenyl]spiro[3H-indole-3,3'-piperidine]-2,6'(1H)-dione (15 mg).

EXAMPLE 109a

Preparation of intermediate 5-bromo-2-(4-fluoro-benzyloxy)-benzaldehyde

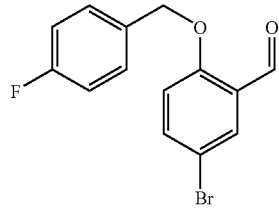

M.W. 309.14 C14H10BrFO2

To a mixture of 5-bromo-2-hydroxy-benzaldehyde (5 g, 25 mmol), KI (2 g) and K2CO3 (7 g, 50 mmol) in DMF (100 mL) was added 1-chloromethyl-4-fluoro-benzene (3.96 g, 28 mmol). The mixture was heated at 140° C. for 2 h, then cooled to room temperature, partitioned between water and ethyl acetate. The organic layer was washed with water for 3 times, dried over anhydrous Na2SO4 and concentrated. The residue was purified by column chromatography to give the title compound (4.5 g).

EXAMPLE 109b

Preparation of 1-[5-bromo-2-(4-fluoro-benzyloxy)phenyl]-3-trimethylsilyoxy-2-aza-1,3-butadiene

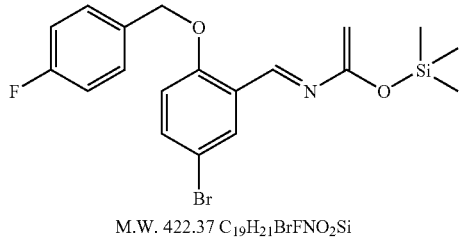

M.W. 422.37 C19H21BrFNO2Si

To a mixture of 5-bromo-2-(4-fluoro-benzyloxy)-benzaldehyde (4.4 g, 14 mmol) in THF (60 mL) at 0° C. was added a solution of lithium bis(trimethylsilyl)amide in THF (1 M, 14 mL, 14 mmol). The mixture was stirred at same temperature for 1 h under argon. Then trimethylsilyl chloride (1.75 mL, 14 mmol) was added dropwise, followed by addition of triethylamine (2.51 mL, 18 mmol) in one portion and a solution of acetyl chloride (1.28 mL, 18 mmol) in diethyl ether (60 mL) dropwise. The cooling bath was removed, and the mixture was stirred at room temperature for 1 h. The mixture was quickly filtered on celite under nitrogen, and filtrate was concentrated under reduced pressure. The residue was dissolved in toluene (14 mL) to give a solution (1 M) of the title compound.

EXAMPLE 109c

Preparation of racemic(2'R,3R,4'S)-2'-[5-bromo-2-(4-fluoro-benzyloxy)-phenyl]-6-chloro-4'-(3-chlorophenyl)spiro[3H-indole-3,3'-piperidine]-2,6'(1H)-dione

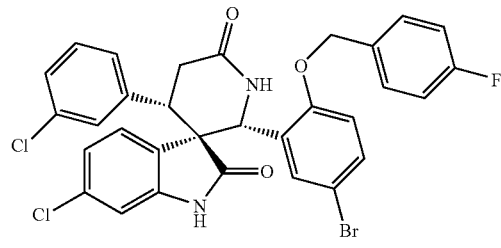

M.W. 640.334 C31H22BrCl2FN2O3

To a solution of 1-[5-bromo-2-(4-fluoro-benzyloxy)phenyl]-3-trimethylsilyoxy-2-aza-1,3-butadiene in toluene (1 M, 12 mL, 12 mmol) was added E/Z-6-chloro-3-(3-chloro-benzylidene)-1-(carboxylic acid tert-butyl ester)-1,3-dihydro-indole-2-one (1.5 g, 3.8 mmol). The reaction mixture was irradiated by microwave at 135° C. for 40 min, then purified by column chromatography to give the title compound as a white solid (160 mg).

m/z (M+H)+: 639

EXAMPLE 110a

Preparation of intermediate toluene-4-sulfonic acid 3-ethyl-oxetan-3-ylmethyl ester

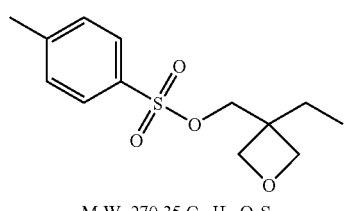

M.W. 270.35 C13H18O4S

To a mixture of (3-ethyl-oxetan-3-yl)-methanol (11.6 g, 0.1 mol) and DMAP (18.3 g, 0.15 mol) in DCM (100 mL) was added 4-methyl-benzenesulfonyl chloride (19 g, 0.1 mol). The mixture was stirred at room temperature for 1 h, then filtered. The filtrate was washed with HCl aq. (1 M) and water, dried over anhydrous Na2SO4 and concentrated to give the title compound (19 g).

EXAMPLE 110b

Preparation of intermediate 5-bromo-2-(3-ethyl-oxetan-3-ylmethoxy)-benzaldehyde

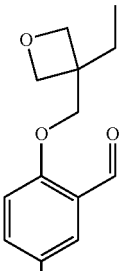

M.W. 229.17 C13H15BrO3

To a mixture of 5-bromo-2-hydroxy-benzaldehyde (14 g, 70 mmol), KI (5 g) and K2CO3 (19 g, 140 mmol) in DMF (100 mL) was added toluene-4-sulfonic acid 3-ethyl-oxetan-3-ylmethyl ester (19 g, 70 mmol). The mixture was heated at 140° C. for 2 h, and then cooled to room temperature, partitioned between water and ethyl acetate. The organic layer was washed with water for 3 times, dried over anhydrous Na2SO4 and concentrated. The residue was purified by column chromatography to give the title compound (10 g).

EXAMPLE 110c

Preparation of intermediate 1-[5-bromo-2-(3-ethyl-oxetan-3-ylmethoxy)phenyl]-3-trimethylsilyoxy-2-aza-1,3-butadiene

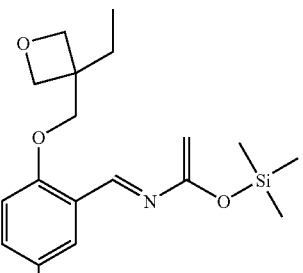

M.W. 412.40 C18H26BrNO3Si

To a mixture of 5-bromo-2-(3-ethyl-oxetan-3-ylmethoxy)-benzaldehyde (5.9 g, 20 mmol) in THF (80 mL) at 0° C. was added a solution of lithium bis(trimethylsilyl)amide in THF (1 M, 20 mL, 20 mmol). The mixture was stirred at same temperature for 1 h under argon. Then trimethylsilyl chloride (2.5 mL, 20 mmol) (Aldrich) was added dropwise, followed by addition of triethylamine (3.6 mL, 26 mmol) in one portion and a solution of acetyl chloride (1.83 mL, 26 mmol) in diethyl ether (80 mL) dropwise. The cooling bath was removed, and the mixture was stirred at room temperature for 1 h. The mixture was quickly filtered on celite under nitrogen, and filtrate was concentrated under reduced pressure. The residue was dissolved in toluene (20 mL) to give a solution (1 M) of the title compound.

EXAMPLE 110d

Preparation of racemic(2'R,3R,4'S)-2'-[5-bromo-2-(3-ethyl-oxetan-3-ylmethoxy)-phenyl]-6-chloro-4'-(3-chlorophenyl)spiro[3H-indole-3,3'-piperidine]-2,6'(1H)-dione

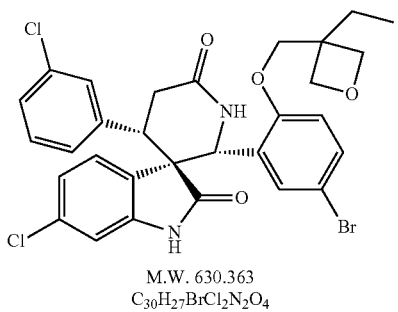

M.W. 630.363
$C_{30}H_{27}BrCl_2N_2O_4$

To a solution of 1-[5-bromo-2-(3-ethyl-oxetan-3-yl-methoxy)phenyl]-3-trimethylsilyoxy-2-aza-1,3-butadiene in toluene (1 M, 12 mL, 12 mmol) was added E/Z-6-chloro-3-(3-chloro-benzylidene)-1-(carboxylic acid tert-butyl ester)-1,3-dihydro-indole-2-one (1.5 g, 3.8 mmol). The reaction mixture was irradiated by microwave at 135° C. for 40 min, then purified by column chromatography to give the title compound as a white solid (200 mg).
m/z (M+H)$^+$: 629.

EXAMPLE 111a

Preparation of intermediate 4-methanesulfonyloxy-piperidine-1-caboxylic acid tert-butyl ester

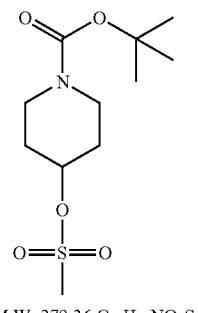

M.W. 279.36 $C_{11}H_{21}NO_5S$

At 0° C., to a solution of 4-hydroxy-piperidine-1-carboxylic acid tert-butyl ester (4 g, 20.20 mmol) and DMAP (3 g, 24 mmol) in DCM (50 mL) was added methanesulfonyl chloride (2.7 g, 24 mmol). After stirred for 2 h, the mixture was filtrated. The filtrate was washed by 0.5N HCl (50 mL), Na$_2$CO$_3$ aqueous solution (1 M, 50 mL) and brine (50 mL), dried over anhydrous Na$_2$SO$_4$, and concentrated to give the title compound as a yellow solid (5 g).

EXAMPLE 111b

Preparation of intermediate 4-(2-formyl-4-trifluoromethyl-phenoxy)-piperidine-1-carboxylic acid tert-butyl ester

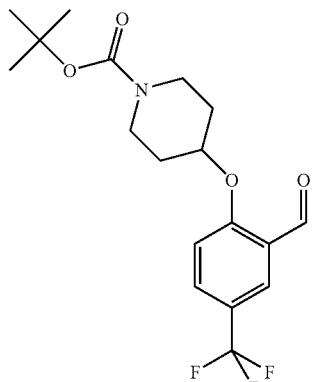

M.W. 373.38 $C_{18}H_{22}F_3NO_4$

A mixture of 2-hydroxy-5-trifluoromethyl-benzaldehyde (1.36 g, 7.17 mmol), 4-methanesulfonyloxy-piperidine-1-carboxylic acid tert-butyl ester (2.2 g, 7.88 mmol) and K$_2$CO$_3$ (2.96 g, 21.5 mmol) in anhydrous N,N-dimethylformamide (15 mL) was heated at 100° C. for 1 h. After cooled to room temperature, the mixture was filtered and the filtrate was concentrated. The residue was dissolved in DCM (50 mL). The solution was washed with water, dried over anhydrous Na$_2$SO$_4$ and concentrated. The residue was purified by chromatography to give the title compound (1.43 g).

EXAMPLE 111c

Preparation of intermediate 1-[2-(1-tert-butoxycarbonyl-piperidin-4-yloxy)]-5-trifluoromethyl-phenyl]-3-trimethylsilyoxy-2-aza-1,3-butadiene

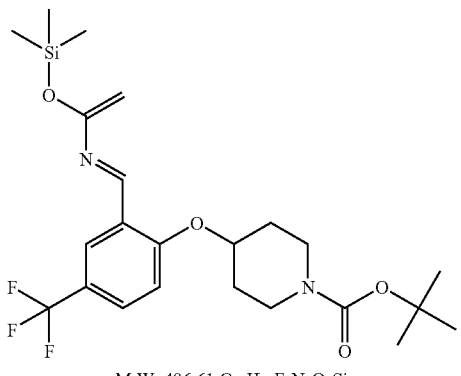

M.W. 486.61 $C_{23}H_{33}F_3N_2O_4Si$

To dry tetrahydrofuran (10 mL) was added a solution of LiHMDS (3.8 mmol, 3.8 mL) in THF (1M) under argon at room temperature, followed by the addition of 4-(2-formyl- 4-trifluoromethyl-phenoxy)-piperidine-1-carboxylic acid tert-butyl ester (1.43 g, 3.83 mmol). After the mixture was stirred at room temperature for 0.5 h, trimethylsilyl chloride (0.48 mL, 3.8 mmol) was added dropwise. Then the temperature of the mixture was lowered to 0° C. on a cooling ice bath. To this mixture was added triethylamine (0.71 ml, 4.87 mmol) in one portion, followed by dropwise addition of a solution of acetyl chloride (0.36 ml, 4.87 mmol) in diethyl ether (20 ml). The cooling bath was removed, and the mixture was stirred at room temperature overnight. The mixture was quickly filtered on celite under nitrogen, and the filtrate was concentrated under reduced pressure to give the title compound as a yellow gum and used for the next step without further purification.

EXAMPLE 111d

Preparation of racemic(2'R,3R,4'S)-2'-[2-(1-tert-butoxycarbonyl-piperidin-4-yloxy)]-5-trifluoromethyl-phenyl]-6-chloro-4'-(3-chlorophenyl)spiro[3H-indole-3,3'-piperidine]-2,6'(1H)-dione

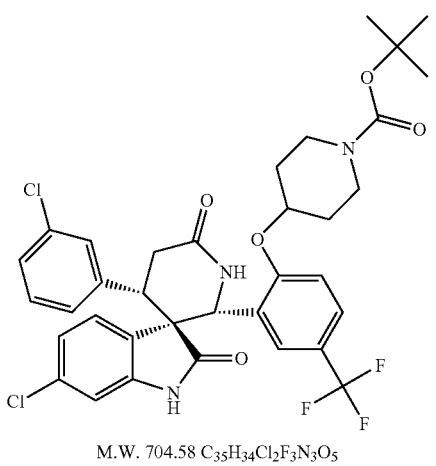

M.W. 704.58 C$_{35}$H$_{34}$Cl$_2$F$_3$N$_3$O$_5$

To a solution of 1-[2-(1-tert-butoxycarbonyl-piperidin-4-yloxy)]-5-trifluoromethyl-phenyl]-3-trimethylsilyoxy-2-aza-1,3-butadiene (2.6 g, 5.4 mmol) in toluene (5.4 mL) was added E/Z-6-chloro-3-(3-chloro-benzylidene)-1-carboxylic acid tert-butyl ester-1,3-dihydro-indole-2-one (300 mg, 0.77 mmol). The mixture was heated at 130° C. for 30 min by microwave irradiation under argon. After cooled to room temperature, the mixture was concentrated and the residue was purified by flash column to give title compound (10 mg).

m/z (M+H)$^+$: 704

EXAMPLE 112a

Preparation of intermediate 5-bromo-2-iodo-benzaldehyde

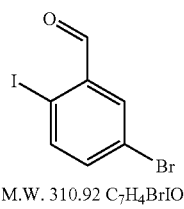

M.W. 310.92 C$_7$H$_4$BrIO

To a solution of 5-bromo-2-iodo-benzomitrile (1.54 g, 5 mmol) in DCM (15 mL) was added a solution of DIBALH (6 mL, 6 mmol) dropwise at 0° C. After the addition, the reaction mixture was warmed to r.t. and stirred for 2 h. Then the mixture was poured into 20 g of ice and 20 mL of 1N HCl, filtered and extracted by DCM (40 mL), washed with aqueous sodium bicarbonate, dried over MgSO$_4$ and concentrated to give crude product (Yield: 1.2 g).

EXAMPLE 112b

Preparation of intermediate 1-(2-iodo-5-bromo-phenyl)-3-trimethylsilyoxy-2-aza-1,3-butadiene

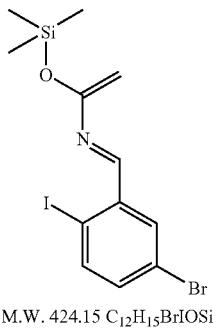

M.W. 424.15 C$_{12}$H$_{15}$BrIOSi

To dry tetrahydrofuran (120 mL) was added a solution of LiHMDS (42 mmol, 42 ml) in THF under argon at room temperature, followed by the addition of 5-bromo-2-iodo-benzaldehyde (13 g, 42 mmol). After the mixture was stirred at room temperature for 0.5 h, trimethylsilyl chloride (5.32 mL, 42 mmol) was added dropwise. Then the temperature of the mixture was lowered to 0° C. on a cooling ice bath. To this mixture was added triethylamine (7.6 mL, 54.4 mmol) in one portion, followed by the dropwise addition of a solution of acetyl chloride (3.9 mL, 54.4 mmol) in diethyl ether (200 mL). The cooling bath was removed, and the mixture was stirred at room temperature for 1 h. The mixture was quickly filtered on celite under nitrogen, and filtrate was concentrated under reduced pressure to give the title compound as a yellow gum and used for the next step without further purification.

EXAMPLE 112c

Preparation of intermediate racemic(2'S,3R,4'S)-2'-(5-bromo-2-iodo-phenyl)-6-chloro-4'-(3-chlorophenyl)spiro[3H-indole-3,3'-piperidine]-2,6'(1H)-dione

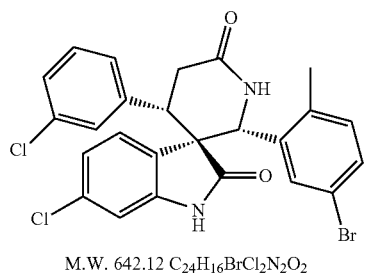

M.W. 642.12 C$_{24}$H$_{16}$BrCl$_2$N$_2$O$_2$

In a manner similar to the method described in 32d, E/Z-6-chloro-3-(3-chloro-benzylidene)-1-carboxylic acid tert-butyl ester-1,3-dihydro-indole-2-one (3.9 g, 8 mmol) was reacted with 1-(5-bromo-2-Iodo)-3-trimethylsilyoxy-2-aza-1,3-butadiene (21 mmol) in toluene to give the title compound as a white solid (Yield: 600 mg).

EXAMPLE 112d

Preparation of racemic(2'R,3R,4'S)-2'-[5-bromo-2-(1-methyl-piperidin-4-ylamino)-phenyl]-6-chloro-4'-(5-chloro-2-methyl-phenyl)spiro[3H-indole-3,3'-piperidine]-2,6'(1H)-dione

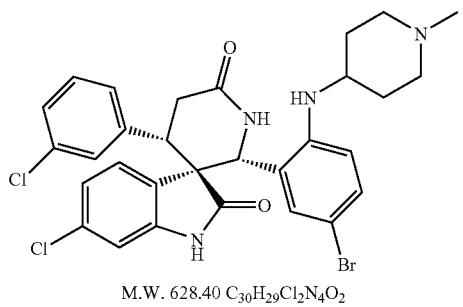

M.W. 628.40 C$_{30}$H$_{29}$Cl$_2$N$_4$O$_2$

To a solution of racemic(2'R,3R,4'S)-6-chloro-4'-(3-chlorophenyl)-2'-(5-bromo-2-iodo-phenyl)spiro[3H-indole-3,3'-piperidine]-2,6'(1H)-dione (32 mg, 0.05 mmol) in DMF (5 mL) was added 1-methyl-piperidin-4-ylamine (8 mg g, 0.075 mmol), Cs$_2$CO$_3$ (33 mg, 0.01 mmol), 2-acetyl-cyclohexanone (1.4 mg) and CuI (1 mg) under argon. The mixture was stirred at r.t. for 5 h, then partitioned between ethyl acetate and water. The organic layer was separated, and the aqueous layer was extracted with ethyl acetate. The combined organic layer was washed with NaHCO$_3$ aqueous solution, dried over MgSO$_4$ and concentrated. The residue was purified with Prep-HPLC to give title compound as a white solid (Yield: 10 mg)

m/z (M+H)$^+$: 627.

EXAMPLE 113a

Preparation of intermediate 2-[2-(tert-Butyl-dimethyl-silanyloxy)-ethoxy]-5-iodo -benzaldehyde

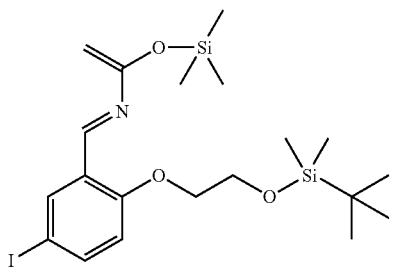

M.W. 406.34 C$_{15}$H$_{23}$IO$_3$Si

To a solution of 5-iodosalicylaldehyde (6.68 g, 26.9 mmol) (Aldrich) in N,N-dimethylformamide (150 mL) was added anhydrous K$_2$CO$_3$ (11.17 g, 80.7 mmol), and (2-bromo-ethoxy)-tert-butyl-dimethyl-silane (7.74 g, 32.3 mmol, Aldrich). The reaction mixture was heated at 65° C. for 18 h. The crude was cooled to room temperature, diluted with ethyl acetate, washed with water, brine. The organic layer was separated, dried over MgSO$_4$, concentrated to give 2-[2-(tert-butyl-dimethyl-silanyloxy)-ethoxy]-5-iodo-benzaldehyde as a yellow oil (Yield 10 g, 100%).

EXAMPLE 113b

Preparation of intermediate 1-[2-(tert-butyl-dimethyl-silanyloxy)-ethoxy]-5-iodo-phenyl]-3-trimethylsilyoxy-2-aza-1,3-butadiene M.W. 519.58
C$_{20}$H$_{34}$INO$_3$Si$_2$ To 1,1,1,3,3,3-hexamethyldisilazane (4.36 mL, 21 mmol) (Aldrich) under nitrogen at room temperature was added n-butyllithium (2.5 M, 8.4 mL, 21 mmol) (Aldrich). The reaction mixture was stirred at room temperature for 10 minutes. Then dry tetrahydrofuran (60 mL) was added, followed by the addition of 2-[2-(tert-butyl -dimethyl-silanyloxy)-ethoxy]-5-iodo-benzaldehyde (8.53 g, 21 mmol). After the mixture was stirred at room temperature for 0.5 h, trimethylsilyl chloride (2.66 mL, 21 mmol) (Aldrich) was added dropwise. Then the temperature of the mixture was lowered to 0° C. on a cooling ice bath. To this mixture was added triethylamine (3.8 mL, 27.2 mmol) in one portion, followed by the dropwise addition of a solution of acetyl chloride (1.94 mL, 27.2 mmol) in diethyl ether (100 mL). The cooling bath was removed, and the mixture was stirred at room temperature for 1 h. The mixture was quickly filtered on celite under nitrogen, and filtrate was concentrated under reduced pressure to give crude 1-[2-(tert -butyl-dimethyl-silanyloxy)-ethoxy]-5-iodo-phenyl]-3-trimethylsilyoxy-2-aza-1,3-butadiene as a yellow oil and used for the next step without further purification.

EXAMPLE 113c

Preparation of intermediate racemic(2'R,3R,4'S)-6-chloro-4'-(3-chlorophenyl)-2'-[5-iodo-2-(2-hydroxy-ethoxy)-phenyl]spiro[3H-indole-3,3'-pipeidine]-2,6' (1H)-dione

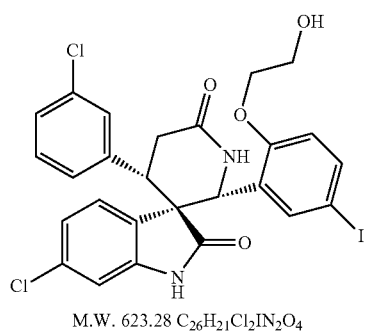

M.W. 623.28 $C_{26}H_{21}Cl_2IN_2O_4$

To a solution of 1-[2-(tert-butyl-dimethyl-silanyloxy)-ethoxy]-5-iodo-phenyl]-3-trimethylsilyoxy-2-aza-1,3-butadiene (21 mmol) in toluene (30 mL) was added E/Z-6-chloro-3-(3-chlorobenzylidene)-2-oxo-2,3-dihydro-indole-1-carboxylic acid tert-butyl ester prepared in Example 1b (1.2 g, 3.1 mmol). The reaction mixture was stirred under nitrogen in a sealed tube at 140° C. for 45 min. After the solution was cooled to room temperature, the reaction mixture was concentrated. The residue was dissolved in dichloromethane (20 mL) and trifluoroactic acid (20 mL) was added. After the reaction mixture was stirred at room temperature for 4 h, the mixture was concentrated. The residue was partitioned between saturated NaHCO₃ solution and ethyl acetae. The aqueous layer was extracted with ethyl acetate. The combined organic layer was dried over Na₂SO₄ and concentrated. The residue was purified by chromatography (EtOAc:CH₂Cl₂=1; 3) to give racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione as a light yellow solid (Yield 0.46 g, 25%).

HRMS(ES⁺) m/z Calcd for $C_{26}H_{21}Cl_2IN_2O_4$+H [(M+H)⁺]: 622.9996. Found: 622.9995.

EXAMPLE 113d

Preparation of racemic(2'R,3'R,4'S)-6-chloro-4'-(3-chlorophenyl)-2'-[2-(2-hydroxy-ethoxy)-5-(2-thiophenyl)-phenyl]-spiro[3H-indole-3,3'-piperidine]-2,6'-dione

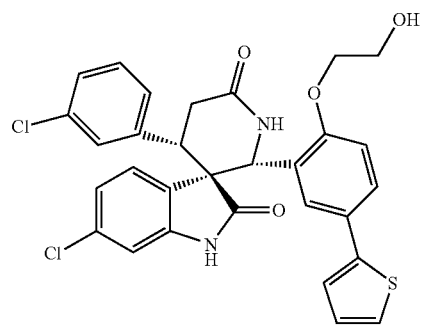

M.W. 579.51 $C_{30}H_{24}Cl_2N_2O_4S$

Racemic(2'R,3'R,4'S)-6-chloro-4'-(3-chlorophenyl)-2'-[2-(2-hydroxy-ethoxy)-5-iodo-phenyl]-spiro[3H-indole-3,3'-piperidine]-2,6'-dione (150 mg, 0.24 mmol), triphenyl phosphine (Aldrich, 25 mg), tris(dibenzylideneacetone) dipalladium (Strem Chemicals, MA, 25 mg), copper iodide (2 mg, Aldrich), and 2-(tributylstannyl)thiophene (585 mg, 1.56 mmol, Aldrich) were combined into 1.4-dioxane (4 mL). The mixture was purged with nitrogen and was stirred at 85° C. for 1.5 h. The reaction mixture was poured into water and was extracted with EtOAc. The combined organic was washed with H₂O, brine, dried with MgSO₄ and concentrated to give a yellow residue. It was chromatographied on an ISCO machine eluting with EtOAc to 5% MeOH/EtOAc followed by recrystalization from CH₂Cl₂/Hexane to give an off-white solid. 20 mg.

HRMS(ES⁺) m/z Calcd for $C_{30}H_{24}Cl_2N_2O_4S$+H [(M+H)⁺]: observed, 579.0905; calculated, 579.0907.

EXAMPLE 114

Preparation of chiral(2'R,3'R,4'S)-6-chloro-4'-(3-chlorophenyl)-2'-[2-(2-hydroxy-ethoxy)-5-(2-furanyl)-phenyl]-spiro[3H-indole-3,3'-piperidine]-2,6'-dione

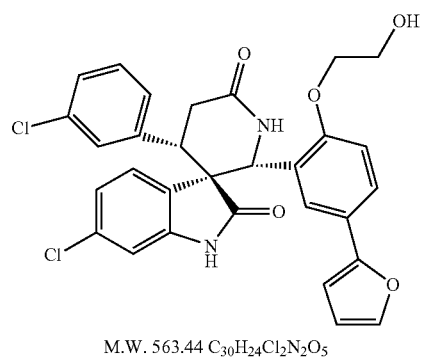

M.W. 563.44 $C_{30}H_{24}Cl_2N_2O_5$

Racemic(2'R,3'R,4'S)-6-chloro-4'-(3-chlorophenyl)-2'-[2-(2-hydroxy-ethoxy)-5-iodo-phenyl]-spiro[3H-indole-3,3'-piperidine]-2,6'-dione (120 mg, 0.19 mmol), triphenyl phosphine (Aldrich, 30 mg), tris(dibenzylideneacetone)dipalladium (Strem Chemicals, MA, 20 mg), CuI (2 mg, Aldrich), and 2-(tributylstannyl)furan (200 mg, 0.56 mmol, Aldrich) were combined into 1,4-dioxane (4 mL). The mixture was purged with nitrogen and was stirred at 80° C. for 1.5 hrs. The reaction mixture was poured into water and was extracted with EtOAc. The combined organic was washed with $H_2O$, brine, dried with $MgSO_4$ and concentrated to give a yellow residue. It was chromatographied on an ISCO machine eluting with EtOAc to 5% MeOH/EtOAc to give a yellow film. 32 mg. The product was then resolved on a SFC machine at 2mL/min., 35% methanol, 100 bar and 30° C. to give two enantiomers.

HRMS($ES^+$) m/z Calcd for $C_{30}H_{24}Cl_2N_2O_5$+H [$(M+H)^+$]: observed, 563.1133; calculated, 563.1135.

EXAMPLE 115

Preparation of racemic(2'R,3'R,4'S)-6-chloro-4'-(3-chlorophenyl)-2'-[2-(2-hydroxy-ethoxy)-5-phenyl-phenyl]-spiro[3H-indole-3,3'-piperidine]-2,6'-dion

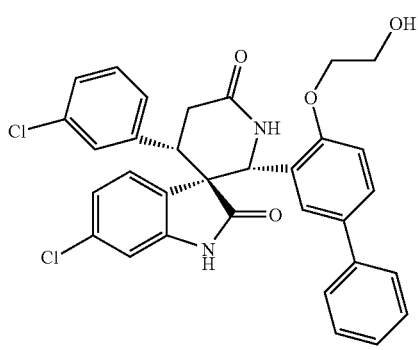

M.W. 573.48 $C_{32}H_{26}Cl_2N_2O_4$

Racemic(2'R,3'R,4'S)-6-chloro-4'-(3-chlorophenyl)-2'-[2-(2-hydroxy-ethoxy)-5-iodo-phenyl]-spiro[3H-indole-3,3'-piperidine]-2,6'-dione (200 mg, 0.32 mmol), triphenyl phosphine (Aldrich, 30 mg), tris(dibenzylideneacetone)dipalladium (Strem Chemicals, MA, 32 mg), CuI (3 mg, Aldrich), and tributylphenyltin (587 mg, 1.60 mmol, Aldrich) were combined into 1.4-dioxane (4 mL). The mixture was purged with nitrogen and was stirred at 80° C. for 2 h. The reaction mixture was diluted with THF, filtered through celite. The filtrate was concentrated to give a brown residue, which was chromatographied on an ISCO machine eluting with 50% EtOAc/Hexane to EtOAc followed by HPLC purification with 25-65% CH3CN/H2O to give a white solid. 7.8 mg.

HRMS($ES^+$) m/z Calcd for $C_{32}H_{26}Cl_2N_2O_4$+H [$(M+H)^+$]: observed, 573.1340; calculated, 573.1343.

EXAMPLE 116a

Preparation of intermediate 4-chloro-2-tert-butyl-dimethylsilanyloxy-benzaldehyde

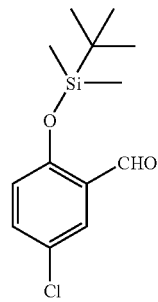

M.W. 270.83 $C_{13}H_{19}ClO_2Si$

To a stirred solution of 5-chloro-2-hydroxy-benzaldehyde (Aldrich, 7.83 g, 50 mmol) in methylene chloride (150 mL) were added imidazole (Aldrich, 3.72 g, 54.6 mmol) and tert-butyl-dimethyl-chloro-silane (Aldrich, 7.84 g, 52 mmol). The mixture was stirred at room temperature for 5 hrs. A second portion of imidazole (1.2 g) was added and mixture was stirred for 1 hr. The mixture was then poured into saturated sodium bicarbonate solution (150 mL). The organic layer was separated and the aqueous layer was extracted with methylene chloride (2×50 mL). The combined extracts were washed with water, brine and dried over magnesium sulfate. Removal of the solvent gave an off white solid. 13.62 g.

EXAMPLE 116b

Preparation of intermediate 1-[2-(tert-butyl-dimethylsilanyloxy)-5-chloro-phenyl]-3-trimethylsilanyloxy-2-aza-1,3-butadiene

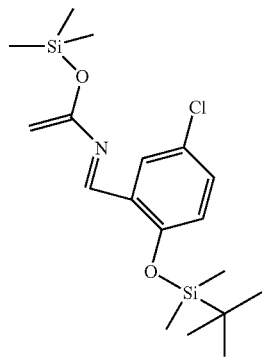

M.W. 384.07 $C_{18}H_{30}ClNO_2Si_2$

To a stirred solution of 1,1,1,3,3,3-hexamethyldisilazane (3.34 g, 20 mmol) at 0° C., n-Buli (2.5 M, 8 mL) was added slowly and the mixture was stirred for 15 min. Then THF (40 mL) was added followed by 4-chloro-2-tert-butyl-dimethylsilanyloxy-benzaldehyde (5.42 g, 20 mmol). The mixture was stirred at rt for 30 min. Then, trimethylsilanyl chloride (26 mmol), acetyl chloride (26 mmol) and trimethylamine (26 mmol) were added and the mixture was stirred at rt for 1 hr. The mixture was quickly passed through a short pad of silica gel and the pad was washed with 30% EtOAc/Hexanes to make sure the azadiene has completely passed through. The filtrate was concentrated at rt and directly used for the next step.

EXAMPLE 116c

Preparation of intermediate racemic(2'R,3R,4'S)-2'-[2-(tert-butyl-dimethylsilanyloxy)-5-chloro-phenyl]-6-chloro-4'-(3-chlorophenyl)-2,6'-dioxo-spiro[3H-indole-3,3'-piperidine]-1-carboxylic acid tert-butyl ester

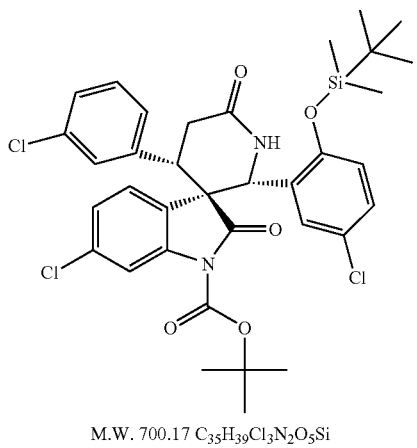

M.W. 700.17 C$_{35}$H$_{39}$Cl$_3$N$_2$O$_5$Si

E/Z-6-chloro-3-(3-chloro-benzylidene)-2-oxo-2,3-dihydro-indole-1-carboxylic acid tert-butyl ester (3.89 g, 10 mmol) and 1-[5-chloro-2-(tert-butyl-dimethylsilanyloxy)-phenyl]-3-trimethylsilanyloxy-2-aza-1,3-butadiene (20 mmol) were combined into toluene (110 mL). The mixture was stirred at 110° C. for 2 hrs. The solvent was removed and the residue was chromatographied (15% -35% EtOAc/Hexanes) to give a foam. 1.66 g. MS (H$^+$), 701.

EXAMPLE 116d

Preparation of racemic(2'R,3R,4'S)-6-chloro-4'-(3-chlorophenyl)-2'-[5-chloro-2-(2-pyrazinyloxy)-phenyl]-spiro-[3H-indole-3,3'-piperidine]-2,6'-dione

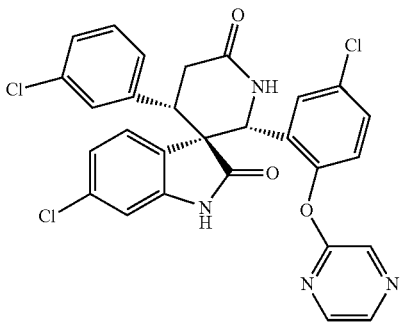

M.W. 565.85, C$_{28}$H$_{19}$Cl$_3$N$_4$O$_3$

To a stirred solution of racemic (2'R,3R,4'S)-2'-[2-(tert-butyl-dimethylsilanyloxy)-5-chloro-phenyl]-6-chloro-4'-(3-chlorophenyl)-2,6'-dioxo-spiro[3H-indole-3,3'-piperidine]-1-carboxylic acid tert-butyl ester (140 mg, 0.2 mmol) in 1,4-dioxane (4 mL), tetra-butylammonium fluoride (Aldrich, 0.4 mmol, 0.4 mL of 1 M solution in THF) was added and the mixture was stirred for 30 min. at rt. Then 2-chloro-pyrazine (Aldrich, 0.40 mmol) was added and the resulting mixture was stirred at reflux for 8 hrs. The solvent was removed and the residue was chromatographied on an ISCO machine (5% MeOH in methylene chloride) to give a brown solid. 24 mg. MS (H$^+$), 565

EXAMPLE 117a

Preparation of intermediate 4-iodo-2-tert-butyl-dimethylsilanyloxy-benzaldehyde

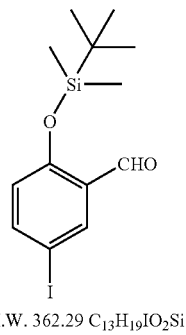

M.W. 362.29 C$_{13}$H$_{19}$IO$_2$Si

To a stirred solution of 5-iodo-2hydroxy-benzaldehyde (Aldrich, 15.5 g, 62.5 mmol) in methylene chloride (100 mL) were added imidazole (Aldrich, 4.28 g, 63 mmol) and tert-butyl-dimethyl-chloro-silane (Aldrich, 9.45 g, 63 mmol). The mixture was stirred at room temperature for 5.5 hrs and then poured into 1 N sodium hydroxide solution (150 mL). The organic layer was separated and the aqueous layer was extracted with methylene chloride (2×50 mL). The combined extracts were washed with water, brine and dried over magnesium sulfate. Removal of the solvent gave an oil, which was chromatographied (hexane as eluent) to give a colorless oil. 16.6 g.

EXAMPLE 117b

Preparation of intermediate 1-[5-bromo-2-(tert-butyl-dimethylsilanyloxy)-phenyl]-3-trimethylsilanyloxy-2-aza-1,3-butadiene

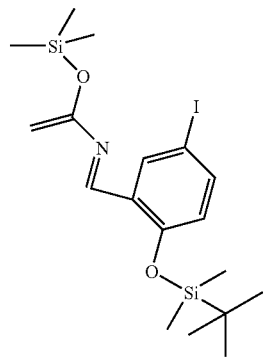

M.W. 475.52 C$_{18}$H$_{30}$INO$_2$Si$_2$

To a stirred solution of 1,1,1,3,3,3-hexamethyldisilazane (6.4 g, 40 mmol) at 0° C., n-BuLi (2.5 M, 16 mL) was added slowly and the mixture was stirred for 15 min. Then THF (80 mL) was added followed by 4-iodo-2-tert-butyl-dimethylsilanyloxy-benzaldehyde (14.48 g, 40 mmol). The mixture was stirred at rt for 30 min. Then, trimethylsilanyl chloride (40 mmol), acetyl chloride (40 mmol) and trimethylamine (40 mmol) were added and the mixture was stirred at rt for 1 hr. The mixture was quickly passed through a short pad of silica gel and the pad was washed with 30 EtOAc/Hexanes to make sure the azadiene has completely passed through. The filtrate was concentrated at rt and directly used for the next step.

EXAMPLE 117c

Preparation of intermediate racemic(2'R,3R,4'S)-2'-[2-(tert-butyl-dimethylsilanyloxy)-5-iodo-phenyl]-6-chloro-4'-(3-chlorophenyl)-2,6'-dioxo-spiro[3H-indole-3,3'-piperidine]-1-carboxylic acid tert-butyl ester

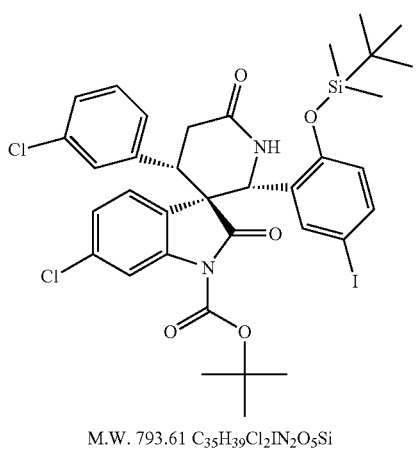

M.W. 793.61 $C_{35}H_{39}Cl_2IN_2O_5Si$

E/Z-6-chloro-3-(3-chloro-benzylidene)-2-oxo-2,3-dihydro-indole-1-carboxylic acid tert-butyl ester (3.85 g, 13 mmol) and 1-[5-bromo-2-(tert-butyl-dimethylsilanyloxy)-phenyl]-3-trimethylsilanyloxy-2-aza-1,3-butadiene (40 mmol) were combined into toluene (110 mL). The mixture was stirred at 110° C. for 2 hrs. The solvent was removed and the residue was chromatographied (15%-35% EtOAc/Hexanes) to give a foam. 4.65 g. MS (H+), 693.

EXAMPLE 117d

Preparation of racemic(2'R,3R,4'S)-6-chloro-4'-(3-chlorophenyl)-2'-[2-hydroxy-5-iodo-phenyl]spiro[3H-indole-3,3'-piperidine]-2,6'-dione

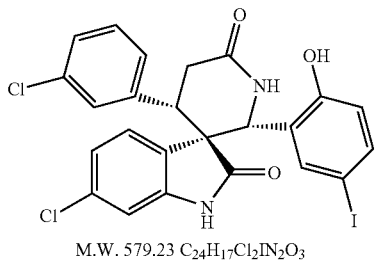

M.W. 579.23 $C_{24}H_{17}Cl_2IN_2O_3$

Racemic(2'R,3R,4'S)-2'-[2-(tert-butyl-dimethylsilanyloxy)-5-iodo-phenyl]-6-chloro-4'-(3-chlorophenyl)-2,6'-dioxo-spiro[3H-indole-3,3'-piperidine]-1-carboxylic acid tert-butyl ester (200 mg, 0.25 mmol) was dissolved in 30% TFA/CH$_2$Cl$_2$ (5 mL) and the solution was stirred at rt for 2 h. The solvent was removed and the residue was partioned between water and methylene chloride. The organic layer was separated and dried with sodium sulfate and concentrated. The residue was chromatographied to give a white solid which was directly used for next step. MS (H+), 579.

EXAMPLE 117e

Preparation of racemic(2'R,3'R,4'S)-6-chloro-4'-(3-chlorophenyl)-2'-[5-(2-furanyl)-2-hydroxy-phenyl]-spiro[3H-indole-3,3'-piperidine]-2,6'-dione

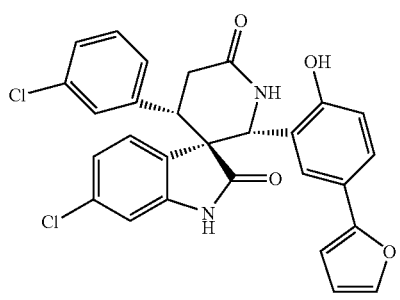

M.W. 519.39, $C_{28}H_{20}Cl_2N_2O_4$

In a manner similar to the method described in Example 114, the title compound was prepared from racemic (2'R,3R,4'S)-6-chloro-4'-(3-chlorophenyl)-2'-[2-hydroxy-5-iodo-phenyl]spiro[3H-indole-3,3'-piperidine]-2,6'-dione.

HRMS(ES+) m/z Calcd for $C_{28}H_{20}Cl_2N_2O_4$+H [(M+H)+]: observed, 519.0873; calculated, 519.0873

EXAMPLE 118

Preparation of racemic(2'R,3'R,4'S)-6-chloro-4'-(3-chlorophenyl)-2'-[2-hydroxy-5-(2-thiofuranyl)-phenyl]-spiro[3H-indole-3,3'-piperidine]-2,6'-dione

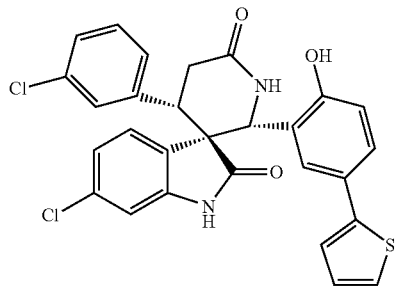

M.W. 535.45, $C_{28}H_{20}Cl_2N_2O_3S$

In a manner similar to the method described in Example 113d, the title compound was prepared from racemic (2'R, 3R,4'S)-6-chloro-4'-(3-chlorophenyl)-2'-[2-hydroxy-5-iodophenyl]spiro[3H-indole-3,3'-piperidine]-2,6'-dione.

MS(ES$^+$) m/z Calcd for $C_{28}H_{20}Cl_2N_2O_3S$+H [(M+H)$^+$]: observed, 535; calculated, 534.

EXAMPLE 119

Preparation of racemic(2'R,3'R,4'S)-6-chloro-4'-(3-chlorophenyl)-2'-[2-hydroxy-5-phenyl]-phenyl-spiro[3H-indole-3,3'-piperidine]-2,6'-dione

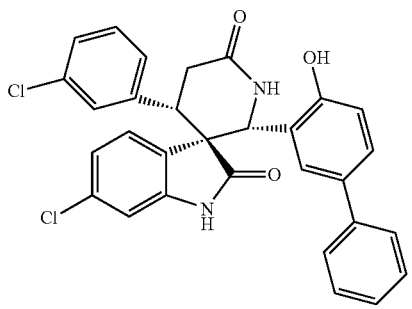

M.W. 529.43, $C_{30}H_{22}Cl_2N_2O_3$

In a manner similar to the method described in Example 115, the title compound was prepared from racemic (2'R,3R,4'S)-6-chloro-4'-(3-chlorophenyl)-2'-[2-hydroxy-5-iodophenyl]spiro[3H-indole-3,3'-piperidine]-2,6'-dione.

HRMS(ES$^+$) m/z Calcd for $C_{30}H_{22}Cl_2N_2O_3$+H [(M+H)$^+$]: observed, 529.1080; calculated, 529.1080.

EXAMPLE 120

Preparation of racemic(2'R,3'R,4'S)-6-chloro-4'-(3-chlorophenyl)-2'-[2-hydroxy-5-(2-thiazolyl)-phenyl]-spiro[3H-indole-3,3'-piperidine]-2,6'-dione

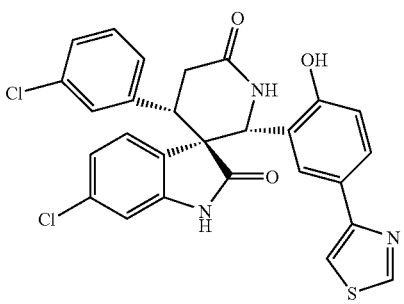

M.W. 536.44, $C_{27}H_{19}Cl_2N_3O_3S$

In a manner similar to the method described in Example 113d, the title compound was prepared from racemic (2'R, 3R,4'S)-6-chloro-4'-(3-chlorophenyl)-2'-[2-hydroxy-5-iodophenyl]spiro[3H-indole-3,3'-piperidine]-2,6'-dione (214d) and 4-(tributylstannyl) thiazole (Synthonix).

HRMS(ES$^+$) m/z Calcd for $C_{27}H_{19}Cl_2N_3O_3S$+H [(M+H)$^-$]: observed, 536.0598; calculated, 536.0597.

EXAMPLE 121

Preparation of racemic(2'R,3'R,4'S)-6-chloro-4'-(3-chlorophenyl)-2'-[2-hydroxy-5-(2-thiazolyl)-phenyl]-spiro[3H-indole-3,3'-piperidine]-2,6'-dione

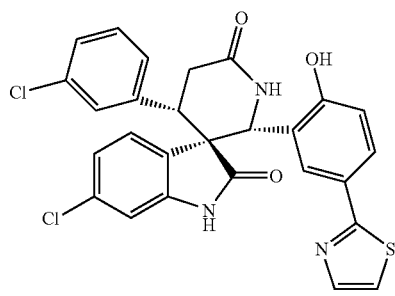

M.W. 536.44, $C_{27}H_{19}Cl_2N_3O_3S$

In a manner similar to the method described in Example 113d, the title compound was prepared from racemic(2'R,3R, 4'S)-6-chloro-4'-(3-chlorophenyl)-2'-[2-hydroxy-5-iodophenyl]spiro[3H-indole-3,3'-piperidine]-2,6'-dione and 2-(tributylstannyl)thiazole (Synthonix).

HRMS(ES$^+$) m/z Calcd for $C_{27}H_{19}Cl_2N_3O_3S$+H [(M+H)$^+$]: observed, 536.0598; calculated, 536.0597.

EXAMPLE 122a

Preparation of intermediate(S)-3-(4-chloro-2-formyl-phenoxy)-pyrrolidine-1-carboxylic acid tert-butyl ester

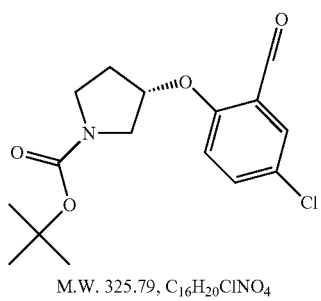

M.W. 325.79, C₁₆H₂₀ClNO₄

To a solution of (R)-1-N-boc-3-hydroxy pyrrolidine (4.89 g, 26.12 mmol, Aldrich) in CH₂Cl₂ (100 mL) at 0° C. was added methanesulfonyl chloride, followed by Et₃N (4.4 mL, 31.35 mmol). The reaction was stirred at room temperature for 2 h, washed with 0.5 N HCl, Water and brine, dried over MgSO₄, filtered and concentrated to give a light yellow oil.

The yellow oil was combined with 5-chlorosalicylaldehyde (4.07 g, 26 mmol, Aldrich) and Cs₂CO₃ (21.2 g, 65 mmol) in DMF (100 ml), heated at 75° C. overnight, poured into water and was extracted with EtOAc (3×). The combined organic was washed with 0.5 N NaOH, water, brine, dried over MgSO₄, filtered and concentrated to give a thick yellow oil (6.82 g, 80% yield), which was used directly for the next step.

EXAMPLE 122b

Preparation of chiral(2'R,3R,4'S)-2'-{2-[3-(tert-butoxycarbonyl)-pyrolidinyloxy]-5-chloro-phenyl}-6-chloro-4'-(3-chlorophenyl)spiro[3H-indole-3,3'-piperidine]-2,6'-dione

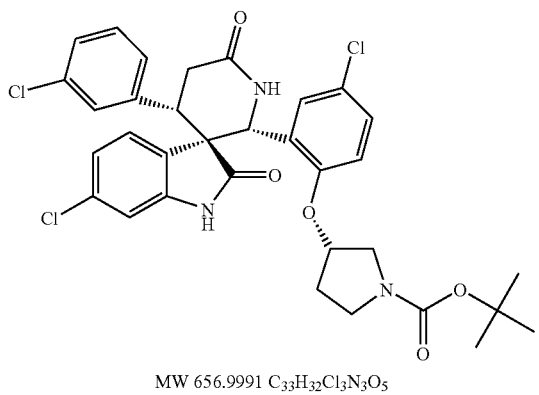

MW 656.9991 C₃₃H₃₂Cl₃N₃O₅

In a manner similar to the method described in examples 48C, 48d, the title diastereomeric compound was prepared in 2 steps starting from intermediate (R)-3-(4-chloro-2-formyl-phenoxy)-pyrrolidine-1-carboxylic acid tert-butyl ester MS (H⁺), 656. Further purification with Chiral SFC gave chiral (2'R,3R,4'S)-2'-{2-[3-(tert-butoxycarbonyl)-pyrolidinyloxy]-5-chloro-phenyl}-6-chloro-4'-(3-chlorophenyl)spiro[3H-indole-3,3'-piperidine]-2,6'-dione
HRMS(ES⁺) m/z Calcd for C₃₃H₃₂Cl₃N₃O₅+H [(M+H)⁺]: observed, 656.1481; calculated, 656.1481.

EXAMPLE 123

Preparation of chiral(2'R,3R,4'S)-6-chloro-4'-(3-chlorophenyl)-2'-[5-chloro-(3-pyrolidinyloxy)-phenyl}spiro[3H-indole-3,3'-piperidine]-2,6'-dione

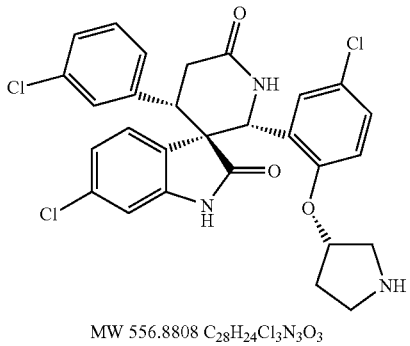

MW 556.8808 C₂₈H₂₄Cl₃N₃O₃

Racemic(2'R,3R,4'S)-2'-{2-[3-(tert-butoxycarbonyl)-pyrolidinyloxy]-5-chloro-phenyl}-6-chloro-4'-(3-chlorophenyl)spiro[3H-indole-3,3'-piperidine]-2,6'-dione (800 mg, 1.22 mmol) was dissolved in 30% TFA/CH₂Cl₂ (15 mL) and the solution was stirred at rt for 30 min. The solvent was removed and the residue was partioned between EtOAc and 10% Na₂CO₃. The organic layer was separated, washed with water, brine and dried with sodium sulfate and concentrated. A yellow solid was obtained which was directly used for next step. MS (H⁺), 556.

In a manner similar, the title compound was prepared from chiral(2'R,3R,4'S)-2'-{2-[3-(tert-butoxycarbonyl)-pyrolidinyloxy]-5-chloro-phenyl}-6-chloro-4'-(3-chlorophenyl) spiro[3H-indole-3,3'-piperidine]-2,6'-dione. MS (H⁺), 556.

EXAMPLE 124

Preparation of chiral(2'R,3R,4'S)-6-chloro-2'-[5-chloro-2-(3-methanesulfonyl-pyrolidinyloxy)-phenyl]-4'-(3-chlorophenyl)spiro[3H-indole-3,3'-piperidine]-2,6'-dione

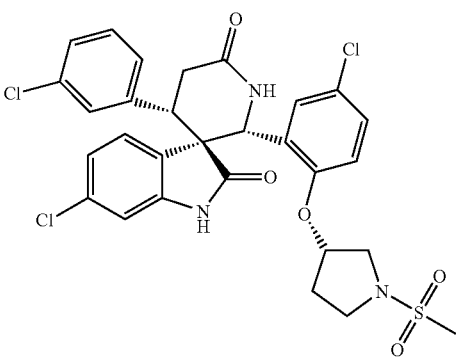

MW 634.97 C₂₉H₂₆Cl₃N₃O₅S

In a manner similar to the method described in example 13a, the title compound was prepared from chiral(2'R,3R,4'S)-6-chloro-4'-(3-chlorophenyl)-2'-[5-chloro-(3-pyrolidinyloxy)-phenyl}spiro[3H-indole-3,3'-piperidine]-2,6'-dione .HRMS(ES⁺) m/z Calcd for $C_{29}H_{26}Cl_3N_3O_5S+H$ [(M+H)⁺]: observed, 634.0729; calculated, 634.0732.

EXAMPLE 125

Preparation of chiral(2'R,3R,4'S)-6-chloro-2'-[5-chloro-2-(3-ethylcarbamoyl-pyrolidinyloxy)-phenyl}-4'-(3-chlorophenyl)spiro[3H-indole-3,3'-piperidine]-2,6'-dione

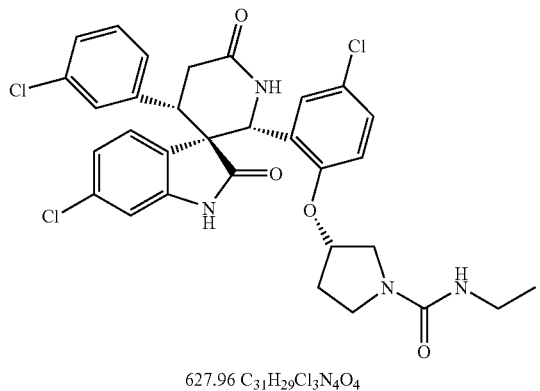

627.96 $C_{31}H_{29}Cl_3N_4O_4$

In a manner similar to the method described in example 29, the title compound was prepared from racemic(2'R,3R,4'S)-6-chloro-4'-(3-chlorophenyl)-2'-[5-chloro-(3-pyrolidinyloxy)-phenyl}spiro[3H-indole-3,3'-piperidine]-2,6'-dione. Subsequent chiral SFC separation gave the title compound.
HRMS(ES⁺) m/z Calcd for $C_{31}H_{29}Cl_3N_4O_4+H$ [(M+H)⁺]: observed, 627.1324; calculated, 627.1327.

EXAMPLE 126

Preparation of chiral(2'R,3R,4'S)-2'-[2-(1-acetyl-3-pyrolidinyloxy)-5-chloro-phenyl]-6-chloro-4'-(3-chlorophenyl)spiro[3H-indole-3,3'-piperidine]-2,6'-dione

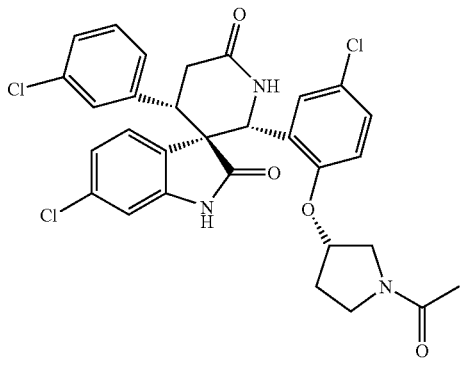

M.W. 570.91, $C_{29}H_{26}Cl_3N_3O_3$

In a manner similar to the method described in example 6a, the title compound was prepared from chiral(2'R,3R,4'S)-6-chloro-4'-(3-chlorophenyl)-2'-[5-chloro-(3-pyrolidinyloxy)-phenyl}spiro[3H-indole-3,3'-piperidine]-2,6'-dione.
HRMS(ES⁺) m/z $C_{29}H_{26}Cl_3N_3O_3+H$ [(M+H)⁺]: observed, 570 calculated, 570.

EXAMPLE 127a

Preparation of intermediate 7-oxa-3-aza-bicyclo[4.1.0]heptane-3-carboxylic acid tert-butyl ester

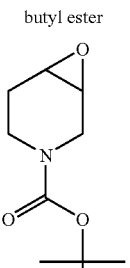

M.W. 199.25, $C_{10}H_{17}NO_3$

To a stirred solution of 3,6-dihydro-2H-pyridine-1-carboxylic acid tert-butyl ester (Aldrich, 15.99 g, 87.28 mmol) in methylene chloride (600 mL) at 0° C., mCPBA (Aldrich, 29.4 g, 77%, 131 mmol) was added and the mixture was stirred overnight. The reaction was quenched with 10% $Na_2S_2O_3$ and the organic layer was separated and washed with 5% sodium carbonate, brine and water and dried over sodium sulfate and concentrated to give a light yellow oil, which was chromatographied (10% EtOAc/Hexane) to yield a colorless oil. 14.93 g. The compound was used directly for the next step.

EXAMPLE 127b

Preparation of intermediate racemic 4-(2-formyl-4-iodo-phenoxy)-3-hydroxy-piperidine-1-carboxylic acid tert-butyl ester

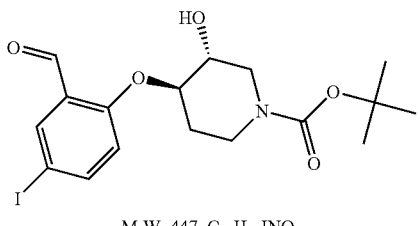

M.W. 447, $C_{17}H_{22}INO_5$

To a stirred solution of 2-hydroxy-5-iodo-benzaldehyde (Aldrich, 4.96 g, 20 mmol) in DMF (80 mL), potassium carbobate (10 g, 60 mmol) and 7-oxa-3-aza-bicyclo[4.1.0] heptane-3-carboxylic acid tert-butyl ester (8 g, 40 mmol) were added and the mixture was stirred at 70° C. for three days and 80° C. for two days. The mixture was poured into 1N HCl and the mixture was extracted with EtOAc (3×50 mL). The extracts were combined and dried over sodium sulfate and concentrated to give an oil, which was chromatographied on an ISCO machine (10-30% EtOAc/Hexanes) to yield an oil, 3.4 g. MS (H+), 348.

EXAMPLE 127c

Preparation of intermediate 3-(tert-butyl-dimethyl-silanyloxy)-4-(2-formyl-4-iodo-phenoxy)-piperidine 1-carboxylic acid tert-butyl ester

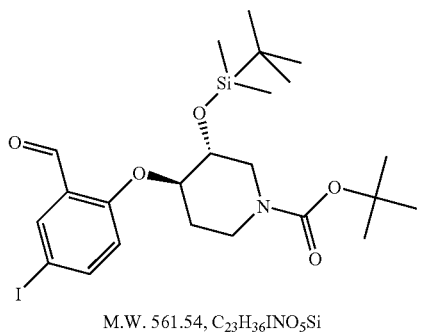

M.W. 561.54, $C_{23}H_{36}INO_5Si$

To a stirred solution of 4-(2-formyl-4-iodo-phenoxy)-3-hydroxy-piperidine-1-carboxylic acid tert-butyl ester (1.12 g, 2.50 mmol) in DMF (7 mL), at 0° C., 2,6-lutidine (Aldrich, 1.16 mL, 10 mmol) was added followed by TBDSOTf (Aldrich, 10 mmol) and the mixture was stirred for 40 min. The reaction mixture was poured into water and extracted with EtOAc (3×25 mL). The extracts were combined and dried and concentrated to give a yellow oil. 1.6 g. Which was purified by chromatorgraphy. MS (H+), 562.

EXAMPLE 127d

Preparation of intermediate 3-(tert-butyl-dimethyl-silanyloxy)-4-[4-iodo-2-(2-aza-3-trimethylsilany-loxy-buta-1,3-dienyl)-phenoxy]-piperidine-1-carboxylic acid tert-butyl ester

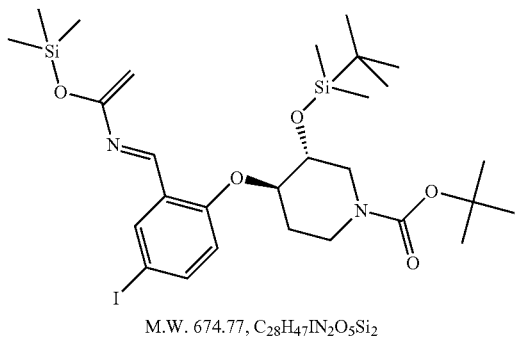

M.W. 674.77, $C_{28}H_{47}IN_2O_5Si_2$

To a stirred solution of bistrimetylsilanyl amine (Aldrich, 0.50 mL, 2.4 mmol) at −20° C., n-Buli (Aldrich, 2.5 M in hexanes, 0.96 mL, 2.4 mmol) was added slowly and the mixture was stirred for 5 min. The THF (10 mL) was added followed by the addition of 3-(tert-butyl-dimethyl-silany-loxy)-4-(2-formyl-4-iodo-phenoxy)-piperidine1-carboxylic acid tert-butyl ester (2.4 mmol, made above) in 10 mL of THF. The mixture was gradually warmed to rt and stirred for 1 hr. The reaction was cooled to 0° C. and TMSCl (Aldrich, 2.4 mmol), Et3N (Aldrich, 2.4 mmol) and acetyl chloride (Aldrich, 2.4 mmol) were added and the mixture was stirred for 2 hrs. The mixture was then filtered through a short pad of celite and the filtrate was concentrated under redeuced pressure to give a thick yellow paste, which was directly used for the next step.

EXAMPLE 127e

Preparation of raceic(2'R,3R,4'S)-6-chloro-4'-(3-chlorophenyl)-2'-[trans-4-(3-hydroxy-1-methane-sulfonyl-piperidinyloxy)-5-iodo-phenyl]spiro[3H-indole-3,3'-piperidine]-2,6 '-dione

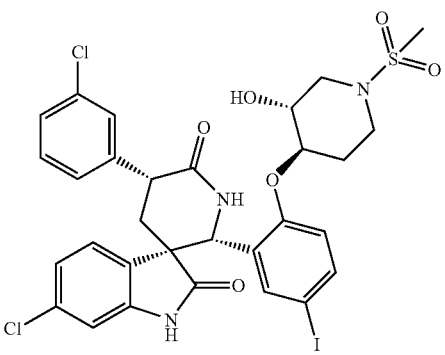

M.W. 757, $C_{30}H_{28}Cl_2IN_3O_6S$ 3-(Tert-butyl-dimethyl-silanyloxy)-4-[4-iodo-2-(2-aza-3-trimethylsilanyloxy-buta-1,3-dienyl)-phenoxy]-piperidine-1-carboxylic acid tert-butyl ester (2.4 mmol) and E/Z-6-chloro-3-[1-(3-chloro-phenyl)-meth-ylidene]-2-oxo-2,3-dihydro-indole-1-carboxylic acid tert-butyl ester in example 1b (375 mg, 0.96 mmol) were combined into 10 mL of toluene and the mixture was stirred at 125° C. for 14 h. The solvent was removed under reduced pressure and the residue was chromatographed on an ISCO machne (EtOAc/Hexanes, 0% to 40%) to yield a yellow foam. 324 mg.

The solid (250 mg, 0.28 mmol) was dissolved in 5 mL of THF. To the stirred solution, tetrabutylammonium fluoride (Aldrich, 1M in THF, 0.6 mL) was added and the mixture was stirred at rt overnight. The solvent was removed and the residue was dissolved in 4 mL of methylene chloride and trifluoro acetic acid (1:1). The mixture was stirred at rt for 30 min. and the solvent was removed to yield a foam, which was directly used for the next step.

The solid was dissolved in THF (3 mL). To the stirred solution, saturated sodium bicarbonate (1.5 mL) was added followed by methane sulfonyl chloride (Aldrich, 2 eq, 0.56 mmol). The reaction mixture was stirred at rt for 1 h and extracted with EtOAc (3×5 mL). The extracts were combined and dried. The residue was purified on a reversed phase HPLC (30-70 acetonitrile/Water) to give an white powder. 9 mg. MS (H+), 756.

EXAMPLE 128a

Preparation of intermediate 5-fluoro-2-(tetrahydro-pyran-4-yloxy)-benzaldehyde

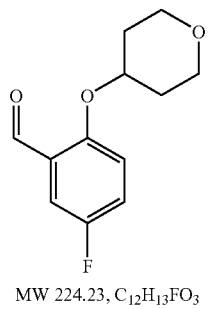

MW 224.23, C₁₂H₁₃FO₃

In a manner similar to the method described in Example 4a, 5-fluoro salicylaldehyde (Aldrich) reacted with methanesulfonic acid tetrahydro-pyran-4-yl ester (Example 32a) and potassium carbonate in dimethylformamide to give a solid. MS (H⁺), 225.

EXAMPLE 128b

Preparation of intermediate 1-[5-fluoro-2-(tetrahydro-pyran-4-yloxy)-phenyl]-3-trimethylsilyoxy-2-aza-1,3-butadiene

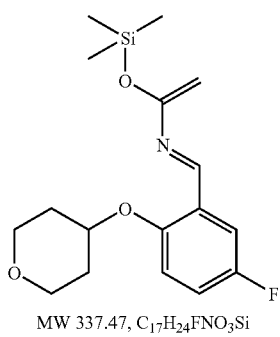

MW 337.47, C₁₇H₂₄FNO₃Si

In a manner similar to the method described in Example 112b, 5-fluoro-2-(tetrahydro-pyran-4-yloxy)-benzaldehyde was treated with LHMDS, acetyl chloride, triethylamine and chloro-triethyl-silane to give the desired compound, which was directly used for the next step.

EXAMPLE 128c

Preparation of racemic(2'R,3'R,4'S)-6-chloro-4'-(3-chloro-phenyl)-2'-[5-fluoro-2-(tetrahydro-pyran-4-yloxy)-phenyl]spiro[3H-indole-3,3'-piperidine]-2,6'-dione

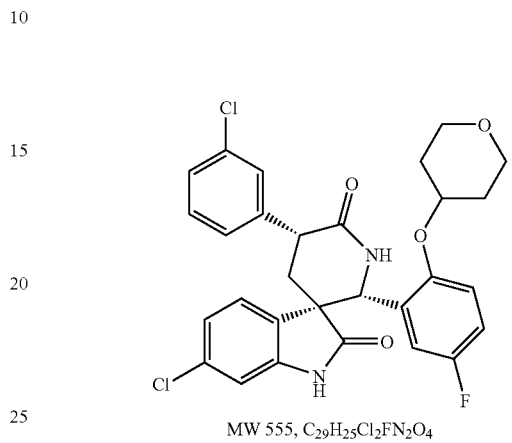

MW 555, C₂₉H₂₅Cl₂FN₂O₄

In a similar manner to the preparation of Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[5-fluoro-2-(tetrahydro-pyran-4-yloxy)-phenyl]-3-trimethylsilyoxy-2-aza-1,3-butadiene gave the desired product. MS(M+H⁺), 555.

EXAMPLE 129a

Preparation of intermediate 6-chloro-3-[1-(3-fluoro-phenyl)-methylidene]-1,3-dihydro-indol-2-one

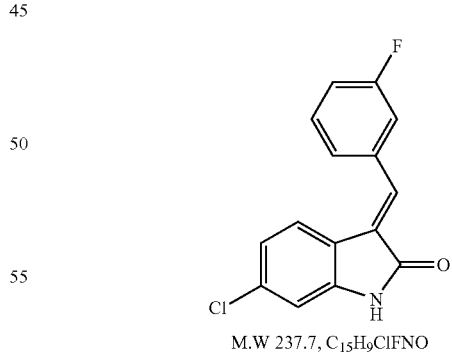

M.W 237.7, C₁₅H₉ClFNO

6-Chloro-1,3-dihydro-indol-2-one (Aldrich, 7.5 g, 44.92 mmol) was treated with 3-fluoro-benzaldehyde (Aldrich, 5.57 g, 44.92 mmol) in methanol (50 mL) and piperdine (0.2 mL). The mixture was heated at 75° C. overnight and then cooled to room temperature. The solid was filtered and dried to give a yellow solid. 8.8 g.

EXAMPLE 129b

Preparation of intermediate 6-chloro-3-[1-(3-fluoro-phenyl)-methylidene]-2-oxo-2,3-dihydro-indole-1-carboxylic acid tert-butyl ester

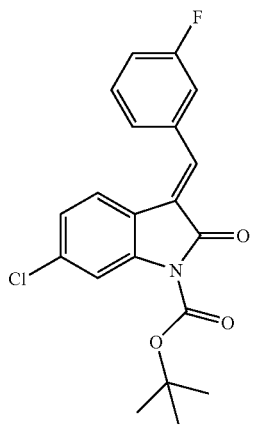

M.W 373.8, $C_{20}H_{17}ClFNO_3$ 6-chloro-3-[1-(3-fluoro-phenyl)-methylidene]-1,3-dihydro-indol-2-one (3.8 g, 13.1 mmol) was treated with (t-BuOCO)$_2$O (Aldrich, 3.05 g, 14 mmol) in methylen chloride (50 mL) and a catalytic amount of DMAP (Aldrich, 25 mg). The mixture was stirred at rt for 5 h and washed quickly with 0.05 N HCl and dried over sodium sulfate. Removed of solvent gave a yellow solid. 4.1 g.

EXAMPLE 129c

Preparation of chiral(2'R,3'R,4'S)-6-chloro-4'-(3-fluoro-phenyl)-2'-[5-fluoro-2-(tetrahydro-pyran-4-yloxy)-phenyl]spiro[3H-indole-3,3'-piperidine]-2,6'-dione

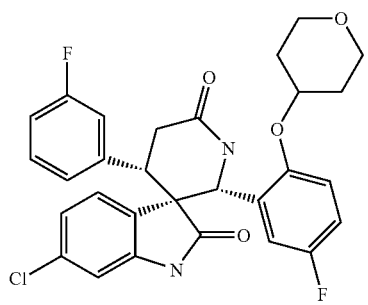

MW 538.98, $C_{29}H_{25}ClF_2N_2O_4$

In a similar manner to the preparation of Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[5-fluoro-2-(tetrahydro-pyran-4-yloxy)-phenyl]-3-trimethylsilanyloxy-2-aza-1,3-butadiene prepared in Example 128b gave the desired product. MS(M+H$^+$), 539.

Chiral SFC separation (30% MeOH, 100 Par, 30° C.) gave the desired enantiomer.

MS(M+H$^+$), 539.

EXAMPLE 130a

Preparation of intermediate methanesulfonic acid tetrahydro-thiopyran-4-yl ester

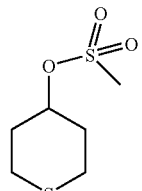

MW 196.29, $C_6H_{12}O_3S_2$

To a stirred solution of 4-hydroxy-tetrahedro-thiopyran (Aldrich, 2.0 g, 17 mmol) in methylene chloride at 0° C., Methane sulfonyl chloride (18 mmol) and triethyl amine (18 mmol) were added slowly and the mixture was stirred 1 h. The reaction was quenched with water and the mixture was extracted with methylene chloride. The extracts were combined and dried with sodium sulfate. Removal of solvent gave an off white solid. 2.15 g.

EXAMPLE 130b

Preparation of intermediate 5-fluoro-2-(tetrahydro-thiopyran-4-yloxy)benzaldehyde

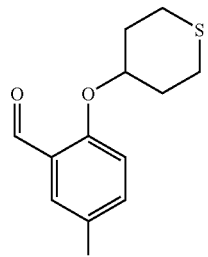

MW 240, $C_{12}H_{13}FO_2S$

In a manner similar to the method described in Example 128a, 5-fluoro salicylaldehyde (Aldrich) reacted with methanesulfonic acid tetrahydro-thiopyran-4-yl ester prepared in Example 130a and potassium carbonate in dimethylformamide to give a solid. MS (H$^+$), 241.

EXAMPLE 130c

Preparation of intermediate 1-[5-fluoro-2-(tetrahydro-thiopyran-4-yloxy)-phenyl]-3-trimethylsilyoxy-2-aza-1,3-butadiene

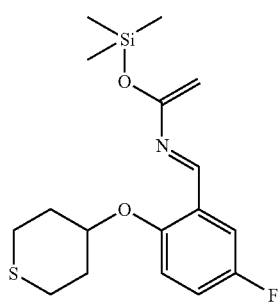

In a manner similar to the method described in Example 112b, 5-fluoro-2-(tetrahydro-thiopyran-4-yloxy)-benzaldehyde was treated with LHMDS, acetyl chloride, triethylamine and trimethyl silane to give the desired compound, which was directly used for the next step.

EXAMPLE 130d

Preparation of racemic(2'R,3'R,4'S)-6-chloro-4'-(3-chlorophenyl)-2'-[5-fluoro-2-(tetrahydro-thiopyran-4-yloxy)-phenyl]spiro[3H-indole-3,3'-piperidine]-2,6'-dione

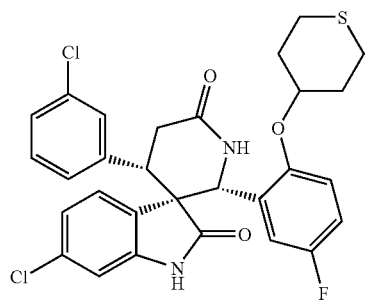

MW, 571.5, C29H25Cl2FN2O3S

In a similar manner to the preparation of Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[5-fluoro-2-(tetrahydro-thiopyran-4-yloxy)-phenyl]-3-trimethylsilanyloxy-2-aza-1,3-butadiene prepared in Example 130c gave the desired product. MS(M+H$^+$), 571.

EXAMPLE 131

Preparation of chiral(2'R,3'R,4'S)-6-chloro-4'-(3-chlorophenyl)-2'-[5-fluoro-2-(1,1-dioxo-tetrahydro-thiopyran-4-yloxy)-phenyl]spiro[3H-indole-3,3'-piperidine]-2,6'-dione

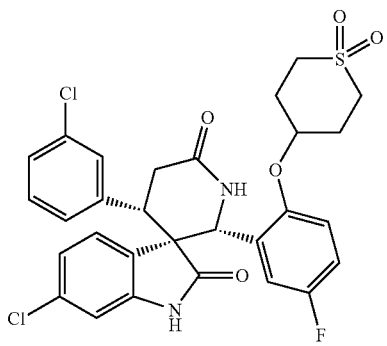

MW 603.5, C$_{29}$H$_{25}$Cl$_2$FN$_2$O$_5$S

To a stirred solution of racemic(2'R,3'R,4'S)-6-chloro-4'-(3-chlorophenyl)-2'-[5-fluoro-2-(tetrahydro-thiopyran-4-yloxy)-phenyl]spiro[3H-indole-3,3'-piperidine]-2,6'-dione (300 mg) in methylene chloride (15 mL), MCPBA (Aldrich, 77%, 180 mg, 0.79 mmol) was added and the mixture was stirred overnight. The reaction was quenched with saturated solution of sodium thiosulfate and the organic layer was separated and washed with sodium bicarbonate solution and dried (MgSO$_4$). Removal of solvent gave the crude, which was chromatographied on a ISCO machine (EtOAc/CH$_2$Cl$_2$) to the desired product as a white solid. 72 mg. MS(M+H$^+$), 603.

The racemate was further separated on SFC at condition of 30% MeOH, 100Par and 30° C. to give the enantiomer. 26 mg. MS(M+H$^+$), 603.

EXAMPLE 132a

Preparation of intermediate methanesulfonic acid cyclohexyl ester

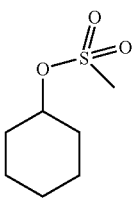

MW 178, C$_7$H$_{14}$O$_3$S

To a stirred solution of cyclohexanol (Aldrich, 10.2 g, 100 mmol) in methylene chloride (250 mL) at 0° C., Methane sulfonyl chloride (8.52 mL, 110 mmol) and triethyl amine (17.5 mL, 125 mmol) were added slowly and the mixture was stirred for 2 hrs. The reaction was quenched with water and the mixture was washed with 0.5 N HCl and brine solution.

The organic layer was dried with sodium sulfate. Removal of solvent gave a yellow oil. 18.05 g.

EXAMPLE 132b

Preparation of intermediate 5-fluoro-2-cyclohexyl-benzaldehyde

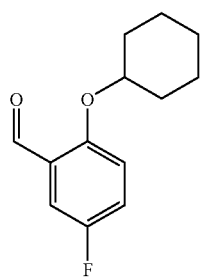

MW, 222.26, $C_{13}H_{15}FO_2$

In a manner similar to the method described in Example 4a, 5-fuloro salicylaldehyde (Aldrich) reacted with methanesulfonic acid cyclohexyl ester and potassium carbonate in dimethylformamide to give a solid. MS(H$^+$), 223.

EXAMPLE 132c

Preparation of intermediate 1-[5-fluoro-2-(cyclohexyloxy)-phenyl]-3-trimethylsilanyloxy-2-aza-1,3-butadiene

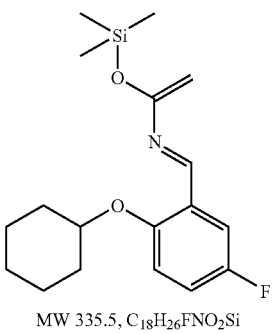

MW 335.5, $C_{18}H_{26}FNO_2Si$

In a manner similar to the method described in Example 112b, 5-fluoro-2-(cyclohexyloxy)-benzaldehyde was treated with LHMDS, acetyl chloride, triethylamine and chloro-trimethyl-silane to give the desired compound, which was directly used for the next step.

EXAMPLE 132d

Preparation of chiral(2'R,3'R,4'S)-6-chloro-4'-(3-chlorophenyl)-2'-[5-fluoro-2-(cyclohexyloxy)-phenyl]spiro[3H-indole-3,3'-piperidine]-2,6'-dione

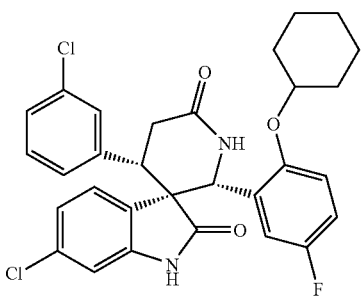

MW 552.14, $C_{30}H_{27}Cl_2FN_2O_3$

In a similar manner to the preparation of Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[5-fluoro-2-(cyclohexyloxy)-phenyl]-3-trimethylsilyoxy-2-aza-1,3-butadiene prepared in Example 132c gave the desired product.

MS(M+H$^+$), 553.

The racemate was further separated on SFC at condition of 30% MeOH, 100Par and 30° C. to give the enantiomer.

MS(M+H$^+$), 553.

EXAMPLE 133a

Preparation of intermediate methanesulfonic acid cyclopentyl ester

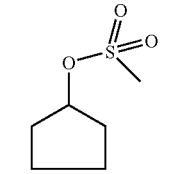

M.W, 164, $C_6H_{12}O_3S$

To a stirred solution of cyclopentanol (Aldrich, 2.58 g, 30 mmol) in methylene chloride (150 mL) at 0° C., Methane sulfonyl chloride (2.55 mL, 33 mmol) and triethyl amine (5.23 mL, 37.5 mmol) were added slowly and the mixture was stirred for 1.5 hrs. The reaction was quenched with water and the mixture was washed with 0.5 N HCl and brine solution. The organic layer was dried with sodium sulfate. Removal of solvent gave a colorless oil. 5.1 g.

EXAMPLE 133b

Preparation of intermediate 2-cyclopentyloxy-5-fluoro-enzaldehyde

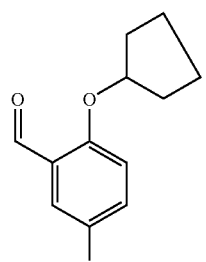

MW, 220.26, $C_{12}H_{13}FO_2$

In a manner similar to the method described in Example 4a, 5-fluoro salicylaldehyde (Aldrich) reacted with methanesulfonic acid cyclopentyl ester prepared in Example 133a and potassium carbonate in dimethylformamide to give a pale yellow oil.

MS (H$^+$), 221.

EXAMPLE 133c

Preparation of intermediate 1-[5-fluoro-2-(cyclopentyloxy)-phenyl]-3-trimethylsilanyloxy-2-aza-1,3-butadiene

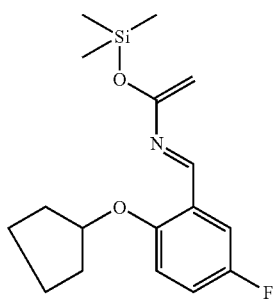

MW, 321.5, $C_{17}H_{24}FNO_2Si$

In a manner similar to the method described in Example 112b, 5-fluoro-2-(cyclopentyloxy)-benzaldehyde was treated with LHMDS, acetyl chloride, triethylamine and chloro-trimethyl-silane to give the desired compound, which was directly used for the next step.

EXAMPLE 133d

Preparation of chiral(2'R,3'R,4'S)-6-chloro-4'-(3-chlorophenyl)-2'-[5-fluoro-2-(cyclopentyloxy)-phenyl]spiro[3H-indole-3,3'-piperidine]-2,6'-dione

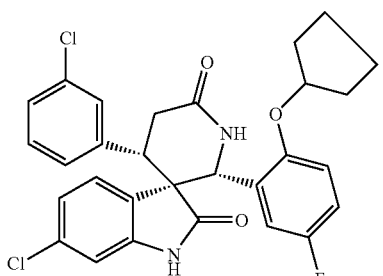

MW, 539.44, $C_{29}H_{25}Cl_2FN_2O_3$

In a similar manner to the preparation of Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[5-fluoro-2-(cyclopentyloxy)-phenyl]-3-trimethylsilanyloxy-2-aza-1,3-butadiene prepared in Example 133c gave the desired product. MS(M+H$^+$), 539.

The racemate was separated by chiral SFC (30% MeOH, 100 Par, 30° C.) to give the desired enantiomer.

EXAMPLE 134a

Preparation of intermediate 5-chloro-2-cyclohexyloxy-benzaldehyde

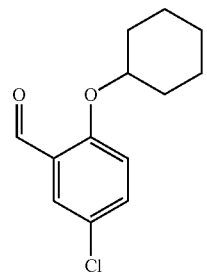

MW, 238.72, $C_{13}H_{15}ClO_2$

In a manner similar to the method described in Example 4a, 5-chloro salicylaldehyde (Aldrich) reacted with methanesulfonic acid cyclohexyl ester prepared in Example 132a and potassium carbonate in dimethylformamide to give a solid. MS (H$^+$), 239.

EXAMPLE 134b

Preparation of intermediate 1-[5-chloro-2-(cyclohexyloxy)-phenyl]-3-trimethylsilanyloxy-2-aza-1,3-butadiene

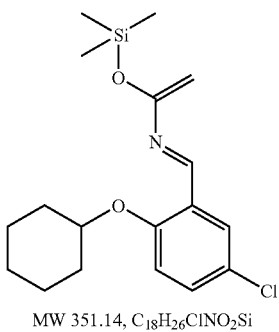

MW 351.14, C$_{18}$H$_{26}$ClNO$_2$Si

In a manner similar to the method described in Example 112b, 5-chloro-2-cyclohexyloxy-benzaldehyde was treated with LHMDS, acetyl chloride, triethylamine and chloro-trimethyl-silane to give the desired compound, which was directly used for the next step.

EXAMPLE 134c

Preparation of racemic(2'R,3'R,4'S)-6-chloro-2'-[5-chloro-2-(cyclohexyloxy-phenyl)]-4'-(3-chloro-phenyl)spiro[3H-indole-3,3'-piperidine]-2,6'-dione

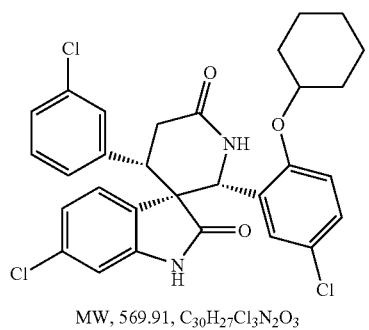

MW, 569.91, C$_{30}$H$_{27}$Cl$_3$N$_2$O$_3$

In a manner similar to the method described in Example 1e, reaction of 6-chloro-3-[1-(3-chloro-phenyl)-methylidene]-2-oxo-2,3-dihydro-indole-1-carboxylic acid tert-butyl ester with 1-[5-chloro-2-(cyclohexyloxy)-phenyl]-3-trimethylsilanyloxy-2-aza-1,3-butadiene gave a white solid.

MS(M+H$^+$), 569.

EXAMPLE 135a

Preparation of intermediate 5-chloro-2-(tetrahydro-thiopyran-4-yloxy)-benzaldehyde

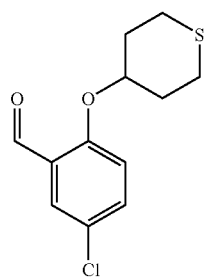

MW, 256.75, C$_{12}$H$_{13}$ClO$_2$S

In a manner similar to the method described in Example 4a, 5-chloro salicylaldehyde (Aldrich) reacted with methanesulfonic acid tetrahydro-thiopyran-4-yl ester prepared in Example 130a and potassium carbonate in dimethylformamide to give a solid. MS (H$^+$), 257.

EXAMPLE 135b

Preparation of intermediate 1-[5-chloro-2-(tetrahydro-thiopyran-4-yloxy)-phenyl]-3-trimethylsilyoxy-2-aza-1,3-butadiene

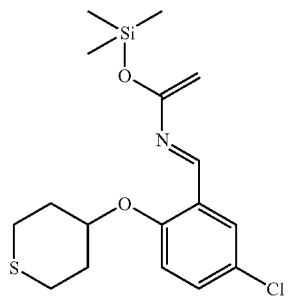

In a manner similar to the method described in Example 112b, 5-chloro-2-(tetrahydro-thiopyran-4-yloxy)-benzaldehyde was treated with LHMDS, acetyl chloride, triethylamine and trimethyl silane to give the desired compound, which was directly used for the next step.

EXAMPLE 135c

Preparation of racemic(2'R,3'R,4'S)-6-chloro2'-[5-chlororo-2-(tetrahydro-thiopyran-4-yloxy)-phenyl]-4'-(3-fluoro-phenyl)-spiro[3H-indole-3,3'-piperidine]-2,6'-dione

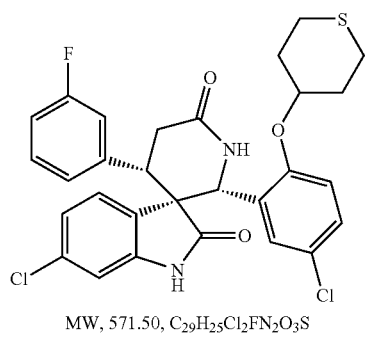

MW, 571.50, C29H25Cl2FN2O3S

In a similar manner to the preparation of Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[5-chloro-2-(tetrahydro-thiopyran-4-yloxy)-phenyl]-3-trimethylsilanyloxy-2-aza-1,3-butadiene gave the desired product.

MS(M+H+), 571.

EXAMPLE 136

Preparation of racemic(2'R,3'R,4'S)-6-chloro-2'-[5-chloro-2-(1,1-dioxo-tetrahydro-thiopyran-4-yloxy)-phenyl]-4'-(3-fluoro-phenyl)spiro[3H-indole-3,3'-piperidine]-2,6'-dione

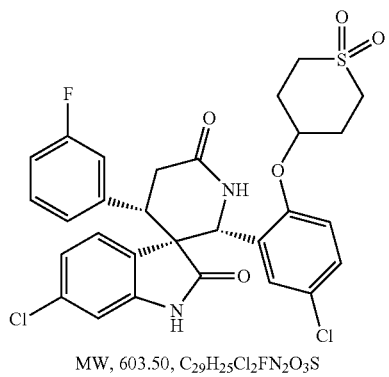

MW, 603.50, C29H25Cl2FN2O3S

In a similar manner to the preparation of Example 131, reaction of (2'R,3'R,4'S)-6-chloro-4'-(3-fluoro-phenyl)-2'-[5-chloro-2-(tetrahydro-thiopyran-4-yloxy)-phenyl]spiro[3H-indole-3,3'-piperidine]-2,6'-dione with MCPBA gave the desired product.

MS(M+H+), 603.

EXAMPLE 137a

Preparation of intermediate 1-[5-fluoro-2-(4-fluoro-phenoxy)-phenyl]-3-trimethylsilanyloxy-2-aza-1,3-butadiene

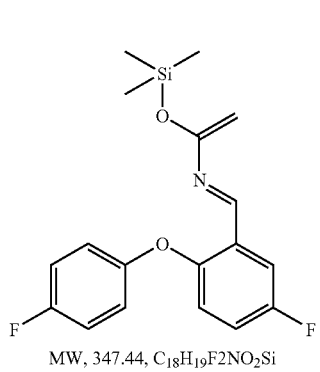

MW, 347.44, C18H19F2NO2Si

In a manner similar to the method described in Example 112b, 5-fluoro-2-(4-fluoro-phenyloxy)-benzaldehyde (VWR) was treated with LHMDS, acetyl chloride, triethylamine and chloro-trimethyl-silane to give the desired compound, which was directly used for the next step.

EXAMPLE 137b

Preparation of racemic(2'R,3'R,4'S)-6-chloro -4'-(3-fluoro-phenyl)-2'-[5-fluoro-2-(4-fuloro-phenoxy-phenyl)]spiro[3H-indole-3,3'-piperidine]-2,6'-dione

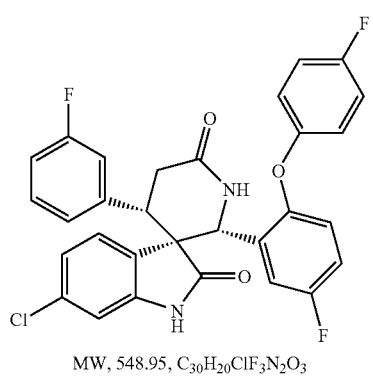

MW, 548.95, C30H20ClF3N2O3

In a manner similar to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[5-fluoro-2-(4-fluoro-phenoxy)-phenyl]-3-trimethylsilanyloxy-2-aza-1,3-butadiene gave a white solid.

MS(M+H+), 549.

EXAMPLE 138a

Preparation of intermediate 1-[5-fluoro-2-(2,4-difluoro-phenyloxy)-phenyl]-3-trimethylsilanyloy-2-aza-1,3-butadiene

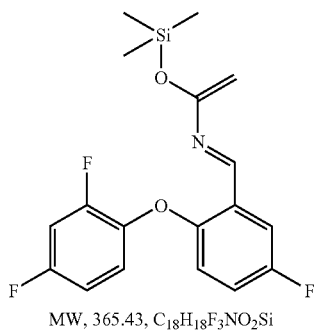

MW, 365.43, $C_{18}H_{18}F_3NO_2Si$

In a manner similar to the method described in Example 112b, 5-fluoro-2-(2,4-fluoro-phenyloxy)-benzaldehyde (VWR) was treated with LHMDS, acetyl chloride, triethylamine and chloro-trimethyl-silane to give the desired compound, which was directly used for the next step.

EXAMPLE 138b

Preparation of intermediate b 3-[1-(3-chloro-phenyl)-methylidene]-6-fluoro-2-oxo-2,3-dihydro-indole-1-carboxylic acid tert-butyl ester

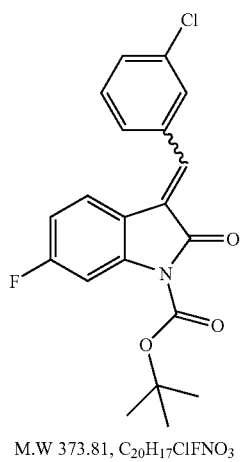

M.W 373.81, $C_{20}H_{17}ClFNO_3$

In a manner similar to the methods described in Examples 1a and 1b, 6-fluoro-1,3-dihydro-indol-2-one (Aldrich) reacted with 3-chloro-benzaldehyde to give 6-fluoro-3-[1-(2,5-difluoro-phenyl)-methylidene]-2-oxo-2,3-dihydro-indole, which was subsequently reacted with (t-BuOCO)$_2$O and DMAP and used directly for next step.

EXAMPLE 138c

Preparation of racemic(2'R,3'R,4'S)-4'-(3-chloro-phenyl)-6-fluoro-2'-[2-(2,4-difluoro-phenyloxy)-5-fluoro-phenyl]spiro[3H-indole-3,3'-piperidine]-2,6'-dione

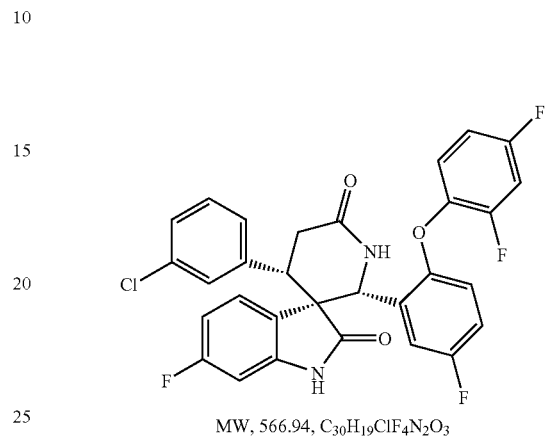

MW, 566.94, $C_{30}H_{19}ClF_4N_2O_3$

In a similar manner to the preparation of Example 1e, reaction of 6-fluoro-3-[1-(3-chloro-phenyl)-methylidene]-2-oxo-2,3-dihydro-indole-1-carboxylic acid tert-butyl ester with 1-[2-(2,4-difluoro-phenyloxy)-5-fluoro-phenyl]-3-trimethylsilanyloxy-2-aza-1,3-butadiene gave the desired product.

MS(M+H$^+$), 567.

EXAMPLE 139a

Preparation of intermediate 5-chloro-2-[(2-chloro-6-fluoro-benzyloxy)-phenyl]-3-trimethylsilanyloxy-2-aza-1,3-butadiene

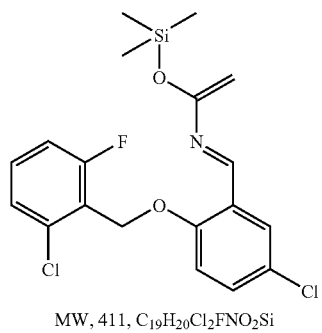

MW, 411, $C_{19}H_{20}Cl_2FNO_2Si$

In a manner similar to the method described in Example 112b, 5-chloro-2-(2-chloro-6-fluoro-benzyloxy)-benzaldehyde (Chembrdg-BB) was treated with LHMDS, acetyl chloride, triethylamine and chloro-trimethyl-silane to give the desired compound, which was directly used for the next step.

EXAMPLE 139b

Preparation of intermediate 6-chloro-3-[1-(2,5-difluoro-phenyl)-methylidene]-2-oxo-2,3-dihydro-indole-1-carboxylic acid tert-butyl ester

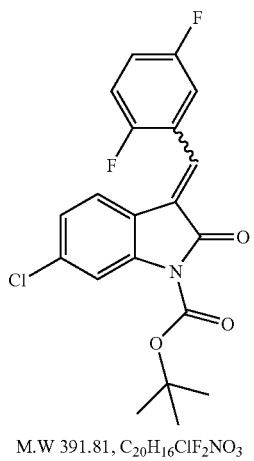

M.W 391.81, C$_{20}$H$_{16}$ClF$_2$NO$_3$

In a manner similar to the methods described in Examplea 1a and 1b, 6-chloro-1,3-dihydro-indol-2-one (Aldrich) reacted with 2,5-difluoro-benzaldehyde to give 6-chloro-3-[1-(2,5-difluoro-phenyl)-methylidene]-2-oxo-2,3-dihydro-indole, which was subsequently reacted with (t-BuOCO)$_2$O and DMAP.

EXAMPLE 139c

Preparation of racemic(2'R,3'R,4'R)-6-chloro-2'-[5-chloro-2-(2-chloro-6-fluoro-benzyloxy)-phenyl]-4'-(2,5-difluoro-phenyl)spiro[3H-indole-3,3'-piperidine]-2,6'-dione

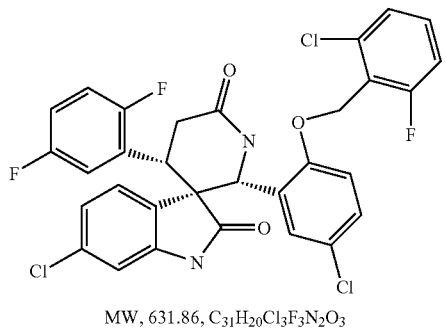

MW, 631.86, C$_{31}$H$_{20}$Cl$_3$F$_3$N$_2$O$_3$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester with 5-chloro-2-[(2-chloro-6-fluoro-benzyloxy)-phenyl]-3-trimethylsilanyloxy-2-aza-1,3-butadiene gave the desired product.

MS(M+H$^+$), 631.

EXAMPLE 140a

Preparation of intermediate 2-(4-cyanophenyloxy)-5-fluoro-benzaldehyde

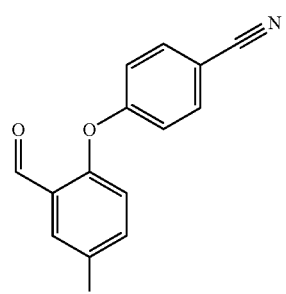

MW, 241, C$_{14}$H$_{18}$FNO$_2$

To stirred solution of 4-cyanophenol (Aldrich, 5.00 g, 42 mmol) in DMF (100 mL), potassium carbonate (63 mmol) and 2-4, difluoro-benzaldehyde (Aldrich, 5.97 g, 42 mmol) were added and the mixture was stirred at 90° C. overnight. The mixture was cooled to room temperature and poured into water. The solid was filtered and dried to give a pale yellow solid. 5.2 g MS (H$^+$), 242.

EXAMPLE 140b

Preparation of intermediate 1-[2-(4-cyano-phenyloxy)-5-fluoro-phenyl]-3-trimethylsilyoxy-2-aza-1,3-butadiene

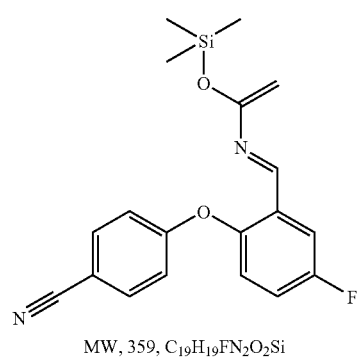

MW, 359, C$_{19}$H$_{19}$FN$_2$O$_2$Si

In a manner similar to the method described in Example 112b, 2-(4-cyano-phenyloxy)-5-fluoro-benzaldehyde was treated with LHMDS, acetyl chloride, triethylamine and chloro-trimethyl-silane to give the desired compound, which was directly used for the next step.

EXAMPLE 140c

Preparation of racemic(2'R,3'R,4'R)-6-chloro-2'-[2-(4-cyano-phenyloxy)-5-fluoro-phenyl]-4'-(2,5-difluoro-phenyl)spiro[3H-indole-3,3'-piperidine]-2,6'-dione

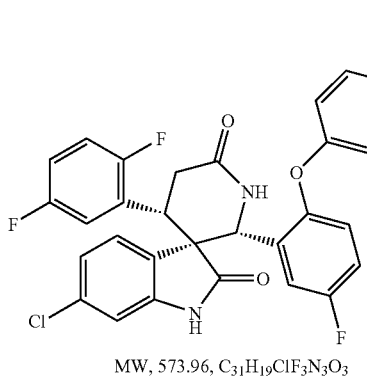

MW, 573.96, C$_{31}$H$_{19}$ClF$_3$N$_3$O$_3$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 1-[2-(4-cyano-phenyloxy)-5-fluoro-phenyl]-3-trimethylsilanyloxy-2-aza-1,3-butadiene gave the desired product. MS(M+H$^+$), 573.

EXAMPLE 141

Preparation of racemic(2'R,3'R,4'S)-6-chloro-2'-[2-(4-cyano-phenyloxy)-5-fluoro-phenyl]-4'-(3-fluoro-phenyl)spiro[3H-indole-3,3'-piperidine]-2,6'-dione

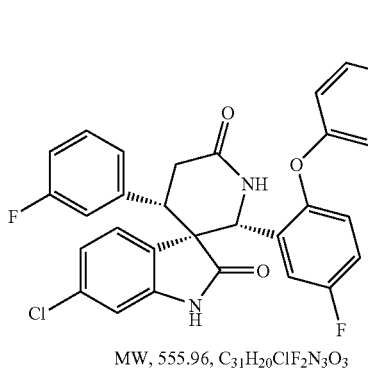

MW, 555.96, C$_{31}$H$_{20}$ClF$_2$N$_3$O$_3$

In a similar manner to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[2-(4-cyano-phenyloxy)-5-fluoro-phenyl]-3-trimethylsilanyloxy-2-aza-1,3-butadiene prepared in Example 140b gave the desired product.
MS(M+H$^+$), 556.

EXAMPLE 142

Preparation of racemic(2'R,3'R,4'S)-4'-(3-chloro-phenyl)-2'-[2-(4-cyano-phenyloxy)-5-fluoro-phenyl]-6-fluoro spiro[3H-indole-3,3'-piperidine]-2,6'-dione

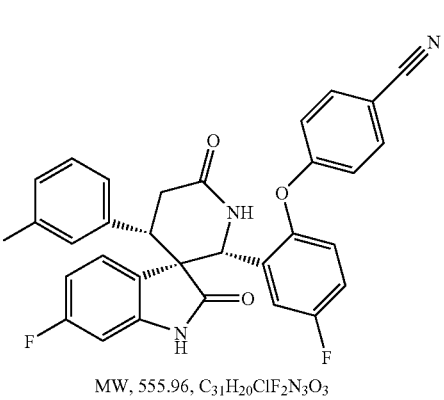

MW, 555.96, C$_{31}$H$_{20}$ClF$_2$N$_3$O$_3$

In a similar manner to the method described in Example 1e, reaction of 6-fluoro-3-[1-(3-chloro-phenyl)-methylidene]-2-oxo-2,3-dihydro-indole-1-carboxylic acid tert-butyl ester prepared in Example 138b with 1-[2-(4-cyano-phenyloxy)-5-fluoro-phenyl]-3-trimethylsilanyloxy-2-aza-1,3-butadiene prepared in Example 140b gave the desired product.
MS(M+H$^+$), 556.

EXAMPLE 143a

Preparation of intermediate 2-(4-methoxy-phenyloxy)-5-fluoro-benzaldehyde

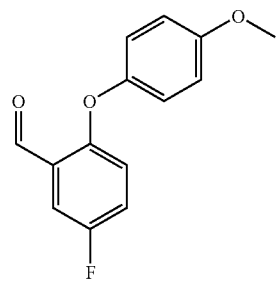

MW, 246, C$_{14}$H$_{11}$FO$_3$

In a similar manner to the method described in Example 140a, 2,4-difluoro-benzaldehyde (Aldrich) was reacted with 4-methoxy-phenol and potassium carbonate to give a solid. MS (H$^+$), 247.

EXAMPLE 143b

Preparation of intermediate 1-[5-fluoro-2-(4-methoxy-phenyloxy)-phenyl]-3-trimethylsilanyloxy-2-aza-1,3-butadiene

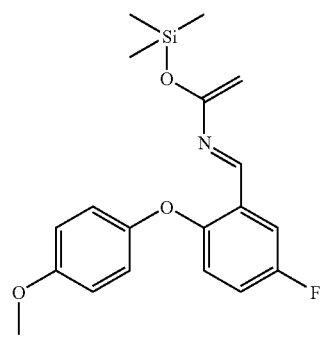

MW, 359, $C_{19}H_{22}FNO_3Si$

In a manner similar to the method described in Example 112b, 2-(4-methoxy-phenyloxy)-5-fluoro-benzaldehyde was treated with LHMDS, acetyl chloride, triethylamine and chloro-trimethyl-silane to give the desired compound, which was directly used for the next step.

EXAMPLE 143c

Preparation of racemic(2'R,3'R,4'S)-6-chloro-2'-[5-fluoro-2-(4-methoxy-phenyloxy)-phenyl]-4'-(3-fluoro-phenyl)spiro[3H-indole-3,3'-piperidine]-2,6'-dione

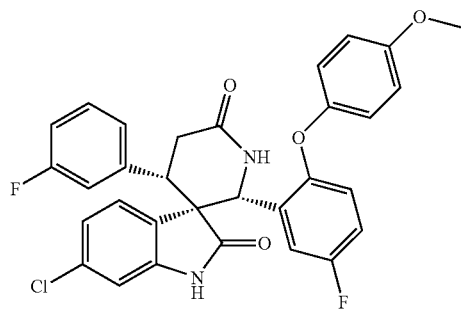

MW, 560.98, $C_{31}H_{23}ClF_2N_2O_4$

In a similar manner to the method described in Example 1e, reaction of 6-chloro-3-[1-(3-difluoro-phenyl)-methylidene]-2-oxo-2,3-dihydro-indole-1-carboxylic acid tert-butyl ester prepared in Example 129b with 1-[2-(4-methoxy-phenyloxy)-5-fluoro-phenyl]-3-trimethylsilanyloxy -2-aza-1,3-butadiene gave the desired product.
MS(M+H⁺), 561.

EXAMPLE 144

Preparation of racemic(2'R,3'R,4'S)-4'-(3-chloro-phenyl)-6-fluoro-2'-[5-fluoro-2-(4-methoxy-phenyloxy)-phenyl]spiro[3H-indole-3,3'-piperidine]-2,6'-dione

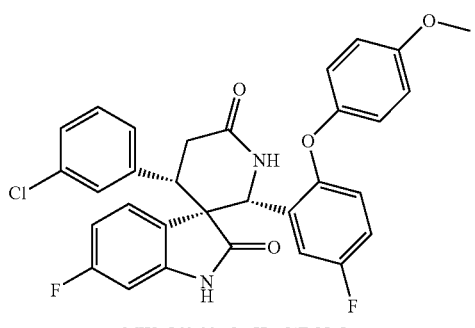

MW, 560.98, $C_{31}H_{23}ClF_2N_2O_4$

In a similar manner to the method described in Example 1e, reaction of 6-fluoro-3-[1-(3-chloro-phenyl)-methylidene]-2-oxo-2,3-dihydro-indole-1-carboxylic acid tert-butyl ester prepared in Example 138b with 1-[2-(4-methoxy-phenyloxy)-5-fluoro-phenyl]-3-trimethylsilanyloxy-2-aza-1,3-butadiene prepared in Example 143b gave the desired product. MS(M+H⁺), 561.

EXAMPLE 145

Preparation of racemic(2'R,3'R,4'R)-6-chloro-2'-[5-fluoro-2-(4-methoxy-phenyloxy)-phenyl]-4'-(2,5-difluoro-phenyl)spiro[3H-indole-3,3'-piperidine]-2,6'-dione

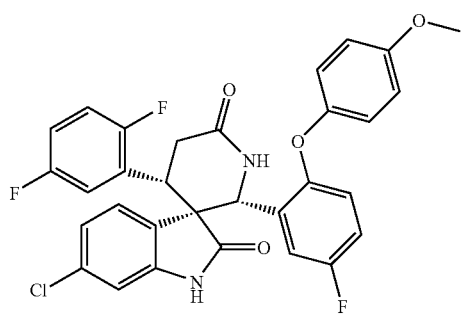

MW, 578.97, $C_{31}H_{22}ClF_3N_2O_4$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 5-fluoro-1-[2-(4-methoxy-phenyloxy)-phenyl]-3-trimethylsilanyloxy-2-aza-1,3-butadiene prepared in Example 143b gave the desired product.
MS(M+H⁺), 579.

EXAMPLE 146

Preparation of chiral(2'R,3'R,4'S)-6-chloro-4'-(3-chloro-phenyl)-2'-[5-fluoro-2-(4-methoxy-phenyloxy)-phenyl]spiro[3H-indole-3,3'-piperidine]-2,6'-dione

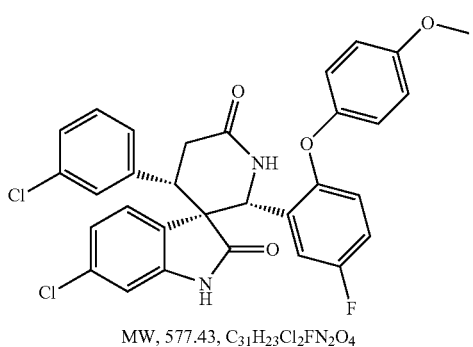

MW, 577.43, $C_{31}H_{23}Cl_2FN_2O_4$

In a similar manner to the method described in Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[2-(4-methoxy-phenyloxy)-5-fluoro-phenyl]-3-trimethylsilanyloxy-2-aza-1,3-butadiene prepared in Example 143b gave the desired product. SFC separation (30% MeOH, 100 par, 30° C.) gave the desired enantiomer.

MS(M+H$^+$), 577.

EXAMPLE 147a

Preparation of intermediate 6-chloro-3-(5-chloro-2-fluoro-benzylidene)-2-oxo-2,3-dihydro-indole-1-carboxylic acid tert-butyl ester

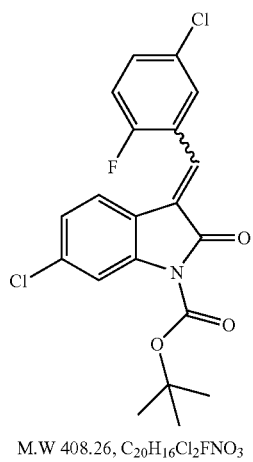

M.W 408.26, $C_{20}H_{16}Cl_2FNO_3$

In a manner similar to the methods described in Examples 1a and 1b, 6-chloro-1,3-dihydro-indol-2-one (Aldrich) reacted with 5-chloro-2-fluoro-benzaldehyde to give 6-chloro-3-[1-(5-chloro-2-fluoro-phenyl)-methylidene]-2-oxo-2,3-dihydro-indole, which was subsequently protected with (t-BuOCO)$_2$O and DMAP.

EXAMPLE 147b

Preparation of chiral(2'R,3'R,4'R)-6-chloro-4'-(5-chloro-2-fluoro-phenyl)-2'-[5-fluoro-2-(4-methoxy-phenyloxy)-phenyl]spiro[3H-indole-3,3'-piperidine]-2,6'-dione

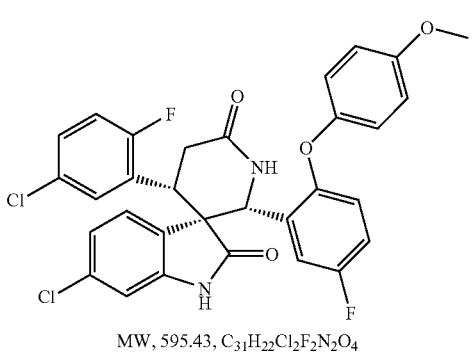

MW, 595.43, $C_{31}H_{22}Cl_2F_2N_2O_4$

In a similar manner to the method described in Example 1e, reaction of 6-chloro-3-[1-(3-fluoro-5-chloro-phenyl)-methylidene]-2-oxo-2,3-dihydro-indole-1-carboxylic acid tert-butyl ester with 1-[2-(4-methoxy-phenyloxy)-5-fluoro-phenyl]-3-trimethylsilanyloxy-2-aza-1,3-butadiene prepared in Example 143b gave the desired product SFC separation (30% MeOH, 100 par, 30° C.) gave the desired enantiomer. MS(M+H$^+$), 595.

EXAMPLE 148a

Preparation of intermediate 4-[2-(tert-butyl-dimethyl-silanyloxy)-ethoxy]-phenol

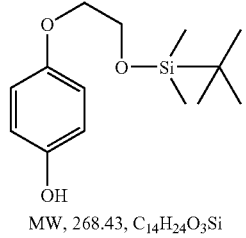

MW, 268.43, $C_{14}H_{24}O_3Si$

To a stirred solution of hydroquinone (Aldrich, 11.01 g, 100 mmol) in DMF (300 mL), (2-bromo-ethoxy)-tert-butyl-dimethyl-silane (Aldrich, 12.0 g, 50 mmol), cesium carbonate (40.7 g, 125 mol) were added and the mixture was stirred at 60° C. overnight. The mixture was poured into water (300 mL) and 6N HCl was added to adjust the "pH" to 6. The mixture was extracted with EtOAc (3×60 mL) and the extracts were combined and dried. Removal of solvent gave the crude, which was chromatographied on a ISCO machine eluting with EtOAc/hexane (0-30%) to give a light brown solid. 5.71 g.

EXAMPLE 148b

Preparation of intermediate 5-fluoro-2-{4-[2-(tert-butyl-dimethyl-silanyloxy)ethoxy]-Phenoxy}-benzaldehyde

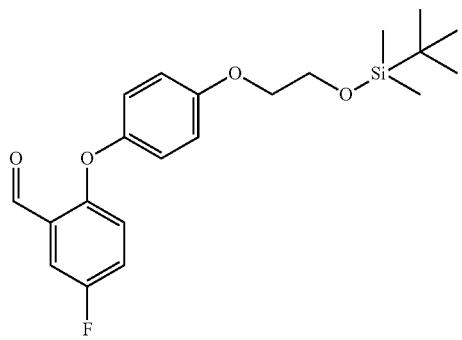

MW, 390.53,
$C_{21}H_{27}FO_4Si$

In a similar manner to the method described in Example 140a, 2,4-difluoro-benzaldehyde (Aldrich) reacted with 4-[2-(tert-butyl-dimethyl-silanyloxy)-ethoxy]-phenol and potassium carbonate to give a light brown oil which solidifies on standing.

MS (H+), 391.

EXAMPLE 148c

Preparation of intermediate 1-[5-fluoro-2-{4-[2-(tert-butyl-dimethyl-silanyloxy)ethoxy]-phenoxy}-phenyl]-3-trimethylsilyloxy-2-aza-1,3-butadiene

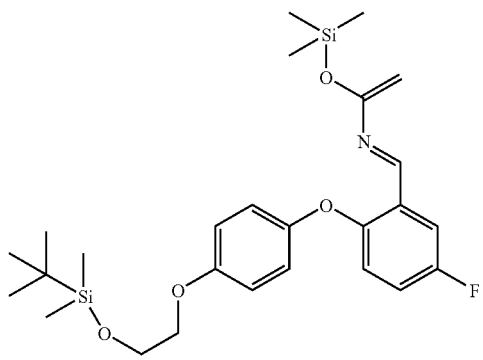

MW, 503.77,
$C_{26}H_{38}FNO_4Si_2$

In a manner similar to the method described in example 112b, 5-fluoro-2-{4-[2-(tert-butyl-dimethyl-silanyloxy)-ethoxy]-phenoxy}-benzaldehyde was treated with LHMDS, acetyl chloride, triethylamine and chloro-trimethyl-silane to give the desired compound, which was directly used for the next step.

EXAMPLE 148d

Preparation of racemic(2'R,3'R,4'R)-6-chloro-2'-{5-fluoro-2-[4-(2-hydroxy-ethoxy) -phenoxy]phenyl}-4'-(2,5-difluoro-phenyl)spiro[3H-indole-3,3'-piperidine]-2,6'-dione

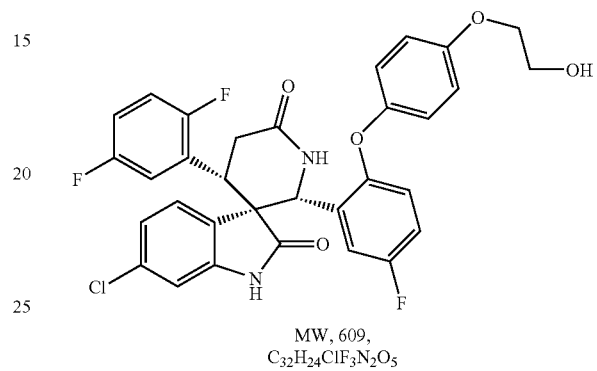

MW, 609,
$C_{32}H_{24}ClF_3N_2O_5$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 1-[5-fluoro-2-{4-[2-(tert-butyl-dimethyl-silanyloxy) -ethoxy]-phenoxy}phenyl]-3-trimethylsilyoxy-2-aza-1,3-butadiene followed by deprotection reaction with tetrabutylammonium fluoride gave the desired product as white solid.
MS(M+H+), 609.

EXAMPLE 149

Preparation of racemic(2'R,3'R,4'R)-6-chloro-4'-(5-chloro-2-fluoro-phenyl)-2'-{5-fluoro-2-[4-(2-hydroxy-ethoxy)-phenoxy]phenyl}spiro[3H-indole-3,3'-piperidine]-2,6'-dione

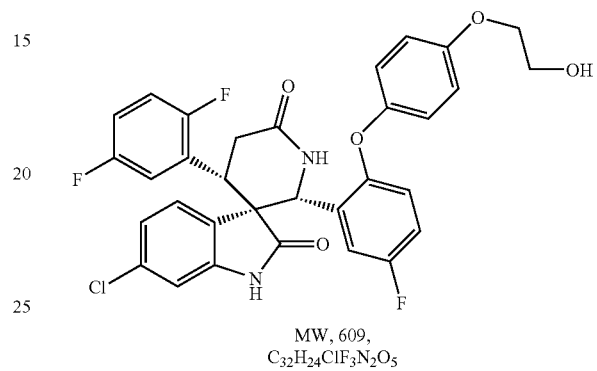

MW, 625.45,
$C_{32}H_{24}Cl_2F_2N_2O_5$

In a similar manner to the method described in Example 1e, reaction of 6-chloro-3-[1-(2-fluoro-5-chloro-phenyl)-methylidene]-2-oxo-2,3-dihydro-indole-1-carboxylic acid tert-butyl ester prepared in Example 147a with 1-[5-fluoro-2-{4-

[2-(tert-butyl-dimethyl-silanyloxy)-ethoxy]-phenoxy}phenyl]-3-trimethylsilanyloxy-2-aza-1,3-butadiene prepared in Example 148c followed by deprotection reaction with tetrabutylammonium fluoride gave the desired product as white solid.
MS(M+H$^+$), 625.

EXAMPLE 150

Preparation of racemic(2'R,3'R,4'S)-6-chloro-4'-(3-fluoro-phenyl)-2'-{5-fluoro-2-[4-(2-hydroxy-ethoxy)-phenoxy]phenyl}spiro[3H-indole-3,3'-piperidine]-2,6'-dione

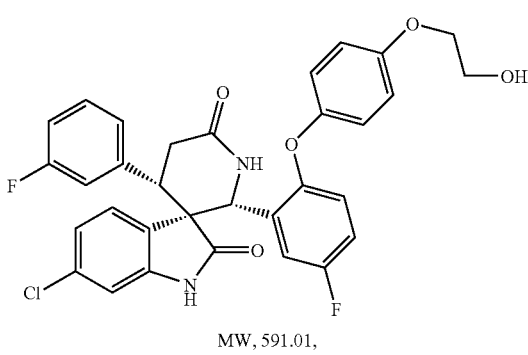

MW, 591.01,
$C_{32}H_{25}ClF_2N_2O_5$

In a similar manner to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[5-fluoro-2-{4-[2-(tert-butyl-dimethyl-silanyloxy)-ethoxy]-phenoxy}phenyl]-3-trimethylsilyoxy-2-aza-1,3-butadiene prepared in Example 148c followed by deprotection reaction with tetrabutylammonium fluoride gave the desired product as white solid.
MS(M+H$^+$), 591.

EXAMPLE 151

Preparation of racemic(2'R,3'R,4'S)-4'-(3-chloro-phenyl)-6-fluoro-2'-{5-fluoro-2-[4-(2-hydroxy-ethoxy)-phenoxy]phenyl}spiro[3H-indole-3,3'-piperidine]-2,6'-dione

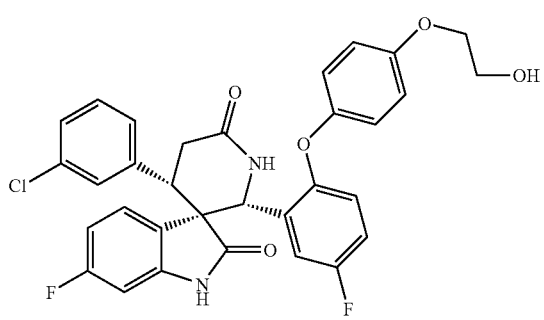

MW 591.01,
$C_{32}H_{25}ClF_2N_2O_5$

In a similar manner to the method described in Example 1e, reaction of 6-fluoro-3-[1-(3-chloro-phenyl)-methylidene]-2-oxo-2,3-dihydro-indole-1-carboxylic acid tert-butyl ester prepared in Example 138b with 1-[5-fluoro-2-{4-[2-(tert-butyl-dimethyl-silanyloxy)-ethoxy]-phenoxy}phenyl]-3-trimethylsilanyloxy-2-aza-1,3-butadiene prepared in Example 148c followed by deprotwction reaction with tetrabutylammonium fluoride gave the desired product as white solid.
MS(M+H$^+$), 591.

EXAMPLE 152

Preparation of racemic(2'R,3'R,4'S)-6-chloro-4'-(3-chloro-phenyl)-2'-{5-fluoro-2-[4-(2-hydroxy-ethoxy)-phenoxy]phenyl}spiro[3H-indole-3,3'-piperidine]-2,6'-dione

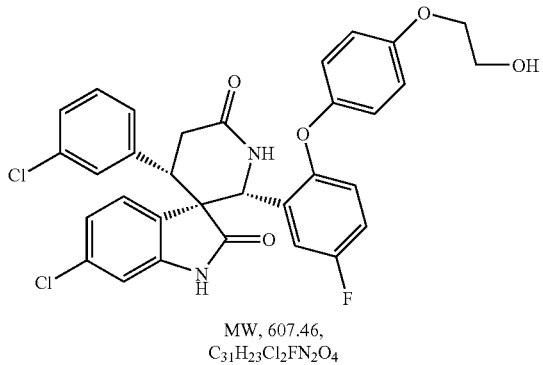

MW, 607.46,
$C_{31}H_{23}Cl_2FN_2O_4$

In a similar manner to the method described in Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[5-fluoro-2-{4-[2-(tert-butyl-dimethyl-silanyloxy)-ethoxy]-phenoxy}phenyl]-3-trimethylsilanyloxy-2-aza-1,3-butadiene prepared in Example 148c, followed by deprotection reaction with tetrabutylammonium fluoride gave the desired product as white solid.
MS(M+H$^+$), 607.

EXAMPLE 153a

Preparation of intermediate 6-chloro-3-[1-(2-chloro-5-trifluoromethyl-phenyl)-methylidene]-2-oxo-2,3-dihydro-indole-1-carboxylic acid tert-butyl ester

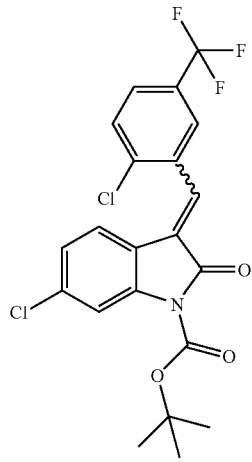

M.W. 458.27,
$C_{21}H_{16}Cl_2F_3NO_3$

In a manner similar to the methods described in Examples 1a and 1b, 6-chloro-1,3-dihydro-indol-2-one (Aldrich) reacted with 2-chloro-5-trifluoromethyl-benzaldehyde (Aldrich) to give 6-chloro-3-[1-(2-chloro-5-trifluoromethyl-phenyl)-methylidene]-2-oxo-2,3-dihydro-indole, which was subsequently reacted with di-tert-butyl-dicarbonate and DMAP and directly used for the next step.

EXAMPLE 153b

Preparation of racemic(2'R,3'R,4'S)-6-chloro-2'-[5-chloro-2-(tetrahydro-pyran-4-yloxy)-phenyl]-4'-(5-chloro-2-trifluoromethyl-phenyl)spiro[3H-indole-3,3'-piperidine]-2,6'-dione

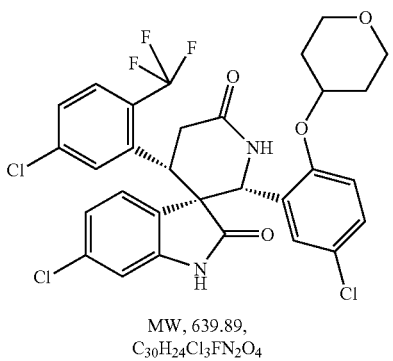

MW, 639.89,
$C_{30}H_{24}Cl_3FN_2O_4$

In a similar manner to the method described in Example 1e, reaction of 6-chloro-3-[1-(3-chloro-2-trifluoromethyl-phenyl)-methylidene]-2-oxo-2,3-dihydro-indole-1-carboxylic acid tert-butyl ester with 1-[5-chloro-2-(tetrahydro-pyran-4-yloxy)-phenyl]-3-trimethylsilanyloxy-2-aza-1,3-butadiene prepared in Example 99b gave the desired product.
MS(M+H$^+$), 639.

EXAMPLE 154a

Preparation of intermediate 1-[5-iodo-2-(cyclohexyloxy)-phenyl]-3-trimethylsilanyloxy-2-aza-1,3-butadiene

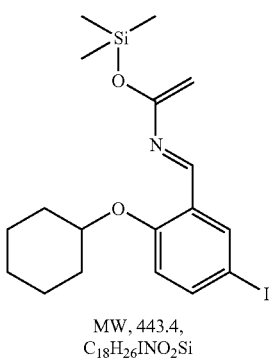

MW, 443.4,
$C_{18}H_{26}INO_2Si$

In a manner similar to the methods described in Example 128a and 112b, 5-iodo-2-hydroxy-benzaldehyde was reacted with methanesulfonic acid cyclohexyl ester and potassium carbonate to give 5-Iodo-2-(cyclohexyloxy)-benzaldehyde, which was subsequently reacted with LHMDS, acetyl chloride, triethylamine and chloro-trimethyl-silane to give the title compound and directly used for the next step.

EXAMPLE 154b

Preparation of racemic(2'R,3'R,4'S)-6-chloro-4'-(5-chloro-2-trifluoromethyl-phenyl)-2'-[5-iodo-2-(tetrahydro-pyran-4-yloxy)-phenyl]spiro[3H-indole-3,3'-piperidine]-2,6'-dione

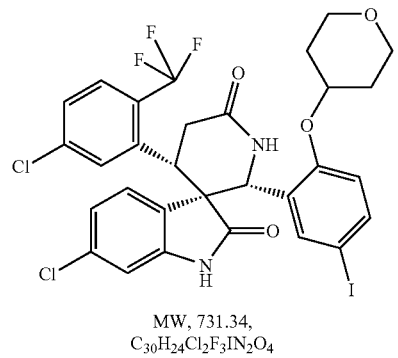

MW, 731.34,
$C_{30}H_{24}Cl_2F_3IN_2O_4$

In a similar manner to the method described in Example 1e, reaction of 6-chloro-3-[1-(3-chloro-2-trifluoromethyl-phenyl)-methylidene]-2-oxo-2,3-dihydro-indole-1-carboxylic acid tert-butyl ester prepared in Example 153a with 1-[5-iodo-2-(tetrahydro-pyran-4-yloxy)-phenyl]-3-trimethylsilanyloxy-2-aza-1,3-butadiene gave the desired product.
MS(M+H$^+$), 731.

EXAMPLE 155

Preparation of (2'R,3'R,4'S)-6-chloro-4'-(5-chloro-2-trifluoromethyl-phenyl)-2'-[2-(cyclohexyloxy)-5-fluoro-phenyl]spiro[3H-indole-3,3'-piperidine]-2,6'-dione

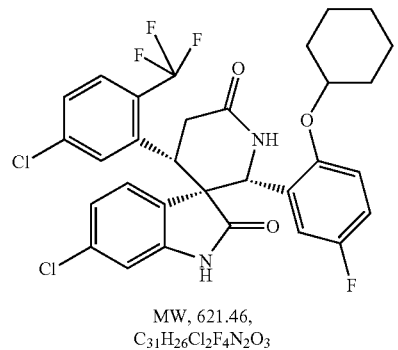

MW, 621.46,
$C_{31}H_{26}Cl_2F_4N_2O_3$

In a similar manner to the method described in Example 1e, reaction of 6-chloro-3-[1-(3-chloro-2-trifluoromethyl-phenyl)-methylidene]-2-oxo-2,3-dihydro-indole-1-carboxylic acid tert-butyl ester prepared in Example 153a with 1-[2-(cyclohexyloxy)-5-fluoro-phenyl]-3-trimethylsilanyloxy-2-aza-1,3-butadiene prepared in Example 132c gave the desired product.
MS(M+H$^+$), 621.

EXAMPLE 156

Preparation of chiral(2'R,3'R,4'S)-6-chloro-2'-[5-chloro-2-(tetrahydro-pyran-4-yloxy)-phenyl]-4'-(3-fluoro-phenyl)spiro[3H-indole-3,3'-piperidine]-2,6'-dione

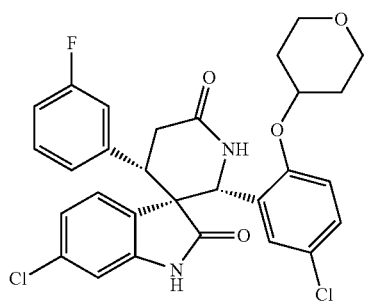

MW, 555.44,
C$_{29}$H$_{25}$Cl$_2$FN$_2$O$_4$

In a similar manner to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[5-chloro-2-(tetrahydro-pyran-4-yloxy)-phenyl]-3-trimethylsilanyloxy-2-aza-1,3-butadiene prepared in example 99b gave the desired product. MS(M+H$^+$), 555.

Chiral SFC separation (30% MeOH, 100 Par, 30° C.) gave the desired enantiomer.

MS(M+H$^+$), 555.

EXAMPLE 157

Preparation of chiral(2'R,3'R,4'S)-6-chloro-2'-[5-fluoro-2-(cyclopentyloxy)-phenyl]-4'-(3-fluoro-phenyl)spiro[3H-indole-3,3'-piperidine]-2,6'-dione

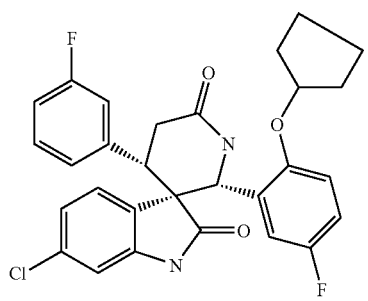

MW, 522.98,
C$_{29}$H$_{25}$ClF$_2$N$_2$O$_3$

In a similar manner to the method described in Example 1e, reaction of 6-chloro-3-[1-(3-fuloro-phenyl)-methylidene]-2-oxo-2,3-dihydro-indole-1-carboxylic acid tert-butyl ester prepared in Example 129b with 1-[5-fluoro-2-(cyclopentyloxy)-phenyl]-3-trimethylsilanyloxy-2-aza-1,3-butadiene prepared in Example 133c gave the desired product. MS(M+H$^+$), 523.

The racemate was further separated on SFC at a condition of 30% MeOH, 100 Par and 30° C. to give the enantiomer.

MS(M+H$^+$), 523.

EXAMPLE 158

Preparation of racemic(2'R,3'R,4'S)-6-chloro-2'-[2-(cyclohexyloxy-5-iodo)-phenyl]-4'-(3-fluoro-phenyl)spiro[3H-indole-3,3'-piperidine]-2,6'-dione

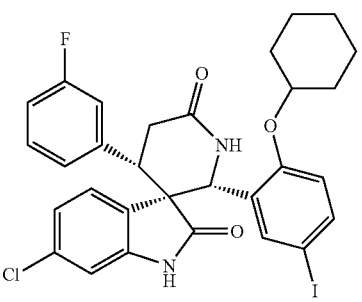

MW, 644.91,
C$_{30}$H$_{27}$ClFIN$_2$O$_3$

In a similar manner to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[2-(cyclohexyloxy-5-iodo)-phenyl]-3-trimethylsilanyloxy-2-aza-1,3-butadiene prepared in Example 154a gave the desired product.

MS(M+H$^+$), 645.

EXAMPLE 159

Preparation of racemic(2'R,3'R,4'S)-6-chloro-2'-[2-(cyclohexyloxy-5-fluoro)-phenyl]-4'-(3-fluoro-phenyl)spiro[3H-indole-3,3'-piperidine]-2,6'-dione

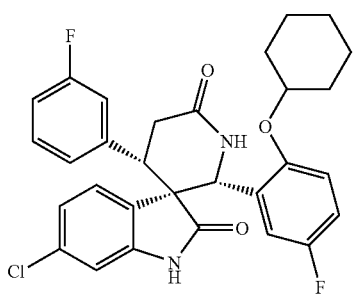

MW, 537.00,
C$_{30}$H$_{27}$ClF$_2$N$_2$O$_3$

In a similar manner to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[2-(cyclohexyloxy-5-fluoro)-phenyl]-3-trimethylsilanyloxy-2-aza-1,3-butadiene prepared in Example 132c gave the desired product.

MS(M+H$^+$), 537.

EXAMPLE 160

Preparation of racemic(2'R,3'R,4'S)-6-chloro-2'-[2-(cyclohexyloxy-5-ethynyl)-phenyl]-4'-(3-fluoro-phenyl)spiro[3H-indole-3,3'-piperidine]-2,6'-dione

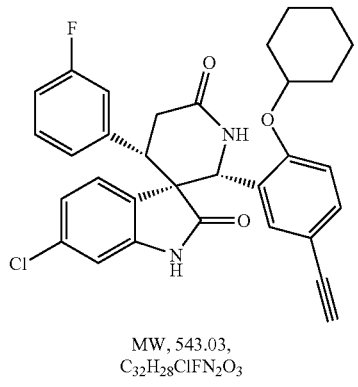

MW, 543.03,
$C_{32}H_{28}ClFN_2O_3$

To a stirred solution of racemic(2'R,3'R,4'S)-6-chloro-2'-[2-(cyclohexyloxy-5-iodo)-phenyl]-4'-(3-fluoro-phenyl)spiro[3H-indole-3,3'-piperidine]-2,6'-dione (100 mg, 0.16 mmol) prepared in Example 158 in DMF (3 mL), trimethylsilyl acetylene (Aldrich, 220 uL, 1.55 mmol), $PdCl_2(PPh_3)_2$ (Aldrich, 5 mg, 0.07 mmol), CuI (Aldrich, 1 mg) and $Et_3N$ (1 mL) were added and the mixture was stirred under nitrogen at 65° C. for 3 h. The mixture was poured into water and the new mixture was extracted with EtOAc (3×10 mL), dried with sodium sulfate. The solvent was removed and the residue was purified on a ISCO machine (2% EtOAc/methylene chloride) to give an off-white solid. The off-white solid was stirred in a mixture of aqueous NaOH (2N, 3 mL) and methanol (3 mL) at rt for 2 h. The mixture was acidified to "pH" 5 and the solid was filtered and dried. 50.8 mg. MS(M+H$^+$), 543.

EXAMPLE 161

Preparation of racemic(2'R,3'R,4'S)-6-chloro-4'-(3-chloro-phenyl)-2'-[2-(cyclohexyloxy)-5-iodo-phenyl]spiro[3H-indole-3,3'-piperidine]-2,6'-dione

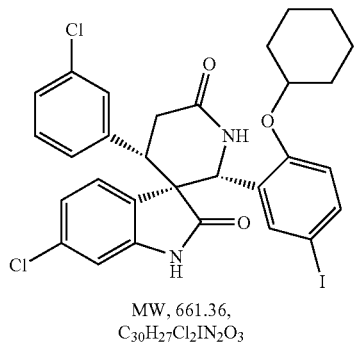

MW, 661.36,
$C_{30}H_{27}Cl_2IN_2O_3$

In a similar manner to the method described in Example 1e, reaction of 6-chloro-3-[1-(3-chloro-phenyl)-methylidene]-2-oxo-2,3-dihydro-indole-1-carboxylic acid tert-butyl ester prepared in Example 1b with 1-[2-(cyclohexyloxy-5-iodo)-phenyl]-3-trimethylsilanyloxy-2-aza-1,3-butadiene prepared in Example 132c gave the desired product. MS(M+H$^+$), 661.

EXAMPLE 162

Preparation of racemic(2'R,3'R,4'S)-6-chloro-4'-(3-chloro-phenyl)-2'-[2-(cyclohexyloxy)-5-ethynyl-phenyl]spiro[3H-indole-3,3'-piperidine]-2,6'-dione

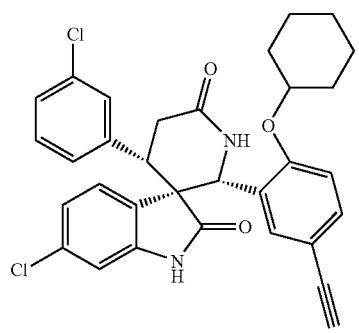

MW, 543.03,
$C_{32}H_{28}Cl_2N_2O_3$

In manner similar to the method described in Example 160, reaction of racemic (2'R,3'R,4'S)-6-chloro-4'-(3-chloro-phenyl)-2'-[2-(cyclohexyloxy-5-iodo)-phenyl]spiro[3H-indole-3,3'-piperidine]-2,6'-dione with trimethylsilyl acetylene, $PdCl_2(PPh_3)_2$, CuI and $Et_3N$, followed by reaction with NaOH in methanol gave a white solid. MS(M+H$^+$), 543.

EXAMPLE 163

Preparation of racemic(2'R,3'R,4'R)-6-chloro-2'-[5-chloro-2-(tetrahydro-thiopyran-4-yloxy)-phenyl]-4'-(2,5-difluoro-phenyl)spiro[3H-indole-3,3'-piperidine]-2,6'-dione

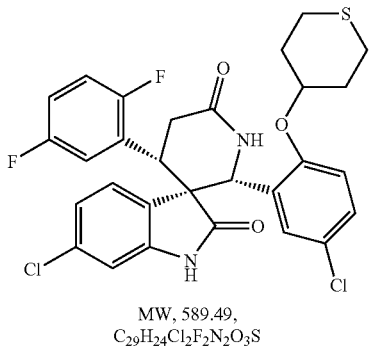

MW, 589.49,
$C_{29}H_{24}Cl_2F_2N_2O_3S$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 1-[5-chloro-2-(tetrahydro-thiopyran-4-yloxy)-phenyl]-3-trimethylsilanyloxy-2-aza-1,3-butadiene prepared in Example 135b gave the desired product.
MS(M+H$^+$), 589.

EXAMPLE 164

Preparation of chiral(2'R,3'R,4'R)-6-chloro-2'-[2-cyclohexyloxy-5-fluoro-phenyl]-4'-(2,5-difluoro-phenyl)spiro[3H-indole-3,3'-piperidine]-2,6'-dione

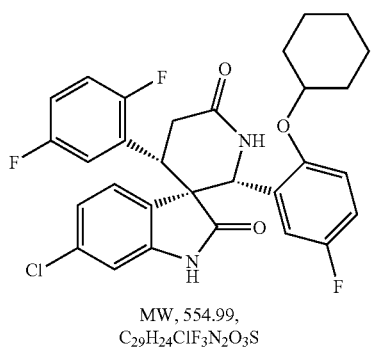

MW, 554.99,
$C_{29}H_{24}ClF_3N_2O_3S$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 1-[5-fluoro-2-(cyclohexyloxy)-phenyl]-3-trimethylsilanyloxy-2-aza-1,3-butadiene prepared in Example 132c gave the desired product. Chiral SFC separation (30% MeOH, 100 Par, 30° C.) gave the desired enantiomer.

MS(M+H$^+$), 555.

EXAMPLE 165

Preparation of racemic(2'R,3'R,4'S)-2'-[5-chloro-2-(cyclohexyloxy)-phenyl]-4'-(3-chloro-phenyl)-6-fluoro spiro[3H-indole-3,3'-piperidine]-2,6'-dione

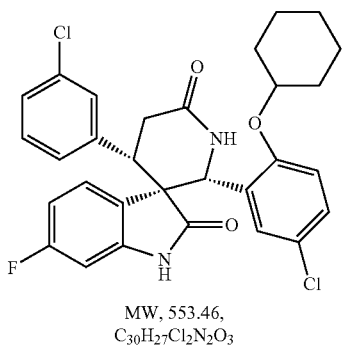

MW, 553.46,
$C_{30}H_{27}Cl_2N_2O_3$

In manner similar to the method described in Example 1e, reaction of 6-fluoro-3-[1-(3-chloro-phenyl)-methylidene]-2-oxo-2,3-dihydro-indole-1-carboxylic acid tert-butyl ester prepared in Example 138b with 1-[5-chloro-2-(cyclohexyloxy)-phenyl]-3-trimethylsilanyloxy-2-aza-1,3-butadiene prepared in Example 134b gave a white solid.

MS(M+H$^+$), 553.

EXAMPLE 166

Preparation of racemic(2'R,3'R,4'S)-4'-(3-chloro-phenyl)-2'-[5-chloro-2-(tetrahedro-thiopyran-4-yloxy-phenyl)]-6-fluoro spiro[3H-indole-3,3'-piperidine]-2,6'-dione

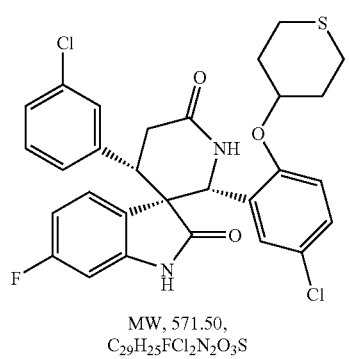

MW, 571.50,
$C_{29}H_{25}FCl_2N_2O_3S$

In manner similar to the method described in Example 1e, reaction of 6-fluoro-3-[1-(3-chloro-phenyl)-methylidene]-2-oxo-2,3-dihydro-indole-1-carboxylic acid tert-butyl ester prepared in Example 138b with 1-[5-chloro-2-(tetrahedro-thiopyran-4-yloxy-phenyl]-3-trimethylsilanyloxy-2-aza-1,3-butadiene prepared in Example 135b gave a white solid.

MS(M+H$^+$), 571.

EXAMPLE 167

Preparation of racemic(2'R,3'R,4'S)-6-chloro-2'-[5-chloro-2-(cyclohexyloxy-phenyl)]-4'-(3-fluoro-phenyl)spiro[3H-indole-3,3'-piperidine]-2,6'-dione

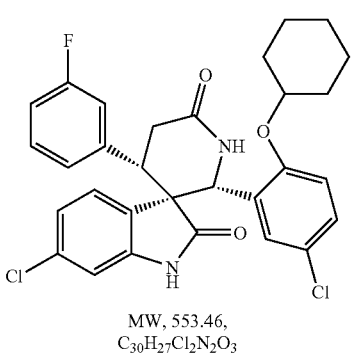

MW, 553.46,
$C_{30}H_{27}Cl_2N_2O_3$

In manner similar to the method described in Example 1e, reaction of 6-chloro-3-[1-(3-fluoro-phenyl)-methylidene]-2-oxo-2,3-dihydro-indole-1-carboxylic acid tert-butyl ester prepared in Example 129b with 1-[5-chloro-2-(cyclohexyloxy)-phenyl]-3-trimethylsilanyloxy-2-aza-1,3-butadiene prepared in Example 134b gave a white solid.

MS(M+H$^+$), 553.

EXAMPLE 168

Preparation of chiral(2'R,3'R,4'R)-6-chloro-2'-[5-chloro-2-(tetrahydro-pyran-4-yloxy)-phenyl]-4'-(2,5-difluoro-phenyl)spiro[3H-indole-3,3'-piperidine]-2,6'-dione

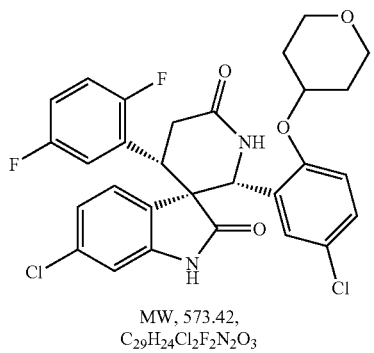

MW, 573.42,
$C_{29}H_{24}Cl_2F_2N_2O_3$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 1-[5-chloro-2-(tetrahedro-pyran-4-yloxy)-phenyl]-3-trimethylsilanyloxy-2-aza-1,3-butadiene prepared in Example 99b gave the desired product. Chiral SFC separation (30% MeOH, 100 Par, 30° C.) gave the desired enantiomer.

MS(M+H$^+$), 573

EXAMPLE 169

Preparation of chiral(2'R,3'R,4'R)-6-chloro-4'-(2,5-difluoro-phenyl)-2'-[5-fluoro-2-(tetrahydro-pyran-4-yloxy)-phenyl]spiro[3H-indole-3,3'-piperidine]-2,6'-dione

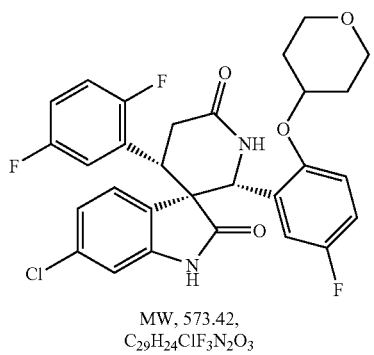

MW, 573.42,
$C_{29}H_{24}ClF_3N_2O_3$

In a similar manner to the method described in Example 1e, reaction of 6-chloro-3-[1-(2,5-difluoro-phenyl)-methylidene]-2-oxo-2,3-dihydro-indole-1-carboxylic acid tert-butyl ester prepared in Example 139b with 1-[5-fluoro-2-(tetrahydro-pyran-4-yloxy)-phenyl]-3-trimethylsilanyloxy-2-aza-1,3-butadiene prepared in Example 128b gave the desired product. Chiral SFC separation (30% MeOH, 100 Par, 30° C.) gave the desired enantiomer. MS(M+H$^+$), 557.

EXAMPLE 170

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$'s showing the biological activity of this invention exhibit activities less than about 10 μM.

Representative values are, for example:

| Example | $IC_{50}$ (μM, 0.2% BSA) |
|---|---|
| 2 | 0.205 |
| 5c | 0.034 |
| 22b | 0.042 |
| 56 | 0.131 |
| 87 | 0.048 |

What is claimed:

1. A compound of the formula

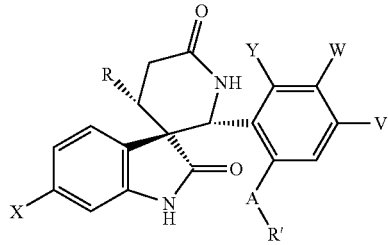

wherein

X is Cl, F or Br

R is a substituted phenyl or substituted heteroaryl with the substituted phenyl or substituted heteroaryl selected from group consisting of:

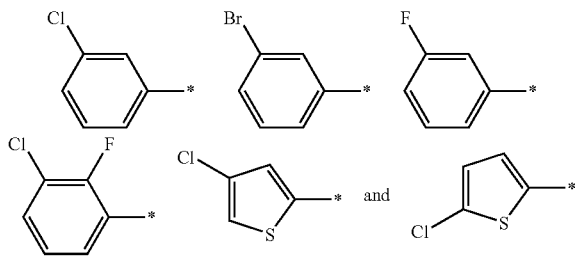

W is selected from the group consisting of F, CI, Br, I, methyl, ethyl, cyclopropyl, cyano, methoxy, hydroxymethyl, COOMe, ethynyl, $CF_3$, vinyl, isopropenyl, 1-propynyl, 3-methyl-1-butynyl, 3,3-dimethyl-1-butynyl, 3-trifluoroethynyl, phenyl, 2-furany, 2-thiophenyl and 4-thiazolyl, Y is hydrogen, F, CI or Me, V is hydrogen, F, CI or methyl, A is selected from the group consisting of O and NH, n=1, 2 or 3, R' is selected from the group consisting of heterocycle, substituted heterocyle, heteroaryl, substitluted heteroaryl, aryl, substituted aryl, substituted cycloalkyl, and $CR_1R_2C(=O)NR_3R_4$ wherein $R_1$, $R_2$ are hydrogen or lower alkyl, or may independently link to form a cyclic structure selected from a substituted or unsubstituted cycloalkyl and $R_3$, $R_4$ are independently selected from the group consisting of hydrogen, lower alkyl, aryl, lower alkenyl, substituted aryl, heteroaryl, substituted heteroaryl, heterocycle, substituted heterocycle, cycloalkyl and substituted cycloalkyl with the proviso that $R_3$, $R_4$ are not both hydrogen, or $R_3/R_4$ may independently link to form a cyclic structure selected from a substituted or unsubstituted heteroaryl, substituted or unsubstituted cycloalkyl, substituted or unsubstituted cycloalkenyl or a substituted or unsubstituted heterocycle and the pharmaceutically acceptable salts and esters thereof.

2. The compound of claim 1 wherein W, X, Y, A, R and R' are as described in claim 1 and V is hydrogen or F.

3. The compound of claim 1 wherein W, X, A, R and R' are as described in claim 1, V is hydrogen or F and Y is hydrogen or F.

4. The compound of claim 1 wherein X, A, R and R' are as described in claim 1, W is F, CI, Br, I or ethynyl, Y is hydrogen or F and V is hydrogen or F.

5. The compound of claim 1 wherein X, R and R' are as described in claim 1, W is F, CI, Br, I or ethynyl, Y is hydrogen or F, V is hydrogen or F and A is O or NH with the proviso that Y and V are not both F.

6. A compound of claim 1 selected from the group consisting of racemic(2'R,3R,4'S)-2'-[2-(1-(tert-butoxycarbonyl)-4-piperidinylmethoxy)-5-iodo-phenyl]-6-chloro-4'-(3-chlorophenyl)spiro[3H-indole-3,3'-piperidine]-2,6'(1H)-dione, racemic(2'R,3R,4'S)-2'-[2-(1-(tert-butoxycarbonyl)-4-piperidinylmethoxy)-5-ethynyl-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinylmethoxy)-5-ethynyl-phenyl]-6-chloro-4'-(3-chlorophenyl)spiro[3H-indole-3,3'-piperidine]-2,6'(1H)-dione, racemic(2'R,3R,4'S)-2'-[2-(1-(tert-butoxycarbonyl)-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione, chiral(2'R,3R,4'S)-2'-[2-(1-acetyl-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione, chiral(2'R,3R,4'S)-2'-[2-(1-acetyl-4-piperidinyloxy)-5-ethynyl-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(1-methyl-4-piperidinyloxy)-phenyl]spiro[3H-indole-3,3'-piperidine]-2,6'(1H)-dione, racemic(2'R,3R,4'S)-2'-[2-(1-acetyl-4-piperidinylamino)-5-iodo-phenyl]-6-chloro-4'-(3-chlorophenyl)spiro[3H-indole-3,3'-piperidine]-2,6'(1H)-dione and racemic(2'R,3R,4'S)-2'-[2-(1-acetyl-4-piperidinylamino)-5-ethynyl-phenyl]-6-chloro-4'-(3-chlorophenyl)spiro[3H-indole-3;3'-piperidine]-2,6'(1H)-dione.

7. A compound of claim 1 selected from the group consisting of racemic(2'R,3R,4'S)-6-chloro-4'-(3-chlorophenyl)-2'-[5-ethynyl-2-(1-propionyl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-{5-ethynyl-2-[1-(3-methanesulfonyl-propyl)-4-piperidinyloxy]-phenyl}spiro[3H-indole-3,3'-piperidine]-2,6'(1H)-dione, racemic(2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(1-methanesulfonyl-4-piperidinyloxy)phenyl]spiro[3H-indole-3,3'-piperidine]-2,6'(1H)-dione, racemic(2'R,3R,4'S)-6-chloro-4'-(3-chlorophenyl)-2'-[2-(1-dimethylcarbamoyl-4-piperidinyloxy)-5-ethynyl-phenyl]spiro[3H-indole-3,3'-piperidine]-2,6'(1H)-dione, racemic(2'R,3R,4'S)-2'-[5-bromo-2-(1-(tert-butoxycarbonyl)-4-piperidinyloxy)-phenyl]-6-chloro-4'-(3-chlorophenyl)spiro[3H-indole-3,3'-piperidine]-2,6'(1H)-dione, racemic(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione, chiral(2'R,3R,4'S)-2'-[2-(1-acetyl-4-piperidinyloxy)-5-bromo-phenyl]-6-chloro-4'-(3-chlorophenyl)spiro[3H-indole-3,3'-piperidine]-2,6'(1H)-dione, racemic(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione, chiral(2'R,3R,4'S)-2'-[3-bromo-6-(1-(tert-butoxycarbonyl)-4-piperidinyloxy)-2-fluoro-phenyl]-6-chloro-4'-(3-chlorophenyl)spiro[3H-indole-3,3'-piperidine]-2,6'(1H)-dione, racemic(2'R,3R,4'S)-2'-[6-(1-acetyl-4-piperidinyloxy)-3-bromo-2-fluoro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-ethyl-4-piperidinyloxy)-5-ethynyl-phenyl]spiro[3H-indole-3,3'-piperidine]-2,6'(1H)-dione, racemic(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione and chiral(2'R,3R,4'S)-2'-[3-bromo-2-fluoro-6-(1-methyl-4-piperidinyloxy)-phenyl]-6-chloro-4'-(3-chlorophenyl)spiro[3H-indole-3,3'-piperidine]-2,6'(1H)-dione.

8. A compound of claim 1 selected from the group consisting of racemic(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione, chiral(2'R,3R,4'S)-2'-[3-bromo-6-(1-dimethylcarbamoyl-4-piperidinyloxy)-2-fluoro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-diethylcarbamoyl-4-piperidinyloxy)-5-ethynyl-phenyl]spiro[3H-indole-3,3'-piperidine]-2,6'(1H)-dione, racemic(2'R,3R,4'S)-6-chloro-4'-(3-chlorophenyl)-2'-{5-iodo-2-[1-(pyrrolidine-1-carbonyl)-4-piperidinyloxy]-phenyl}spiro[3H-indole-3,3'-piperidine]-2,6'(1H)-dione, racemic(2'R,3R,4'S)-6-chloro4'-(3-chlorophenyl)-2'-{5-ethynyl-2-[1-(pyrrolidine-1-carbonyl)-4-piperidinyloxy]-phenyl}spiro[3H-indole-3,3'-piperidine]-2,6'(1H)-dione, racemic(2'R,3R,4'S)-6-chloro-4'-(3-chlorophenyl)-2'-[5-ethynyl-2-(1-isopropyl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-{5-ethynyl-2-[1-(2-oxo-imidazolidine-1-carbonyl)-4-piperidinyloxy]-phenyl}spiro[3H-indole-3,3'-piperidine]-2,6'(1H)-dione, racemic(2'R,3R,4'S)-2'-[6-(1-(tert-butoxycarbonyl)-4-piperidinyloxy)-3-chloro-2-fluoro-phenyl]-6-chloro-4'-(3-chlorophenyl)spiro[3H-indole-3,3'-piperidine]-2,6'(1H)-dione, racemic(2'R,3R,4'S)-2'-[6-(1-acetyl-4-piperidinyloxy)-3-chloro-2-fluoro-phenyl]-6-chloro-4'-(3-chlorophenyl)spiro[3H-indole-3,3'-piperidine]-2,6'(1H)-dione, racemic(2'R,3R,4'S)-6-chloro-2'-[3-chloro-6-(1-dimethylcarbamoyl-4-piperidinyloxy)-2-fluoro-phenyl]-4'-(3-chlorophenyl)spiro[3H-indole-3,3'-piperidine]-2,6'(1H)-dione, racemic(2'R,3R,4'S)-6-chloro-2-[3-chloro-6-(1-methylcarbamoyl-4-piperidinyloxy)-2-fluoro-phenyl]-4'-(3-chlorophenyl)spiro[3H-indole-3,3'-piperidine]-2,6'(1H)-dione, racemic(2'R,3R,4'S)-2'-[3-bromo-6-(1-methylcarbamoyl-4-piperidinyloxy)-2-fluoro-phenyl]-6-chloro-4'-(3-chlorophenyl)spiro[3H-indole-3,3'-piperidine]-2,6'(1H)-dione and racemic(2'R,3R,4'S)-6-chloro-4'-(3-chlorophenyl)-2'-[2-(1-dimethylcarbamoyl-4-piperidinyloxy)-5-iodo-phenyl]spiro[3H-indole-3,3'-piperidine]-2,6'(1H)-dione.

9. A compound of claim 1 selected from the group consisting of racemic(2'R,3R,4'S)-6-chloro-4'-(3-chlorophenyl)-2'-{5-ethynyl--[1-(4-methylpiperazine-1-carbonyl)-4-piperidinyloxyFphenyl}spiro[3H-indole-3,3'-piperidine]-2,6'(1H)-dione, racemic(2'R,3R,4'S)-6-chloro-4'-(3-chlorophenyl)-2'-[5-Iodo-2-(tetrahydro-pyran-4-yloxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(tetrahydro-pyran-4-yloxy)-phenyl]spiro[3H-indole-3,3'-piperidine]-2,6'(1H)-dione, racemic(2'R,3R,4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione, chiral(2'R,3R,4'S)-2'-[5-bromo-2-(tetrahydro-pyran-4-yloxy)-phenyl]-6-chloro-4'-(3-chlorophenyl)spiro[3H-indole-3,3'-piperidine]-2,6'(1H)-dione, racemic(2'R,3R,4'S)-2'-{5-bromo-2[-1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione, chiral(2'R,3R,4'S)-2'-{5-bromo-2-[1-(1-pyrrolidine-carbonyl)-4-piperidinyloxy]-phenyl}-6-chloro-4'-(3-chlorophenyl)spiro[3H-indole-3,3'-piperidine]-2,6'(1H)-dione, racemic(2'R,3R,4'S)-2'-[5-bromo-2-(1-dimethylcarbamoyl-4-piperidinyloxy)-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-ethoxycarbonyl-4-piperidinyloxy)-5-iodo-phenyl]spiro[3H-indole-3,3'-piperidine]-2,6'(1H)-dione, racemic(2'R,3R,4'S)-2'-[5-bromo-2-(1-ethoxycarbonyl-4-piperidinyloxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-isobutyryl-4-piperidinyloxy)-phenyl]-6-chloro-4'-(3-chlorophenyl)spiro[3H-indole-3,3'-piperidine]-2,6'(1H)-dione and racemic(2'R,3R,4'S)-2'-[5-bromo-2-(1-isopropoxycarbonyl-4-piperidinyloxy)-phenyl]-6-chloro-4'-(3-chlorophenyl)spiro[3H-indole-3,3'-piperidine]-2,6'(1H)-dione.

10. A compound of claim 1 selected from the group consisting of racemic(2'R,3R,4'S)-6-chloro-4'-(3-chlorophenyl)-2'-[5-iodo-2-(1-isobutyryl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-[5-iodo-2-(1-isopropoxycarbonyl-4-piperidinyloxy)-phenyl]spiro[3H-indole-3,3'-piperidine]-2,6'(1H)-dione, racemic(2'R,3R,4'S)-6-chloro-4'-(3-chlorophenyl)-2'-{2-[1-(2-hydroxy-ethyl)-4-piperidinyloxy]-5-iodo-phenyl}spiro[3H-indole-3,3'-piperidine]-2,6'(1H)-dione, racemic(2'R,3R,4'S)-6-chloro-4'-(3-chlorophenyl)-2'-[5-iodo-2-(1-methoxycarbonylmethyl-4-piperidinyloxy)-phenyl]spiro[3H-indole-3,3'-piperidine]-2,6'(1H)-dione, racemic(2'R,3R,4'S)-2'-[2-(1-tert-butoxycarbonylmethyl-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(1-hydroxycarbonylmethyl-4-piperidinyloxy)-5-iodo-phenyl]spiro[3H-indole-3,3'-piperidine]-2,6'(1H)-dione, racemic(2'R,3R,4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione, chiral(2'R,3R,4'S)-2'-[2-(1-carbamoylmethyl-4-piperidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-tert-butoxycarbonyl-3-pyrrolidinyloxy)-phenyl]-6-chloro-4'-(3-chlorophenyl)spiro[3H-indole-3,3'-piperidine]-2,6'(1H)-dione, racemic(2'R,3R,4'S)-2'-[2-(1-tert-butoxycarbonyl-3-pyrrolidinyloxy)-5-iodo-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1)-dione, chiral(2'R,3R,4'S)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione and racemic(2'R,3R,4'S)-2'-[5-bromo-2-(4-methoxy-phenoxy)-phenyl]-6-chloro-4'-(3-chlorophenyl)spiro[3H-indole-3,3'-piperidine]-2,6'(1H)-dione.

11. A compound of claim 1 selected from the group consisting of racemic(2'R,3R,4'S)-2'-[5-bromo-2-(2,5-dimethyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2-methoxy-4-methoxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-hydroxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-2'-{5-Bromo-2-[4-(2-hydroxy-1,1-dimethyl-ethylcarbamoyl)-phenoxy]-phenyl}-6-chloro-4'-(3-chlorophenyl)spiro[3H-indole-3,3'-piperidine]-2,6'(1H)-dione, racemic(2'R,3R,4'S)-2'-{5-bromo-2[4-(2-pyrrolidin-1-yl-ethylcarbamoyl)-phenoxy]-phenyl}-6-chloro-4'-(3-chlorophenyl)spiro[3H-indole-3,3'- piperidine]-2,6'(1H)-dione, racemic(2'R,3R,4'S)-2'-[5-bromo-2-(4-carbamoyl-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2-chloro-4-methoxycarbonyl-phenoxy)-phenyl]-6-chloro-4'-(3-chlorophenyl)spiro[3H-indole-3,3'-piperidine]-2,6'(1H)-dione, racemic(2'R,3R,4'S)-6-chloro-2'-[5-chloro-2-(4-methoxycarbonyl-phenoxy)-phenyl]-4'-(3-chlorophenyl)spiro[3H-indole-3,3'-piperidine]-2,6'(1H)-dione, racemic(2'R,3R,4'S)-6-chloro-4'-(3-chlorophenyl)-2'-{2-[4-(2-hydroxy-ethoxy)-phenoxy]-5-iodo-phenyl}spiro[3H-indole-3,3'-piperidine]-2,6'(1H)-dione, chiral(2'R,3R,4'S)-6-chloro-4'-(3-chlorophenyl)-2'-{2'-[4-(2-hydroxy-ethoxy)-phenoxy]-5-iodo-phenyl}spiro[3H-indole-3,3'-piperidine]-2,6'(1H)-dione, racemic(2'R,3R,4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione, chiral(2'R,3R,4'S)-6-chloro-4'-(3-chlorophenyl)-2'-{5-ethynyl-2-[4-(2-hydroxy-ethoxy)-phenoxy]-phenyl}spiro[3H-indole-3,3'-piperidine]-2,6'(1H)-dione, racemic(2'R,3R,4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione and chiral(2'R,3R,4'S)-6-chloro-2'-{5-chloro-2-[4-(2-hydroxy-ethoxy)-phenoxy]-phenyl}-4'-(3-chlorophenyl)spiro[3H-indole-3,3'-piperidine]-2,6'(1H)-dione.

12. A compound of claim 1 selected from the group consisting of racemic(2'R,3R,4'S)-2'-[5-bromo-2-(2,6-dimethyl-4-pyridinyloxy)-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[2-(4-cyano-phenoxy)-5-iodo-phenyl]spiro[3H-indole-3,3'-piperidine]-2,6'(1H)-dione, chiral(2'R,3R,4'S)-6-chloro-4'-(3-chlorophenyl)-2'-[2-(4-cyano-phenoxy)-5-iodo-phenyl]spiro[3H-indole-3,3'-piperidine]-2,6'(1H)-dione, racemic(2'R,3R,4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione, chiral(2'R,3R,4'S)-6-chloro-4'-(3-chlorophenyl)-2'-[2-(4-cyano-phenoxy)-5-ethynyl-phenyl]spiro[3H-indole-3,3'-piperidine]-2,6'(1H)-dione, racemic(2'R,3R,4'S)-6-chloro-4'-(3-chlorophenyl)-2'-[5-iodo-2-(4-methoxy-phenoxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(4-methoxy-phenoxy)-phenyl]spiro[3H-indole-3,3'-piperidine]-2,6'(1H)-dione, racemic(2'R,3R,4'S)-6-chloro-4'-(3-chlorophenyl)-2'-[5-iodo-2-(4-methoxycarbonyl-phenoxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(4-methoxycarbonyl-phenoxy)-phenyl]spiro[3H-indole-3,3'-piperidine]-2,6'(1H)-dione, racemic(2'R,3R,4'S)-6-chloro-4'-(3-chlorophenyl)-2'-[2-(4-hydroxycarbonyl-phenoxy)-5-iodo-phenyl]spiro[3H-indole-3,3'-piperidine]-2,6'(1H)-dione, racemic(2'R,3R,4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione and chiral(2'R,3R,4'S)-2'-[2-(4-carbamoyl-phenoxy)-5-ethynyl-phenyl]-6-chloro-4'-(3-chlorophenyl)spiro[3H-indole-3,3'-piperidine]-2,6'(1H)-dione.

13. A compound of claim 1 selected from the group consisting of racemic(2'R,3R,4'S)-6-chloro-4'-(3-chlorophenyl)-2'-[2-(2,6-dimethyl-4-pyridinyloxy)-5-iodo-phenyl]spiro[3H-indole-3,3'-piperidine]-2,6'(1H)-dione, racemic(2'R,3R,4'S)-6-chloro-4'-(3-chlorophenyl)-2'-[2-(2,6-dimethyl-4-pyridinyloxy)-5-ethynyl-phenyl]spiro[3H-indole-3,3'-piperidine]-2,6'(1H)-dione, racemic(2'R,3R,4'S)-2'-[5-bromo-2-(4-fluoro-phenoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(4-trifluoromethyl-phenoxy)-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-chloro-2-(4-trifluoromethyl-phenoxy)-phenyl]spiro[3H-indole-3,3'-piperidine]-2,6'(1H)-dione, racemic(2'R,3R,4'S)-2'-[5-bromo-2-(3-cyano-phenoxy)-phenyl]-6-chloro-4'-(3-chlorophenyl)spiro[3H-indole-3,3'-piperidine]-2,6'(1H)-dione, racemic(2'R,3R,4'S)-2'-{5-bromo-2-[4-(3-hydroxy-propyl)-phenoxy]-phenyl}-6-chloro-4'-(3-chlorophenyl)spiro[3H-indole-3,3'-piperidine]-2,6'(1H)-dione, racemic(2'R,3R,4'S)-6-chloro-2'-[5-chloro-2-(4-cyano-phenoxy)-phenyl]-4'-(3-chlorophenyl)spiro[3H-indole-3,3'-piperidine]-2,6'(1H)-dione, chiral(2'R,3R,4'S)-6-chloro-2'-[5-chloro-2-(4-cyano-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-methylsulfanyl-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-methylsulfonyl-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-methylsulfinyl-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-nitro-phenoxy)-phenyl]-4'-(3-chlorophenyl)spiro[3H-indole-3,3'-piperidine]-2,6'(1H)-dione and racemic(2'R,3R,4'S)-2'-[2-(4-amino-phenoxy)-5-chloro-phenyl]-6-chloro-4'-(3-chlorophenyl)spiro[3H-indole-3,3'-piperidine]-2,6'(1H)-dione.

14. A compound of claim 1 selected from the group consisting of chiral(2'R,3R,4'S)-2'-[2-(4-amino-phenoxy)-5-chloro-phenyl]-6-chloro-4'-(3-chlorophenyl)spiro[3H-indole-3,3'-piperidine]-2,6'(1H)-dione, racemic(2'R,3R,4'S)-2'-[2-(4-acetylamino-phenoxy)-5-chloro-phenyl]-6-chloro-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-iodo-2-(1,3,5-trimethyl-1H-pyrazol-4-yloxy)-phenyl]spiro[3H-indole-3,3'-piperidine]-2,6'(1H)-dione, racemic(2'R,3R,4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione, chiral(2'R,3R,4'S)-6-chloro-4'-(3-chlorophenyl)-2'-[5-ethynyl-2-(1,3,5-trimethyl-1H-pyrazol-4-yloxy)-phenyl]spiro[3H-indole-3,3'-piperidine]-2,6'(1H)-dione, racemic(2'R,3R,4'S)-2'-[5-bromo-2-(1,3,5-trimethyl-1H-pyrazol-4-yloxy)-phenyl]-6-chloro-4'-(3-chlorophenyl)spiro[3H-indole-3,3'-piperidine]-2,6'(1H)-dione, racemic(2'R,3R,4'S)-6-chloro-2'-[5-chloro-2-(1,4-dioxa-spiro[4.5]dec-8-yloxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(4-oxo-cyclohexyloxy)-phenyl]-4'-(3-chlorophenyl)spiro[3H-indole-3,3'-piperidine]-2,6'(1H)-dione, racemic(2'S,3R,4'S)-6-chloro-2'-[2-chloro-6-(4-methoxy-phenoxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione, chiral(2'R,3R,4'S)-6-chloro-2'-[5-chloro-2-(cis-4-hydroxy-cyclohexyloxy)-phenyl]-4'-(3-chlorophenyl)spiro[3H-indole-3,3'-piperidine]-2,6'(1H)-dione, racemic(2'R,3R,4'S)-6-chloro-2'-[5-chloro-2-(trans-4-hydroxy-cyclohexyloxy)-phenyl]-4'-(3-chlorophenyl)spiro[3H-indole-3,3'-piperidine]-2,6'(1H)-dione, chiral(2'R,3R,4'S)-6-chloro-2'-

[5-chloro-2-(trans-4-hydroxy-cyclohexyloxy)-phenyl]-4'-(3-chlorophenyl)spiro[3H-indole-3,3'-piperidine]-2,6'(1H)-dione and racemic(2'R,3R,4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione.

15. A compound of claim 1 selected from the group consisting of racemic(2'R,3R,4'S)-6-chloro-2'-[5-chloro-4-fluoro-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'S)-6-chloro-2'-[5-chloro-4-methyl-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione, chiral(2'R,3R,4'S)-6-chloro-4'-(3-chlorophenyl)-2'-[5-chloro-2-(2,2,6,6-tetramethyl-tetrahydro-pyran-4-yloxy)-phenyl]spiro[3H-indole-3,3'-piperidine]-2,6'(1H)-dione, racemic(2'R,3R,4'S)-6-chloro-2'-[5-chloro-2-(tetrahydro-pyran-4-yloxy)-phenyl]]-4'-(3-chlorophenyl)spiro[3H-indole-3,3'-piperidine]-2,6'(1H)-dione, racemic(2'R,3R,4'R)-6-chloro-4'-(3-chloro-2-fluoro-phenyl)-2'-[5-chloro-2-(tetrahydro-pyran-4-yloxy)-phenyl]]spiro[3H-indole-3,3'-piperidine]-2,6'(1H)-dione, racemic(2'R,3R,4'R)-6-chloro-4'-(3-chloro-4-fluoro-phenyl)-2'-[5-chloro-2-(tetrahydro-pyran-4-yloxy)-phenyl]]spiro[3H-indole-3,3'-piperidine]-2,6'(1H)-dione, racemic(2'R,3R,4'S)-2'-{5-bromo-2-[2-(4-acetyl-piperazin-1-yl)-1,1-dimethyl-2-oxo-ethoxy]-phenyl}-6-chloro-4'-(3-chlorophenyl)spiro[3H-indole-3,3'-piperidine]-2,6'(1H)-dione, racemic(2'R,3R,4'S)-2'-{5-bromo-2-[2-(4,4-difluoro-piperidin-1-yl)-1,1-dimethyl-2-oxo-ethoxy]-phenyl}-6-chloro-4'-(3-chlorophenyl)spiro[3H-indole-3,3'-piperidine]-2,6'(1H)-dione, racemic(2'R,3R,4'S)-2'-{5-bromo-2-[1-methyl-1-(2,2,2-trifluoro-ethylcarbamoyl)-ethoxy]-phenyl}-6-chloro-4'-(3-chlorophenyl)spiro[3H-indole-3,3'-piperidine]-2,6'(1H)-dione, racemic(2'R,3R,4'S)-2'-[5-bromo-2-(1-dimethylcarbamoyl-1-methyl-ethoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2-dimethylcarbamoyl-2-methyl-propoxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(2,2-dimethyl-3-oxo-3-pyrrolidin-1-yl-propoxy)-phenyl]-6-chloro-4'-(3-chlorophenyl)spiro[3H-indole-3,3'-piperidine]-2,6'(1H)-dione and racemic(2'R,3R,4'S)-2'-[5-bromo-2-(3-methyl-oxetan-3-ylmethoxy)-phenyl]-6-chloro-4'-(3-chlorophenyl)spiro[3H-indole-3,3'-piperidine]-2,6'(1H)-dione.

16. A compound of claim 1 selected from the group consisting of chiral(2'R,3R,4'S)-6-chloro-4'-(3-chlorophenyl)-2'-[5-bromo-2-(3-methyl-oxetan-3-ylmethoxy) phenyl]spiro[3H-indole-3,3'-piperidine]-2,6'(1H)-dione, racemic(2'R,3R,4'S)-2'-[5-bromo-2-(4-fluoro-benzyloxy)-phenyl]-6-chloro-4'-(3-chlorophenyl)spiro[3H-indole-3,3'-piperidine]-2,6'(1H)-dione, racemic(2'R,3R,4'S)-2'-[5-bromo-2-(3-ethyl-oxetan-3-ylmethoxy)-phenyl]-6-chloro-4'-(3-chlorophenyl)spiro[3H-indole-3,3'-piperidine]-2,6'(1H)-dione, racemic(2'R,3R,4'S)-2'-[2-(1-tert-butoxycarbonyl-piperidin-4-yloxy)]-5-trifluoromethyl-phenyl]-6-chloro-4'-(3-chlorophenyl)spiro[3H-indole-3,3'-piperidine]-2,6'(1H)-dione, racemic(2'R,3R,4'S)-2'-[5-bromo-2-(1-methyl-piperidin-4-ylamino)-phenyl]-6-chloro-4'-(5-chloro-2-methyl-phenyl)spiro[3H-indole-3,3'-piperidine]-2,6'(1H)-dione and racemic(2'R,3R,4'S)-6-chloro-4'-(3-chlorophenyl)-2'-[5-chloro-2-(2-pyrazinyloxy)-phenyl]-spiro-[3H-indole-3,3'-piperidine]-2,6'-dione.

17. A compound of claim 1 selected from the group consisting of chiral(2'R,3R,4'S)-2'-{2-[3-(tert-butoxycarbonyl)-pyrolidinyloxy]-5-chloro-phenyl}-6-chloro-4'-(3-chlorophenyl)spiro[3H-indole-3,3'-piperidine]-2,6'-dione, chiral (2'R,3R,4'S)-6-chloro-4'-(3-chlorophenyl)-2'-[5-chloro-(3-pyrolidinyloxy)-phenyl}spiro[3H-indole-3,3'-piperidine]-2,6'-dione, chiral(2'R,3R,4'S)-6-chloro-2'-[5-chloro-2-(3-methanesulfonyl-pyrolidinyloxy)-phenyl]-4'-(3-chlorophenyl)spiro[3H-indole-3,3'-piperidine]-2,6'-dione, chiral(2'R,3R,4'S)-6-chloro-2'-[5-chloro-2-(3-ethylcarbamoyl-pyrolidinyloxy)-phenyl}-4'-(3-chlorophenyl)spiro[3H-indole-3,3'-piperidine]-2,6'-dione, chiral(2'R,3R,4'S)-2'-[2-(1-acetyl-3-pyrolidinyloxy)-5-chloro-phenyl]-6-chloro-4'-(3-chlorophenyl)spiro[3H-indole-3,3'-piperidine]-2,6'-dione, racemic(2'R,3R,4'S)-6-chloro-4'-(3-chlorophenyl)-2'-[trans-4-(3-hydroxy-1-methanesulfonyl-piperidinyloxy)-5-iodo-phenyl]spiro[3H-indole-3,3'-piperidine]-2,6'-dione, racemic(2'R,3'R,4'S)-6-chloro-4'-(3-chloro-phenyl)-2'-[5-fluoro-2-(tetrahydro-pyran-4-yloxy)-phenyl]spiro[3H-indole-3,3'-piperidine]-2,6'-dione, chiral(2'R,3'R,4'S)-6-chloro-4'-(3-fluoro-phenyl)-2'-[5-fluoro-2-(tetrahydro-pyran-4-yloxy)-phenyl]spiro[3H-indole-3,3'-piperidine]-2,6'-dione, racemic(2'R,3'R,4'S)-6-chloro-4'-(3-chlorophenyl)-2'-[5-fluoro-2-(tetrahydro-thiopyran-4-yloxy)-phenyl]spiro[3H-indole-3,3'-piperidine]-2,6'-dione, chiral(2'R,3'R,4'S)-6-chloro-4'-(3-chlorophenyl)-2'-[5-fluoro-2-(1,1-dioxo-tetrahydro-thiopyran-4-yloxy)-phenyl]spiro[3H-indole-3,3'-piperidine]-2,6'-dione, chiral(2'R,3'R,4'S)-6-chloro-4'-(3-chlorophenyl)-2'-[5-fluoro-2-(cyclohexyloxy)-phenyl]spiro[3H-indole-3,3'-piperidine]-2,6'-dione, chiral(2'R,3'R,4'S)-6-chloro-4'-(3-chlorophenyl)-2'-[5-fluoro-2-(cyclopentyloxy)-phenyl]spiro[3H-indole-3,3'-piperidine]-2,6'-dione and racemic(2'R,3'R,4'S)-6-chloro-2'-[5-chloro-2-(cyclohexyloxy-phenyl)]-4'-(3-chloro-phenyl) spiro[3H-indole-3,3'-piperidine]-2,6'-dione.

18. A compound of claim 1 selected from the group consisting of racemic(2'R,3'R,4'S)-6-chloro2'-[5-chlororo-2-(tetrahydro-thiopyran-4-yloxy)-phenyl]-4'-(3-fluoro-phenyl)-spiro[3H-indole-3,3'-piperidine]-2,6'-dione, racemic (2'R,3'R,4'S)-6-chloro-2'-[5-chloro-2-(1,1-dioxo-tetrahydro-thiopyran-4-yloxy)-phenyl]-4'-(3-fluoro-phenyl) spiro[3H-indole-3,3'-piperidine]-2,6'-dione, racemic(2'R,3'R,4'S)-6-chloro -4'-(3-fluoro -phenyl)-2'-[5-fluoro-2-(4-fuloro-phenoxy-phenyl)]spiro[3H-indole-3,3'-piperidine]-2,6'-dione, racemic(2'R,3'R,4'S)-4'-(3-chloro-phenyl)-6-fluoro-2'-[2-(2,4-difluoro-phenyloxy)-5-fluoro-phenyl]spiro[3H-indole-3,3'-piperidine]-2,6'-dione, racemic(2'R,3'R,4'R)-6-chloro-2'-[5-chloro-2-(2-chloro-6-fluoro-benzyloxy)-phenyl]-4'-(2,5-difluoro-phenyl)spiro[3H-indole-3,3'-piperidine]-2,6'-dione, racemic(2'R,3'R,4'R)-6-chloro-2'-[2-(4-cyano-phenyloxy)-5-fluoro-phenyl]-4'-(2,5-difluoro-phenyl)spiro[3H-indole-3,3'-piperidine]-2,6'-dione, racemic(2'R,3'R,4'S)-6-chloro-2'-[2-(4-cyano-phenyloxy)-5-fluoro-phenyl]-4'-(3-fluoro-phenyl) spiro[3H-indole-3,3'-piperidine]-2,6'-dione, racemic(2'R,3'R,4'S)-4'-(3-chloro-phenyl)-2'-[2-(4-cyano-phenyloxy)-5-fluoro-phenyl]-6-fluoro spiro[3H-indole-3,3'-piperidine]-2,6'-dione, racemic (2'R,3'R,4'S)-6-chloro-2'-[5-fluoro-2-(4-methoxy-phenyloxy)-phenyl]-4'-(3-fluoro-phenyl)spiro[3H-indole-3,3'-piperidine]-2,6'-dione, racemic(2'R,3'R,4'S)-4'-(3-chloro-phenyl)-6-fluoro-2'-[5-fluoro-2-(4-methoxy-phenyloxy)-phenyl]spiro[3H-indole-3,3'-piperidine]-2,6'-dione, racemic (2'R,3'R,4'R)-6-chloro-2'-[5-fluoro-2-(4-methoxy-phenyloxy)-phenyl]-4'-(2,5-difluoro-phenyl)spiro[3H-indole-3,3'-piperidine]-2,6'-dione, chiral(2'R,3'R,4'S)-6-chloro-4'-(3-chloro-phenyl)-2'-[5-fluoro-2-(4-methoxy-phenyloxy)-phenyl]spiro[3H-indole-3,3'-piperidine]-2,6'- dione, chiral(2'R,3'R,4'R)-6-chloro-4'-(5-chloro-2-fluoro-phenyl)-2'-[5-fluoro-2-(4-methoxy-phenyloxy)-phenyl]spiro[3H-indole-3,3'-piperidine]-2,6'-dione and racemic(2'R,3'R,4'R)-6-chloro-2'-{5-fluoro-2-[4-(2-hydroxy-ethoxy)-phenoxy]phenyl}-4'-(2,5-difluoro-phenyl)spiro[3H-indole-3,3'-piperidine]-2,6'-dione.

19. A compound of claim 1 selected from the group consisting of racemic(2'R,3'R,4'R)-6-chloro-4'-(5-chloro-2-fluoro-phenyl)-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-6-chloro-4'-(3-fluoro-phenyl)-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-4'-(3-chloro -phenyl)-6-fluoro-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-6-chloro-4'-(3-chloro-phenyl)-2'-{5-fluoro-2-[4-(2-hydroxy-ethoxy)-phenoxy]phenyl}spiro[3H-indole-3,3'-piperidine]-2,6'-dione, racemic(2'R,3'R,4'S)-6-chloro-2'-[5-chloro-2-(tetrahydro-pyran-4-yloxy)-phenyl]-4'-(5-chloro-2-trifluoromethyl-phenyl)spiro[3H-indole-3,3'-piperidine]-2,6'-dione, racemic(2'R,3'R,4'S)-6-chloro-4'-(5-chloro-2-trifluoromethyl-phenyl)-2'-[5-iodo-2-(tetrahydro-pyran-4-yloxy)-phenyl]spiro[3H-indole-3,3'-piperidine]-2,6'-dione, (2'R, 3'R,4'S)-6-chloro-4'-(5-chloro-2-trifluoromethyl-phenyl)-2'-[2-(cyclohexyloxy)-5-fluoro-phenyl]spiro[3H-indole-3,3'-piperidine]-2,6'-dione, chiral(2'R,3'R,4'S)-6-chloro-2'-[5-chloro-2-(tetrahydro-pyran-4-yloxy)-phenyl]-4'-(3-fluoro-phenyl)spiro[3H-indole-3,3'-piperidine]-2,6'-dione, chiral(2'R,3'R,4'S)-6-chloro-2'-[5-fluoro-2-(cyclopentyloxy)-phenyl]-4'-(3-fluoro-phenyl)spiro[3H-indole-3,3'-piperidine]-2,6'-dione, racemic(2'R,3'R,4'S)-6-chloro-2'-[2-(cyclohexyloxy-5-iodo)-phenyl]-4'-(3-fluoro-phenyl) spiro[3H-indole-3,3'-piperidine]-2,6'-dione, racemic(2'R,3'R,4'S)-6-chloro-2'-[2-(cyclohexyloxy-5-fluoro)-phenyl]-4'-(3-fluoro-phenyl) spiro[3H-indole-3,3'-piperidine]-2,6'-dione, racemic(2'R,3'R,4'S)-6-chloro-2'-[2-(cyclohexyloxy-5-ethynyl)-phenyl]-4'-(3-fluoro-phenyl)spiro[3H-indole-3,3'-piperidine]-2,6'-dione, racemic(2'R,3'R,4'S)-6-chloro-4'-(3-chloro-phenyl)-2'-[2-(cyclohexyloxy)-5-iodo-phenyl] spiro[3H-indole-3,3'-piperidine]-2,6'-dione and racemic(2'R,3'R,4'S)-6-chloro-4'-(3-chloro-phenyl)-2'-[2-(cyclohexyloxy)-5-ethynyl-phenyl]spiro[3H-indole-3,3'-piperidine]-2,6'-dione.

20. A compound of claim 1 selected from the group consisting of racemic(2'R,3'R,4'R)-6-chloro-2'-[5-chloro-2-(tetrahydro-thiopyran-4-yloxy)-phenyl]-4'-(2,5-difluoro-phenyl)spiro[3H-indole-3,3'-piperidine]-2,6'-dione, chiral(2'R, 3'R,4'R)-6-chloro-2'[2-cyclohexyloxy-5-fluoro-phenyl]-4'-(2,5-difluoro-phenyl) spiro[3H-indole-3,3'-piperidine]-2,6'-dione, racemic(2'R,3'R,4'S)-2'-[5-chloro-2-(cyclohexyloxy)-phenyl]-4'-(3-chloro-phenyl)-6-fluoro spiro[3H-indole-3,3'-piperidine]-2,6'-dione, racemic(2'R,3'R,4'S)-4'-(3-chloro-phenyl)-2'-[5-chloro-2-(tetrahedro-thiopyran-4-yloxy-phenyl)]-6-fluoro spiro[3H-indole-3,3'-piperidine]-2,6'-dione, racemic(2'R,3'R,4'S)-6-chloro-2'-[5-chloro-2-(cyclohexyloxy-phenyl)]-4'-(3-fluoro -phenyl)spiro[3H-indole-3,3'-piperidine]-2,6'-dione, chiral(2'R,3'R,4'R)-6-chloro-2'-[5-chloro-2-(tetrahydro-pyran-4-yloxy)-phenyl]-4'-(2,5-difluoro-phenyl)spiro[3H-indole-3,3'-piperidine]-2,6'-dione and chiral(2'R,3'R,4'R)-6-chloro-4'-(2,5-difluoro-phenyl)-2'-[5-fluoro-2-(tetrahydro-pyran-4-yloxy)-phenyl]spiro[3H-indole-3,3'-piperidine]-2,6'-dione.

21. A pharmaceutical composition comprising a compound of the formula

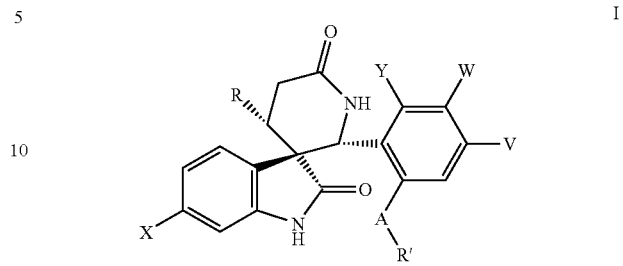

wherein
X is Cl, F or Br
R is a substituted phenyl or substituted heteroaryl with the substituted phenyl or substituted heteroaryl selected from group consisting of:

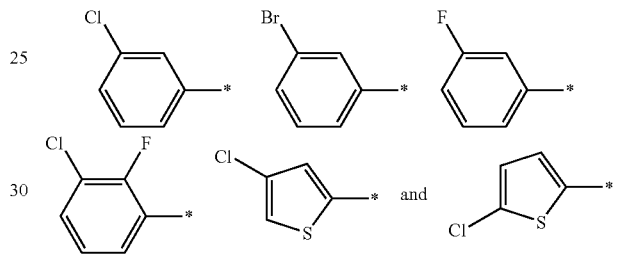

W is selected from the group consisting of F, Cl, Br, I, methyl, ethyl, cyclopropyl, cyano, methoxy, hydroxymethyl, COOMe, ethynyl, $CF_3$, vinyl, isopropenyl, 1-propynyl, 3-methyl-1-butynyl, 3,3-dimethyl-1-butynyl, 3-trifluoroethynyl, phenyl, 2-furany, 2-thiophenyl and 4-thiazolyl,
Y is hydrogen, F, Cl or Me,
V is hydrogen, F, Cl or methyl,
A is selected from the group consisting of O and NH,
n =1, 2 or 3
R' is selected from the group consisting of heterocycle, substituted heterocyle, heteroaryl, substitluted heteroaryl, aryl, substituted aryl, substituted cycloalkyl and $CR_1R_2C(=O)NR_3R_4$ wherein
$R_1$, $R_2$ are hydrogen or lower alkyl,
or may independently link to form a cyclic structure selected from a substituted or unsubstituted cycloalkyl and
$R_3$, $R_4$ are independently selected from the group consisting of hydrogen, lower alkyl, arid, lower alkenyl, substituted aryl, heteroaryl, substituted heteroaryl, heterocycle, substituted heterocycle, cycloalkyl and substituted cycloalkyl with the proviso that $R_3$, $R_4$ are not both hydrogen,
or $R_3/R_4$ may independently link to form a cyclic
structure selected from a substituted or unsubstituted heteroaryl, substituted or unsubstituted cycloalkyl, substituted or unsubstituted cycloalkenyl or a substituted or unsubstituted heterocycle and the pharmaceutically acceptable salts and esters thereof together with a pharmaceutically acceptable carrier or excipient.

22. A compound selected from the group consisting of racemic(2'R,3R,4'S)-6-chloro-2'-(5-chloro-2-imidazol-1-ylphenyl)-4'-(3-chlorophenyl) spiro[3H-indole-3,3'-piperidine]-2,6'(1H)-dione, racemic(2'R,3'R,4'S)-6-chloro-4'-(3-chlorophenyl)-2'-[2-(2-hydroxy-ethoxy)-5-(2-thiophenyl)-phenyl]-spiro[3H-indole-3,3'-piperidine]-2,6'-dione, chiral (2'R, 3'R, 4'S)-6-chloro-4'-(3-chlorophenyl)-2'-[2-(2-hydroxy-ethoxy)-5-(2-furanyl)-phenyl]-spiro[3H-indole-3,3'-piperidine]-2,6'-dione, racemic(2'R,3'R,4'S)-6-chloro-4'-(3-chlorophenyl)-2'-[2-(2-hydroxy-ethoxy)-5-phenyl-phenyl]-spiro[3H-indole-3,3'-piperidine]-2,6'-dione, racemic(2'R, 3R,4'S)-6-chloro-4'-(3-chlorophenyl)-2'-[2-hydroxy-5-iodophenyl]spiro[3H-indole-3,3'-piperidine]-2,6'-dione, racemic (2'R,3'R,4'S)-6-chloro-4'-(3-chlorophenyl)-2'-[5-(2-furanyl)-2-hydroxy-phenyl]-spiro[3H-indole-3,3'-piperidine]-2,6'-dione, racemic(2'R,3'R,4'S)-6-chloro-4'-(3-chlorophenyl)-2'-[2-hydroxy-5-(2-thiofuranyl)-phenyl]-spiro[3H-indole-3,3'-piperidine]-2,6'-dione, racemic(2'R, 3'R,4'S)-6-chloro-4'-(3-chlorophenyl)-2'-[2-hydroxy-5-phenyl]-phenyl-spiro[3H-indole-3,3'-piperidine]-2,6'-dione, racemic(2'R,3'R,4'S)-6-chloro-4'-(3-chlorophenyl)-2'-[2-hydroxy-5-(2-thiazolyl)-phenyl]-spiro[3H-indole-3,3'-piperidine]-2,6'-dione and racemic(2'R,3'R,4'S)-6-chloro-4'-(3-chlorophenyl)-2'-[2-hydroxy-5-(2-thiazolyl)-phenyl]-spiro[3H-indole-3,3'-piperidine]-2,6'-dione.

* * * * *